US012741034B2

(12) United States Patent
Burns et al.

(10) Patent No.: US 12,741,034 B2

(45) **Date of Patent: *Sep. 22, 2026**

(54) COMPOSITIONS AND METHODS FOR TREATING SENSORINEURAL HEARING LOSS USING OTOFERLIN DUAL VECTOR SYSTEMS

(71) Applicant: Decibel Therapeutics, Inc., Boston, MA (US)

(72) Inventors: Joseph Burns, Newton, MA (US); Kathryn Ellis, Arlington, MA (US); Adam Palermo, Somerville, MA (US); Martin Schwander, Auburndale, MA (US); Jonathon Whitton, Cambridge, MA (US)

(73) Assignee: Decibel Therapeutics, Inc., Boston, MA (US)

( * ) Notice: Subject to any disclaimer, the term of this patent is extended or adjusted under 35 U.S.C. 154(b) by 125 days.

This patent is subject to a terminal disclaimer.

(21) Appl. No.: 18/933,398

(22) Filed: Oct. 31, 2024

(65) Prior Publication Data

US 2025/0127926 A1 Apr. 24, 2025

Related U.S. Application Data

(63) Continuation of application No. 18/142,133, filed on May 2, 2023, now abandoned, which is a continuation of application No. 16/395,999, filed on Apr. 26, 2019, now Pat. No. 11,660,353.

(60) Provisional application No. 62/663,739, filed on Apr. 27, 2018.

(51) Int. Cl.

| | |
|---|---|
| ***A61K 48/00*** | (2006.01) |
| ***C07K 14/47*** | (2006.01) |
| ***C12N 15/09*** | (2006.01) |
| ***C12N 15/86*** | (2006.01) |
| *A61K 9/00* | (2006.01) |

(52) U.S. Cl.

CPC ........ *A61K 48/005* (2013.01); *A61K 48/0075* (2013.01); *C07K 14/47* (2013.01); *C12N 15/86* (2013.01); *A61K 9/0048* (2013.01); *C12N 2750/14143* (2013.01)

(58) Field of Classification Search

CPC ................................ A61K 48/00; C12N 15/09

See application file for complete search history.

(56) References Cited

U.S. PATENT DOCUMENTS

| | | | |
|---|---|---|---|
| 6,436,392 | B1 | 8/2002 | Engelhardt et al. |
| 6,544,786 | B1 | 4/2003 | Xiao et al. |
| 6,808,922 | B1 | 10/2004 | Bebbington et al. |
| 6,897,045 | B2 | 5/2005 | Engelhardt et al. |
| 7,803,622 | B2 | 9/2010 | Engelhardt et al. |
| 8,236,557 | B2 | 8/2012 | Dongsheng et al. |
| 8,298,818 | B2 | 10/2012 | Boye et al. |
| 10,214,572 | B2 | 2/2019 | Boye et al. |
| 11,325,956 | B2 | 5/2022 | Boye et al. |
| 11,525,139 | B2 | 12/2022 | Simons et al. |
| 11,660,353 | B2 | 5/2023 | Burns et al. |
| 11,781,145 | B2 | 10/2023 | Simons et al. |
| 11,807,867 | B2 | 11/2023 | Simons et al. |
| 2003/0219741 | A1 | 11/2003 | Isogai et al. |
| 2004/0072154 | A1 | 4/2004 | Morris et al. |
| 2007/0161031 | A1 | 7/2007 | Trinklein et al. |
| 2007/0161110 | A1 | 7/2007 | Iida et al. |
| 2008/0249052 | A1 | 10/2008 | Duan et al. |
| 2010/0003218 | A1 | 1/2010 | Duan et al. |
| 2010/0266551 | A1 | 10/2010 | Richard et al. |
| 2012/0003190 | A1 | 1/2012 | Yamoah et al. |
| 2012/0087862 | A1 | 4/2012 | Hood et al. |
| 2013/0210895 | A1 | 8/2013 | Boye et al. |
| 2014/0249208 | A1 | 9/2014 | Bancel et al. |
| 2014/0256802 | A1 | 9/2014 | Boye et al. |
| 2015/0065562 | A1 | 3/2015 | Yazicioglu et al. |
| 2015/0209406 | A1 | 7/2015 | Chen |
| 2016/0022836 | A1 | 1/2016 | Banfi et al. |
| 2016/0076054 | A1 | 3/2016 | Auricchio et al. |
| 2018/0015172 | A1 | 1/2018 | Muzyczka et al. |
| 2018/0055908 | A1 | 3/2018 | Petit et al. |
| 2018/0327779 | A1 | 11/2018 | Colella et al. |
| 2019/0002916 | A1 | 1/2019 | Kalatzis et al. |
| 2019/0153050 | A1 | 5/2019 | Boye et al. |

(Continued)

FOREIGN PATENT DOCUMENTS

| | | | |
|---|---|---|---|
| WO | WO-01/025465 | A1 | 4/2001 |
| WO | WO-2001/070972 | A2 | 9/2001 |

(Continued)

OTHER PUBLICATIONS

U.S. Appl. No. 17/290,082, Dyka et al., Apr. 29, 2021.

(Continued)

*Primary Examiner* — James Joseph Graber

(74) *Attorney, Agent, or Firm* — Clark & Elbing LLP

(57) ABSTRACT

The disclosure features compositions and methods for the treatment of sensorineural hearing loss and auditory neuropathy, particularly forms of the disease that are associated with mutations in otoferlin (OTOF), by way of OTOF gene therapy. The disclosure provides a variety of compositions that include a first nucleic acid vector that contains a polynucleotide encoding an N-terminal portion of an OTOF protein and a second nucleic acid vector that contains a polynucleotide encoding a C-terminal portion of an OTOF protein. These vectors can be used to increase the expression of OTOF in a subject, such as a human subject suffering from sensorineural hearing loss.

16 Claims, 41 Drawing Sheets

Specification includes a Sequence Listing.

(56) References Cited

U.S. PATENT DOCUMENTS

2019/0185864 A1 6/2019 Simons et al.
2019/0309326 A1 10/2019 Maclaren et al.
2020/0155705 A1 5/2020 Burns et al.
2020/0157573 A1 5/2020 Boye et al.
2021/0130421 A1 5/2021 Boye et al.
2021/0236654 A1 8/2021 Burns et al.
2021/0388045 A1 12/2021 Burns et al.
2021/0395778 A1 12/2021 Dyka et al.
2021/0395781 A1 12/2021 Burns et al.
2022/0064671 A1 3/2022 Maranga et al.
2022/0265865 A1 8/2022 Burns et al.
2023/0149565 A1 5/2023 Boye et al.
2024/0011039 A1 1/2024 Simons et al.
2024/0131186 A1 4/2024 Burns et al.
2024/0148905 A1 5/2024 Palermo et al.
2024/0309399 A1 9/2024 Hu et al.

FOREIGN PATENT DOCUMENTS

WO WO-2008/088895 A2 7/2008
WO WO-2009/100438 A2 8/2009
WO WO-2013/075008 A1 5/2013
WO WO-2013/158879 A1 10/2013
WO WO-2014/140051 A1 9/2014
WO WO-2014/170480 A1 10/2014
WO WO-2014/193716 A2 12/2014
WO WO-2016/131981 A1 8/2016
WO WO-2016/139321 A1 9/2016
WO WO-2017/049252 A1 3/2017
WO WO-2017/100791 A1 6/2017
WO WO-2017/216560 A1 12/2017
WO WO-2018/039375 A1 3/2018
WO WO-2018/145111 A1 8/2018
WO WO-2018/162748 A1 9/2018
WO WO-2018/204734 A1 11/2018
WO WO-2019/162396 A1 8/2019
WO WO-2019/165292 A1 8/2019
WO WO-2019/183641 A1 9/2019
WO WO-2019/210181 A1 10/2019
WO WO-2020/093018 A1 5/2020
WO WO-2020/097372 A1 5/2020
WO WO-2020/148458 A1 7/2020
WO WO-2020/163743 A1 8/2020
WO WO-2021/087296 A1 5/2021
WO WO-2024/173835 A2 8/2024

OTHER PUBLICATIONS

U.S. Appl. No. 16/952,016, Boye et al., Nov. 18, 2020.
U.S. Appl. No. 17/916,308, Boye et al., Sep. 30, 2022.
Akil et al., "Dual AAV gene therapy restores hearing in a mouse model for human genetic Deafness," International Symposium on Inner Ear Therapies (ISIET), Marrakech, Morocco. 21 (2017) (Abstract only).
Akil et al., "Dual AAV-mediated gene therapy restores hearing in a DFNB9 mouse model," Proc Natl Acad Sci U S A. 116(10):4496-4501 (Published Feb. 19, 2019).
Al-Moyed et al., "A dual AAV viral vector approach partially restores exocytosis and rescues hearing in deaf otoferlin knock-out mice," ARO Abstracts, Abstract PS 134. 41:76 (Published Feb. 9, 2018) (Abstract only).
Alemi, "Progress Report: AOS Research Grant: Restoration of Hearing in the Otoferlin Knockout Mouse using Viral Gene Therapy," 145th Annual Meeting of the American Otological Society, Inc, Apr. 21-22, San Diego, California. 68 (2012) (Abstract only).
Belyantseva et al., "Myosin XVa localizes to the tips of inner ear sensory cell stereocilia and is essential for staircase formation of the hair bundle," Proc Natl Acad Sci U S A. 100(24):13958-63 (2003).
Boëda et al., "A specific promoter of the sensory cells of the inner ear defined by transgenesis," Hum Mol Genet. 10(15):1581-1589 (2001) (10 pages).
Caberlotto et al., "Usher type 1G protein sans is a critical component of the tip-link complex, a structure controlling actin polymerization in stereocilia," Proc Natl Acad Sci U S A. 108(14):5825-30 (2011) (14 pages).
Choi et al., "Identities and frequencies of mutations of the otoferlin gene (OTOF) causing DFNB9 deafness in Pakistan," available in PMC Oct. 1, 2012, published in final edited form as: Clin Genet. 75(3):237-243 (2009) (10 pages).
Duan et al., "Expanding AAV Packaging Capacity with Trans-splicing or Overlapping Vectors: A Quantitative Comparison," Mol Ther. 4(4):383-91 (2001).
GenBank Accession No. JN953192.1, "Mus musculus targeted KO-first, conditional ready, IacZ-tagged mutant allele Myo15:tm1a(EUCOMM)Wtsi; transgenic," retrieved from <https://www.ncbi.nlm.nih.gov/nuccore/JN953192>, dated Nov. 5, 2011 (11 pages).
Ghosh et al., "A Hybrid Vector System Expands Adeno-associated Viral Vector Packaging Capacity in a Transgene-independent Manner," The American Society of Gene Therapy. 16(1):124-130 (2008).
Ghosh et al., "Efficient Transgene Reconstitution with Hybrid Dual AAV Vectors Carrying the Minimized Bridging Sequences," Hum Gene Ther. 22(1):77-83 (2011).
McClements et al., "Adeno-associated Virus (AAV) Dual Vector Strategies for Gene Therapy Encoding Large Transgenes," Yale J Biol Med. 90(4):611-623 (2017).
Schlabach et al., "Synthetic design of strong promoters," Proc Natl Acad Sci U S A. 107(6):2538-43 (2010).
GenBank Accession No. JN957158.1, "Mus musculus targeted non-conditional, IacZ-tagged mutant allele Myo15:tm1e(EUCOMM)Wtsi; transgenic," retrieved from <https://www.ncbi.nlm.nih.gov/nucleotide/JN957158.1>, dated Nov. 5, 2011 (12 pages).
Trapani et al., "Improved dual AAV vectors with reduced expression of truncated proteins are safe and effective in the retina of a mouse model of Stargardt disease," Hum Mol Genet. 24(23):6811-25 (2015).
Trapani et al., "Effective delivery of large genes to the retina by dual AAV vectors," EMBO Mol Med. 6(2):194-211 (2014).
Xu et al., "Trans-Splicing Adeno-Associated Viral Vector-Mediated Gene Therapy Is Limited by the Accumulation of Spliced mRNA but Not by Dual Vector Coinfection Efficiency," available in PMC Jun. 19, 2008, published in final edited form as: Hum Gene Ther. 15(9):896-905 (2004) (17 pages).
Yasunaga et al., "OTOF Encodes Multiple Long and Short Isoforms: Genetic Evidence That the Long Ones Underlie Recessive Deafness DFNB9," Am J Hum Genet. 67(3):591-600 (2000).
Michalski et al., "Genetics of auditory mechano-electrical transduction," Pflugers Arch. 467(1):49-72 (2015).
Skarnes et al., "A conditional knockout resource for the genome-wide study of mouse gene function," available in PMC Feb. 14, 2013, published in final edited form as: Nature. 474(7351):337-342 (2011) (18 pages).
Boye et al., "Transduction and Tropism of an Abbreviated Form of CMV-Chicken β-Actin Promoter (CBA) With AAV in Mouse Retina," ARVO Annual Meeting Abstract May 2006, published in: Investigative Opthalmology & Visual Science. 47: 852 (2006) (2 pages) (Abstract only).
Lovell, "Mouse DNA sequence from clone RP23-135F6 on chromosome 11," European Nucleotide Archive, EMBL-EBI. (2012) (15 pages).
Higashimoto et al., "The woodchuck hepatitis virus post-transcriptional regulatory element reduces readthrough transcription from retroviral vectors," Gene Ther. 14(17):1298-304 (2007).
Al-Moyed et al., "A dual-AAV approach restores fast exocytosis and partially rescues auditory function in deaf otoferlin knock-out mice," EMBO Mol Med. 11(1):e9396 (2019) (13 pages).
Wang, Aihui, Dissertation: "Molecular Cloning of an Unconventional Myosin MYO15 and the Identification of Mutations of MYO15 Responsible for Human Nonsyndromic Deafness DFNB3," Doctor of Philosophy, Graduate Program in Genetics, Michigan State University (1999) (140 pages).

(56) References Cited

OTHER PUBLICATIONS

Liang et al., "Characterization of the Human and Mouse Unconventional Myosin XV Genes Responsible for Hereditary Deafness DFNB3 and Shaker 2," Genomics. 61(3):243-258 (1999).
Yuhe, Liu, "Preparation of adeno-associated virus vector and its application in cochlea transgenic research," Chinese Journal of Otology. 4(4):343-347 (2006) (6 pages).
Hirsch et al., "Delivering Transgenic DNA Exceeding the Carrying Capacity of AAV Vectors," available in PMC Aug. 3, 2016, published in final edited form as: Methods Mol Biol. 13382:21-39 (2016) (20 pages).
Majewski and Ott, "GT Repeats Are Associated with Recombination on Human Chromosome 22," Genome Res. 10(8): 1108-1144 (Aug. 2000) (7 pages).
Lostal et al., "Full-Length Dystrophin Reconstitution with Adeno-Associated Viral Vectors," Human Gene Ther. 25(6): 552-562 (Jun. 2014) (11 pages).
Gao et al., "The Dystrophin Complex: structure, function and implications for therapy," available in PMC Jul. 1, 2016, published in final edited form as: Compr Physiol. 5(3): 1223-1239 (Jul. 2015) (33 pages).
Dyka et al., "Dual adeno-associated virus vectors result in efficient in vitro and in vivo expression of an oversized gene, MYO7A," Human Gene Ther Methods. 25(2): 166-77 (Apr. 2014) (12 pages).
Pryadkina et al., "A comparison of AAV strategies distinguishes overlapping vectors for efficient systemic delivery of the 6.2 kb Dysferlin coding sequence," Mol Ther Methods Clin Dev. 2: 15009 (Mar. 2015) (12 pages).
Geleoc et al., "Sound strategies for hearing restoration," available in PMC Aug. 29, 2014, published in final edited form as: Science. 344(6184):1241062 (May 2014) (20 pages).
Corns et al., "Mechanotransduction is required for establishing and maintaining mature inner hair cells and regulating efferent innervation," Nat Commun. 9(1):4015 (Oct. 2018) (15 pages).
Yoshimura et al., "Enhanced viral-mediated cochlear gene delivery in adult mice by combining canal fenestration with round window membrane inoculation," Scientific Reports. 8:2980 (with supplemental material) (Feb. 2018) (14 pages).
Pangrsic et al., "Otoferlin: a multi-C2 domain protein essential for hearing," Trends in Neurosciences. 35(11): 671-680 (2012) (10 pages).
Holt et al., "Split otoferlins reunited," EMBO Molecular Medicine. 11:(1)e9995 (Jan. 2019) (3 pages).
Suzuki et al., "Cochlear gene therapy with ancestral AAV in adult mice: complete transduction of inner hair cells without cochlear dysfunction," Scientific Reports. 7(1):45524 (Apr. 2017) (11 pages).
Tertrais et al., "Viral Transfer of Mini-Otoferlins Partially Restores the Fast Component of Exocytosis and Uncovers Ultrafast Endocytosis in Auditory Hair Cells of Otoferlin Knock-Out Mice," J. Neurosci. 39(18):3394-3411 (May 2019) (18 pages).
Petrs-Silva et al., "Novel Properties of Tyrosine-mutant AAV2 Vectors in the Mouse Retina," Molecular Therapy. 19(2):293-301 (Feb. 2011) (9 pages).
American Academy of Audiology, "Children's Hospital of Philadelphia Performs First Gene Therapy Procedure to Treat Genetic Hearing Loss in United States," <https://www.audiology.org/childrens-hospital-of-philadelphia-performs-first-gene-therapy-procedure-to-treat-genetic-hearing-loss-in-united-states/>, dated Jan. 26, 2024 (2 pages).
Yoshimura et al., "Targeted Allele Suppression Prevents Progressive Hearing Loss in the Mature Murine Model of Human TMC1 Deafness," Molecular Therapy. 27(3):681-690 (with supplemental material) (Mar. 2019) (17 pages).
Akil et al., "Surgical Method for Virally Mediated Gene Delivery to the Mouse Inner Ear through the Round Window Membrane," Journal of Visualized Experiments. 97(1):e52187 (Mar. 2015) (7 pages).
Liu et al., "Specific and Efficient Transduction of Cochlear Inner Hair Cells with Recombinant Adeno-associated Virus Type 3 Vector," Molecular Therapy. 12(4):725-733 (Oct. 2005) (9 pages).
"Basics of sound, the Ear, and Hearing," Hearing Loss: Determining Eligibility for Social Security Benefits. Edited by Robert A. Dobie and Susan Van Hemel, 42-68 (2004) (61 pages).
Akil et al., "AAV-Mediated Gene Delivery to the Inner Ear," Adeno-Associated Virus Vectors: Design and Delivery. Methods in Molecular Biology. Edited by Michael J. Castle, 271-282 (2019) [published online on Jan. 1, 2019] (16 pages).
Langouet-Astrie et al., "Characterization of intravitreally delivered capsid mutant AAV2-Cre vector to induce tissue-specific mutations in murine retinal ganglion cells," Experimental Eye Research. 151(1):61-67 (Jul. 2016) (7 pages).
Li et al., "A novel bispecific molecule delivered by recombinant AAV2 suppresses ocular inflammation and choroidal neovascularization," J. Cell. Mol. Med. 21(8):1555-1571 (Aug. 2017) (17 pages).
Lopes-Pacheco et al., "Self-complementary and tyrosine-mutant rAAV vectors enhance transduction in cystic fibrosis bronchial epithelial cells," Experimental Cell Research. 372:99-107 (Sep. 2018) (9 pages).
Petrs-Silva et al., "High-efficiency Transduction of the Mouse Retina by Tyrosine-mutant AAV Serotype Vectors," Molecular Therapy. 17(3):463-471 (Mar. 2009) (9 pages).
Kilpatrick et al., "Adeno-associated virus-mediated gene delivery into the scala media of the normal and deafened adult mouse ear," Gene Therapy. 18(6):569-578 (Jan. 2011) (10 pages).
Tao et al., "Delivery of Adeno-Associated Virus Vectors in Adult Mammalian Inner-Ear Cell Subtypes Without Auditory Dysfunction," Human Gene Therapy. 29(4):492-506 (Nov. 2017) (15 pages).
Zhang et al., "Cochlear Gene Therapy for Sensorineural Hearing Loss: Current Status and Major Remaining Hurdles for Translational Success," Front. Mol. Neurosci. 11(221):1-15 (Jun. 2018) (15 pages).
Roux et al., "Otoferlin, Defective in a Human Deafness Form, Is Essential for Exocytosis at the Auditory Ribbon Synapse," Cell. 127(2):277-289 (Oct. 2006) (13 pages).
"Genetic Hearing Loss With No Associated Abnormalities," Hereditary Hearing Loss and Its Syndromes, Third Edition. Helga V. Toriello and Shelley D. Smith. 164-165 (2013) (4 pages).
Ahmed et al., "Emerging Gene Therapies for Genetic Hearing Loss," Jaro. 18(5):649-670 (Aug. 2017) (22 pages).
Zhang et al., "Temperature sensitive auditory neuropathy," Hearing Research. 335(1):53-63 (Jan. 2016) (11 pages).
Hamosh et al. "Otoferlin; Otof," Omim. (Apr. 2015) (8 pages) retrieved via The Wayback Machine on Jul. 29, 2015, URL: <https://web.archive.org/web/20150729163826/http://omim.org/entry/603681>.
Kim et al., "Direct isolation and identification of promoters in the human genome," Genome Res. 15(6):830-9 (Jun. 2005) (11 pages).
GenPept Accession NP_001274418.1, dated Apr. 23, 2017, (4 pages) retrieved from https://www.ncbi.nlm.nih.gov/protein/566559996?sat=46&satkey=73202094.
McClements et al., "A fragmented adeno-associated viral dual vector strategy for treatment of diseases caused by mutations in large genes leads to expression of hybrid transcripts," J Genet Syndr Gene Ther. 7(5):311 (Nov. 14, 2016) (16 pages).
Avraham, "What's hot about otoferlin," EMBO J. 35(23):2502-4 (Dec. 1, 2016).
NCBI Reference Sequence: NM_001632.5, "*Homo sapiens* alkaline phosphatase, placental (ALPP), mRNA" (Apr. 4, 2024) (5 pages).
NCBI Reference Sequence: NP_000251.3, "unconventional myosin-VIIa isoform 1 [*Homo sapiens*]" (Dec. 11, 2024) (5 pages).
GenBank: U39226.1, "Human myosin VIIA (USH1B) mRNA, complete cds" (Jul. 11, 1996) (4 pages).
Akil et al., "Restoration of Hearing in the VGLUT3 Knockout Mouse Using Virally Mediated Gene Therapy," Neuron. 75:283-293 (2012).
Al-Hussaini et al., "Mature retinal pigment epithelium cells are retained in the cell cycle and proliferate in vivo," Mol Vis. 14:1784-91 (2008).
Allocca et al., "Serotype-dependent packaging of large genes in adeno-associated viral vectors results in effective gene delivery in mice," J Clin Invest. 118(5):1955-64 (May 2008) (11 pages).

(56) References Cited

OTHER PUBLICATIONS

Chen et al., "Molecular cloning and domain structure of human myosin-VIIa, the gene product defective in Usher syndrome 1B," Genomics 36(3):440-8 (Sep. 15, 1996).
Daya et al., "Gene therapy using adeno-associated virus vectors," Clin Microbiol Rev. 21(4):583-93 (Oct. 2008).
Dong et al., "Characterization of genome integrity for oversized recombinant AAV vector," Mol Ther. 18(1):87-92 (Jan. 2010).
Duan et al., "Circular intermediates of recombinant adeno-associated virus have defined structural characteristics responsible for long-term episomal persistence in muscle tissue," J Virol. 72(11):8568-77 (Nov. 1998).
Hashimoto et al., "Lentiviral gene replacement therapy of retinas in a mouse model for Usher syndrome type 1B," Gene Ther. 14(7):584-94 (Apr. 2007) (21 pages).
Jacobson et al., "Usher syndromes due to MYO7A, PCDH15, USH2A or GPR98 mutations share retinal disease mechanism," Hum Mol Genet. 17(15):2405-15 (Aug. 1, 2008).
Lai et al., "Evidence for the failure of adeno-associated virus serotype 5 to package a viral genome > or = 8.2 kb," Mol Ther. 18(1):75-9 (Jan. 2010).
Li et al., "High-efficiency transduction of fibroblasts and mesenchymal stem cells by tyrosine-mutant AAV2 vectors for their potential use in cellular therapy," Hum Gene Ther. 21(11):1527-43 (Nov. 2010) (18 pages).
Lopes et al., "Retinal gene therapy with a large MYO7A cDNA using adeno-associated virus," Gene Ther. 20(8):824-33 (Aug. 2013) (21 pages).
Weil et al., "Human myosin VIIA responsible for the Usher 1B syndrome: a predicted membrane-associated motor protein expressed in developing sensory epithelia," Proc Natl Acad Sci USA. 93(8):3232-7 (Apr. 16, 1996).
Wu et al., "Effect of genome size on AAV vector packaging," Mol Ther. 18(1):80-6 (Jan. 2010).
Yan et al., "Inverted terminal repeat sequences are important for intermolecular recombination and circularization of adeno-associated virus genomes," J Virol. 79(1):364-79 (Jan. 2005).

Dual hybrid: Myo15-hOTOF

SEQUENCE LISTING

```
Sequence total quantity: 44
SEQ ID NO: 1            moltype = AA  length = 1997
FEATURE                 Location/Qualifiers
source                  1..1997
                        mol_type = protein
                        organism = Homo sapiens
SEQUENCE: 1
MALLIHLKTV SELRGRGDRI AKVTFRGQSF YSRVLENCED VADFDETFRW PVASSIDRNE  60
MLEIQVFNYS KVFSNKLIGT FRMVLQKVVE ESHVEVTDTL IDDNNAIIKT SLCVEVRYQA  120
TDGTVGSWDD GDFLGDESLQ EEEKDSQETD GLLPGSRPSS RPPGEKSFRR AGRSVFSAMK  180
LGKNRSHKEE PQRPDEPAVL EMEDLDHLAI RLGDGLDPDS VSLASVTALT TNVSNKRSKP  240
DIKMEPSAGR PMDYQVSITV IEARQLVGLN MDPVVCVEVG DDKKYTSMKE STNCPYYNEY  300
FVFDFHVSPD VMFDKIIKIS VIHSKNLLRS GTLVGSFKMD VGTVYSQPEH QFHHKWAILS  360
DPDDISSGLK GYVKCDVAVV GKGDNIKTPH KANETDEDDI EGNLLLPEGV PPERQWARFY  420
VKIYRAEGLP RMNTSLMANV KKAFIGENKD LVDPYVQVFF AGQKGKTSVQ KSSYEPLWNE  480
QVVFTDLFPP LCKRMKVQIR DSDKVNDVAI GTHFIDLRKI SNDGDKGFLP TLGPAWVNMY  540
GSTRNYTLLD EHQDLNEGLG EGVSFRARLL LGLAVEIVDT SNPELTSSTE VQVEQATPIS  600
ESCAGKMEEF FLFGAFLEAS MIDRRNGDKP ITFEVTIGNY GNEVDGLSRP QRPRPRKEPG  660
DEEEVDLIQN ASDDEAGDAG DLASVSSTPP MRPQVTDRNY FHLPYLERKP CIYIKSWWPD  720
QRRRLYNANI MDHIADKLEE GLNDIQEMIK TEKSYPERRL RGVLEELSCG CCRFLSLADK  780
DQGHSSRTRL DRERLKSCMR ELENMGQQAR MLRAQVKRHT VRDKLRLCQN FLQKLRFLAD  840
EPQHSIPDIF IWMMSNNKRV AYARVPSKDL LFSIVEEETG KDCAKVKTLF LKLPGKRGFG  900
SAGWTVQAKV ELYLWLGLSK QRKEFLCGLP CGFQEVKAAQ GLGLHAFPPV SLVYTKKQAF  960
QLRAHMYQAR SLFAADSSGL SDPFARVFFI NQSQCTEVLN ETLCPTWDQM LVFDNLELYG  1020
EAHELRDDPP IIVIEIYDQD SMGKADFMGR TFAKPLVKMA DEAYCPPRFP PQLEYYQIYR  1080
GNATAGDLLA AFELLQIGPA GKADLPPING PVDVDRGPIM PVPMGIRPVL SKYRVEVLFW  1140
GLRDLKRVNL AQVDRPRVDI ECAGKGVQSS LIHNYKKNPN FNTLVKWFEV DLPENELLHP  1200
PLNIRVVDCR AFGRYTLVGS HAVSSLRRFI YRPPDRSAPS WNTTVRLLRR CRVLCNGGSS  1260
SHSTGEVVVT MEPEVPIKKL ETMVKLDATS EAVVKVDVAE EEKEKKKKKK GTAEEPEEEE  1320
PDESMLDWWS KYFASIDTMK EQLRQQEPSG IDLEEKEEVD NTEGLKGSMK GKEKARAAKE  1380
EKKKKTQSSG SGQGSEAPEK KKPKIDELKV YPKELESEFD NFEDWLHTFN LLRGKTGDDE  1440
DGSTEEERIV GRFKGSLCVY KVPLPEDVSR EAGYDSTYGM FQGIPSNDPI NVLVRVYVVR  1500
ATDLHPADIN GKADPYIAIR LGKTDIRDKE NYISKQLNPV FGKSFDIEAS FPMESMLTVA  1560
VYDWDLVGTD DLIGETKIDL ENRFYSKHRA TCGIAQTYST HGYNIWRDPM KPSQILTRLC  1620
KDGKVDGPHF GPPGRVKVAN RVFTGPSEIE DENGQRKPTD EHVALLALRH WEDIPRAGCR  1680
LVPEHVETRP LLNPDKPGIE QGRLELWVDM FPMDMPAPGT PLDISPRKPK KYELRVIIWN  1740
TDEVVLEDDD FFTGEKSSDI FVRGWLKGQQ EDKQDTDVHY HSLTGEGNFN WRYLFPFDYL  1800
AAEEKIVISK KESMFSWDET EYKIPARLTL QIWDADHFSA DDFLGAIELD LNRFPRGAKT  1860
AKQCTMEMAT GEVDVPLVSI FKQKRVKGWW PLLARNENDE FELTGKVEAE LHLLTAEEAE  1920
```

-continued

```
KNPVGLARNE PDPLEKPNRP DTSFIWFLNP LKSARYFLWH TYRWLLLKLL LLLLLLLLLA  1980
LFLYSVPGYL VKKILGA                                                 1997

SEQ ID NO: 2           moltype = AA  length = 1230
FEATURE                Location/Qualifiers
source                 1..1230
                       mol_type = protein
                       organism = Homo sapiens
SEQUENCE: 2
MIKTEKSYPE RRLRGVLEEL SCGCCRFLSL ADKDQGHSSR TRLDRERLKS CMRELENMGQ  60
QARMLRAQVK RHTVRDKLRL CQNFLQKLRF LADEPQHSIP DIFIWMMSNN KRVAYARVPS  120
KDLLFSIVEE ETGKDCAKVK TLFLKLPGKR GFGSAGWTVQ AKVELYLWLG LSKQRKEFLC  180
GLPCGFQEVK AAQGLGLHAF PPVSLVYTKK QAFQLRAHMY QARSLFAADS SGLSDPFARV  240
FFINQSQCTE VLNETLCPTW DQMLVFDNLE LYGEAHELRD DPPIIVIEIY DQDSMGKADF  300
MGRTFAKPLV KMADEAYCPP RFPPQLEYYQ IYRGNATAGD LLAAFELLQI GPAGKADLPP  360
INGPVDVDRG PIMPVPMGIR PVLSKYRVEV LFWGLRDLKR VNLAQVDRPR VDIECAGKGV  420
QSSLIHNYKK NPNFNTLVKW FEVDLPENEL LHPPLNIRVV DCRAFGRYTL VGSHAVSSLR  480
RFIYRPPDRS APSWNTTGEV VVTMEPEVPI KKLETMVKLD ATSEAVVKVD VAEEEKEKKK  540
KKKGTAEEPE EEEPDESMLD WWSKYFASID TMKEQLRQQE PSGIDLEEKE EVDNTEGLKG  600
SMKGKEKARA AKEEKKKKTQ SSGSGQGSEA PEKKKPKIDE LKVYPKELES EFDNFEDWLH  660
TFNLLRGKTG DDEDGSTEEE RIVGRFKGSL CVYKVPLPED VSREAGYDST YGMFQGIPSN  720
DPINVLVRVY VVRATDLHPA DINGKADPYI AIRLGKTDIR DKENYISKQL NPVFGKSFDI  780
EASFPMESML TVAVYDWDLV GTDDLIGETK IDLENRFYSK HRATCGIAQT YSTHGYNIWR  840
DPMKPSQILT RLCKDGKVDG PHFGPPGRVK VANRVFTGPS EIEDENGQRK PTDEHVALLA  900
LRHWEDIPRA GCRLVPEHVE TRPLLNPDKP GIEQGRLELW VDMFPMDMPA PGTPLDISPR  960
KPKKYELRVI IWNTDEVVLE DDDFFTGEKS SDIFVRGWLK GQQEDKQDTD VHYHSLTGEG  1020
NFNWRYLFPF DYLAAEEKIV ISKKESMFSW DETEYKIPAR LTLQIWDADH FSADDFLGAI  1080
ELDLNRFPRG AKTAKQCTME MATGEVDVPL VSIFKQKRVK GWWPLLARNE NDEFELTGKV  1140
EAELHLLTAE EAEKNPVGLA RNEPDPLEKP NRPDTSFIWF LNPLKSARYF LWHTYRWLLL  1200
KLLLLLLLLL LLALFLYSVP GYLVKKILGA                                   1230

SEQ ID NO: 3           moltype = AA  length = 1230
FEATURE                Location/Qualifiers
source                 1..1230
                       mol_type = protein
                       organism = Homo sapiens
SEQUENCE: 3
MIKTEKSYPE RRLRGVLEEL SCGCCRFLSL ADKDQGHSSR TRLDRERLKS CMRELENMGQ  60
QARMLRAQVK RHTVRDKLRL CQNFLQKLRF LADEPQHSIP DIFIWMMSNN KRVAYARVPS  120
KDLLFSIVEE ETGKDCAKVK TLFLKLPGKR GFGSAGWTVQ AKVELYLWLG LSKQRKEFLC  180
GLPCGFQEVK AAQGLGLHAF PPVSLVYTKK QAFQLRAHMY QARSLFAADS SGLSDPFARV  240
FFINQSQCTE VLNETLCPTW DQMLVFDNLE LYGEAHELRD DPPIIVIEIY DQDSMGKADF  300
MGRTFAKPLV KMADEAYCPP RFPPQLEYYQ IYRGNATAGD LLAAFELLQI GPAGKADLPP  360
INGPVDVDRG PIMPVPMGIR PVLSKYRVEV LFWGLRDLKR VNLAQVDRPR VDIECAGKGV  420
QSSLIHNYKK NPNFNTLVKW FEVDLPENEL LHPPLNIRVV DCRAFGRYTL VGSHAVSSLR  480
RFIYRPPDRS APSWNTTGEV VVTMEPEVPI KKLETMVKLD ATSEAVVKVD VAEEEKEKKK  540
KKKGTAEEPE EEEPDESMLD WWSKYFASID TMKEQLRQQE PSGIDLEEKE EVDNTEGLKG  600
SMKGKEKARA AKEEKKKKTQ SSGSGQGSEA PEKKKPKIDE LKVYPKELES EFDNFEDWLH  660
TFNLLRGKTG DDEDGSTEEE RIVGRFKGSL CVYKVPLPED VSREAGYDST YGMFQGIPSN  720
DPINVLVRVY VVRATDLHPA DINGKADPYI AIRLGKTDIR DKENYISKQL NPVFGKSFDI  780
EASFPMESML TVAVYDWDLV GTDDLIGETK IDLENRFYSK HRATCGIAQT YSTHGYNIWR  840
DPMKPSQILT RLCKDGKVDG PHFGPPGRVK VANRVFTGPS EIEDENGQRK PTDEHVALLA  900
LRHWEDIPRA GCRLVPEHVE TRPLLNPDKP GIEQGRLELW VDMFPMDMPA PGTPLDISPR  960
KPKKYELRVI IWNTDEVVLE DDDFFTGEKS SDIFVRGWLK GQQEDKQDTD VHYHSLTGEG  1020
NFNWRYLFPF DYLAAEEKIV ISKKESMFSW DETEYKIPAR LTLQIWDADH FSADDFLGAI  1080
ELDLNRFPRG AKTAKQCTME MATGEVDVPL VSIFKQKRVK GWWPLLARNE NDEFELTGKV  1140
EAELHLLTAE EAEKNPVGLA RNEPDPLEKP NRPDTAFVWF LNPLKSIKYL ICTRYKWLII  1200
KIVLALLGLL MLGLFLYSLP GYMVKKLLGA                                   1230

SEQ ID NO: 4           moltype = AA  length = 1307
FEATURE                Location/Qualifiers
source                 1..1307
                       mol_type = protein
                       organism = Homo sapiens
SEQUENCE: 4
MMTDTQDGPS ESSQIMRSLT PLINREEAFG EAGEAGLWPS ITHTPDSQEE GLNDIQEMIK  60
TEKSYPERRL RGVLEELSCG CCRFLSLADK DQGHSSRTRL DRERLKSCMR ELENMGQQAR  120
MLRAQVKRHT VRDKLRLCQN FLQKLRFLAD EPQHSIPDIF IWMMSNNKRV AYARVPSKDL  180
LFSIVEEETG KDCAKVKTLF LKLPGKRGFG SAGWTVQAKV ELYLWLGLSK QRKEFLCGLP  240
CGFQEVKAAQ GLGLHAFPPV SLVYTKKQAF QLRAHMYQAR SLFAADSSGL SDPFARVFFI  300
NQSQCTEVLN ETLCPTWDQM LVFDNLELYG EAHELRDDPP IIVIEIYDQD SMGKADFMGR  360
TFAKPLVKMA DEAYCPPRFP PQLEYYQIYR GNATAGDLLA AFELLQIGPA GKADLPPING  420
PVDVDRGPIM PVPMGIRPVL SKYRVEVLFW GLRDLKRVNL AQVDRPRVDI ECAGKGVQSS  480
LIHNYKKNPN FNTLVKWFEV DLPENELLHP PLNIRVVDCR AFGRYTLVGS HAVSSLRRFI  540
YRPPDRSAPS WNTTVRLLRR CRVLCNGGSS SHSTGEVVVT MEPEVPIKKL ETMVKLDATS  600
EAVVKVDVAE EEKEKKKKKK GTAEEPEEEE PDESMLDWWS KYFASIDTMK EQLRQQEPSG  660
IDLEEKEEVD NTEGLKGSMK GKEKARAAKE EKKKKTQSSG SGQGSEAPEK KKPKIDELKV  720
YPKELESEFD NFEDWLHTFN LLRGKTGDDE DGSTEEERIV GRFKGSLCVY KVPLPEDVSR  780
EAGYDSTYGM FQGIPSNDPI NVLVRVYVVR ATDLHPADIN GKADPYIAIR LGKTDIRDKE  840
```

```
NYISKQLNPV FGKSFDIEAS FPMESMLTVA VYDWDLVGTD DLIGETKIDL ENRFYSKHRA  900
TCGIAQTYST HGYNIWRDPM KPSQILTRLC KDGKVDGPHF GPPGRVKVAN RVFTGPSEIE  960
DENGQRKPTD EHVALLALRH WEDIPRAGCR LVPEHVETRP LLNPDKPGIE QGRLELWVDM  1020
FPMDMPAPGT PLDISPRKPK KYELRVIIWN TDEVVLEDDD FFTGEKSSDI FVRGWLKGQQ  1080
EDKQDTDVHY HSLTGEGNFN WRYLFPFDYL AAEEKIVISK KESMFSWDET EYKIPARLTL  1140
QIWDADHFSA DDFLGAIELD LNRFPRGAKT AKQCTMEMAT GEVDVPLVSI FKQKRVKGWW  1200
PLLARNENDE FELTGKVEAE LHLLTAEEAE KNPVGLARNE PDPLEKPNRP DTSFIWFLNP  1260
LKSARYFLWH TYRWLLLKLL LLLLLLLLLA LFLYSVPGYL VKKILGA                1307

SEQ ID NO: 5            moltype = AA  length = 1997
FEATURE                 Location/Qualifiers
source                  1..1997
                        mol_type = protein
                        organism = Homo sapiens
SEQUENCE: 5
MALLIHLKTV SELRGRGDRI AKVTFRGQSF YSRVLENCED VADFDETFRW PVASSIDRNE  60
MLEIQVFNYS KVFSNKLIGT FRMVLQKVVE ESHVEVTDTL IDDNNAIIKT SLCVEVRYQA  120
TDGTVGSWDD GDFLGDESLQ EEEKDSQETD GLLPGSRPSS RPPGEKSFRR AGRSVFSAMK  180
LGKNRSHKEE PQRPDEPAVL EMEDLDHLAI RLGDGLDPDS VSLASVTALT TNVSNKRSKP  240
DIKMEPSAGR PMDYQVSITV IEARQLVGLN MDPVVCVEVG DDKKYTSMKE STNCPYYNEY  300
FVFDFHVSPD VMFDKIIKIS VIHSKNLLRS GTLVGSFKMD VGTVYSQPEH QFHHKWAILS  360
DPDDISSGLK GYVKCDVAVV GKGDNIKTPH KANETDEDDI EGNLLLPEGV PPERQWARFY  420
VKIYRAEGLP RMNTSLMANV KKAFIGENKD LVDPYVQVFF AGQKGKTSVQ KSSYEPLWNE  480
QVVFTDLFPP LCKRMKVQIR DSDKVNDVAI GTHFIDLRKI SNDGDKGFLP TLGPAWVNMY  540
GSTRNYTLLD EHQDLNEGLG EGVSFRARLL LGLAVEIVDT SNPELTSSTE VQVEQATPIS  600
ESCAGKMEEF FLFGAFLEAS MIDRRNGDKP ITFEVTIGNY GNEVDGLSRP QRPRPRKEPG  660
DEEEVDLIQN ASDDEAGDAG DLASVSSTPP MRPQVTDRNY FHLPYLERKP CIYIKSWWPD  720
QRRRLYNANI MDHIADKLEE GLNDIQEMIK TEKSYPERRL RGVLEELSCG CCRFLSLADK  780
DQGHSSRTRL DRERLKSCMR ELENMGQQAR MLRAQVKRHT VRDKLRLCQN FLQKLRFLAD  840
EPQHSIPDIF IWMMSNNKRV AYARVPSKDL LFSIVEEETG KDCAKVKTLF LKLPGKRGFG  900
SAGWTVQAKV ELYLWLGLSK QRKEFLCGLP CGFQEVKAAQ GLGLHAFPPV SLVYTKKQAF  960
QLRAHMYQAR SLFAADSSGL SDPFARVFFI NQSQCTEVLN ETLCPTWDQM LVFDNLELYG  1020
EAHELRDDPP IIVIEIYDQD SMGKADFMGR TFAKPLVKMA DEAYCPPRFP PQLEYYQIYR  1080
GNATAGDLLA AFELLQIGPA GKADLPPING PVDVDRGPIM PVPMGIRPVL SKYRVEVLFW  1140
GLRDLKRVNL AQVDRPRVDI ECAGKGVQSS LIHNYKKNPN FNTLVKWFEV DLPENELLHP  1200
PLNIRVVDCR AFGRYTLVGS HAVSSLRRFI YRPPDRSAPS WNTTVRLLRR CRVLCNGGSS  1260
SHSTGEVVVT MEPEVPIKKL ETMVKLDATS EAVVKVDVAE EEKEKKKKKK GTAEEPEEEE  1320
PDESMLDWWS KYFASIDTMK EQLRQQEPSG IDLEEKEEVD NTEGLKGSMK GKEKARAAKE  1380
EKKKKTQSSG SGQGSEAPEK KKPKIDELKV YPKELESEFD NFEDWLHTFN LLRGKTGDDE  1440
DGSTEEERIV GRFKGSLCVY KVPLPEDVSR EAGYDSTYGM FQGIPSNDPI NVLVRVYVVR  1500
ATDLHPADIN GKADPYIAIR LGKTDIRDKE NYISKQLNPV FGKSFDIEAS FPMESMLTVA  1560
VYDWDLVGTD DLIGETKIDL ENRFYSKHRA TCGIAQTYST HGYNIWRDPM KPSQILTRLC  1620
KDGKVDGPHF GPPGRVKVAN RVFTGPSEIE DENGQRKPTD EHVALLALRH WEDIPRAGCR  1680
LVPEHVETRP LLNPDKPGIE QGRLELWVDM FPMDMPAPGT PLDISPRKPK KYELRVIIWN  1740
TDEVVLEDDD FFTGEKSSDI FVRGWLKGQQ EDKQDTDVHY HSLTGEGNFN WRYLFPFDYL  1800
AAEEKIVISK KESMFSWDET EYKIPARLTL QIWDADHFSA DDFLGAIELD LNRFPRGAKT  1860
AKQCTMEMAT GEVDVPLVSI FKQKRVKGWW PLLARNENDE FELTGKVEAE LHLLTAEEAE  1920
KNPVGLARNE PDPLEKPNRP DTAFVWFLNP LKSIKYLICT RYKWLIIKIV LALLGLLMLG  1980
LFLYSLPGYM VKKLLGA                                                 1997

SEQ ID NO: 6            moltype = AA  length = 1997
FEATURE                 Location/Qualifiers
source                  1..1997
                        mol_type = protein
                        organism = Mus musculus
SEQUENCE: 6
MALIVHLKTV SELRGKGDRI AKVTFRGQSF YSRVLENCEG VADFDETFRW PVASSIDRNE  60
VLEIQIFNYS KVFSNKLIGT FCMVLQKVVE ENRVEVTDTL MDDSNAIIKT SLSMEVRYQA  120
TDGTVGPWDD GDFLGDESLQ EEKDSQETDG LLPGSRPSTR ISGEKSFRRA GRSVFSAMKL  180
GKTRSHKEEP QRQDEPAVLE MEDLDHLAIQ LGDGLDPDSV SLASVTALTS NVSNKRSKPD  240
IKMEPSAGRP MDYQVSITVI EARQLVGLNM DPVVCVEVGD DKKYTSMKES TNCPYYNEYF  300
VFDFHVSPDV MFDKIIKISV IHSKNLLRSG TLVGSFKMDV GTVYSQPEHQ FHHKWAILSD  360
PDDISAGLKG YVKCDVAVVG KGDNIKTPHK ANETDEDDIE GNLLLPEGVP PERQWARFYV  420
KIYRAEGLPR MNTSLMANVK KAFIGENKDL VDPYVQVFFA GQKGKTSVQK SSYEPLWNEQ  480
VVFTDLFPPL CKRMKVQIRD SDKVNDVAIG THFIDLRKIS NDGDKGFLPT LGPAWVNMYG  540
STRNYTLLDE HQDLNEGLGE GVSFRARLML GLAVEILDTS NPELTSSTEV QVEQATPVSE  600
SCTGRMEEFF LFGAFLEASM IDRKNGDKPI TFEVTIGNYG NEVDGMSRPL RPRPRKEPGD  660
EEEVDLIQNS SDDEGDEAGD LASVSSTPPM RPQITDRNYF HLPYLERKPC IYIKSWWPDQ  720
RRRLYNANIM DHIADKLEEG LNDVQEMIKT EKSYPERRLR GVLEELSCGC HRFLSLSDKD  780
QGRSSRTRLD RERLKSCMRE LESMGQQAKS LRAQVKRHTV RDKLRSCQNF LQKLRFLADE  840
PQHSIPDVFI WMMSNNKRIA YARVPSKDLL FSIVEEELGK DCAKVKTLFL KLPGKRGFGS  900
AGWTVQAKLE LYLWLGLSKQ RKDFLCGLPC GFEEVKAAQG LGLHSFPPIS LVYTKKQAFQ  960
LRAHMYQARS LFAADSSGLS DPFARVFFIN QSQCTEVLNE TLCPTWDQML VFDNLELYGE  1020
AHELRDDPPI IVIEIYDQDS MGKADFMGRT FAKPLVKMAD EAYCPPRFPP QLEYYQIYRG  1080
SATAGDLLAA FELLQIGPSG KADLPPINGP VDMDRGPIMP VPVGIRPVLS KYRVEVLFWG  1140
LRDLKRVNLA QVDRPRVDIE CAGKGVQSSL IHNYKKNPNF NTLVKWFEVD LPENELLHPP  1200
LNIRVVDCRA FGRYTLVGSH AVSSLRRFIY RPPDRSAPNW NTTVRLLRGC HRLRNGGPSS  1260
RPTGEVVVSM EPEEPVKKLE TMVKLDATSD AVVKVDVAED EKERKKKKKK GPSEEPEEEE  1320
PDESMLDWWS KYFASIDTMK EQLRQHETSG TDLEEKEEME SAEGLKGPMK SKEKSRAAKE  1380
```

-continued

EKKKKNQSPG PGQGSEAPEK KKAKIDELKV YPKELESEFD SFEDWLHTFN LLRGKTGDDE 1440
DGSTEEERIV GRFKGSLCVY KVPLPEDVSR EAGYDPTYGM FQGIPSNDPI NVLVRIYVVR 1500
ATDLHPADIN GKADPYIAIK LGKTDIRDKE NYISKQLNPV FGKSFDIEAS FPMESMLTVA 1560
VYDWDLVGTD DLIGETKIDL ENRFYSKHRA TCGIAQTYSI HGYNIWRDPM KPSQILTRLC 1620
KEGKVDGPHF GPHGRVRVAN RVFTGPSEIE DENGQRKPTD EHVALSALRH WEDIPRVGCR 1680
LVPEHVETRP LLNPDKPGIE QGRLELWVDM FPMDMPAPGT PLDISPRKPK KYELRVIVWN 1740
TDEVVLEDDD FFTGEKSSDI FVRGWLKGQQ EDKQDTDVHY HSLTGEGNFN WRYLFPFDYL 1800
AAEEKIVMSK KESMFSWDET EYKIPARLTL QIWDADHFSA DDFLGAIELD LNRFPRGAKT 1860
AKQCTMEMAT GEVDVPLVSI FKQKRVKGWW PLLARNENDE FELTGKVEAE LHLLTAEEAE 1920
KNPVGLARNE PDPLEKPNRP DTSFIWFLNP LKSARYFLWH TYRWLLLKFL LLFLLLLLFA 1980
LFLYSLPGYL AKKILGA 1997

SEQ ID NO: 7 moltype = AA length = 1977
FEATURE Location/Qualifiers
source 1..1977
mol_type = protein
organism = Mus musculus
SEQUENCE: 7
MALIVHLKTV SELRGKGDRI AKVTFRGQSF YSRVLENCEG VADFDETFRW PVASSIDRNE 60
VLEIQIFNYS KVFSNKLIGT FCMVLQKVVE ENRVEVTDTL MDDSNAIIKT SLSMEVRYQA 120
TDGTVGPWDD GDFLGDESLQ EEKDSQETDG LLPGSRPSTR ISGEKSFRRA GRSVFSAMKL 180
GKTRSHKEEP QRQDEPAVLE MEDLDHLAIQ LGDGLDPDSV SLASVTALTS NVSNKRSKPD 240
IKMEPSAGRP MDYQVSITVI EARQLVGLNM DPVVCVEVGD DKKYTSMKES TNCPYYNEYF 300
VFDFHVSPDV MFDKIIKISV IHSKNLLRSG TLVGSFKMDV GTVYSQPEHQ FHHKWAILSD 360
PDDISAGLKG YVKCDVAVVG KGDNIKTPHK ANETDEDDIE GNLLLPEGVP PERQWARFYV 420
KIYRAEGLPR MNTSLMANVK KAFIGENKDL VDPYVQVFFA GQKGKTSVQK SSYEPLWNEQ 480
VVFTDLFPPL CKRMKVQIRD SDKVNDVAIG THFIDLRKIS NDGDKGFLPT LGPAWVNMYG 540
STRNYTLLDE HQDLNEGLGE GVSFRARLML GLAVEILDTS NPELTSSTEV QVEQATPVSE 600
SCTGRMEEFF LFGAFLEASM IDRKNGDKPI TFEVTIGNYG NEVDGMSRPL RPRPRKEPGD 660
EEEVDLIQNS SDDEGDEAGD LASVSSTPPM RPQITDRNYF HLPYLERKPC IYIKSWWPDQ 720
RRRLYNANIM DHIADKLEEG LNDVQEMIKT EKSYPERRLR GVLEELSCGC HRFLSLSDKD 780
QGRSSRTRLD RERLKSCMRE LESMGQQAKS LRAQVKRHTV RDKLRSCQNF LQKLRFLADE 840
PQHSIPDVFI WMMSNNKRIA YARVPSKDLL FSIVEEELGK DCAKVKTLFL KLPGKRGFGS 900
AGWTVQAKLE LYLWLGLSKQ RKDFLCGLPC GFEEVKAAQG LGLHSFPPIS LVYTKKQAFQ 960
LRAHMYQARS LFAADSSGLS DPFARVFFIN QSQCTEVLNE TLCPTWDQML VFDNLELYGE 1020
AHELRDDPPI IVIEIYDQDS MGKADFMGRT FAKPLVKMAD EAYCPPRFPP QLEYYQIYRG 1080
SATAGDLLAA FELLQIGPSG KADLPPINGP VDMDRGPIMP VPVGIRPVLS KYRVEVLFWG 1140
LRDLKRVNLA QVDRPRVDIE CAGKGVQSSL IHNYKKNPNF NTLVKWFEVD LPENELLHPP 1200
LNIRVVDCRA FGRYTLVGSH AVSSLRRFIY RPPDRSAPNW NTTGEVVVSM EPEEPVKKLE 1260
TMVKLDATSD AVVKVDVAED EKERKKKKKK GPSEEPEEEE PDESMLDWWS KYFASIDTMK 1320
EQLRQHETSG TDLEEKEEME SAEGLKGPMK SKEKSRAAKE EKKKKNQSPG PGQGSEAPEK 1380
KKAKIDELKV YPKELESEFD SFEDWLHTFN LLRGKTGDDE DGSTEEERIV GRFKGSLCVY 1440
KVPLPEDVSR EAGYDPTYGM FQGIPSNDPI NVLVRIYVVR ATDLHPADIN GKADPYIAIK 1500
LGKTDIRDKE NYISKQLNPV FGKSFDIEAS FPMESMLTVA VYDWDLVGTD DLIGETKIDL 1560
ENRFYSKHRA TCGIAQTYSI HGYNIWRDPM KPSQILTRLC KEGKVDGPHF GPHGRVRVAN 1620
RVFTGPSEIE DENGQRKPTD EHVALSALRH WEDIPRVGCR LVPEHVETRP LLNPDKPGIE 1680
QGRLELWVDM FPMDMPAPGT PLDISPRKPK KYELRVIVWN TDEVVLEDDD FFTGEKSSDI 1740
FVRGWLKGQQ EDKQDTDVHY HSLTGEGNFN WRYLFPFDYL AAEEKIVMSK KESMFSWDET 1800
EYKIPARLTL QIWDADHFSA DDFLGAIELD LNRFPRGAKT AKQCTMEMAT GEVDVPLVSI 1860
FKQKRVKGWW PLLARNENDE FELTGKVEAE LHLLTAEEAE KNPVGLARNE PDPLEKPNRP 1920
DTSFIWFLNP LKSARYFLWH TYRWLLLKFL LLFLLLLLFA LFLYSLPGYL AKKILGA 1977

SEQ ID NO: 8 moltype = AA length = 1992
FEATURE Location/Qualifiers
source 1..1992
mol_type = protein
organism = Mus musculus
SEQUENCE: 8
MALIVHLKTV SELRGKGDRI AKVTFRGQSF YSRVLENCEG VADFDETFRW PVASSIDRNE 60
VLEIQIFNYS KVFSNKLIGT FCMVLQKVVE ENRVEVTDTL MDDSNAIIKT SLSMEVRYQA 120
TDGTVGPWDD GDFLGDESLQ EEKDSQETDG LLPGSRPSTR ISGEKSFRSK GREKTKGGRD 180
GEHKAGRSVF SAMKLGKTRS HKEEPQRQDE PAVLEMEDLD HLAIQLGDGL DPDSVSLASV 240
TALTSNVSNK RSKPDIKMEP SAGRPMDYQV SITVIEARQL VGLNMDPVVC VEVGDDKKYT 300
SMKESTNCPY YNEYFVFDFH VSPDVMFDKI IKISVIHSKN LLRSGTLVGS FKMDVGTVYS 360
QPEHQFHHKW AILSDPDDIS AGLKGYVKCD VAVVGKGDNI KTPHKANETD EDDIEGNLLL 420
PEGVPPERQW ARFYVKIYRA EGLPRMNTSL MANVKKAFIG ENKDLVDPYV QVFFAGQKGK 480
TSVQKSSYEP LWNEQVVFTD LFPPLCKRMK VQIRDSDKVN DVAIGTHFID LRKISNDGDK 540
GFLPTLGPAW VNMYGSTRNY TLLDEHQDLN EGLGEGVSFR ARLMLGLAVE ILDTSNPELT 600
SSTEVQVEQA TPVSESCTGR MEEFFLFGAF LEASMIDRKN GDKPITFEVT IGNYGNEVDG 660
MSRPLRPRPR KEPGDEEEVD LIQNSSDDEG DEAGDLASVS STPPMRPQIT DRNYFHLPYL 720
ERKPCIYIKS WWPDQRRRLY NANIMDHIAD KLEEGLNDVQ EMIKTEKSYP ERRLRGVLEE 780
LSCGCHRFLS LSDKDQGRSS RTRLDRERLK SCMRELESMG QQAKSLRAQV KRHTVRDKLR 840
SCQNFLQKLR FLADEPQHSI PDVFIWMMSN NKRIAYARVP SKDLLFSIVE EELGKDCAKV 900
KTLFLKLPGK RGFGSAGWTV QAKLELYLWL GLSKQRKDFL CGLPCGFEEV KAAQGLGLHS 960
FPPISLVYTK KQAFQLRAHM YQARSLFAAD SSGLSDPFAR VFFINQSQCT EVLNETLCPT 1020
WDQMLVFDNL ELYGEAHELR DDPPIIVIEI YDQDSMGKAD FMGRTFAKPL VKMADEAYCP 1080
PRFPPQLEYY QIYRGSATAG DLLAAFELLQ IGPSGKADLP PINGPVDMDR GPIMPVPVGI 1140
RPVLSKYRVE VLFWGLRDLK RVNLAQVDRP RVDIECAGKG VQSSLIHNYK KNPNFNTLVK 1200
WFEVDLPENE LLHPPLNIRV VDCRAFGRYT LVGSHAVSSL RRFIYRPPDR SAPNWNTTGE 1260

-continued

```
VVVSMEPEEP VKKLETMVKL DATSDAVVKV DVAEDEKERK KKKKKGPSEE PEEEEPDESM  1320
LDWWSKYFAS IDTMKEQLRQ HETSGTDLEE KEEMESAEGL KGPMKSKEKS RAAKEEKKKK  1380
NQSPGPGQGS EAPEKKKAKI DELKVYPKEL ESEFDSFEDW LHTFNLLRGK TGDDEDGSTE  1440
EERIVGRFKG SLCVYKVPLP EDVSREAGYD PTYGMFQGIP SNDPINVLVR IYVVRATDLH  1500
PADINGKADP YIAIKLGKTD IRDKENYISK QLNPVFGKSF DIEASFPMES MLTVAVYDWD  1560
LVGTDDLIGE TKIDLENRFY SKHRATCGIA QTYSIHGYNI WRDPMKPSQI LTRLCKEGKV  1620
DGPHFGPHGR VRVANRVFTG PSEIEDENGQ RKPTDEHVAL SALRHWEDIP RVGCRLVPEH  1680
VETRPLLNPD KPGIEQGRLE LWVDMFPMDM PAPGTPLDIS PRKPKKYELR VIVWNTDEVV  1740
LEDDDFFTGE KSSDIFVRGW LKGQQEDKQD TDVHYHSLTG EGNFNWRYLF PFDYLAAEEK  1800
IVMSKKESMF SWDETEYKIP ARLTLQIWDA DHFSADDFLG AIELDLNRFP RGAKTAKQCT  1860
MEMATGEVDV PLVSIFKQKR VKGWWPLLAR NENDEFELTG KVEAELHLLT AEEAEKNPVG  1920
LARNEPDPLE KPNRPDTAFV WFLNPLKSIK YLICTRYKWL IIKIVLALLG LLMLALFLYS  1980
LPGYMVKKLL GA                                                      1992

SEQ ID NO: 9            moltype = AA  length = 1977
FEATURE                 Location/Qualifiers
source                  1..1977
                        mol_type = protein
                        organism = Mus musculus
SEQUENCE: 9
MALIVHLKTV SELRGKGDRI AKVTFRGQSF YSRVLENCEG VADFDETFRW PVASSIDRNE  60
VLEIQIFNYS KVFSNKLIGT FCMVLQKVVE ENRVEVTDTL MDDSNAIIKT SLSMEVRYQA  120
TDGTVGPWDD GDFLGDESLQ EEKDSQETDG LLPGSRPSTR ISGEKSFRRA GRSVFSAMKL  180
GKTRSHKEEP QRQDEPAVLE MEDLDHLAIQ LGDGLDPDSV SLASVTALTS NVSNKRSKPD  240
IKMEPSAGRP MDYQVSITVI EARQLVGLNM DPVVCVEVGD DKKYTSMKES TNCPYYNEYF  300
VFDFHVSPDV MFDKIIKISV IHSKNLLRSG TLVGSFKMDV GTVYSQPEHQ FHHKWAILSD  360
PDDISAGLKG YVKCDVAVVG KGDNIKTPHK ANETDEDDIE GNLLLPEGVP PERQWARFYV  420
KIYRAEGLPR MNTSLMANVK KAFIGENKDL VDPYVQVFFA GQKGKTSVQK SSYEPLWNEQ  480
VVFTDLFPPL CKRMKVQIRD SDKVNDVAIG THFIDLRKIS NDGDKGFLPT LGPAWVNMYG  540
STRNYTLLDE HQDLNEGLGE GVSFRARLML GLAVEILDTS NPELTSSTEV QVEQATPVSE  600
SCTGRMEEFF LFGAFLEASM IDRKNGDKPI TFEVTIGNYG NEVDGMSRPL RPRPRKEPGD  660
EEEVDLIQNS SDDEGDEAGD LASVSSTPPM RPQITDRNYF HLPYLERKPC IYIKSWWPDQ  720
RRRLYNANIM DHIADKLEEG LNDVQEMIKT EKSYPERRLR GVLEELSCGC HRFLSLSDKD  780
QGRSSRTRLD RERLKSCMRE LESMGQQAKS LRAQVKRHTV RDKLRSCQNF LQKLRFLADE  840
PQHSIPDVFI WMMSNNKRIA YARVPSKDLL FSIVEEELGK DCAKVKTLFL KLPGKRGFGS  900
AGWTVQAKLE LYLWLGLSKQ RKDFLCGLPC GFEEVKAAQG LGLHSFPPIS LVYTKKQAFQ  960
LRAHMYQARS LFAADSSGLS DPFARVFFIN QSQCTEVLNE TLCPTWDQML VFDNLELYGE  1020
AHELRDDPPI IVIEIYDQDS MGKADFMGRT FAKPLVKMAD EAYCPPRFPP QLEYYQIYRG  1080
SATAGDLLAA FELLQIGPSG KADLPPINGP VDMDRGPIMP VPVGIRPVLS KYRVEVLFWG  1140
LRDLKRVNLA QVDRPRVDIE CAGKGVQSSL IHNYKKNPNF NTLVKWFEVD LPENELLHPP  1200
LNIRVVDCRA FGRYTLVGSH AVSSLRRFIY RPPDRSAPNW NTTGEVVVSM EPEEPVKKLE  1260
TMVKLDATSD AVVKVDVAED EKERKKKKKK GPSEEPEEEE PDESMLDWWS KYFASIDTMK  1320
EQLRQHETSG TDLEEKEEME SAEGLKGPMK SKEKSRAAKE EKKKKNQSPG PGQGSEAPEK  1380
KKAKIDELKV YPKELESEFD SFEDWLHTFN LLRGKTGDDE DGSTEEERIV GRFKGSLCVY  1440
KVPLPEDVSR EAGYDPTYGM FQGIPSNDPI NVLVRIYVVR ATDLHPADIN GKADPYIAIK  1500
LGKTDIRDKE NYISKQLNPV FGKSFDIEAS FPMESMLTVA VYDWDLVGTD DLIGETKIDL  1560
ENRFYSKHRA TCGIAQTYSI HGYNIWRDPM KPSQILTRLC KEGKVDGPHF GPHGRVRVAN  1620
RVFTGPSEIE DENGQRKPTD EHVALSALRH WEDIPRVGCR LVPEHVETRP LLNPDKPGIE  1680
QGRLELWVDM FPMDMPAPGT PLDISPRKPK KYELRVIVWN TDEVVLEDDD FFTGEKSSDI  1740
FVRGWLKGQQ EDKQDTDVHY HSLTGEGNFN WRYLFPFDYL AAEEKIVMSK KESMFSWDET  1800
EYKIPARLTL QIWDADHFSA DDFLGAIELD LNRFPRGAKT AKQCTMEMAT GEVDVPLVSI  1860
FKQKRVKGWW PLLARNENDE FELTGKVEAE LHLLTAEEAE KNPVGLARNE PDPLEKPNRP  1920
DTAFVWFLNP LKSIKYLICT RYKWLIIKIV LALLGLLMLA LFLYSLPGYM VKKLLGA     1977

SEQ ID NO: 10           moltype = DNA  length = 7171
FEATURE                 Location/Qualifiers
source                  1..7171
                        mol_type = other DNA
                        organism = Homo sapiens
SEQUENCE: 10
atcggagggg ggtcgggagg aggaggagga ggcagcggca gagaagagag aggcgtgtga  60
gccgtgctcc accggctagc tccttcccgc tgctcctgcc tggcagtgcc aggcagccca  120
caccagcatg gccttgctca tccacctcaa gacagtctcg gagctgcggg gcaggggcga  180
ccggatcgcc aaagtgactt tccgagggca atccttctac tctcgggtcc tggagaactg  240
tgaggatgtg gctgactttg atgagacatt tcggtggccg gtggccagca gcatcgacag  300
aaatgagatg ctggagattc aggttttcaa ctacagcaaa gtcttcagca acaagctcat  360
cgggaccttc cgcatggtgc tgcagaaggt ggtagaggag agccatgtgg aggtgactga  420
cacgctgatt gatgacaaca atgctatcat caagaccagc ctgtgcgtgg aggtccggta  480
tcaggccact gacggcacag tgggctcctg ggacgatggg gacttcctgg gagatgagtc  540
tcttcaagag gaagagaagg acagccaaga gacggatgga ctgctcccag gctcccggcc  600
cagctcccgg cccccaggag agaagagctt ccggagagcc gggaggagcg tgttctccgc  660
catgaagctc ggcaaaaacc ggtctcacaa ggaggagccc caaagaccag atgaaccggc  720
ggtgctggag atggaagacc ttgaccatct ggccattcgg ctaggagatg gactggatcc  780
cgactcggtg tctctagcct cagtcacagc tctcaccact aatgtctcca acaagcgatc  840
taagccagac attaagatgg agccaagtgc tgggcggccc atggattacc aggtcagcat  900
cacggtgatc gaggcccggc agctggtggg cttgaacatg gaccctgtgg tgtgcgtgga  960
ggtgggtgac gacaagaagt acacatccat gaaggagtcc actaactgcc cctattacaa  1020
cgagtacttc gtcttcgact tccatgtctc tccggatgtc atgtttgaca agatcatcaa  1080
gatttcggtg attcactcca agaacctgct gcgcagtggc accctggtgg gctccttcaa  1140
```

-continued

```
aatggacgtg ggaaccgtgt actcgcagcc agagcaccag ttccatcaca agtgggccat  1200
cctgtctgac cccgatgaca tctcctcggg gctgaagggc tacgtgaagt gtgacgttgc  1260
cgtggtgggc aaaggggaca acatcaagac gccccacaag gccaatgaga ccgacgaaga  1320
tgacattgag gggaacttgc tgctccccga gggggtgccc cccgaacgcc agtgggcccg  1380
gttctatgtg aaaatttacc gagcagaggg gctgccccgt atgaacacaa gcctcatggc  1440
caatgtaaag aaggctttca tcggtgaaaa caaggacctc gtggacccct acgtgcaagt  1500
cttctttgct ggccagaagg gcaagacttc agtgcagaag agcagctatg agcccctgtg  1560
gaatgagcag gtcgtcttta cagacctctt cccccactc tgcaaacgca tgaaggtgca  1620
gatccgagac tcggacaagg tcaacgacgt ggccatcggc acccacttca ttgacctgcg  1680
caagatttct aatgacggag acaaaggctt cctgcccaca ctgggcccag cctgggtgaa  1740
catgtacggc tccacacgta actacacgct gctggatgag catcaggacc tgaacgaggg  1800
cctgggggag ggtgtgtcct tccgggcccg gctcctgctg ggcctggctg tggagatcgt  1860
agacacctcc aaccctgagc tcaccagctc cacagaggtg caggtggagc aggccacgcc  1920
catctcggag agctgtgcag gtaaaatgga agaattcttt ctctttggag ccttcctgga  1980
ggcctcaatg atcgaccgga gaaacggaga caagcccatc acctttgagg tcaccatagg  2040
caactatggg aacgaagttg atggcctgtc ccggccccag cggcctcggc cccggaagga  2100
gccgggggat gaggaagaag tagacctgat tcagaacgca agtgatgacg aggccggtga  2160
tgccggggac ctggcctcag tctcctccac tccaccaatg cggccccagg tcaccgacag  2220
gaactacttc catctgccct acctggagcg aaagccctgc atctacatca agagctggtg  2280
gccggaccag cgccgccgcc tctacaatgc caacatcatg gaccacattg ccgacaagct  2340
ggaagaaggc ctgaacgaca tacaggagat gatcaaaacg gagaagtcct accctgagcg  2400
tcgcctgcgg ggcgtcctgg aggagctgag ctgtggctgc tgccgcttcc tctccctcgc  2460
tgacaaggac cagggccact catcccgcac caggcttgac cgggagcgcc tcaagtcctg  2520
catgagggag ctggaaaaca tggggcagca ggccaggatg ctgcgggccc aggtgaagcg  2580
gcacacggtg cgggacaagc tgaggctgtg ccagaacttc ctgcagaagc tgcgcttcct  2640
ggcggacgag ccccagcaca gcattcccga catcttcatc tggatgatga gcaacaacaa  2700
gcgtgtcgcc tatgcccgtg tgccctccaa ggacctgctc ttctccatcg tggaggagga  2760
gactggcaag gactgcgcca aggtcaagac gctcttcctt aagctgccag ggaagcgggg  2820
cttcggctcg gcaggctgga cagtgcaggc caaggtggag ctgtacctgt ggctgggcct  2880
cagcaaacag cgcaaggagt tcctgtgcgg cctgccctgt ggcttccagg aggtcaaggc  2940
agcccagggc ctgggcctgc atgccttccc acccgtcagc ctggtctaca ccaagaagca  3000
ggcgttccag ctccgagcgc acatgtacca ggcccgcagc ctctttgccg ccgacagcag  3060
cggactctca gacccctttg cccgcgtctt cttcatcaat cagagtcagt gcacagaggt  3120
gctgaatgag accctgtgtc ccacctggga ccagatgctg gtgttcgaca acctggagct  3180
ctatggtgaa gctcatgagc tgagggacga tccgcccatc attgtcattg aaatctatga  3240
ccaggattcc atgggcaaag ctgacttcat gggccggacc ttcgccaaac ccctggtgaa  3300
gatggcagac gaggcgtact gcccaccccg cttcccacct cagctcgagt actaccagat  3360
ctaccgtggc aacgccacag ctggagacct gctggcggcc ttcgagctgc tgcagattgg  3420
accagcaggg aaggctgacc tgccccccat caatggcccg gtggacgtgg accgaggtcc  3480
catcatgccc gtgcccatgg gcatccggcc cgtgctcagc aagtaccgag tggaggtgct  3540
gttctggggc ctacgggacc taaagcgggt gaacctggcc caggtggacc ggccacgggt  3600
ggacatcgag tgtgcaggga agggggtgca gtcgtccctg atccacaatt ataagaagaa  3660
ccccaacttc aacaccctcg tcaagtggtt tgaagtggac ctcccagaga acgagctgct  3720
gcacccgccc ttgaacatcc gtgtggtgga ctgccgggcc ttcggtcgct acacactggt  3780
gggctcccat gccgtcagct ccctgcgacg cttcatctac cggcccccag accgctcggc  3840
ccccagctgg aacaccacgg tcaggcttct ccggcgctgc cgtgtgctgt gcaatggggg  3900
ctcctcctct cactccacag ggaggttgt ggtgactatg gagccagagg tacccatcaa  3960
gaaactggag accatggtga agctggacgc gacttctgaa gctgttgtca aggtggatgt  4020
ggctgaggag gagaaggaga agaagaagaa gaagaagggc actgcggagg agccagagga  4080
ggaggagcca gacgagagca tgctggactg gtggtccaag tactttgcct ccattgacac  4140
catgaaggag caacttcgac aacaagagcc ctctggaatt gacttggagg agaaggagga  4200
agtggacaat accgagggcc tgaaggggtc aatgaagggc aaggagaagg caaggctgc  4260
caaagaggag aagaagaaga aaactcagag ctctggctct ggccaggggt ccgaggcccc  4320
cgagaagaag aaacccaaga ttgatgagct taaggtatac cccaaagagc tggagtccga  4380
gtttgataac tttgaggact ggctgcacac tttcaacttg cttcggggca agaccgggga  4440
tgatgaggat ggctccaccg aggaggagcg cattgtggga cgcttcaagg gctccctctg  4500
cgtgtacaaa gtgccactcc cagaggacgt gtcccgggaa gccggctacg actccaccta  4560
cggcatgttc cagggcatcc cgagcaatga ccccatcaat gtgctggtcc gagtctatgt  4620
ggtccgggcc acggacctgc accctgctga catcaacggc aaagctgacc cctacatcgc  4680
catccggcta ggcaagactg acatccgcga caaggagaac tacatctcca agcagctcaa  4740
ccctgtcttt gggaagtcct ttgacatcga ggcctccttc cccatggaat ccatgctgac  4800
ggtggctgtg tatgactggg acctggtggg cactgatgac ctcattgggg aaaccaagat  4860
cgacctggag aaccgcttct acagcaagca ccgcgccacc tgcggcatcg cccagaccta  4920
ctccacacat ggctacaata tctggcggga ccccatgaag cccagccaga tcctgacccg  4980
cctctgcaaa gacggcaaag tggacggccc ccactttggg ccccctggga gagtgaaggt  5040
ggccaaccgc gtcttcactg ggccctctga gattgaggac gagaacggtc agaggaagcc  5100
cacagacgag catgtggcgc tgttggccct gaggcactgg gaggacatcc cccgcgcagg  5160
ctgccgcctg gtgccagagc atgtggagac gaggccgctg ctcaaccccg acaagccggg  5220
catcgagcag ggccgcctgg agctgtgggt ggacatgttc cccatggaca tgccagcccc  5280
tgggacgcct ctggacatct cacctcggaa gcccaagaag tacgagctgc gggtcatcat  5340
ctggaacaca gatgaggtgg tcttggagga cgacgacttc ttcacagggg agaagtccag  5400
tgacatcttc gtgagggggt ggctgaaggg ccagcaggag gacaagcagg acacagacgt  5460
ccactaccac tccctcactg gcgagggcaa cttcaactgg cgctacctgt tccccttcga  5520
ctacctggcg gcggaggaga agatcgtcat ctccaagaag gagtccatgt tctcctggga  5580
cgagaccgag tacaagatcc ccgcgcggct caccctgcag atctgggatg cggaccactt  5640
ctccgctgac gacttcctgg gggccatcga gctggacctg aaccggttcc cgcggggcgc  5700
aaagacagcc aagcagtgca ccatggagat ggccaccggg gaggtggacg tgcccctcgt  5760
gtccatcttc aagcaaaagc gcgtcaaagg ctggtggccc ctcctggccc gcaatgagaa  5820
cgatgagttt gagctcacgg gcaaggtgga ggctgagctg catttactga cagcagagga  5880
```

```
ggcagagaag aacccagtgg gcctggcccg caatgaacct gacccccctag agaaacccaa  5940
ccggcccgac acgagcttca tctggttcct gaaccctctc aagtcggctc gctacttctt  6000
gtggcacacg tatcgctggc tgctcctcaa actgttgctg ctcctgctgc tgctcctcct  6060
cctcgccctg ttcctctact ctgtgcctgg ctacctggtc aagaaaatcc tcggggcctg  6120
agcccagtgg cctcctggcc ggcccgacac ggccttcgtc tggttcctca accctctcaa  6180
gtccatcaag tacctcatct gcacccggta caagtggctc atcatcaaga tcgtgctggc  6240
gctgttgggg ctgctcatgt tggggctctt cctctacagc ctccctggct acatggtcaa  6300
aaagctcctt ggggcatgaa ggccgccagc tcccgccagc cgctccccag ccctgccgca  6360
tttcctttca gtggcttgga ctctttccca tctcccctgg ggagcctgag gagcccagcg  6420
tccactcttc atgccttggg ccgagcctgc ctcctgcttg cggggggccgc ctgtcctcac  6480
tgccccaggc tgcggcttgc ccagtcccgc ccctctgacc cctgcctgtg ggctggggag  6540
ccttggatgg ggtggggacc tggaatgggt ctctcttgcc ccacctggct gaggcgccac  6600
ccttcttcag gcccaggctc cagaggaaga ctcctgaaac cctccccagg tcttccaagt  6660
acaggattga agctttagtg aaattaacca aggaccatgg gtcagtgccc agggctttaa  6720
aaagaatgaa cgagcaaaag gtatccccgc cgtgacccct gcagatagca ccggtctttg  6780
atccgcagca ggggccagac cctgccccaca agtcccagcg cggctgcttc tgccactgct  6840
gggctccact tggctcctct cacttcccag ggggtcgcct gtcctgcctg tgggtttcca  6900
tggcttccca gagctccctc tgccccagcc agcgcctcca ggcccagctg aggagctgtg  6960
agaagcagca gaggggactc cccatcccgg gcacaccctg tcctcccacc cctgcccccct  7020
tgcccttcca gccctttcag ctgcagctgg gagctggccc gtcaagtgct gcccctgcct  7080
gtgtctgggt ttctgttggc tgtttttctt ttcttgagtg gtgatttttc tctaaataaa  7140
agaagtcaag cactgaaaaa aaaaaaaaaa a                                 7171

SEQ ID NO: 11          moltype = DNA  length = 4969
FEATURE                Location/Qualifiers
source                 1..4969
                       mol_type = other DNA
                       organism = Homo sapiens
SEQUENCE: 11
ccgtgagttc tgcccaggcc ctgtgagctc accagagcca cagactcaca gcccagaggt  60
ggcttcttcc ttcaggaact gaagaacccc catgaacacc aacatctcca ggttctgaga  120
acagaacctg ggaaattgat gacttcctca tgatgaccga tactcaggat ggccctagcg  180
agagctccca gatcatgagg aagaaggcct gaacgacata caggagatga tcaaaacgga  240
gaagtcctac cctgagcgtc gcctgcgggg cgtcctggag gagctgagct gtggctgctg  300
ccgcttcctc tccctcgctg acaaggacca gggccactca tcccgcacca ggcttgaccg  360
ggagcgcctc aagtcctgca tgagggagct ggaaaacatg ggcagcaggg ccaggatgct  420
gcgggcccag gtgaagcggc acacggtgcg ggacaagctg aggctgtgcc agaacttcct  480
gcagaagctg cgcttcctgg cggacgagcc ccagcacagc attcccgaca tcttcatctg  540
gatgatgagc aacaacaagc gtgtcgccta tgcccgtgtg ccctccaagg acctgctctt  600
ctccatcgtg gaggaggaga ctggcaagga ctgcgccaag gtcaagacgc tcttccttaa  660
gctgccaggg aagcggggct tcggctcggc aggctggaca gtgcaggcca aggtggagct  720
gtacctgtgg ctgggcctca gcaaacagcg caaggagttc ctgtgcggcc tgccctgtgg  780
cttccaggag gtcaaggcag cccagggcct gggcctgcat gccttcccac ccgtcagcct  840
ggtctacacc aagaagcagg cgttccagct ccgagcgcac atgtaccagg cccgcagcct  900
ctttgccgcc gacagcagcg gactctcaga cccctttgcc cgcgtcttct tcatcaatca  960
gagtcagtgc acagaggtgc tgaatgagac cctgtgtccc acctgggacc agatgctggt  1020
gttcgacaac ctggagctct atggtgaagc tcatgagctg agggacgatc cgcccatcat  1080
tgtcattgaa atctatgacc aggattccat gggcaaagct gacttcatgg gccggacctt  1140
cgccaaaccc ctggtgaaga tggcagacga ggcgtactgc ccaccccgct tcccacctca  1200
gctcgagtac taccagatct accgtggcaa cgccacagct ggagacctgc tggcggcctt  1260
cgagctgctg cagattggac cagcagggaa ggctgacctg cccccccatca atggcccggt  1320
ggacgtggac cgaggtccca tcatgcccgt gcccatgggc atccggcccg tgctcagcaa  1380
gtaccgagtg gaggtgctgt tctggggcct acgggaccta aagcgggtga acctggccca  1440
ggtggaccgg ccacgggtgg acatcgagtg tgcagggaag ggggtgcagt cgtccctgat  1500
ccacaattat aagaagaacc ccaacttcaa caccctcgtc aagtggtttg aagtggacct  1560
cccagagaac gagctgctgc acccgccctt gaacatccgt gtggtggact gccgggcctt  1620
cggtcgctac acactggtgg gctcccatgc cgtcagctcc ctgcgacgct tcatctaccg  1680
gccccccagac cgctcggccc ccagctggaa caccacgggg gaggttgtgg tgactatgga  1740
gccagaggta cccatcaaga aactggagac catggtgaag ctggacgcga cttctgaagc  1800
tgttgtcaag gtggatgtgg ctgaggagga gaaggagaag aagaagaaga agaagggcac  1860
tgcggaggag ccagaggagg aggagccaga cgagagcatg ctggactggt ggtccaagta  1920
ctttgcctcc attgacacca tgaaggagca acttcgacaa caagagccct ctggaattga  1980
cttggaggag aaggaggaag tggacaatac cgagggcctg aaggggtcaa tgaagggcaa  2040
ggagaaggca agggctgcca aagaggagaa gaagaagaaa actcagagct ctggctctgg  2100
ccaggggtcc gaggcccccg agaagaagaa acccaagatt gatgagctta aggtataccc  2160
caaagagctg gagtccgagt ttgataactt tgaggactgg ctgcacactt tcaacttgct  2220
tcggggcaag accggggatg atgaggatgg ctccaccgag gaggagcgca ttgtgggacg  2280
cttcaagggc tccctctgcg tgtacaaagt gccactccca gaggacgtgt cccgggaagc  2340
cggctacgac tccacctacg gcatgttcca gggcatcccg agcaatgacc ccatcaatgt  2400
gctggtccga gtctatgtgg tccgggccac ggacctgcac cctgctgaca tcaacggcaa  2460
agctgacccc tacatcgcca tccggctagg caagactgac atccgcgaca aggagaacta  2520
catctccaag cagctcaacc ctgtctttgg gaagtccttt gacatcgagg cctccttccc  2580
catggaatcc atgctgacgg tggctgtgta tgactgggac ctggtgggca ctgatgacct  2640
cattggggaa accaagatcg acctggagaa ccgcttctac agcaagcacc gcgccacctg  2700
cggcatcgcc cagacctact ccacacatgg ctacaatatc tggcgggacc ccatgaagcc  2760
cagccagatc ctgacccgcc tctgcaaaga cggcaaagtg gacggccccc actttgggcc  2820
ccctgggaga gtgaaggtgg ccaaccgcgt cttcactggg ccctctgaga ttgaggacga  2880
gaacggtcag aggaagccca cagacgagca tgtggcgctg ttggccctga ggcactggga  2940
ggacatcccc cgcgcaggct gccgcctggt gccagagcat gtggagacga ggccgctgct  3000
```

-continued

```
caaccccgac aagccgggca tcgagcaggg ccgcctggag ctgtgggtgg acatgttccc  3060
catggacatg ccagcccctg ggacgcctct ggacatctca cctcggaagc ccaagaagta  3120
cgagctgcgg gtcatcatct ggaacacaga tgaggtggtc ttggaggacg acgacttctt  3180
cacaggggag aagtccagtg acatcttcgt gagggggtgg ctgaagggcc agcaggagga  3240
caagcaggac acagacgtcc actaccactc cctcactggc gagggcaact tcaactggcg  3300
ctacctgttc cccttcgact acctggcggc ggaggagaag atcgtcatct ccaagaagga  3360
gtccatgttc tcctgggacg agaccgagta caagatcccc gcgcggctca ccctgcagat  3420
ctgggatgcg gaccacttct ccgctgacga cttcctgggg gccatcgagc tggacctgaa  3480
ccggttcccg cggggcgcaa agacagccaa gcagtgcacc atggagatgg ccaccgggga  3540
ggtggacgtg cccctcgtgt ccatcttcaa gcaaaagcgc gtcaaaggct ggtggcccct  3600
cctggcccgc aatgagaacg atgagtttga gctcacgggc aaggtggagg ctgagctgca  3660
tttactgaca gcagaggagg cagagaagaa cccagtgggc ctggcccgca atgaacctga  3720
cccccctagag aaacccaacc ggcccgacac gagcttcatc tggttcctga accctctcaa  3780
gtcggctcgc tacttcttgt ggcacacgta tcgctggctg ctcctcaaac tgttgctgct  3840
cctgctgctg ctcctcctcc tcgccctgtt cctctactct gtgcctggct acctggtcaa  3900
gaaaatcctc ggggcctgag cccagtggcc tcctggccgg cccgacacgg ccttcgtctg  3960
gttcctcaac cctctcaagt ccatcaagta cctcatctgc acccggtaca agtggctcat  4020
catcaagatc gtgctggcgc tgttggggct gctcatgttg gggctcttcc tctacagcct  4080
ccctggctac atggtcaaaa agctccttgg ggcatgaagg ccgccagctc ccgccagccg  4140
ctccccagcc ctgccgcatt tcctttcagt ggcttggact ctttcccatc tcccctgggg  4200
agcctgagga gcccagcgtc cactcttcat gccttgggcc gagcctgcct cctgcttgcg  4260
ggggccgcct gtcctcactg ccccaggctg cggcttgccc agtcccgccc ctctgacccc  4320
tgcctgtggg ctggggagcc ttggatgggg tggggacctg gaatgggtct ctcttgcccc  4380
acctggctga ggcgccaccc ttcttcaggc ccaggctcca gaggaagact cctgaaaccc  4440
tccccaggtc ttccaagtac aggattgaag ctttagtgaa attaaccaag gaccatgggt  4500
cagtgcccag ggctttaaaa agaatgaacg agcaaaaggt atccccgccg tgacccctgc  4560
agatagcacc ggtctttgat ccgcagcagg ggccagaccc tgcccacaag tcccagcgcg  4620
gctgcttctg ccactgctgg gctccacttg gctcctctca cttcccaggg ggtcgcctgt  4680
cctgcctgtg ggtttccatg gcttcccaga gctccctctg ccccagccag cgcctccagg  4740
cccagctgag gagctgtgag aagcagcaga ggggactccc catcccgggc acaccctgtc  4800
ctcccacccc tgccccttg cccttccagc cctttcagct gcagctggga gctggcccgt  4860
caagtgctgc ccctgcctgt gtctgggttt ctgttggctg tttttctttt cttgagtggt  4920
gatttttctc taaataaaag aagtcaagca ctgaaaaaaa aaaaaaaaa            4969

SEQ ID NO: 12            moltype = DNA  length = 4771
FEATURE                  Location/Qualifiers
source                   1..4771
                         mol_type = other DNA
                         organism = Homo sapiens
SEQUENCE: 12
ccgtgagttc tgcccaggcc ctgtgagctc accagagcca cagactcaca gcccagaggt  60
ggcttcttcc ttcaggaact gaagaacccc catgaacacc aacatctcca ggttctgaga  120
acagaacctg ggaaattgat gacttcctca tgatgaccga tactcaggat ggccctagcg  180
agagctccca gatcatgagg aagaaggcct gaacgacata caggagatga tcaaaacgga  240
gaagtcctac cctgagcgtc gcctgcgggg cgtcctggag gagctgagct gtggctgctg  300
ccgcttcctc tccctcgctg acaaggacca gggccactca tcccgcacca ggcttgaccg  360
ggagcgcctc aagtcctgca tgagggagct ggaaaacatg ggcagcagg ccaggatgct  420
gcgggcccag gtgaagcggc acacggtgcg ggacaagctg aggctgtgcc agaacttcct  480
gcagaagctg cgcttcctgg cggacgagcc ccagcacagc attcccgaca tcttcatctg  540
gatgatgagc aacaacaagc gtgtcgccta tgcccgtgtg ccctccaagg acctgctctt  600
ctccatcgtg gaggaggaga ctggcaagga ctgcgccaag gtcaagacgc tcttccttaa  660
gctgccaggg aagcggggct tcggctcggc aggctggaca gtgcaggcca aggtggagct  720
gtacctgtgg ctgggcctca gcaaacagcg caaggagttc ctgtgcggcc tgccctgtgg  780
cttccaggag gtcaaggcag cccagggcct gggcctgcat gccttcccac ccgtcagcct  840
ggtctacacc aagaagcagg cgttccagct ccgagcgcac atgtaccagg cccgcagcct  900
ctttgccgcc gacagcagcg gactctcaga ccccttttgcc cgcgtcttct tcatcaatca  960
gagtcagtgc acagaggtgc tgaatgagac cctgtgtccc acctgggacc agatgctggt  1020
gttcgacaac ctggagctct atggtgaagc tcatgagctg agggacgatc cgcccatcat  1080
tgtcattgaa atctatgacc aggattccat gggcaaagct gacttcatgg gccggacctt  1140
cgccaaaccc ctggtgaaga tggcagacga ggcgtactgc ccaccccgct tcccacctca  1200
gctcgagtac taccagatct accgtggcaa cgccacagct ggagacctgc tggcggcctt  1260
cgagctgctg cagattggac cagcagggaa ggctgacctg cccccccatca atggcccggt  1320
ggacgtggac cgaggtccca tcatgcccgt gcccatgggc atccggcccg tgctcagcaa  1380
gtaccgagtg gaggtgctgt tctggggcct acgggaccta aagcgggtga acctggccca  1440
ggtggaccgg ccacgggtgg acatcgagtg tgcagggaag ggggtgcagt cgtccctgat  1500
ccacaattat aagaagaacc ccaacttcaa caccctcgtc aagtggtttg aagtggacct  1560
cccagagaac gagctgctgc acccgccctt gaacatccgt gtggtggact gccgggcctt  1620
cggtcgctac acactggtgg gctcccatgc cgtcagctcc ctgcgacgct tcatctaccg  1680
gccccccagac cgctcggccc ccagctggaa caccacgggg gaggttgtgg tgactatgga  1740
gccagaggta cccatcaaga aactggagac catggtgaag ctggacgcga cttctgaagc  1800
tgttgtcaag gtggatgtgg ctgaggagga gaaggagaag aagaagaaga agaagggcac  1860
tgcggaggag ccagaggagg aggagccaga cgagagcatg ctggactggt ggtccaagta  1920
ctttgcctcc attgacacca tgaaggagca acttcgacaa caagagccct ctggaattga  1980
cttggaggag aaggaggaag tggacaatac cgagggcctg aaggggtcaa tgaagggcaa  2040
ggagaaggca agggctgcca aagaggagaa gaagaagaaa actcagagct ctggctctgg  2100
ccaggggtcc gaggcccccg agaagaagaa acccaagatt gatgagctta aggtataccc  2160
caaagagctg gagtccgagt ttgataactt tgaggactgg ctgcacactt tcaacttgct  2220
tcggggcaag accggggatg atgaggatgg ctccaccgag gaggagcgca ttgtgggacg  2280
cttcaagggc tccctctgcg tgtacaaagt gccactccca gaggacgtgt cccgggaagc  2340
```

-continued

```
cggctacgac tccacctacg gcatgttcca gggcatcccg agcaatgacc ccatcaatgt  2400
gctggtccga gtctatgtgg tccgggccac ggacctgcac cctgctgaca tcaacggcaa  2460
agctgacccc tacatcgcca tccggctagg caagactgac atccgcgaca aggagaacta  2520
catctccaag cagctcaacc ctgtctttgg gaagtccttt gacatcgagg cctccttccc  2580
catggaatcc atgctgacgg tggctgtgta tgactgggac ctggtgggca ctgatgacct  2640
cattggggaa accaagatcg acctggagaa ccgcttctac agcaagcacc gcgccacctg  2700
cggcatcgcc cagacctact ccacacatgg ctacaatatc tggcgggacc ccatgaagcc  2760
cagccagatc ctgacccgcc tctgcaaaga cggcaaagtg gacggccccc actttgggcc  2820
ccctgggaga gtgaaggtgg ccaaccgcgt cttcactggg ccctctgaga ttgaggacga  2880
gaacggtcag aggaagccca cagacgagca tgtggcgctg ttggccctga ggcactggga  2940
ggacatcccc cgcgcaggct gccgcctggt gccagagcat gtggagacga ggccgctgct  3000
caaccccgac aagccgggca tcgagcaggg ccgcctggag ctgtgggtgg acatgttccc  3060
catggacatg ccagcccctg ggacgcctct ggacatctca cctcggaagc ccaagaagta  3120
cgagctgcgg gtcatcatct ggaacacaga tgaggtggtc ttggaggacg acgacttctt  3180
cacaggggag aagtccagtg acatcttcgt gaggggggtgg ctgaagggcc agcaggagga  3240
caagcaggac acagacgtcc actaccactc cctcactggc gagggcaact tcaactggcg  3300
ctacctgttc cccttcgact acctggcggc ggaggagaag atcgtcatct ccaagaagga  3360
gtccatgttc tcctgggacg agaccgagta caagatcccc gcgcggctca ccctgcagat  3420
ctgggatgcg gaccacttct ccgctgacga cttcctgggg gccatcgagc tggacctgaa  3480
ccggttcccg cggggcgcaa agacagccaa gcagtgcacc atggagatgg ccaccgggga  3540
ggtggacgtg cccctcgtgt ccatcttcaa gcaaaagcgc gtcaaaggct ggtggcccct  3600
cctggcccgc aatgagaacg atgagtttga gctcacgggc aaggtggagg ctgagctgca  3660
tttactgaca gcagaggagg cagagaagaa cccagtgggc ctggcccgca atgaacctga  3720
cccccctagag aaacccaacc ggcccgacac ggccttcgtc tggttcctca accctctcaa  3780
gtccatcaag tacctcatct gcacccggta caagtggctc atcatcaaga tcgtgctggc  3840
gctgttgggg ctgctcatgt tggggctctt cctctacagc ctccctggct acatggtcaa  3900
aaagctcctt ggggcatgaa ggccgccagc tcccgccagc cgctccccag ccctgccgca  3960
tttcctttca gtggcttgga ctctttccca tctcccctgg ggagcctgag gagcccagcg  4020
tccactcttc atgccttggg ccgagcctgc ctcctgcttg cgggggccgc ctgtcctcac  4080
tgccccaggc tgcggcttgc ccagtcccgc ccctctgacc cctgcctgtg ggctggggag  4140
ccttggatgg ggtggggacc tggaatgggt ctctcttgcc ccacctggct gaggcgccac  4200
ccttcttcag gcccaggctc cagaggaaga ctcctgaaac cctccccagg tcttccaagt  4260
acaggattga agctttagtg aaattaacca aggaccatgg gtcagtgccc agggctttaa  4320
aaagaatgaa cgagcaaaag gtatccccgc cgtgacccct gcagatagca ccggtctttg  4380
atccgcagca ggggccagac cctgcccaca agtcccagcg cggctgcttc tgccactgct  4440
gggctccact tggctcctct cacttcccag ggggtcgcct gtcctgcctg tgggtttcca  4500
tggcttccca gagctccctc tgccccagcc agcgcctcca ggcccagctg aggagctgtg  4560
agaagcagca gaggggactc cccatcccgg gcacaccctg tcctcccacc cctgcccccct  4620
tgcccttcca gccctttcag ctgcagctgg gagctggccc gtcaagtgct gcccctgcct  4680
gtgtctgggt ttctgttggc tgtttttctt ttcttgagtg gtgatttttc tctaaataaa  4740
agaagtcaag cactgaaaaa aaaaaaaaaa a                                 4771

SEQ ID NO: 13           moltype = DNA  length = 5123
FEATURE                 Location/Qualifiers
source                  1..5123
                        mol_type = other DNA
                        organism = Homo sapiens
SEQUENCE: 13
ccgtgagttc tgcccaggcc ctgtgagctc accagagcca cagactcaca gcccagaggt  60
ggcttcttcc ttcaggaact gaagaacccc catgaacacc aacatctcca ggttctgaga  120
acagaacctg ggaaattgat gacttcctca tgatgaccga tactcaggat ggccctagcg  180
agagctccca gatcatgagg tccctcactc ccctgatcaa cagggaggag gcatttgggg  240
aggctgggga ggcggggctg tggcccagca tcacccacac tcctgattca caggaagaag  300
gcctgaacga catacaggag atgatcaaaa cggagaagtc ctaccctgag cgtcgcctgc  360
ggggcgtcct ggaggagctg agctgtggct gctgccgctt cctctccctc gctgacaagg  420
accagggcca ctcatcccgc accaggcttg accgggagcg cctcaagtcc tgcatgaggg  480
agctggaaaa catggggcag caggccagga tgctgcgggc ccaggtgaag cggcacacgg  540
tgcgggacaa gctgaggctg tgccagaact tcctgcagaa gctgcgcttc ctggcggacg  600
agccccagca cagcattccc gacatcttca tctggatgat gagcaacaac aagcgtgtcg  660
cctatgcccg tgtgccctcc aaggacctgc tcttctccat cgtggaggag gagactggca  720
aggactgcgc caaggtcaag acgctcttcc ttaagctgcc agggaagcgg ggcttcggct  780
cggcaggctg gacagtgcag gccaaggtgg agctgtacct gtggctgggc ctcagcaaac  840
agcgcaagga gttcctgtgc ggcctgccct gtggcttcca ggaggtcaag gcagcccagg  900
gcctgggcct gcatgccttc ccacccgtca gcctggtcta caccaagaag caggcgttcc  960
agctccgagc gcacatgtac caggcccgca gcctctttgc cgccgacagc agcggactct  1020
cagacccctt tgcccgcgtc ttcttcatca atcagagtca gtgcacagag gtgctgaatg  1080
agaccctgtg tcccacctgg gaccagatgc tggtgttcga caacctggag ctctatggtg  1140
aagctcatga gctgagggac gatccgccca tcattgtcat tgaaatctat gaccaggatt  1200
ccatgggcaa agctgacttc atgggccgga ccttcgccaa acccctggtg aagatggcag  1260
acgaggcgta ctgcccaccc cgcttcccac ctcagctcga gtactaccag atctaccgtg  1320
gcaacgccac agctggagac ctgctggcgg ccttcgagct gctgcagatt ggaccagcag  1380
ggaaggctga cctgcccccc atcaatggcc cggtggacgt ggaccgaggt cccatcatgc  1440
ccgtgcccat gggcatccgg cccgtgctca gcaagtaccg agtggaggtg ctgttctggg  1500
gcctacggga cctaaagcgg gtgaacctgg cccaggtgga ccggccacgg gtggacatcg  1560
agtgtgcagg gaagggggtg cagtcgtccc tgatccacaa ttataagaag aaccccaact  1620
tcaacaccct cgtcaagtgg tttgaagtgg acctcccaga gaacgagctg ctgcacccgc  1680
ccttgaacat ccgtgtggtg gactgccggg ccttcggtcg ctacacactg gtgggctccc  1740
atgccgtcag ctccctgcga cgcttcatct accggccccc agaccgctcg gcccccagct  1800
ggaacaccac ggtcaggctt ctccggcgct gccgtgtgct gtgcaatggg ggctcctcct  1860
```

-continued

```
ctcactccac aggggaggtt gtggtgacta tggagccaga ggtacccatc aagaaactgg  1920
agaccatggt gaagctggac gcgacttctg aagctgttgt caaggtggat gtggctgagg  1980
aggagaagga gaagaagaag aagaagaagg gcactgcgga ggagccagag gaggaggagc  2040
cagacgagag catgctggac tggtggtcca agtactttgc ctccattgac accatgaagg  2100
agcaacttcg acaacaagag ccctctggaa ttgacttgga ggagaaggag gaagtggaca  2160
ataccgaggg cctgaagggg tcaatgaagg gcaaggagaa ggcaagggct gccaaagagg  2220
agaagaagaa gaaaactcag agctctggct ctggccaggg gtccgaggcc cccgagaaga  2280
agaaacccaa gattgatgag cttaaggtat accccaaaga gctggagtcc gagtttgata  2340
actttgagga ctggctgcac actttcaact tgcttcgggg caagaccggg gatgatgagg  2400
atggctccac cgaggaggag cgcattgtgg gacgcttcaa gggctccctc tgcgtgtaca  2460
aagtgccact cccagaggac gtgtcccggg aagccggcta cgactccacc tacggcatgt  2520
tccagggcat cccgagcaat gaccccatca atgtgctggt ccgagtctat gtggtccggg  2580
ccacggacct gcaccctgct gacatcaacg gcaaagctga ccccctacatc gccatccggc  2640
taggcaagac tgacatccgc gacaaggaga actacatctc caagcagctc aaccctgtct  2700
ttgggaagtc ctttgacatc gaggcctcct tccccatgga atccatgctg acggtggctg  2760
tgtatgactg ggacctggtg ggcactgatg acctcattgg ggaaaccaag atcgacctgg  2820
agaaccgctt ctacagcaag caccgcgcca cctgcggcat cgcccagacc tactccacac  2880
atggctacaa tatctggcgg gaccccatga agcccagcca gatcctgacc cgcctctgca  2940
aagacggcaa agtggacggc ccccactttg ggcccccctgg gagagtgaag gtggccaacc  3000
gcgtcttcac tgggccctct gagattgagg acgagaacgg tcagaggaag cccacagacg  3060
agcatgtggc gctgttggcc ctgaggcact gggaggacat cccccgcgca ggctgccgcc  3120
tggtgccaga gcatgtggag acgaggccgc tgctcaaccc cgacaagccg ggcatcgagc  3180
agggccgcct ggagctgtgg gtggacatgt tccccatgga catgccagcc cctgggacgc  3240
ctctggacat ctcacctcgg aagcccaaga agtacgagct gcgggtcatc atctggaaca  3300
cagatgaggt ggtcttggag gacgacgact tcttcacagg ggagaagtcc agtgacatct  3360
tcgtgagggg gtggctgaag ggccagcagg aggacaagca ggacacagac gtccactacc  3420
actccctcac tggcgagggc aacttcaact ggcgctacct gttccccttc gactacctgg  3480
cggcggagga gaagatcgtc atctccaaga aggagtccat gttctcctgg gacgagaccg  3540
agtacaagat ccccgcgcgg ctcaccctgc agatctggga tgcggaccac ttctccgctg  3600
acgacttcct gggggccatc gagctggacc tgaaccggtt cccgcggggc gcaaagacag  3660
ccaagcagtg caccatggag atggccaccg gggaggtgga cgtgcccctc gtgtccatct  3720
tcaagcaaaa gcgcgtcaaa ggctggtggc ccctcctggc ccgcaatgag aacgatgagt  3780
ttgagctcac gggcaaggtg gaggctgagc tgcatttact gacagcagag gaggcagaga  3840
agaacccagt gggcctggcc cgcaatgaac ctgacccccct agagaaaccc aaccggcccg  3900
acacgagctt catctggttc ctgaaccctc tcaagtcggc tcgctacttc ttgtggcaca  3960
cgtatcgctg gctgctcctc aaactgttgc tgctcctgct gctgctcctc ctcctcgccc  4020
tgttcctcta ctctgtgcct ggctacctgg tcaagaaaat cctcggggcc tgagcccagt  4080
ggcctcctgg ccggcccgac acggccttcg tctggttcct caaccctctc aagtccatca  4140
agtacctcat ctgcacccgg tacaagtggc tcatcatcaa gatcgtgctg gcgctgttgg  4200
ggctgctcat gttggggctc ttcctctaca gcctccctgg ctacatggtc aaaaagctcc  4260
ttggggcatg aaggccgcca gctcccgcca gccgctcccc agccctgccg catttccttt  4320
cagtggcttg gactctttcc catctcccct ggggagcctg aggagcccag cgtccactct  4380
tcatgccttg ggccgagcct gcctcctgct tgcgggggcc gcctgtcctc actgccccag  4440
gctgcggctt gcccagtccc gcccctctga cccctgcctg tgggctgggg agccttggat  4500
ggggtgggga cctggaatgg gtctctcttg ccccacctgg ctgaggcgcc acccttcttc  4560
aggcccaggc tccagaggaa gactcctgaa accctcccca ggtcttccaa gtacaggatt  4620
gaagctttag tgaaattaac caaggaccat gggtcagtgc ccagggcttt aaaaagaatg  4680
aacgagcaaa aggtatcccc gccgtgaccc ctgcagatag caccggtctt tgatccgcag  4740
caggggccag accctgccca caagtcccag cgcggctgct tctgccactg ctgggctcca  4800
cttggctcct ctcacttccc agggggtcgc ctgtcctgcc tgtgggtttc catggcttcc  4860
cagagctccc tctgccccag ccagcgcctc caggcccagc tgaggagctg tgagaagcag  4920
cagaggggac tccccatccc gggcacaccc tgtcctccca cccctgcccc cttgcccttc  4980
cagccctttc agctgcagct gggagctggc ccgtcaagtg ctgcccctgc ctgtgtctgg  5040
gtttctgttg gctgttttc ttttcttgag tggtgatttt tctctaaata aaagaagtca  5100
agcactgaaa aaaaaaaaa aaa                                           5123

SEQ ID NO: 14          moltype = DNA  length = 6973
FEATURE                Location/Qualifiers
source                 1..6973
                       mol_type = other DNA
                       organism = Homo sapiens
SEQUENCE: 14
atcggagggg ggtcgggagg aggaggagga ggcagcggca gagaagagag aggcgtgtga  60
gccgtgctcc accggctagc tccttcccgc tgctcctgcc tggcagtgcc aggcagccca  120
caccagcatg gccttgctca tccacctcaa gacagtctcg gagctgcggg gcaggggcga  180
ccggatcgcc aaagtgactt tccgagggca atccttctac tctcgggtcc tggagaactg  240
tgaggatgtg gctgactttg atgagacatt tcggtggccg gtggccagca gcatcgacag  300
aaatgagatg ctggagattc aggttttcaa ctacagcaaa gtcttcagca acaagctcat  360
cgggaccttc cgcatggtgc tgcagaaggt ggtagaggag agccatgtgg aggtgactga  420
cacgctgatt gatgacaaca atgctatcat caagaccagc ctgtgcgtgg aggtccggta  480
tcaggccact gacggcacag tgggctcctg ggacgatggg gacttcctgg gagatgagtc  540
tcttcaagag gaagagaagg acagccaaga gacggatgga ctgctcccag gctcccggcc  600
cagctcccgg cccccaggag agaagagctt ccggagagcc gggaggagcg tgttctccgc  660
catgaagctc ggcaaaaacc ggtctcacaa ggaggagccc caaagaccag atgaaccggc  720
ggtgctggag atggaagacc ttgaccatct ggccattcgg ctaggagatg gactggatcc  780
cgactcggtg tctctagcct cagtcacagc tctcaccact aatgtctcca acaagcgatc  840
taagccagac attaagatgg agccaagtgc tgggcggccc atggattacc aggtcagcat  900
cacggtgatc gaggcccggc agctggtggg cttgaacatg gaccctgtgg tgtgcgtgga  960
ggtgggtgac gacaagaagt acacatccat gaaggagtcc actaactgcc cctattacaa  1020
```

-continued

```
cgagtacttc gtcttcgact tccatgtctc tccggatgtc atgtttgaca agatcatcaa  1080
gatttcggtg attcactcca agaacctgct gcgcagtggc accctggtgg gctccttcaa  1140
aatggacgtg ggaaccgtgt actcgcagcc agagcaccag ttccatcaca agtgggccat  1200
cctgtctgac cccgatgaca tctcctcggg gctgaagggc tacgtgaagt gtgacgttgc  1260
cgtggtgggc aaaggggaca acatcaagac gccccacaag gccaatgaga ccgacgaaga  1320
tgacattgag gggaacttgc tgctccccga gggggtgccc cccgaacgcc agtgggcccg  1380
gttctatgtg aaaatttacc gagcagaggg gctgccccgt atgaacacaa gcctcatggc  1440
caatgtaaag aaggctttca tcggtgaaaa caaggacctc gtggacccct acgtgcaagt  1500
cttctttgct ggccagaagg gcaagacttc agtgcagaag agcagctatg agcccctgtg  1560
gaatgagcag gtcgtcttta cagacctctt cccccactc tgcaaacgca tgaaggtgca  1620
gatccgagac tcggacaagg tcaacgacgt ggccatcggc acccacttca ttgacctgcg  1680
caagatttct aatgacggag acaaaggctt cctgcccaca ctgggcccag cctgggtgaa  1740
catgtacggc tccacacgta actacacgct gctggatgag catcaggacc tgaacgaggg  1800
cctgggggag ggtgtgtcct tccgggcccg gctcctgctg ggcctggctg tggagatcgt  1860
agacacctcc aaccctgagc tcaccagctc cacagaggtg caggtggagc aggccacgcc  1920
catctcggag agctgtgcag gtaaaatgga agaattcttt ctctttggag ccttcctgga  1980
ggcctcaatg atcgaccgga gaaacggaga caagcccatc acctttgagg tcaccatagg  2040
caactatggg aacgaagttg atggcctgtc ccggccccag cggcctcggc cccggaagga  2100
gccgggggat gaggaagaag tagacctgat tcagaacgca agtgatgacg aggccggtga  2160
tgccggggac ctggcctcag tctcctccac tccaccaatg cggccccagg tcaccgacag  2220
gaactacttc catctgccct acctggagcg aaagccctgc atctacatca agagctggtg  2280
gccggaccag cgccgccgcc tctacaatgc caacatcatg gaccacattg ccgacaagct  2340
ggaagaaggc ctgaacgaca tacaggagat gatcaaaacg gagaagtcct accctgagcg  2400
tcgcctgcgg ggcgtcctgg aggagctgag ctgtggctgc tgccgcttcc tctccctcgc  2460
tgacaaggac cagggccact catcccgcac caggcttgac cgggagcgcc tcaagtcctg  2520
catgagggag ctggaaaaca tggggcagca ggccaggatg ctgcgggccc aggtgaagcg  2580
gcacacggtg cgggacaagc tgaggctgtg ccagaacttc ctgcagaagc tgcgcttcct  2640
ggcggacgag ccccagcaca gcattcccga catcttcatc tggatgatga gcaacaacaa  2700
gcgtgtcgcc tatgcccgtg tgccctccaa ggacctgctc ttctccatcg tggaggagga  2760
gactggcaag gactgcgcca aggtcaagac gctcttcctt aagctgccag ggaagcgggg  2820
cttcggctcg gcaggctgga cagtgcaggc caaggtggag ctgtacctgt ggctgggcct  2880
cagcaaacag cgcaaggagt tcctgtgcgg cctgccctgt ggcttccagg aggtcaaggc  2940
agcccagggc ctgggcctgc atgccttccc acccgtcagc ctggtctaca ccaagaagca  3000
ggcgttccag ctccgagcgc acatgtacca ggcccgcagc ctctttgccg ccgacagcag  3060
cggactctca gaccccttttg cccgcgtctt cttcatcaat cagagtcagt gcacagaggt  3120
gctgaatgag accctgtgtc ccacctggga ccagatgctg gtgttcgaca acctggagct  3180
ctatggtgaa gctcatgagc tgagggacga tccgcccatc attgtcattg aaatctatga  3240
ccaggattcc atgggcaaag ctgacttcat gggccggacc ttcgccaaac ccctggtgaa  3300
gatggcagac gaggcgtact gcccaccccg cttcccacct cagctcgagt actaccagat  3360
ctaccgtggc aacgccacag ctggagacct gctggcggcc ttcgagctgc tgcagattgg  3420
accagcaggg aaggctgacc tgcccccat caatggcccg gtggacgtgg accgaggtcc  3480
catcatgccc gtgcccatgg gcatccggcc cgtgctcagc aagtaccgag tggaggtgct  3540
gttctggggc ctacgggacc taaagcgggt gaacctggcc caggtggacc ggccacgggt  3600
ggacatcgag tgtgcaggga agggggtgca gtcgtccctg atccacaatt ataagaagaa  3660
ccccaacttc aacaccctcg tcaagtggtt tgaagtggac ctcccagaga acgagctgct  3720
gcacccgccc ttgaacatcc gtgtggtgga ctgccgggcc ttcggtcgct acacactggt  3780
gggctcccat gccgtcagct ccctgcgacg cttcatctac cggcccccag accgctcggc  3840
ccccagctgg aacaccacgg tcaggcttct ccggcgctgc cgtgtgctgt gcaatggggg  3900
ctcctcctct cactccacag gggaggttgt ggtgactatg gagccagagg tacccatcaa  3960
gaaactggag accatggtga agctggacgc gacttctgaa gctgttgtca aggtggatgt  4020
ggctgaggag gagaaggaga agaagaagaa gaagaagggc actgcggagg agccagagga  4080
ggaggagcca gacgagagca tgctggactg gtggtccaag tactttgcct ccattgacac  4140
catgaaggag caacttcgac aacaagagcc ctctggaatt gacttggagg agaaggagga  4200
agtggacaat accgaggccc tgaaggggtc aatgaagggc aaggagaagg caagggctgc  4260
caaagaggag aagaagaaga aaactcagag ctctggctct ggccaggggt ccgaggcccc  4320
cgagaagaag aaacccaaga ttgatgagct taaggtatac cccaaagagc tggagtccga  4380
gtttgataac tttgaggact ggctgcacac tttcaacttg cttcggggca agaccgggga  4440
tgatgaggat ggctccaccg aggaggagcg cattgtggga cgcttcaagg gctccctctg  4500
cgtgtacaaa gtgccactcc cagaggacgt gtcccgggaa gccggctacg actccaccta  4560
cggcatgttc cagggcatcc cgagcaatga ccccatcaat gtgctggtcc gagtctatgt  4620
ggtccgggcc acggacctgc accctgctga catcaacggc aaagctgacc cctacatcgc  4680
catccggcta ggcaagactg acatccgcga caaggagaac tacatctcca agcagctcaa  4740
ccctgtcttt gggaagtcct ttgacatcga ggcctccttc cccatggaat ccatgctgac  4800
ggtggctgtg tatgactggg acctggtggg cactgatgac ctcattgggg aaaccaagat  4860
cgacctggag aaccgcttct acagcaagca ccgcgccacc tgcggcatcg cccagaccta  4920
ctccacacat ggctacaata tctggcggga ccccatgaag cccagccaga tcctgacccg  4980
cctctgcaaa gacggcaaag tggacggccc ccactttggg cccccctggga gagtgaaggt  5040
ggccaaccgc gtcttcactg ggccctctga gattgaggac gagaacggtc agaggaagcc  5100
cacagacgag catgtggcgc tgttggccct gaggcactgg gaggacatcc cccgcgcagg  5160
ctgccgcctg gtgccagagc atgtggagac gaggccgctg ctcaaccccg acaagccggg  5220
catcgagcag ggccgcctgg agctgtgggt ggacatgttc cccatggaca tgccagcccc  5280
tgggacgcct ctggacatct cacctcggaa gcccaagaag tacgagctgc gggtcatcat  5340
ctggaacaca gatgaggtgg tcttggagga cgacgacttc ttcacagggg agaagtccag  5400
tgacatcttc gtgagggggt ggctgaaggg ccagcaggag gacaagcagg acacagacgt  5460
ccactaccac tccctcactg gcgagggcaa cttcaactgg cgctacctgt tcccccttcga  5520
ctacctggcg gcggaggaga agatcgtcat ctccaagaag gagtccatgt tctcctggga  5580
cgagaccgag tacaagatcc ccgcgcggct caccctgcag atctgggatg cggaccactt  5640
ctccgctgac gacttcctgg gggccatcga gctggacctg aaccggttcc cgcggggcgc  5700
aaagacagcc aagcagtgca ccatggagat ggccaccggg gaggtggacg tgcccctcgt  5760
```

-continued

```
gtccatcttc aagcaaaagc gcgtcaaagg ctggtggccc ctcctggccc gcaatgagaa  5820
cgatgagttt gagctcacgg gcaaggtgga ggctgagctg catttactga cagcagagga  5880
ggcagagaag aacccagtgg gcctggcccg caatgaacct gacccccctag agaaacccaa  5940
ccggcccgac acggccttcg tctggttcct caaccctctc aagtccatca agtacctcat  6000
ctgcacccgg tacaagtggc tcatcatcaa gatcgtgctg gcgctgttgg ggctgctcat  6060
gttggggctc ttcctctaca gcctccctgg ctacatggtc aaaaagctcc ttggggcatg  6120
aaggccgcca gctcccgcca gccgctcccc agccctgccg catttccttt cagtggcttg  6180
gactctttcc catctcccct ggggagcctg aggagcccag cgtccactct tcatgccttg  6240
ggccgagcct gcctcctgct tgcgggggcc gcctgtcctc actgccccag gctgcggctt  6300
gcccagtccc gcccctctga cccctgcctg tgggctgggg agccttggat ggggtgggga  6360
cctggaatgg gtctctcttg ccccacctgg ctgaggcgcc acccttcttc aggcccaggc  6420
tccagaggaa gactcctgaa accctcccca ggtcttccaa gtacaggatt gaagctttag  6480
tgaaattaac caaggaccat gggtcagtgc ccagggcttt aaaaagaatg aacgagcaaa  6540
aggtatcccc gccgtgaccc ctgcagatag caccggtctt tgatccgcag caggggccag  6600
accctgccca caagtcccag cgcggctgct tctgccactg ctgggctcca cttggctcct  6660
ctcacttccc agggggtcgc ctgtcctgcc tgtgggtttc catggcttcc cagagctccc  6720
tctgccccag ccagcgcctc caggcccagc tgaggagctg tgagaagcag cagaggggac  6780
tccccatccc gggcacaccc tgtcctccca cccctgcccc cttgcccttc cagccctttc  6840
agctgcagct gggagctggc ccgtcaagtg ctgcccctgc ctgtgtctgg gtttctgttg  6900
gctgtttttc ttttcttgag tggtgatttt tctctaaata aaagaagtca agcactgaaa  6960
aaaaaaaaaa aaa                                                    6973

SEQ ID NO: 15          moltype = DNA  length = 7125
FEATURE                Location/Qualifiers
source                 1..7125
                       mol_type = other DNA
                       organism = Mus musculus
SEQUENCE: 15
ttggttgcct tggtctctgt gggcagcagc aggaggaggc ggcagcagcc agagaagagg  60
gaggcgtgtg agccacactc caccagcgag cttcttcccg ctgctctgga actgcccagg  120
ctctccccac cagcatggcc ctgattgttc acctcaagac tgtctcagag ctccgaggca  180
aaggtgaccg gattgccaaa gtcactttcc gagggcagtc tttctactcc cgggtcctgg  240
agaactgcga gggtgtggct gactttgatg agacgttccg gtggccagtg gccagcagca  300
tcgaccggaa tgaagtgttg gagattcaga ttttcaacta cagcaaagtc ttcagcaaca  360
agctgatagg gaccttctgc atggtgctgc agaaagtggt ggaggagaat cgggtagagg  420
tgaccgacac gctgatggat gacagcaatg ctatcatcaa gaccagcctg agcatggagg  480
tccggtatca ggccacagat ggcactgtgg gcccctggga tgatggagac ttcctgggag  540
atgaatccct ccaggaggag aaggacagcc aggagacaga tggcctgcta cctggttccc  600
gacccagcac ccggatatct ggcgagaaga gctttcgcag agcgggaagg agtgtgttct  660
cggccatgaa actcggcaaa actcggtccc acaaagagga gccccaaaga caagatgagc  720
cagcagtgct ggagatggag gacctggacc acctagccat tcagctgggg gatgggctgg  780
atcctgactc cgtgtctcta gcctcggtca ccgctctcac cagcaatgtc tccaacaaac  840
ggtctaagcc agatattaag atggagccca gtgctggaag gcccatggat taccaggtca  900
gcatcacagt gattgaggct cggcagctgg tgggcttgaa catggaccct gtggtgtgtg  960
tggaggtggg tgatgacaag aaatacacgt caatgaagga gtccacaaac tgcccttact  1020
acaacgagta ctttgtcttc gacttccatg tctctcctga tgtcatgttt gacaagatca  1080
tcaagatctc ggttatccat tctaagaacc tgcttcggag cggcaccctg gtgggttcct  1140
tcaaaatgga tgtggggact gtgtattccc agcctgaaca ccagttccat cacaaatggg  1200
ccatcctgtc agaccccgat gacatctctg ctgggttgaa gggttatgta aagtgtgatg  1260
tcgctgtggt gggcaaggga gacaacatca agacacccca caaggccaac gagacggatg  1320
aggacgacat tgaagggaac ttgctgctcc ccgagggcgt gcccccccgaa cggcagtggg  1380
cacggttcta tgtgaaaatt taccgagcag agggactgcc ccggatgaac acaagcctca  1440
tggccaacgt gaagaaggcg ttcatcggtg agaacaagga cctcgtcgac ccctatgtgc  1500
aagtcttctt tgctggacaa aagggcaaaa catcagtgca gaagagcagc tatgagccgc  1560
tatggaatga gcaggtcgtc ttcacagact tgttcccccc actctgcaaa cgcatgaagg  1620
tgcagatccg ggactctgac aaggtcaatg atgtggccat cggcacccac ttcatcgacc  1680
tgcgcaagat ttccaacgat ggagacaaag gcttcctgcc taccctcggt ccagcctggg  1740
tgaacatgta cggctccacg cgcaactaca cactgctgga cgagcaccag gacttgaatg  1800
aaggcctggg ggagggtgtg tccttccggg cccgcctcat gttgggacta gctgtggaga  1860
tcctggacac ctccaaccca gagctcacca gctccacgga ggtgcaggtg gagcaggcca  1920
cgcctgtctc ggagagctgc acagggagaa tggaagaatt ttttctattt ggagccttct  1980
tggaagcctc aatgattgac cggaaaaatg gggacaagcc aattaccttt gaggtgacca  2040
taggaaacta cggcaatgaa gtcgatggta tgtcccggcc cctgaggcct cggccccgga  2100
aagagcctgg ggatgaagaa gaggtagacc tgattcagaa ctccagtgac gatgaaggtg  2160
acgaagccgg ggacctggcc tcggtgtcct ccaccccacc tatgcggccc cagatcacgg  2220
acaggaacta tttccacctg ccctacctgg agcgcaagcc ctgcatctat atcaagagct  2280
ggtggcctga ccagaggcgg cgcctctaca atgccaacat catggatcac attgctgaca  2340
agctggaaga aggcctgaat gatgtacagg agatgatcaa aacggagaag tcctacccgg  2400
agcgccgcct gcggggtgtg ctagaggaac tcagctgtgg ctgccaccgc ttcctctccc  2460
tctcggacaa ggaccagggc cgctcgtccc gcaccaggct ggatcgagag cgtcttaagt  2520
cctgtatgag ggagttggag agcatgggac agcaggccaa gagcctgagg gctcaggtga  2580
agcggcacac tgttcgggac aagctgaggt catgccagaa ctttctgcag aagctacgct  2640
tcctggcgga tgagccccag cacagcattc ctgatgtgtt catttggatg atgagcaaca  2700
acaaacgtat cgcctatgcc cgcgtgcctt ccaaagacct gctcttctcc atcgtggagg  2760
aggaactggg caaggactgc gccaaagtca agaccctctt cctgaagctg ccagggaaga  2820
ggggcttcgg ctcggcaggc tggacagtac aggccaagct ggagctctac ctgtggctgg  2880
gcctcagcaa gcagcgaaag gacttcctgt gtggtctgcc ctgtggcttc gaggaggtca  2940
aggcagccca aggcctgggc ctgcattcct ttccgcccat cagcctagtc tacaccaaga  3000
agcaagcctt ccagctccga gcacacatgt atcaggcccg aagcctcttt gctgctgaca  3060
```

```
gcagtgggct ctctgatccc tttgcccgtg tcttcttcat caaccagagc caatgcactg  3120
aggttctaaa cgagacactg tgtcccacct gggaccagat gctggtattt gacaacctgg  3180
agctgtacgg tgaagctcac gagttacgag atgatccccc catcattgtc attgaaatct  3240
acgaccagga cagcatgggc aaagccgact tcatgggccg gaccttcgcc aagcccctgg  3300
tgaagatggc agatgaagca tactgcccac ctcgcttccc gccgcagctt gagtactacc  3360
agatctaccg aggcagtgcc actgccggag acctactggc tgccttcgag ctgctgcaga  3420
ttgggccatc agggaaggct gacctgccac ccatcaatgg cccagtggac atggacagag  3480
ggcccatcat gcctgtgccc gtgggaatcc ggccagtgct cagcaagtac cgagtggagg  3540
tgctgttctg ggcctgaggg gacctaaaga gggtgaacct ggcccaggtg gaccgaccac  3600
gggtggacat cgagtgtgca ggaaaggggg tacaatcctc cctgattcac aattataaga  3660
agaaccccaa cttcaacacg ctggtcaagt ggtttgaagt ggacctcccg gagaatgagc  3720
tcctgcaccc acccttgaac atccgagtgg tagattgccg ggcctttgga cgatacaccc  3780
tggtgggttc ccacgcagtc agctcactga ggcgcttcat ctaccgacct ccagaccgct  3840
cagcccccaa ctggaacacc acagtcaggc tgctccgggg ctgccacagg ctgcgcaatg  3900
ggggcccctc ttctcgcccc acaggggagg ttgtagtaag catggagcct gaggagccag  3960
ttaagaagct ggagaccatg gtgaaactgg atgcgacttc tgatgctgtg gtcaaggtgg  4020
atgtggctga agatgagaag gaaaggaaga agaagaaaaa gaaaggcccg tcagaggagc  4080
cagaggagga agagcccgat gagagcatgc tggattggtg gtccaagtac ttcgcctcca  4140
tcgacacaat gaaggagcaa cttcgacaac atgagacctc tggaactgac ttggaagaga  4200
aggaagagat ggaaagcgct gagggcctga agggaccaat gaagagcaag gagaagtcca  4260
gagctgcaaa ggaggagaaa aagaagaaaa accagagccc tggccctggc cagggatcgg  4320
aggctcctga gaagaagaaa gccaagatcg atgagcttaa ggtgtacccc aaggagctgg  4380
aatcggagtt tgacagcttt gaggactggc tgcacacctt caacctgttg aggggcaaga  4440
cgggagatga tgaggatggc tccacagagg aggagcgcat agtaggccga ttcaagggct  4500
ccctctgtgt gtacaaagtg ccactcccag aagatgtatc tcgagaagct ggctatgatc  4560
ccacctatgg aatgttccag ggcatcccaa gcaatgaccc catcaatgtg ctggtccgaa  4620
tctatgtggt ccgggccaca gacctgcacc cggccgacat caatggcaaa gctgacccct  4680
atattgccat caagttaggc aagaccgaca tccgagacaa ggagaactac atctccaagc  4740
agctcaaccc tgtgtttggg aagtcctttg acattgaggc ctccttcccc atggagtcca  4800
tgttgacagt ggccgtgtac gactgggatc tggtgggcac tgatgacctc atcggagaaa  4860
ccaagattga cctggaaaac cgcttctaca gcaagcatcg cgccacctgc ggcatcgcac  4920
agacctattc catacatggc tacaatatct ggagggaccc catgaagccc agccagatcc  4980
tgacacgcct ctgtaaagag ggcaaagtgg acggccccca ctttggtccc catgggagag  5040
tgagggttgc caaccgtgtc ttcacggggc cttcagaaat agaggatgag aatggtcaga  5100
ggaagcccac agatgagcac gtggcactgt ctgctctgag acactgggag gacatccccc  5160
gggtgggctg ccgccttgtg ccggaacacg tggagaccag gccgctgctc aaccctgaca  5220
agccaggcat tgagcagggc cgcctggagc tgtgggtgga catgttcccc atggacatgc  5280
cagcccctgg gacacctctg gatatatccc ccaggaaacc caagaagtac gagctgcggg  5340
tcatcgtgtg gaacacagac gaggtggtcc tggaagacga tgatttcttc acgggagaga  5400
agtccagtga cattttgtg agggggtgc tgaagggcca gcaggaggac aaacaggaca  5460
cagatgtcca ctatcactcc ctcacggggg agggcaactt caactggaga tacctcttcc  5520
ccttcgacta cctagcggcc gaagagaaga tcgttatgtc caaaaaggag tctatgttct  5580
cctgggatga gacggagtac aagatccctg cgcggctcac cctgcagatc tgggacgctg  5640
accacttctc ggctgacgac ttcctggggg ctatcgagct ggacctgaac cggttcccga  5700
ggggcgctaa gacagccaag cagtgcacca tggagatggc caccggggag gtggacgtac  5760
ccctggtttc catctttaaa cagaaacgtg tcaaaggctg gtggcccctc ctggcccgca  5820
atgagaatga tgagtttgag ctcacaggca aagtggaggc ggagctacac ctactcacgg  5880
cagaggaggc agagaagaac cctgtgggcc tggctcgcaa tgaacctgat cccctagaaa  5940
aacccaatcg gccggacaca agcttcatct ggttcttgaa ccctctcaag tctgcccgct  6000
acttcctgtg gcatacctac cgctggctac tcctcaaatt cctgctgctc ttcctcctgc  6060
tgctgctctt cgccctgttt ctctactctc tgcctggcta cctggccaag aagatccttg  6120
gggcctgagc cctgcagtcg cctaggcctg ccggcctgac acggcattcg tctggttcct  6180
gaacccactc aaatctatca agtacctcat ctgcacccgg tacaagtggc tgatcatcaa  6240
gatcgtgctg gcgctgctgg ggctgctcat gctggccctc ttcctttaca gcctcccagg  6300
ctacatggtc aagaagctcc taggggcctg aagtgtgccc caccccagcc cgctccagca  6360
tccctccagg ggctgctgcg tattttgcct tccctcacct ggactctctc ccaactccct  6420
gaggagccct cccacgcctg ccagccttga gcaagacacc tgcttgctgg acttcatccc  6480
caccccacac ccaaactgtt gcttgcctga tcttgtccca ggcctgcctg gggtttgggg  6540
cacagttggc ctccaaaacc agataccctc ttgtctaaag taccaggttc ctctgcccaa  6600
ccccaagagt ggtagtggcc caaccctccc tgtgctttcc aaatcttgtc ttaaggcacc  6660
agtgaaatta accaagaaac gcggagcaat gcccaaggct ctgatgagta ggaacacgtg  6720
gaaagcacca ggaatgccag cagaggcgag gcggcacacc tctctgcaga gcatccaggc  6780
cgagcggcgg gcagcggcca gctgcttctg cgcatgctct cctcttggct ctgcttcttt  6840
ctcacagtca cagtcacttc acagcttagc cttgggcttc ccatcacttc caggggtgcc  6900
tctgccttgg ccagtgtgtg tcagctagta cacaagctcc aagtgtgaat caggtgtact  6960
ggccgtcctg aagactgact gccctgtcct tcctgccgac agccacaccc gagtgtacac  7020
ttaaagcggt gcccttctgc ctctgtgggc ctgctggctg ctgttccttt cttgagtgtg  7080
attttttttt tctctccctc aataaaataa atcaaactct gagac                 7125

SEQ ID NO: 16          moltype = DNA  length = 7065
FEATURE                Location/Qualifiers
source                 1..7065
                       mol_type = other DNA
                       organism = Mus musculus
SEQUENCE: 16
ttggttgcct tggtctctgt gggcagcagc aggaggaggc ggcagcagcc agagaagagg  60
gaggcgtgtg agccacactc caccagcgag cttcttcccg ctgctctgga actgcccagg  120
ctctccccac cagcatggcc ctgattgttc acctcaagac tgtctcagag ctccgaggca  180
aaggtgaccg gattgccaaa gtcactttcc gagggcagtc tttctactcc cgggtcctgg  240
```

-continued

```
agaactgcga gggtgtggct gactttgatg agacgttccg gtggccagtg gccagcagca  300
tcgaccggaa tgaagtgttg gagattcaga ttttcaacta cagcaaagtc ttcagcaaca  360
agctgatagg gaccttctgc atggtgctgc agaaagtggt ggaggagaat cgggtagagg  420
tgaccgacac gctgatggat gacagcaatg ctatcatcaa gaccagcctg agcatggagg  480
tccggtatca ggccacagat ggcactgtgg gcccctggga tgatggagac ttcctgggag  540
atgaatccct ccaggaggag aaggacagcc aggagacaga tggctgcta cctggttccc  600
gacccagcac ccggatatct ggcgagaaga gctttcgcag agcgggaagg agtgtgttct  660
cggccatgaa actcggcaaa actcggtccc acaaagagga gccccaaaga caagatgagc  720
cagcagtgct ggagatggag gacctggacc acctagccat tcagctgggg gatgggctgg  780
atcctgactc cgtgtctcta gcctcggtca ccgctctcac cagcaatgtc tccaacaaac  840
ggtctaagcc agatattaag atggagccca gtgctggaag gcccatggat taccaggtca  900
gcatcacagt gattgaggct cggcagctgg tgggcttgaa catggaccct gtggtgtgtg  960
tggaggtggg tgatgacaag aaatacacgt caatgaagga gtccacaaac tgcccttact  1020
acaacgagta ctttgtcttc gacttccatg tctctcctga tgtcatgttt gacaagatca  1080
tcaagatctc ggttatccat tctaagaacc tgcttcggag cggcaccctg gtgggttcct  1140
tcaaaatgga tgtggggact gtgtattccc agcctgaaca ccagttccat cacaaatggg  1200
ccatcctgtc agaccccgat gacatctctg ctgggttgaa gggttatgta aagtgtgatg  1260
tcgctgtggt gggcaaggga gacaacatca agacacccca caaggccaac gagacggatg  1320
aggacgacat tgaagggaac ttgctgctcc ccgagggcgt gcccccgaa cggcagtggg  1380
cacggttcta tgtgaaaatt taccgagcag agggactgcc ccggatgaac acaagcctca  1440
tggccaacgt gaagaaggcg ttcatcggtg agaacaagga cctcgtcgac ccctatgtgc  1500
aagtcttctt tgctggacaa aagggcaaaa catcagtgca gaagagcagc tatgagccgc  1560
tatggaatga gcaggtcgtc ttcacagact tgttccccc actctgcaaa cgcatgaagg  1620
tgcagatccg ggactctgac aaggtcaatg atgtggccat cggcacccac ttcatcgacc  1680
tgcgcaagat ttccaacgat ggagacaaag gcttcctgcc taccctcggt ccagcctggg  1740
tgaacatgta cggctccacg cgcaactaca cactgctgga cgagcaccag gacttgaatg  1800
aaggcctggg ggagggtgtg tccttccggg cccgcctcat gttgggacta gctgtggaga  1860
tcctggacac ctccaaccca gagctcacca gctccacgga ggtgcaggtg gagcaggcca  1920
cgcctgtctc ggagagctgc acagggagaa tggaagaatt ttttctattt ggagccttct  1980
tggaagcctc aatgattgac cggaaaaatg gggacaagcc aattaccttt gaggtgacca  2040
taggaaacta cggcaatgaa gtcgatggta tgtcccggcc cctgaggcct cggccccgga  2100
aagagcctgg ggatgaagaa gaggtagacc tgattcagaa ctccagtgac gatgaaggtg  2160
acgaagccgg ggacctggcc tcggtgtcct ccaccccacc tatgcggccc cagatcacgg  2220
acaggaacta tttccacctg ccctacctgg agcgcaagcc ctgcatctat atcaagagct  2280
ggtggcctga ccagaggcgg cgcctctaca atgccaacat catggatcac attgctgaca  2340
agctggaaga aggcctgaat gatgtacagg agatgatcaa aacggagaag tcctacccgg  2400
agcgccgcct gcggggtgtg ctagaggaac tcagctgtgg ctgccaccgc ttcctctccc  2460
tctcggacaa ggaccagggc cgctcgtccc gcaccaggct ggatcgagag cgtcttaagt  2520
cctgtatgag ggagttggag agcatgggac agcaggccaa gagcctgagg gctcaggtga  2580
agcggcacac tgttcgggac aagctgaggt catgccagaa ctttctgcag aagctacgct  2640
tcctggcgga tgagccccag cacagcattc ctgatgtgtt catttggatg atgagcaaca  2700
acaaacgtat cgcctatgcc cgcgtgcctt ccaaagacct gctcttctcc atcgtggagg  2760
aggaactggg caaggactgc gccaaagtca agaccctctt cctgaagctg ccagggaaga  2820
ggggcttcgg ctcggcaggc tggacagtac aggccaagct ggagctctac ctgtggctgg  2880
gcctcagcaa gcagcgaaag gacttcctgt gtggtctgcc ctgtggcttc gaggaggtca  2940
aggcagccca aggcctgggc ctgcattcct ttccgcccat cagcctagtc tacaccaaga  3000
agcaagcctt ccagctccga gcacacatgt atcaggcccg aagcctcttt gctgctgaca  3060
gcagtgggct ctctgatccc tttgcccgtg tcttcttcat caaccagagc caatgcactg  3120
aggttctaaa cgagacactg tgtcccacct gggaccagat gctggtattt gacaacctgg  3180
agctgtacgg tgaagctcac gagttacgag atgatccccc catcattgtc attgaaatct  3240
acgaccagga cagcatgggc aaagccgact tcatgggccg gaccttcgcc aagcccctgg  3300
tgaagatggc agatgaagca tactgcccac ctcgcttccc gccgcagctt gagtactacc  3360
agatctaccg aggcagtgcc actgccggag acctactggc tgccttcgag ctgctgcaga  3420
ttgggccatc agggaaggct gacctgccac ccatcaatgg cccagtggac atggacagag  3480
ggcccatcat gcctgtgccc gtgggaatcc ggccagtgct cagcaagtac cgagtggagg  3540
tgctgttctg ggcctgagg gacctaaaga gggtgaacct ggcccaggtg gaccgaccac  3600
gggtggacat cgagtgtgca ggaaaggggg tacaatcctc cctgattcac aattataaga  3660
agaaccccaa cttcaacacg ctggtcaagt ggtttgaagt ggacctcccg gagaatgagc  3720
tcctgcaccc acccttgaac atccgagtgg tagattgccg ggcctttgga cgatacaccc  3780
tggtgggttc ccacgcagtc agctcactga ggcgcttcat ctaccgacct ccagaccgct  3840
cagcccccaa ctggaacacc acaggggagg ttgtagtaag catggagcct gaggagccag  3900
ttaagaagct ggagaccatg gtgaaactgg atgcgacttc tgatgctgtg gtcaaggtgg  3960
atgtggctga agatgagaag gaaaggaaga agaagaaaaa gaaaggcccg tcagaggagc  4020
cagaggagga agagcccgat gagagcatgc tggattggtg gtccaagtac ttcgcctcca  4080
tcgacacaat gaaggagcaa cttcgacaac atgagacctc tggaactgac ttggaagaga  4140
aggaagagat ggaaagcgct gagggcctga agggaccaat gaagagcaag gagaagtcca  4200
gagctgcaaa ggaggagaaa aagaagaaaa accagagccc tggccctggc cagggatcgg  4260
aggctcctga gaagaagaaa gccaagatcg atgagcttaa ggtgtacccc aaggagctgg  4320
aatcggagtt tgacagcttt gaggactggc tgcacacctt caacctgttg aggggcaaga  4380
cgggagatga tgaggatggc tccacagagg aggagcgcat agtaggccga ttcaagggct  4440
ccctctgtgt gtacaaagtg ccactcccag aagatgtatc tcgagaagct ggctatgatc  4500
ccacctatgg aatgttccag ggcatcccaa gcaatgaccc catcaatgtg ctggtccgaa  4560
tctatgtggt ccgggccaca gacctgcacc cggccgacat caatggcaaa gctgacccct  4620
atattgccat caagttaggc aagaccgaca tccgagacaa ggagaactac atctccaagc  4680
agctcaaccc tgtgtttggg aagtcctttg acattgaggc ctccttcccc atggagtcca  4740
tgttgacagt ggccgtgtac gactgggatc tggtgggcac tgatgacctc atcggagaaa  4800
ccaagattga cctggaaaac cgcttctaca gcaagcatcg cgccacctgc ggcatcgcac  4860
agacctattc catacatggc tacaatatct ggagggaccc catgaagccc agccagatcc  4920
tgacacgcct ctgtaaagag ggcaaagtgg acggccccca ctttggtccc catgggagag  4980
```

```
tgagggttgc caaccgtgtc ttcacggggc cttcagaaat agaggatgag aatggtcaga  5040
ggaagcccac agatgagcac gtggcactgt ctgctctgag acactgggag gacatccccc  5100
gggtgggctg ccgccttgtg ccggaacacg tggagaccag gccgctgctc aaccctgaca  5160
agccaggcat tgagcagggc cgcctggagc tgtgggtgga catgttcccc atggacatgc  5220
cagcccctgg gacacctctg gatatatccc ccaggaaacc caagaagtac gagctgcggg  5280
tcatcgtgtg gaacacagac gaggtggtcc tggaagacga tgatttcttc acgggagaga  5340
agtccagtga catttttgtg agggggtggc tgaagggcca gcaggaggac aaacaggaca  5400
cagatgtcca ctatcactcc ctcacggggg agggcaactt caactggaga tacctcttcc  5460
ccttcgacta cctagcggcc gaagagaaga tcgttatgtc caaaaaggag tctatgttct  5520
cctgggatga gacggagtac aagatccctg cgcggctcac cctgcagatc tgggacgctg  5580
accacttctc ggctgacgac ttcctggggg ctatcgagct ggacctgaac cggttcccga  5640
ggggcgctaa gacagccaag cagtgcacca tggagatggc caccggggag gtggacgtac  5700
ccctggtttc catctttaaa cagaaacgtg tcaaaggctg gtggcccctc ctggcccgca  5760
atgagaatga tgagtttgag ctcacaggca aagtggaggc ggagctacac ctactcacgg  5820
cagaggaggc agagaagaac cctgtgggcc tggctcgcaa tgaacctgat cccctagaaa  5880
aacccaatcg gccggacaca agcttcatct ggttcttgaa ccctctcaag tctgcccgct  5940
acttcctgtg gcatacctac cgctggctac tcctcaaatt cctgctgctc ttcctcctgc  6000
tgctgctctt cgccctgttt ctctactctc tgcctggcta cctggccaag aagatccttg  6060
gggcctgagc cctgcagtcg cctaggcctg ccggcctgac acggcattcg tctggttcct  6120
gaacccactc aaatctatca agtacctcat ctgcacccgg tacaagtggc tgatcatcaa  6180
gatcgtgctg gcgctgctgg ggctgctcat gctggccctc ttcctttaca gcctcccagg  6240
ctacatggtc aagaagctcc taggggcctg aagtgtgccc caccccagcc cgctcccagca 6300
tccctccagg ggctgctgcg tattttgcct tccctcacct ggactctctc ccaactccct  6360
gaggagccct cccacgcctg ccagccttga gcaagacacc tgcttgctgg acttcatccc  6420
caccccacac ccaaactgtt gcttgcctga tcttgtccca ggcctgcctg ggtttgggg   6480
cacagttggc ctccaaaacc agataccctc ttgtctaaag taccaggttc ctctgcccaa  6540
ccccaagagt ggtagtggcc caaccctccc tgtgctttcc aaatcttgtc ttaaggcacc  6600
agtgaaatta accaagaaac gcggagcaat gcccaaggct ctgatgagta ggaacacgtg  6660
gaaagcacca ggaatgccag cagaggcgag gcggcacacc tctctgcaga gcatccaggc  6720
cgagcggcgg gcagcggcca gctgcttctg cgcatgctct cctcttggct ctgcttcttt  6780
ctcacagtca cagtcacttc acagcttagc cttgggcttc ccatcacttc caggggtgcc  6840
tctgccttgg ccagtgtgtg tcagctagta cacaagctcc aagtgtgaat caggtgtact  6900
ggccgtcctg aagactgact gccctgtcct tcctgccgac agccacaccc gagtgtacac  6960
ttaaagcggt gcccttctgc ctctgtgggc ctgctggctg ctgttccttt cttgagtgtg  7020
attttttttt tctctccctc aataaaataa atcaaactct gagac                  7065

SEQ ID NO: 17          moltype = DNA  length = 6907
FEATURE                Location/Qualifiers
source                 1..6907
                       mol_type = other DNA
                       organism = Mus musculus
SEQUENCE: 17
ttggttgcct tggtctctgt gggcagcagc aggaggaggc ggcagcagcc agagaagagg  60
gaggcgtgtg agccacactc caccagcgag cttcttcccg ctgctctgga actgcccagg  120
ctctccccac cagcatggcc ctgattgttc acctcaagac tgtctcagag ctccgaggca  180
aaggtgaccg gattgccaaa gtcactttcc gagggcagtc tttctactcc cgggtcctgg  240
agaactgcga gggtgtggct gactttgatg agacgttccg gtggccagtg gccagcagca  300
tcgaccggaa tgaagtgttg gagattcaga ttttcaacta cagcaaagtc ttcagcaaca  360
agctgatagg gaccttctgc atggtgctgc agaaagtggt ggaggagaat cgggtagagg  420
tgaccgacac gctgatggat gacagcaatg ctatcatcaa gaccagcctg agcatggagg  480
tccggtatca ggccacagat ggcactgtgg gcccctggga tgatggagac ttcctgggag  540
atgaatccct ccaggaggag aaggacagcc aggagacaga tgggctgcta cctggttccc  600
gacccagcac ccggatatct ggcgagaaga gctttcgcag caaaggcaga gagaagacca  660
agggaggcag agatggcgag cacaaagcgg gaaggagtgt gttctcggcc atgaaactcg  720
gcaaaactcg gtcccacaaa gaggagcccc aaagacaaga tgagccagca gtgctggaga  780
tggaggacct ggaccaccta gccattcagc tgggggatgg gctggatcct gactccgtgt  840
ctctagcctc ggtcaccgct ctcaccagca atgtctccaa caaacggtct aagccagata  900
ttaagatgga gcccagtgct ggaaggccca tggattacca ggtcagcatc acagtgattg  960
aggctcggca gctggtgggc ttgaacatgg accctgtggt gtgtgtggag gtgggtgatg  1020
acaagaaata cacgtcaatg aaggagtcca caaactgccc ttactacaac gagtactttg  1080
tcttcgactt ccatgtctct cctgatgtca tgtttgacaa gatcatcaag atctcggtta  1140
tccattctaa gaacctgctt cggagcggca ccctggtggg ttccttcaaa atggatgtgg  1200
ggactgtgta ttcccagcct gaacaccagt tccatcacaa atgggccatc ctgtcagacc  1260
ccgatgacat ctctgctggg ttgaagggtt atgtaaagtg tgatgtcgct gtggtgggca  1320
agggagacaa catcaagaca ccccacaagg ccaacgagac ggatgaggac gacattgaag  1380
ggaacttgct gctccccgag ggcgtgcccc ccgaacggca gtgggcacgg ttctatgtga  1440
aaatttaccg agcagaggga ctgcccccgga tgaacacaag cctcatggcc aacgtgaaga 1500
aggcgttcat cggtgagaac aaggacctcg tcgacccccta tgtgcaagtc ttctttgctg 1560
gacaaaaggg caaaacatca gtgcagaaga gcagctatga gccgctatgg aatgagcagg  1620
tcgtcttcac agacttgttc cccccactct gcaaacgcat gaaggtgcag atccgggact  1680
ctgacaaggt caatgatgtg gccatcggca cccacttcat cgacctgcgc aagatttcca  1740
acgatggaga caaaggcttc ctgcctaccc tcggtccagc ctgggtgaac atgtacggct  1800
ccacgcgcaa ctacacactg ctggacgagc accaggactt gaatgaaggc ctgggggagg  1860
gtgtgtcctt ccgggcccgc ctcatgttgg gactagctgt ggagatcctg gacacctcca  1920
acccagagct caccagctcc acggaggtgc aggtggagca ggccacgcct gtctcggaga  1980
gctgcacagg gagaatggaa gaatttttc tatttggagc cttcttggaa gcctcaatga   2040
ttgaccggaa aaatggggac aagccaatta cctttgaggt gaccatagga aactacggca  2100
atgaagtcga tggtatgtcc cggcccctga ggcctcggcc ccggaaagag cctggggatg  2160
aagaagaggt agacctgatt cagaactcca gtgacgatga aggtgacgaa gccggggacc  2220
```

-continued

```
tggcctcggt gtcctccacc ccacctatgc ggccccagat cacggacagg aactatttcc  2280
acctgcccta cctggagcgc aagccctgca tctatatcaa gagctggtgg cctgaccaga  2340
ggcggcgcct ctacaatgcc aacatcatgg atcacattgc tgacaagctg gaagaaggcc  2400
tgaatgatgt acaggagatg atcaaaaacgg agaagtccta cccggagcgc cgcctgcggg  2460
gtgtgctaga ggaactcagc tgtggctgcc accgcttcct ctccctctcg gacaaggacc  2520
agggccgctc gtcccgcacc aggctggatc gagagcgtct taagtcctgt atgagggagt  2580
tggagagcat gggacagcag gccaagagcc tgagggctca ggtgaagcgg cacactgttc  2640
gggacaagct gaggtcatgc cagaactttc tgcagaagct acgcttcctg gcggatgagc  2700
cccagcacag cattcctgat gtgttcattt ggatgatgag caacaacaaa cgtatcgcct  2760
atgcccgcgt gccttccaaa gacctgctct tctccatcgt ggaggaggaa ctgggcaagg  2820
actgcgccaa agtcaagacc ctcttcctga agctgccagg gaagaggggc ttcggctcgg  2880
caggctggac agtacaggcc aagctggagc tctacctgtg gctgggcctc agcaagcagc  2940
gaaaggactt cctgtgtggt ctgccctgtg gcttcgagga ggtcaaggca gcccaaggcc  3000
tgggcctgca ttcctttccg cccatcagcc tagtctacac caagaagcaa gccttccagc  3060
tccgagcaca catgtatcag gcccgaagcc tctttgctgc tgacagcagt gggctctctg  3120
atccctttgc ccgtgtcttc ttcatcaacc agagccaatg cactgaggtt ctaaacgaga  3180
cactgtgtcc cacctgggac cagatgctgg tatttgacaa cctggagctg tacggtgaag  3240
ctcacgagtt acgagatgat ccccccatca ttgtcattga aatctacgac caggacagca  3300
tgggcaaagc cgacttcatg ggccggacct tcgccaagcc cctggtgaag atggcagatg  3360
aagcatactg cccacctcgc ttcccgccgc agcttgagta ctaccagatc taccgaggca  3420
gtgccactgc cggagaccta ctggctgcct tcgagctgct gcagattggg ccatcaggga  3480
aggctgacct gccacccatc aatggcccag tggacatgga cagagggccc atcatgcctg  3540
tgcccgtggg aatccggcca gtgctcagca agtaccgagt ggaggtgctg ttctggggcc  3600
tgagggacct aaagagggtg aacctggccc aggtggaccg accacgggtg gacatcgagt  3660
gtgcaggaaa gggggtacaa tcctccctga ttcacaatta taagaagaac cccaacttca  3720
acacgctggt caagtggttt gaagtggacc tcccggagaa tgagctcctg cacccaccct  3780
tgaacatccg agtggtagat tgccgggcct ttggacgata caccctggtg ggttcccacg  3840
cagtcagctc actgaggcgc ttcatctacc gacctccaga ccgctcagcc cccaactgga  3900
acaccacagg ggaggttgta gtaagcatgg agcctgagga gccagttaag aagctggaga  3960
ccatggtgaa actggatgcg acttctgatg ctgtggtcaa ggtggatgtg gctgaagatg  4020
agaaggaaag gaagaagaag aaaaagaaag gcccgtcaga ggagccagag gaggaagagc  4080
ccgatgagag catgctggat tggtggtcca agtacttcgc ctccatcgac acaatgaagg  4140
agcaacttcg acaacatgag acctctggaa ctgacttgga agagaaggaa gagatggaaa  4200
gcgctgaggg cctgaaggga ccaatgaaga gcaaggagaa gtccagagct gcaaaggagg  4260
agaaaaagaa gaaaaaccag agccctggcc ctggccaggg atcggaggct cctgagaaga  4320
agaaagccaa gatcgatgag cttaaggtgt accccaagga gctggaatcg gagtttgaca  4380
gctttgagga ctggctgcac accttcaacc tgttgagggg caagacggga gatgatgagg  4440
atggctccac agaggaggag cgcatagtag gccgattcaa gggctccctc tgtgtgtaca  4500
aagtgccact cccagaagat gtatctcgag aagctggcta tgatcccacc tatggaatgt  4560
tccagggcat cccaagcaat gaccccatca atgtgctggt ccgaatctat gtggtccggg  4620
ccacagacct gcacccggcc gacatcaatg gcaaagctga cccctatatt gccatcaagt  4680
taggcaagac cgacatccga gacaaggaga actacatctc caagcagctc aaccctgtgt  4740
ttgggaagtc ctttgacatt gaggcctcct tccccatgga gtccatgttg acagtggccg  4800
tgtacgactg ggatctggtg ggcactgatg acctcatcgg agaaaccaag attgacctgg  4860
aaaaccgctt ctacagcaag catcgcgcca cctgcggcat cgcacagacc tattccatac  4920
atggctacaa tatctggagg gaccccatga agcccagcca gatcctgaca cgcctctgta  4980
aagagggcaa agtggacggc ccccactttg gtccccatgg gagagtgagg gttgccaacc  5040
gtgtcttcac ggggccttca gaaatagagg atgagaatgg tcagaggaag cccacagatg  5100
agcacgtggc actgtctgct ctgagacact gggaggacat cccccgggtg ggctgccgcc  5160
ttgtgccgga acacgtggag accaggccgc tgctcaaccc tgacaagcca ggcattgagc  5220
agggccgcct ggagctgtgg gtggacatgt tccccatgga catgccagcc cctgggacac  5280
ctctggatat atcccccagg aaacccaaga agtacgagct gcgggtcatc gtgtggaaca  5340
cagacgaggt ggtcctggaa gacgatgatt tcttcacggg agagaagtcc agtgacattt  5400
ttgtgagggg gtggctgaag ggccagcagg aggacaaaca ggacacagat gtccactatc  5460
actccctcac gggggagggc aacttcaact ggagatacct cttccccttc gactacctag  5520
cggccgaaga gaagatcgtt atgtccaaaa aggagtctat gttctcctgg gatgagacgg  5580
agtacaagat ccctgcgcgg ctcaccctgc agatctggga cgctgaccac ttctcggctg  5640
acgacttcct gggggctatc gagctggacc tgaaccggtt cccgaggggc gctaagacag  5700
ccaagcagtg caccatggag atggccaccg gggaggtgga cgtacccctg gtttccatct  5760
ttaaacagaa acgtgtcaaa ggctggtggc ccctcctggc ccgcaatgag aatgatgagt  5820
ttgagctcac aggcaaagtg gaggcggagc tacacctact cacggcagag gaggcagaga  5880
agaaccctgt gggcctggct cgcaatgaac ctgatcccct agaaaaaccc aaccggcctg  5940
acacggcatt cgtctggttc ctgaacccac tcaaatctat caagtacctc atctgcaccc  6000
ggtacaagtg gctgatcatc aagatcgtgc tggcgctgct ggggctgctc atgctggccc  6060
tcttccttta cagcctccca ggctacatgg tcaagaagct cctaggggcc tgaagtgtgc  6120
cccaccccag cccgctccag catccctcca ggggctgctg cgtattttgc cttccctcac  6180
ctggactctc tcccaactcc ctgaggagcc ctcccacgcc tgccagcctt gagcaagaca  6240
cctgcttgct ggacttcatc cccaccccac acccaaactg ttgcttgcct gatcttgtcc  6300
caggcctgcc tggggtttgg ggcacagttg gcctccaaaa ccagataccc tcttgtctaa  6360
agtaccaggt tcctctgccc aaccccaaga gtggtagtgg cccaaccctc cctgtgcttt  6420
ccaaatcttg tcttaaggca ccagtgaaat taaccaagaa acgcggagca atgcccaagg  6480
ctctgatgag taggaacacg tggaaagcac caggaatgcc agcagaggcg aggcggcaca  6540
cctctctgca gagcatccag gccgagcggc gggcagcggc cagctgcttc tgcgcatgct  6600
ctcctcttgg ctctgcttct ttctcacagt cacagtcact tcacagctta gccttgggct  6660
tcccatcact tccaggggtg cctctgcctt ggccagtgtg tgtcagctag tacacaagct  6720
ccaagtgtga atcaggtgta ctggccgtcc tgaagactga ctgccctgtc cttcctgccg  6780
acagccacac ccgagtgtac acttaaagcg gtgcccttct gcctctgtgg gcctgctggc  6840
tgctgttcct ttcttgagtg tgattttttt tttctctccc tcaataaaat aaatcaaact  6900
ctgagac                                                            6907
```

```
SEQ ID NO: 18          moltype = DNA  length = 6862
FEATURE                Location/Qualifiers
source                 1..6862
                       mol_type = other DNA
                       organism = Mus musculus
SEQUENCE: 18
ttggttgcct tggtctctgt gggcagcagc aggaggaggc ggcagcagcc agagaagagg  60
gaggcgtgtg agccacactc caccagcgag cttcttcccg ctgctctgga actgcccagg  120
ctctccccac cagcatggcc ctgattgttc acctcaagac tgtctcagag ctccgaggca  180
aaggtgaccg gattgccaaa gtcactttcc gagggcagtc tttctactcc cgggtcctgg  240
agaactgcga gggtgtggct gactttgatg agacgttccg gtggccagtg gccagcagca  300
tcgaccggaa tgaagtgttg gagattcaga ttttcaacta cagcaaagtc ttcagcaaca  360
agctgatagg gaccttctgc atggtgctgc agaaagtggt ggaggagaat cgggtagagg  420
tgaccgacac gctgatggat gacagcaatg ctatcatcaa gaccagcctg agcatggagg  480
tccggtatca ggccacagat ggcactgtgg gcccctggga tgatggagac ttcctgggag  540
atgaatccct ccaggaggag aaggacagcc aggagacaga tgggctgcta cctggttccc  600
gacccagcac ccggatatct ggcgagaaga gctttcgcag agcgggaagg agtgtgttct  660
cggccatgaa actcggcaaa actcggtccc acaaagagga gccccaaaga caagatgagc  720
cagcagtgct ggagatggag gacctggacc acctagccat tcagctgggg gatgggctgg  780
atcctgactc cgtgtctcta gcctcggtca ccgctctcac cagcaatgtc tccaacaaac  840
ggtctaagcc agatattaag atggagccca gtgctggaag gcccatggat taccaggtca  900
gcatcacagt gattgaggct cggcagctgg tgggcttgaa catggaccct gtggtgtgtg  960
tggaggtggg tgatgacaag aaatacacgt caatgaagga gtccacaaac tgcccttact  1020
acaacgagta ctttgtcttc gacttccatg tctctcctga tgtcatgttt gacaagatca  1080
tcaagatctc ggttatccat tctaagaacc tgcttcggag cggcaccctg gtgggttcct  1140
tcaaaatgga tgtggggact gtgtattccc agcctgaaca ccagttccat cacaaatggg  1200
ccatcctgtc agaccccgat gacatctctg ctgggttgaa gggttatgta aagtgtgatg  1260
tcgctgtggt gggcaaggga gacaacatca agacacccca caaggccaac gagacggatg  1320
aggacgacat tgaagggaac ttgctgctcc ccgagggcgt gccccccgaa cggcagtggg  1380
cacggttcta tgtgaaaatt taccgagcag agggactgcc ccggatgaac acaagcctca  1440
tggccaacgt gaagaaggcg ttcatcggtg agaacaagga cctcgtcgac ccctatgtgc  1500
aagtcttctt tgctggacaa aagggcaaaa catcagtgca gaagagcagc tatgagccgc  1560
tatggaatga gcaggtcgtc ttcacagact tgttcccccc actctgcaaa cgcatgaagg  1620
tgcagatccg ggactctgac aaggtcaatg atgtggccat cggcacccac ttcatcgacc  1680
tgcgcaagat ttccaacgat ggagacaaag gcttcctgcc taccctcggt ccagcctggg  1740
tgaacatgta cggctccacg cgcaactaca cactgctgga cgagcaccag gacttgaatg  1800
aaggcctggg ggagggtgtg tccttccggg cccgcctcat gttgggacta gctgtggaga  1860
tcctggacac ctccaaccca gagctcacca gctccacgga ggtgcaggtg gagcaggcca  1920
cgcctgtctc ggagagctgc acagggagaa tggaagaatt ttttctattt ggagccttct  1980
tggaagcctc aatgattgac cggaaaaatg gggacaagcc aattaccttt gaggtgacca  2040
taggaaacta cggcaatgaa gtcgatggta tgtcccggcc ccctgaggcct cggccccgga  2100
aagagcctgg ggatgaagaa gaggtagacc tgattcagaa ctccagtgac gatgaaggtg  2160
acgaagccgg ggacctggcc tcggtgtcct ccaccccacc tatgcggccc cagatcacgg  2220
acaggaacta tttccacctg ccctacctgg agcgcaagcc ctgcatctat atcaagagct  2280
ggtggcctga ccagaggcgg cgcctctaca atgccaacat catggatcac attgctgaca  2340
agctggaaga aggcctgaat gatgtacagg agatgatcaa aacggagaag tcctacccgg  2400
agcgccgcct gcggggtgtg ctagaggaac tcagctgtgg ctgccaccgc ttcctctccc  2460
tctcggacaa ggaccagggc cgctcgtccc gcaccaggct ggatcgagag cgtcttaagt  2520
cctgtatgag ggagttggag agcatgggac agcaggccaa gagcctgagg gctcaggtga  2580
agcggcacac tgttcgggac aagctgaggt catgccagaa ctttctgcag aagctacgct  2640
tcctggcgga tgagccccag cacagcattc ctgatgtgtt catttggatg atgagcaaca  2700
acaaacgtat cgcctatgcc cgcgtgcctt ccaaagacct gctcttctcc atcgtggagg  2760
aggaactggg caaggactgc gccaaagtca agaccctctt cctgaagctg ccagggaaga  2820
ggggcttcgg ctcggcaggc tggacagtac aggccaagct ggagctctac ctgtggctgg  2880
gcctcagcaa gcagcgaaag gacttcctgt gtggtctgcc ctgtggcttc gaggaggtca  2940
aggcagccca aggcctgggc ctgcattcct ttccgcccat cagcctagtc tacaccaaga  3000
agcaagcctt ccagctccga gcacacatgt atcaggcccg aagcctcttt gctgctgaca  3060
gcagtgggct ctctgatccc tttgcccgtg tcttcttcat caaccagagc caatgcactg  3120
aggttctaaa cgagacactg tgtcccacct gggaccagat gctggtattt gacaacctgg  3180
agctgtacgg tgaagctcac gagttacgag atgatccccc catcattgtc attgaaatct  3240
acgaccagga cagcatgggc aaagccgact tcatgggccg gaccttcgcc aagcccctgg  3300
tgaagatggc agatgaagca tactgcccac ctcgcttccc gccgcagctt gagtactacc  3360
agatctaccg aggcagtgcc actgccggag acctactggc tgccttcgag ctgctgcaga  3420
ttgggccatc agggaaggct gacctgccac ccatcaatgg cccagtggac atggacagag  3480
ggcccatcat gcctgtgccc gtgggaatcc ggccagtgct cagcaagtac cgagtggagg  3540
tgctgttctg ggggcctgagg gacctaaaga gggtgaacct ggcccaggtg gaccgaccac  3600
gggtggacat cgagtgtgca ggaaaggggg tacaatcctc cctgattcac aattataaga  3660
agaaccccaa cttcaacacg ctggtcaagt ggtttgaagt ggacctcccg gagaatgagc  3720
tcctgcaccc acccttgaac atccgagtgg tagattgccg ggcctttgga cgatacaccc  3780
tggtgggttc ccacgcagtc agctcactga ggcgcttcat ctaccgacct ccagaccgct  3840
cagcccccaa ctggaacacc acaggggagg ttgtagtaag catggagcct gaggagccag  3900
ttaagaagct ggagaccatg gtgaaactgg atgcgacttc tgatgctgtg gtcaaggtgg  3960
atgtggctga agatgagaag gaaaggaaga agaagaaaaa gaaaggcccg tcagaggagc  4020
cagaggagga agagcccgat gagagcatgc tggattggtg gtccaagtac ttcgcctcca  4080
tcgacacaat gaaggagcaa cttcgacaac atgagacctc tggaactgac ttggaagaga  4140
aggaagagat ggaaagcgct gagggcctga agggaccaat gaagagcaag gagaagtcca  4200
gagctgcaaa ggaggagaaa aagaagaaaa accagagccc tggccctggc cagggatcgg  4260
aggctcctga gaagaagaaa gccaagatcg atgagcttaa ggtgtacccc aaggagctgg  4320
```

-continued

```
aatcggagtt tgacagcttt gaggactggc tgcacacctt caacctgttg aggggcaaga  4380
cgggagatga tgaggatggc tccacagagg aggagcgcat agtaggccga ttcaagggct  4440
ccctctgtgt gtacaaagtg ccactcccag aagatgtatc tcgagaagct ggctatgatc  4500
ccacctatgg aatgttccag ggcatcccaa gcaatgaccc catcaatgtg ctggtccgaa  4560
tctatgtggt ccgggccaca gacctgcacc cggccgacat caatggcaaa gctgacccct  4620
atattgccat caagttaggc aagaccgaca tccgagacaa ggagaactac atctccaagc  4680
agctcaaccc tgtgtttggg aagtcctttg acattgaggc ctccttcccc atggagtcca  4740
tgttgacagt ggccgtgtac gactgggatc tggtgggcac tgatgacctc atcggagaaa  4800
ccaagattga cctggaaaac cgcttctaca gcaagcatcg cgccacctgc ggcatcgcac  4860
agacctattc catacatggc tacaatatct ggagggaccc catgaagccc agccagatcc  4920
tgacacgcct ctgtaaagag ggcaaagtgg acggccccca ctttggtccc catgggagag  4980
tgagggttgc caaccgtgtc ttcacggggc cttcagaaat agaggatgag aatggtcaga  5040
ggaagcccac agatgagcac gtggcactgt ctgctctgag acactgggag gacatccccc  5100
gggtgggctg ccgccttgtg ccggaacacg tggagaccag gccgctgctc aaccctgaca  5160
agccaggcat tgagcagggc cgcctggagc tgtgggtgga catgttcccc atggacatgc  5220
cagcccctgg gacacctctg gatatatccc ccaggaaacc caagaagtac gagctgcggg  5280
tcatcgtgtg gaacacagac gaggtggtcc tggaagacga tgatttcttc acgggagaga  5340
agtccagtga catttttgtg agggggtggc tgaagggcca gcaggaggac aaacaggaca  5400
cagatgtcca ctatcactcc ctcacggggg agggcaactt caactggaga tacctcttcc  5460
ccttcgacta cctagcggcc gaagagaaga tcgttatgtc caaaaaggag tctatgttct  5520
cctgggatga gacggagtac aagatccctg cgcggctcac cctgcagatc tgggacgctg  5580
accacttctc ggctgacgac ttcctggggg ctatcgagct ggacctgaac cggttcccga  5640
ggggcgctaa gacagccaag cagtgcacca tggagatggc caccggggag gtggacgtac  5700
ccctggtttc catctttaaa cagaaacgtg tcaaaggctg gtggcccctc ctggcccgca  5760
atgagaatga tgagtttgag ctcacaggca aagtggaggc ggagctacac ctactcacgg  5820
cagaggaggc agagaagaac cctgtgggcc tggctcgcaa tgaacctgat cccctagaaa  5880
aacccaaccg gcctgacacg gcattcgtct ggttcctgaa cccactcaaa tctatcaagt  5940
acctcatctg cacccggtac aagtggctga tcatcaagat cgtgctggcg ctgctggggc  6000
tgctcatgct ggccctcttc ctttacagcc tcccaggcta catggtcaag aagctcctag  6060
gggcctgaag tgtgccccac cccagcccgc tccagcatcc ctccaggggc tgctgcgtat  6120
tttgccttcc ctcacctgga ctctctccca actccctgag gagccctccc acgcctgcca  6180
gccttgagca agacacctgc ttgctggact tcatccccac cccacaccca aactgttgct  6240
tgcctgatct tgtcccaggc ctgcctgggg tttggggcac agttggcctc caaaaccaga  6300
taccctcttg tctaaagtac caggttcctc tgcccaaccc caagagtggt agtggcccaa  6360
ccctccctgt gctttccaaa tcttgtctta aggcaccagt gaaattaacc aagaaacgcg  6420
gagcaatgcc caaggctctg atgagtagga acacgtggaa agcaccagga atgccagcag  6480
aggcgaggcg gcacacctct ctgcagagca tccaggccga gcggcgggca gcggccagct  6540
gcttctgcgc atgctctcct cttggctctg cttctttctc acagtcacag tcacttcaca  6600
gcttagcctt gggcttccca tcacttccag gggtgcctct gccttggcca gtgtgtgtca  6660
gctagtacac aagctccaag tgtgaatcag gtgtactggc cgtcctgaag actgactgcc  6720
ctgtccttcc tgccgacagc cacacccgag tgtacactta aagcggtgcc cttctgcctc  6780
tgtgggcctg ctggctgctg ttcctttctt gagtgtgatt tttttttct ctccctcaat  6840
aaaataaatc aaactctgag ac                                          6862

SEQ ID NO: 19          moltype = DNA  length = 77
FEATURE                Location/Qualifiers
source                 1..77
                       mol_type = other DNA
                       organism = synthetic construct
SEQUENCE: 19
gggattttgc cgatttcggc ctattggtta aaaaatgagc tgatttaaca aaaatttaac  60
gcgaatttta acaaaat                                                77

SEQ ID NO: 20          moltype = DNA  length = 82
FEATURE                Location/Qualifiers
source                 1..82
                       mol_type = other DNA
                       organism = synthetic construct
SEQUENCE: 20
gtaagtatca aggttacaag acaggtttaa ggagaccaat agaaactggg cttgtcgaga  60
cagagaagac tcttgcgttt ct                                          82

SEQ ID NO: 21          moltype = DNA  length = 51
FEATURE                Location/Qualifiers
source                 1..51
                       mol_type = other DNA
                       organism = synthetic construct
SEQUENCE: 21
gataggcacc tattggtctt actgacatcc actttgcctt tctctccaca g          51

SEQ ID NO: 22          moltype = DNA  length = 48
FEATURE                Location/Qualifiers
source                 1..48
                       mol_type = other DNA
                       organism = synthetic construct
SEQUENCE: 22
gcctgcaaga actggttcag cagcctgagc cacttcgtga tccacctg              48

SEQ ID NO: 23          moltype = DNA  length = 548
```

-continued

```
FEATURE                Location/Qualifiers
source                 1..548
                       mol_type = other DNA
                       organism = synthetic construct
SEQUENCE: 23
gatccaatca acctctggat tacaaaattt gtgaaagatt gactggtatt cttaactatg  60
ttgctccttt tacgctatgt ggatacgctg ctttaatgcc tttgtatcat gctattgctt  120
cccgtatggc tttcattttc tcctccttgt ataaatcctg gttgctgtct ctttatgagg  180
agttgtggcc cgttgtcagg caacgtggcg tggtgtgcac tgtgtttgct gacgcaaccc  240
ccactggttg gggcattgcc accacctgtc agctcctttc cgggactttc gctttccccc  300
tccctattgc cacggcggaa ctcatcgccg cctgccttgc ccgctgctgg acaggggctc  360
ggctgttggg cactgacaat tccgtggtgt tgtcggggaa atcatcgtcc tttccttggc  420
tgctcgcctg tgttgccacc tggattctgc gcgggacgtc cttctgctac gtcccttcgg  480
ccctcaatcc agcggacctt ccttcccgcg gcctgctgcc ggctctgcgg cctcttccgc  540
gtcttcga                                                           548

SEQ ID NO: 24          moltype = DNA  length = 454
FEATURE                Location/Qualifiers
source                 1..454
                       mol_type = genomic DNA
                       organism = Mus musculus
SEQUENCE: 24
ctgcagctca gcctactact tgctttccag gctgttccta gttcccatgt cagctgcttg  60
tgctttccag agacaaaaca ggaataatag atgtcattaa atatacattg ggccccaggc  120
ggtcaatgtg gcagcctgag cctcctttcc atctctgtgg aggcagacat aggaccccca  180
acaaacagca tgcaggttgg gagccagcca caggacccag gtaaggggcc ctgggtcctt  240
aagcttctgc cactggctcc ggcattgcag agagaagaga aggggcggca gagctgaacc  300
ttagccttgc cttcctgggt acccttctga gcctcactgt cttctgtgag atgggcaaag  360
tgcgggtgtg actccttggc aacggtgtta caccagggca ggtaaagttg tagttatttg  420
tggggtacac caggactgtt aaaggtgtaa ctat                              454

SEQ ID NO: 25          moltype = DNA  length = 1157
FEATURE                Location/Qualifiers
source                 1..1157
                       mol_type = genomic DNA
                       organism = Mus musculus
SEQUENCE: 25
ggtctcaccc agcattttca cttctaataa gttcaaatgt gatacggcac ctttctaaaa  60
attagttttc agggaaatag ggttcaaaac tggtagtggt agggtccatt ctcacgaccc  120
ccaggcctgc taaccctgac caagctacct attacttacc ctcctctttc tcctcctcct  180
ctttctcctt ctcctgcttc ccctcttcct tctccctccc ttcctctccc tcctccccct  240
ccttggctgt gatcagatcc agagcctgaa tgagcctcct gaccccacac ccccactagc  300
atgggcctgc aagtgcccag aagtccctcc tgcctcctaa actgcccagc cgatccatta  360
gctcttcctt cttcccagtg aaagaagcag gcacagcctg tccctcccgt tctacagaaa  420
ggaagctaca gcacagggag ggccaaaggc cttcctggga ctagacagtt gatcaacagc  480
aggactggag agctgggctc catttttgtt ccttggtgcc ctgcccctcc ccatgacctg  540
cagagacatt cagcctgcca ggctttatga ggtgggagct gggctctccc tgatgtatta  600
ttcagctccc tggagttggc cagctcctgt tacactggcc acagccctgg gcatccgctt  660
ctcacttcta gtttcccctc caaggtaatg tggtgggtca tgatcattct atcctggctt  720
cagggacctg actccacttt ggggccattc gaggggtcta gggtagatga tgtccccctg  780
tggggattaa tgtcctgctc tgtaaaactg agctagctga gatccaggag ggcttggcca  840
gagacagcaa gttgttgcca tggtgacttt aaagccaggt tgctgcccca gcacaggcct  900
cccagtctac cctcactaga aaacaacacc caggcacttt ccaccacctc tcaaaggtga  960
aacccaaggc tggtctagag aatgaattat ggatcctcgc tgtccgtgcc acccagctag  1020
tcccagcggc tcagacactg aggagagact gtaggttcag ctacaagcaa aaagacctag  1080
ctggtctcca agcagtgtct ccaagtccct gaacctgtga cacctgcccc aggcatcatc  1140
aggcacagag ggccacc                                                 1157

SEQ ID NO: 26          moltype = DNA  length = 76
FEATURE                Location/Qualifiers
source                 1..76
                       mol_type = genomic DNA
                       organism = Mus musculus
SEQUENCE: 26
cccatgtcag ctgcttgtgc tttccagaga caaaacagga ataatagatg tcattaaata  60
tacattgggc cccagg                                                  76

SEQ ID NO: 27          moltype = DNA  length = 95
FEATURE                Location/Qualifiers
source                 1..95
                       mol_type = genomic DNA
                       organism = Mus musculus
SEQUENCE: 27
agcctgagcc tcctttccat ctctgtggag gcagacatag gacccccaac aaacagcatg  60
caggttggga gccagccaca ggacccaggt aaggg                             95

SEQ ID NO: 28          moltype = DNA  length = 171
FEATURE                Location/Qualifiers
source                 1..171
```

```
                        mol_type = other DNA
                        organism = synthetic construct
SEQUENCE: 28
cccatgtcag ctgcttgtgc tttccagaga caaaacagga ataatagatg tcattaaata  60
tacattgggc cccaggagcc tgagcctcct ttccatctct gtggaggcag acataggacc  120
cccaacaaac agcatgcagg ttgggagcca gccacaggac ccaggtaagg g           171

SEQ ID NO: 29           moltype = DNA  length = 171
FEATURE                 Location/Qualifiers
source                  1..171
                        mol_type = other DNA
                        organism = synthetic construct
SEQUENCE: 29
agcctgagcc tcctttccat ctctgtggag gcagacatag gacccccaac aaacagcatg  60
caggttggga gccagccaca ggacccaggt aagggcccat gtcagctgct tgtgctttcc  120
agagacaaaa caggaataat agatgtcatt aaatatacat tgggccccag g           171

SEQ ID NO: 30           moltype = DNA  length = 184
FEATURE                 Location/Qualifiers
source                  1..184
                        mol_type = genomic DNA
                        organism = Mus musculus
SEQUENCE: 30
cccatgtcag ctgcttgtgc tttccagaga caaaacagga ataatagatg tcattaaata  60
tacattgggc cccaggcggt caatgtggca gcctgagcct cctttccatc tctgtggagg  120
cagacatagg acccccaaca aacagcatgc aggttgggag ccagccacag gacccaggta  180
aggg                                                               184

SEQ ID NO: 31           moltype = DNA  length = 82
FEATURE                 Location/Qualifiers
source                  1..82
                        mol_type = genomic DNA
                        organism = Mus musculus
SEQUENCE: 31
tgaggtggga gctgggctct ccctgatgta ttattcagct ccctggagtt ggccagctcc  60
tgttacactg gccacagccc tg                                           82

SEQ ID NO: 32           moltype = DNA  length = 106
FEATURE                 Location/Qualifiers
source                  1..106
                        mol_type = genomic DNA
                        organism = Mus musculus
SEQUENCE: 32
cacaggcctc ccagtctacc ctcactagaa aacaacaccc aggcactttc caccacctct  60
caaaggtgaa acccaaggct ggtctagaga atgaattatg gatcct                 106

SEQ ID NO: 33           moltype = DNA  length = 188
FEATURE                 Location/Qualifiers
source                  1..188
                        mol_type = other DNA
                        organism = synthetic construct
SEQUENCE: 33
tgaggtggga gctgggctct ccctgatgta ttattcagct ccctggagtt ggccagctcc  60
tgttacactg gccacagccc tgcacaggcc tcccagtcta ccctcactag aaaacaacac  120
ccaggcactt tccaccacct ctcaaaggtg aaacccaagg ctggtctaga gaatgaatta  180
tggatcct                                                           188

SEQ ID NO: 34           moltype = DNA  length = 188
FEATURE                 Location/Qualifiers
source                  1..188
                        mol_type = other DNA
                        organism = synthetic construct
SEQUENCE: 34
cacaggcctc ccagtctacc ctcactagaa aacaacaccc aggcactttc caccacctct  60
caaaggtgaa acccaaggct ggtctagaga atgaattatg gatccttgag gtgggagctg  120
ggctctccct gatgtattat tcagctccct ggagttggcc agctcctgtt acactggcca  180
cagccctg                                                           188

SEQ ID NO: 35           moltype = DNA  length = 430
FEATURE                 Location/Qualifiers
source                  1..430
                        mol_type = genomic DNA
                        organism = Mus musculus
SEQUENCE: 35
tgaggtggga gctgggctct ccctgatgta ttattcagct ccctggagtt ggccagctcc  60
tgttacactg gccacagccc tgggcatccg cttctcactt ctagtttccc ctccaaggta  120
atgtggtggg tcatgatcat tctatcctgg cttcagggac ctgactccac tttggggcca  180
ttcgaggggt ctagggtaga tgatgtcccc ctgtggggat taatgtcctg ctctgtaaaa  240
ctgagctagc tgagatccag gagggcttgg ccagagacag caagttgttg ccatggtgac  300
```

-continued

```
tttaaagcca ggttgctgcc ccagcacagg cctcccagtc taccctcact agaaaacaac  360
acccaggcac tttccaccac ctctcaaagg tgaaacccaa ggctggtcta gagaatgaat  420
tatggatcct                                                         430

SEQ ID NO: 36          moltype = DNA  length = 1611
FEATURE                Location/Qualifiers
source                 1..1611
                       mol_type = other DNA
                       organism = synthetic construct
SEQUENCE: 36
ctgcagctca gcctactact tgctttccag gctgttccta gttcccatgt cagctgcttg  60
tgctttccag agacaaaaca ggaataatag atgtcattaa atatacattg gccccaggc  120
ggtcaatgtg gcagcctgag cctcctttcc atctctgtgg aggcagacat aggaccccca  180
acaaacagca tgcaggttgg gagccagcca caggacccag gtaaggggcc ctgggtcctt  240
aagcttctgc cactggctcc ggcattgcag agagaagaga aggggcggca gagctgaacc  300
ttagccttgc cttcctgggt acccttctga gcctcactgt cttctgtgag atgggcaaag  360
tgcgggtgtg actccttggc aacggtgtta caccagggca ggtaaagttg tagttatttg  420
tggggtacac caggactgtt aaaggtgtaa ctatggtctc acccagcatt ttcacttcta  480
ataagttcaa atgtgatacg gcacctttct aaaaattagt tttcagggaa atagggttca  540
aaactggtag tggtagggtc cattctcacg acccccaggc ctgctaaccc tgaccaagct  600
acctattact taccctcctc tttctcctcc tcctctttct ccttctcctg cttcccctct  660
tccttctccc tcccttcctc tccctcctcc ccctccttgg ctgtgatcag atccagagcc  720
tgaatgagcc tcctgacccc acacccccac tagcatgggc ctgcaagtgc ccagaagtcc  780
ctcctgcctc ctaaactgcc cagccgatcc attagctctt ccttcttccc agtgaaagaa  840
gcaggcacag cctgtccctc ccgttctaca gaaaggaagc tacagcacag ggagggccaa  900
aggccttcct gggactagac agttgatcaa cagcaggact ggagagctgg gctccatttt  960
tgttccttgg tgccctgccc ctccccatga cctgcagaga cattcagcct gccaggcttt  1020
atgaggtggg agctgggctc tccctgatgt attattcagc tccctggagt tggccagctc  1080
ctgttacact ggccacagcc ctgggcatcc gcttctcact tctagtttcc cctccaaggt  1140
aatgtggtgg gtcatgatca ttctatcctg gcttcaggga cctgactcca ctttggggcc  1200
attcgagggg tctagggtag atgatgtccc cctgtgggga ttaatgtcct gctctgtaaa  1260
actgagctag ctgagatcca ggagggcttg gccagagaca gcaagttgtt gccatggtga  1320
ctttaaagcc aggttgctgc cccagcacag gcctcccagt ctaccctcac tagaaaacaa  1380
cacccaggca ctttccacca cctctcaaag gtgaaaccca aggctggtct agagaatgaa  1440
ttatggatcc tcgctgtccg tgccacccag ctagtcccag cggctcagac actgaggaga  1500
gactgtaggt tcagctacaa gcaaaaagac ctagctggtc tccaagcagt gtctccaagt  1560
ccctgaacct gtgacacctg ccccaggcat catcaggcac agagggccac c           1611

SEQ ID NO: 37          moltype = DNA  length = 1611
FEATURE                Location/Qualifiers
source                 1..1611
                       mol_type = other DNA
                       organism = synthetic construct
SEQUENCE: 37
ggtctcaccc agcattttca cttctaataa gttcaaatgt gatacggcac ctttctaaaa  60
attagttttc agggaaatag ggttcaaaac tggtagtggt agggtccatt ctcacgaccc  120
ccaggcctgc taaccctgac caagctacct attacttacc ctcctctttc tcctcctcct  180
ctttctcctt ctcctgcttc ccctcttcct tctccctccc ttcctctccc tcctccccct  240
ccttggctgt gatcagatcc agagcctgaa tgagcctcct gaccccacac ccccactagc  300
atgggcctgc aagtgcccag aagtccctcc tgcctcctaa actgcccagc cgatccatta  360
gctcttcctt cttcccagtg aaagaagcag gcacagcctg tccctcccgt tctacagaaa  420
ggaagctaca gcacagggag ggccaaaggc cttcctggga ctagacagtt gatcaacagc  480
aggactggag agctgggctc catttttgtt ccttggtgcc ctgcccctcc ccatgacctg  540
cagagacatt cagcctgcca ggctttatga ggtgggagct gggctctccc tgatgtatta  600
ttcagctccc tggagttggc cagctcctgt tacactggcc acagccctgg gcatccgctt  660
ctcacttcta gtttcccctc caaggtaatg tggtgggtca tgatcattct atcctggctt  720
cagggacctg actccacttt ggggccattc gaggggtcta gggtagatga tgtccccctg  780
tggggattaa tgtcctgctc tgtaaaactg agctagctga gatccaggag ggcttggcca  840
gagacagcaa gttgttgcca tggtgacttt aaagccaggt tgctgcccca gcacaggcct  900
cccagtctac cctcactaga aaacaacacc caggcacttt ccaccacctc tcaaaggtga  960
aacccaaggc tggtctagag aatgaattat ggatcctcgc tgtccgtgcc acccagctag  1020
tcccagcggc tcagacactg aggagagact gtaggttcag ctacaagcaa aaagacctag  1080
ctggtctcca agcagtgtct ccaagtccct gaacctgtga cacctgcccc aggcatcatc  1140
aggcacagag ggccaccctg cagctcagcc tactacttgc tttccaggct gttcctagtt  1200
cccatgtcag ctgcttgtgc tttccagaga caaaacagga ataatagatg tcattaaata  1260
tacattgggc cccaggcggt caatgtggca gcctgagcct cctttccatc tctgtggagg  1320
cagacatagg acccccaaca aacagcatgc aggttgggag ccagccacag gacccaggta  1380
aggggccctg ggtccttaag cttctgccac tggctccggc attgcagaga gaagagaagg  1440
ggcggcagag ctgaacctta gccttgcctt cctgggtacc cttctgagcc tcactgtctt  1500
ctgtgagatg ggcaaagtgc gggtgtgact ccttggcaac ggtgttacac cagggcaggt  1560
aaagttgtag ttatttgtgg ggtacaccag gactgttaaa ggtgtaacta t           1611

SEQ ID NO: 38          moltype = DNA  length = 425
FEATURE                Location/Qualifiers
source                 1..425
                       mol_type = other DNA
                       organism = synthetic construct
SEQUENCE: 38
aatcaacctc tggattacaa aatttgtgaa agattgactg gtattcttaa ctatgttgct  60
```

```
ccttttacgc tatgtggata cgctgcttta atgcctttgt atcatgctat tgcttcccgt  120
atggctttca ttttctcctc cttgtataaa tcctggttag ttcttgccac ggcggaactc  180
atcgccgcct gccttgcccg ctgctggaca ggggctcggc tgttgggcac tgacaattcc  240
gtggtgttta tttgtgaaat ttgtgatgct attgctttat ttgtaaccat ctagctttat  300
ttgtgaaatt tgtgatgcta ttgctttatt tgtaaccatt ataagctgca ataaacaagt  360
taacaacaac aattgcattc attttatgtt tcaggttcag ggggagatgt gggaggtttt  420
ttaaa                                                              425

SEQ ID NO: 39          moltype = DNA  length = 865
FEATURE                Location/Qualifiers
source                 1..865
                       mol_type = genomic DNA
                       organism = Homo sapiens
SEQUENCE: 39
ccccgggtgc gcggcgtcgg tggtgccggc ggggggcgcc aggtcgcagg cggtgtaggg  60
ctccaggcag gcggcgaagg ccatgacgtg cgctatgaag gtctgctcct gcacgccgtg  120
aaccaggtgc gcctgcgggc cgcgcgcgaa caccgccacg tcctcgcctg cgtgggtctc  180
ttcgtccagg ggcactgctg actgctgccg atactcgggg ctcccgctct cgctctcggt  240
aacatccggc cgggcgccgt ccttgagcac atagcctgga ccgtttccgt ataggaggac  300
cgtgtaggcc ttcctgtccc gggccttgcc agcggccagc ccgatgaagg agctccctcg  360
cagggggtag cctccgaagg agaagacgtg ggagtggtcg gcagtgacga ggctcagcgt  420
gtcctcctcg ctggtgagct ggcccgccct ctcaatggcg tcgtcgaaca tgatcgtctc  480
agtcagtgcc cggtaagccc tgctttcatg atgaccatgg tcgatgcgac caccctccac  540
gaagaggaag aagccgcggg ggtgtctgct cagcaggcgc agggcagcct ctgtcatctc  600
catcagggag gggtccagtg tggagtctcg gtggatctcg tatttcatgt ctccaggctc  660
aaagagaccc atgagatggg tcacagacgg gtccagggaa gcctgcatga gctcagtgcg  720
gttccacacg taccgggcac cctggcgttc gccgagccat tcctgcacca gattcttccc  780
gtccagcctg gtcccacctt ggctgtagtc atctgggtac tcagggtctg ggttcccat  840
gcgaaacatg tactttcggc ctcca                                        865

SEQ ID NO: 40          moltype = DNA  length = 437
FEATURE                Location/Qualifiers
source                 1..437
                       mol_type = other DNA
                       organism = Homo sapiens
SEQUENCE: 40
ccccgggtgc gcggcgtcgg tggtgccggc ggggggcgcc aggtcgcagg cggtgtaggg  60
ctccaggcag gcggcgaagg ccatgacgtg cgctatgaag gtctgctcct gcacgccgtg  120
aaccaggtgc gcctgcgggc cgcgcgcgaa caccgccacg tcctcgcctg cgtgggtctc  180
ttcgtccagg ggcactgctg actgctgccg atactcgggg ctcccgctct cgctctcggt  240
aacatccggc cgggcgccgt ccttgagcac atagcctgga ccgtttccgt ataggaggac  300
cgtgtaggcc ttcctgtccc gggccttgcc agcggccagc ccgatgaagg agctccctcg  360
cagggggtag cctccgaagg agaagacgtg ggagtggtcg gcagtgacga ggctcagcgt  420
gtcctcctcg ctggtga                                                 437

SEQ ID NO: 41          moltype = DNA  length = 428
FEATURE                Location/Qualifiers
source                 1..428
                       mol_type = other DNA
                       organism = Homo sapiens
SEQUENCE: 41
gctggcccgc cctctcaatg gcgtcgtcga acatgatcgt ctcagtcagt gcccggtaag  60
ccctgctttc atgatgacca tggtcgatgc gaccaccctc cacgaagagg aagaagccgc  120
gggggtgtct gctcagcagg cgcagggcag cctctgtcat ctccatcagg gaggggtcca  180
gtgtggagtc tcggtggatc tcgtatttca tgtctccagg ctcaaagaga cccatgagat  240
gggtcacaga cgggtccagg gaagcctgca tgagctcagt gcggttccac acgtaccggg  300
caccctggcg ttcgccgagc cattcctgca ccagattctt cccgtccagc ctggtcccac  360
cttggctgta gtcatctggg tactcagggt ctggggttcc catgcgaaac atgtactttc  420
ggcctcca                                                           428

SEQ ID NO: 42          moltype = DNA  length = 287
FEATURE                Location/Qualifiers
source                 1..287
                       mol_type = other DNA
                       organism = Homo sapiens
SEQUENCE: 42
ccccgggtgc gcggcgtcgg tggtgccggc ggggggcgcc aggtcgcagg cggtgtaggg  60
ctccaggcag gcggcgaagg ccatgacgtg cgctatgaag gtctgctcct gcacgccgtg  120
aaccaggtgc gcctgcgggc cgcgcgcgaa caccgccacg tcctcgcctg cgtgggtctc  180
ttcgtccagg ggcactgctg actgctgccg atactcgggg ctcccgctct cgctctcggt  240
aacatccggc cgggcgccgt ccttgagcac atagcctgga ccgtttc                287

SEQ ID NO: 43          moltype = DNA  length = 290
FEATURE                Location/Qualifiers
source                 1..290
                       mol_type = other DNA
                       organism = Homo sapiens
SEQUENCE: 43
cgtataggag gaccgtgtag gccttcctgt cccgggcctt gccagcggcc agcccgatga  60
```

-continued

```
aggagctccc tcgcaggggg tagcctccga aggagaagac gtgggagtgg tcggcagtga  120
cgaggctcag cgtgtcctcc tcgctggtga gctggcccgc cctctcaatg gcgtcgtcga  180
acatgatcgt ctcagtcagt gcccggtaag ccctgctttc atgatgacca tggtcgatgc  240
gaccaccctc cacgaagagg aagaagccgc gggggtgtct gctcagcagg             290

SEQ ID NO: 44          moltype = DNA  length = 288
FEATURE                Location/Qualifiers
source                 1..288
                       mol_type = other DNA
                       organism = Homo sapiens
SEQUENCE: 44
cgcagggcag cctctgtcat ctccatcagg gaggggtcca gtgtggagtc tcggtggatc  60
tcgtatttca tgtctccagg ctcaaagaga cccatgagat gggtcacaga cgggtccagg  120
gaagcctgca tgagctcagt gcggttccac acgtaccggg caccctggcg ttcgccgagc  180
cattcctgca ccagattctt cccgtccagc ctggtcccac cttggctgta gtcatctggg  240
tactcagggt ctggggttcc catgcgaaac atgtactttc ggcctcca               288
```

COMPOSITIONS AND METHODS FOR TREATING SENSORINEURAL HEARING LOSS USING OTOFERLIN DUAL VECTOR SYSTEMS

SEQUENCE LISTING

The instant application contains a Sequence Listing which has been submitted electronically in XML file format and is hereby incorporated by reference in its entirety. Said XML copy, created on Oct. 29, 2024, is named 51124-042006_Sequence_Listing_10_29_24.xml and is 121,642 bytes in size.

FIELD OF THE INVENTION

Described herein are compositions and methods for the treatment of sensorineural hearing loss and auditory neuropathy, particularly forms of the disease that are associated with mutations in otoferlin (OTOF), by way of OTOF gene therapy. The disclosure provides dual vector systems that include a first nucleic acid vector that contains a polynucleotide encoding an N-terminal portion of an OTOF protein and a second nucleic acid vector that contains a polynucleotide encoding a C-terminal portion of an OTOF protein. These vectors can be used to increase the expression of or provide wild-type OTOF to a subject, such as a human subject suffering from sensorineural hearing loss.

BACKGROUND

Sensorineural hearing loss is a type of hearing loss caused by defects in the cells of the inner ear or the neural pathways that project from the inner ear to the brain. Although sensorineural hearing loss is often acquired, and can be caused by noise, infections, head trauma, ototoxic drugs, or aging, there are also congenital forms of sensorineural hearing loss associated with autosomal recessive mutations. One such form of autosomal recessive sensorineural hearing loss is associated with mutation of the otoferlin (OTOF) gene, which is implicated in prelingual nonsyndromic hearing loss. In recent years, efforts to treat hearing loss have increasingly focused on gene therapy as a possible solution; however, OTOF is too large to allow for treatment using standard gene therapy approaches. There is a need for new therapeutics to treat OTOF-related sensorineural hearing loss.

SUMMARY OF THE INVENTION

The present invention provides compositions and methods for treating sensorineural hearing loss or auditory neuropathy in a subject, such as a human subject. The compositions and methods of the disclosure pertain to dual vector systems for the delivery of a polynucleotide encoding an otoferlin (OTOF) protein to a subject having or at risk of developing sensorineural hearing loss or auditory neuropathy (e.g., a subject with a mutation in OTOF). For example, using the compositions and methods described herein, a first nucleic acid vector and a second nucleic acid vector that each encode a portion of a functional OTOF protein may be delivered to a subject by way of viral gene therapy. The compositions and methods described herein may also be used to increase expression of a WT OTOF protein in a cochlear hair cell (e.g., an inner hair cell).

In a first aspect, the invention provides a composition comprising: a first nucleic acid vector containing a promoter selected from the group consisting of a myosin 15 (Myo15) promoter, a vesicular glutamate transporter 3 (VGLUT3) promoter, and a fibroblast growth factor 8 (FGF8) promoter operably linked to a first coding polynucleotide that encodes an N-terminal portion of an otoferlin (OTOF) protein; and a second nucleic acid vector containing a second coding polynucleotide that encodes a C-terminal portion of an OTOF protein and a polyadenylation (poly(A)) sequence positioned at the 3' end of the second coding polynucleotide; wherein the first coding polynucleotide partially overlaps with the second coding polynucleotide, wherein neither the first nor second nucleic acid vector encodes a full-length OTOF protein, and, when introduced into a mammalian cell, the two first and second nucleic acid vectors undergo homologous recombination to form a recombined nucleic acid that encodes a full-length OTOF protein.

In another aspect, the invention provides a dual vector system comprising: a first nucleic acid vector containing a promoter selected from the group consisting of a myosin 15 (Myo15) promoter, a vesicular glutamate transporter 3 (VGLUT3) promoter, and a fibroblast growth factor 8 (FGF8) promoter operably linked to a first coding polynucleotide that encodes an N-terminal portion of an otoferlin (OTOF) protein; and a second nucleic acid vector containing a second coding polynucleotide that encodes a C-terminal portion of an OTOF protein and a polyadenylation (poly(A)) sequence positioned at the 3' end of the second coding polynucleotide; wherein the first coding polynucleotide partially overlaps with the second coding polynucleotide, wherein neither the first nor second nucleic acid vector encodes a full-length OTOF protein, and, when introduced into a mammalian cell, the two first and second nucleic acid vectors undergo homologous recombination to form a recombined nucleic acid that encodes a full-length OTOF protein.

In another aspect, the invention provides a composition comprising: a first nucleic acid vector containing a promoter selected from the group consisting of a CAG promoter, a cytomegalovirus (CMV) promoter, a Myo15 promoter, a Myosin 7A (Myo7A) promoter, a Myosin 6 (Myo6) promoter, a POU Class 4 Homeobox 3 (POU4F3) promoter, an OTOF promoter, an FGF8 promoter, and a VGLUT3 promoter operably linked to a first coding polynucleotide that encodes an N-terminal portion of a human OTOF protein; and a second nucleic acid vector containing a second coding polynucleotide that encodes a C-terminal portion of a human OTOF protein and a polyadenylation (poly(A)) sequence positioned at the 3' end of the second coding polynucleotide; wherein the first coding polynucleotide partially overlaps with the second coding polynucleotide, wherein neither the first nor second nucleic acid vector encodes a full-length OTOF protein, and, when introduced into a mammalian cell, the two first and second nucleic acid vectors undergo homologous recombination to form a recombined nucleic acid that encodes a full-length OTOF protein.

In another aspect, the invention provides a dual vector system comprising: a first nucleic acid vector containing a promoter selected from the group consisting of a CAG promoter, a cytomegalovirus (CMV) promoter, a Myo15 promoter, a Myosin 7A (Myo7A) promoter, a Myosin 6 (Myo6) promoter, a POU Class 4 Homeobox 3 (POU4F3) promoter, an OTOF promoter, an FGF8 promoter, and a VGLUT3 promoter operably linked to a first coding polynucleotide that encodes an N-terminal portion of a human OTOF protein; and a second nucleic acid vector containing a second coding polynucleotide that encodes a C-terminal portion of a human OTOF protein and a polyadenylation (poly(A)) sequence positioned at the 3' end of the second coding polynucleotide; wherein the first coding polynucleotide partially overlaps with the second coding polynucleotide, wherein neither the first nor second nucleic acid vector encodes a full-length OTOF protein, and, when introduced into a mammalian cell, the two first and second nucleic acid vectors undergo homologous recombination to form a recombined nucleic acid that encodes a full-length OTOF protein.

In some embodiments of any of the foregoing aspects, the first and second nucleic acid vectors are adeno-associated virus (AAV) vectors. In some embodiments of any of the foregoing aspects, the serotype of the AAV vectors is selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a composition comprising: a first nucleic acid vector containing a promoter selected from the group consisting of a CAG promoter, a CMV promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of an OTOF protein; and a second nucleic acid vector containing a second coding polynucleotide that encodes a C-terminal portion of an OTOF protein and a polyadenylation (poly(A)) sequence positioned at the 3' end of the second coding polynucleotide; wherein the first coding polynucleotide partially overlaps with the second coding polynucleotide, wherein neither the first nor second nucleic acid vector encodes a full-length OTOF protein, and, when introduced into a mammalian cell, the two first and second nucleic acid vectors undergo homologous recombination to form a recombined nucleic acid that encodes a full-length OTOF protein, and wherein the first and second nucleic acid vectors are AAV vectors having a serotype selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a dual vector system comprising: a first nucleic acid vector containing a promoter selected from the group consisting of a CAG promoter, a CMV promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of an OTOF protein; and a second nucleic acid vector containing a second coding polynucleotide that encodes a C-terminal portion of an OTOF protein and a polyadenylation (poly(A)) sequence positioned at the 3' end of the second coding polynucleotide; wherein the first coding polynucleotide partially overlaps with the second coding polynucleotide, wherein neither the first nor second nucleic acid vector encodes a full-length OTOF protein, and, when introduced into a mammalian cell, the two first and second nucleic acid vectors undergo homologous recombination to form a recombined nucleic acid that encodes a full-length OTOF protein, and wherein the first and second nucleic acid vectors are AAV vectors having a serotype selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a composition comprising: a first nucleic acid vector containing a promoter operably linked to a first coding polynucleotide that encodes an N-terminal portion of a human OTOF protein; and a second nucleic acid vector containing a second coding polynucleotide that encodes a C-terminal portion of a human OTOF protein and a polyadenylation (poly(A)) sequence positioned at the 3' end of the second coding polynucleotide; wherein the first coding polynucleotide partially overlaps with the second coding polynucleotide, wherein neither the first nor second nucleic acid vector encodes a full-length OTOF protein, and, when introduced into a mammalian cell, the two first and second nucleic acid vectors undergo homologous recombination to form a recombined nucleic acid that encodes a full-length OTOF protein, and wherein the first and second nucleic acid vectors are AAV vectors having a serotype selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a dual vector system comprising: a first nucleic acid vector containing a promoter operably linked to a first coding polynucleotide that encodes an N-terminal portion of a human OTOF protein; and a second nucleic acid vector containing a second coding polynucleotide that encodes a C-terminal portion of a human OTOF protein and a polyadenylation (poly(A)) sequence positioned at the 3' end of the second coding polynucleotide; wherein the first coding polynucleotide partially overlaps with the second coding polynucleotide, wherein neither the first nor second nucleic acid vector encodes a full-length OTOF protein, and, when introduced into a mammalian cell, the two first and second nucleic acid vectors undergo homologous recombination to form a recombined nucleic acid that encodes a full-length OTOF protein, and wherein the first and second nucleic acid vectors are AAV vectors having a serotype selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In some embodiments of any of the foregoing aspects, the first and second coding polynucleotides that encode the OTOF protein (e.g., the human OTOF protein) do not contain introns.

In some embodiments of any of the foregoing aspects, the OTOF protein is a mammalian OTOF protein.

In some embodiments of any of the foregoing aspects, the OTOF protein is a murine OTOF protein. In some embodiments of any of the foregoing aspects, the murine OTOF protein has at least 85% sequence identity (e.g., 85%, 86%, 87%, 88%, 89%, 90%, 91%, 92%, 93%, 94%, 95%, 96%, 97%, 98%, 99%, or 100% identity) to the sequence of SEQ ID NO: 6, SEQ ID NO: 7, SEQ ID NO: 8, or SEQ ID NO: 9. In some embodiments of any of the foregoing aspects, the OTOF protein comprises or consists of the sequence of SEQ ID NO: 6.

In some embodiments of any of the foregoing aspects, the OTOF protein is a human OTOF protein. In some embodiments of any of the foregoing aspects, the human OTOF protein has at least 85% sequence identity (e.g., 85%, 86%, 87%, 88%, 89%, 90%, 91%, 92%, 93%, 94%, 95%, 96%, 97%, 98%, 99%, or 100% identity) to the sequence of SEQ ID NO: 1, SEQ ID NO: 2, SEQ ID NO:3, SEQ ID NO: 4, or SEQ ID NO: 5. In some embodiments of any of the foregoing aspects, the OTOF protein comprises or consists of the sequence of SEQ ID NO: 1.

In some embodiments of any of the foregoing aspects, the serotype of the AAV vectors is AAV1. In some embodiments of any of the foregoing aspects, the serotype of the AAV vectors is AAV9. In some embodiments of any of the foregoing aspects, the serotype of the AAV vectors is AAV6. In some embodiments of any of the foregoing aspects, the serotype of the AAV vectors is Anc80. In some embodiments of any of the foregoing aspects, the serotype of the AAV vectors is Anc80L65. In some embodiments of any of the foregoing aspects, the serotype of the AAV vectors is DJ/9. In some embodiments of any of the foregoing aspects, the serotype of the AAV vectors is 7m8. In some embodiments of any of the foregoing aspects, the serotype of the AAV vectors is AAV2. In some embodiments of any of the foregoing aspects, the serotype of the AAV vectors is PHP.B. In some embodiments of any of the foregoing aspects, the serotype of the AAV vectors is AAV8. In some embodiments of any of the foregoing aspects, the first and second nucleic acid vectors have the same serotype (e.g., both the first and second nucleic acid vector are AAV vectors having an AAV1 serotype or an AAV9 serotype). In some embodiments of any of the foregoing aspects, the first and second nucleic acid vectors have different serotypes (e.g., the first nucleic acid vector is an AAV having an AAV1 serotype, and the second nucleic acid vector is an AAV having an AAV9 serotype).

In some embodiments of any of the foregoing aspects, each of the first and second coding polynucleotides encode about half of the OTOF protein sequence.

In some embodiments of any of the foregoing aspects, wherein the first coding polynucleotide overlaps with the second coding polynucleotide by at least 1 kilobase (kb).

In some embodiments of any of the foregoing aspects, the region of overlap between the first and second coding polynucleotides is centered at an OTOF exon boundary. In some embodiments of any of the foregoing aspects, the first coding polynucleotide encodes an N-terminal portion of the OTOF protein containing the OTOF N-terminus to 500 kb 3' of the exon boundary at the center of the overlap region; and the second coding polynucleotide encodes a C-terminal portion of the OTOF protein containing 500 kb 5' of the exon boundary at the center of the overlap region to the OTOF C-terminus.

In some embodiments of any of the foregoing aspects, the exon boundary at the center of the overlap region is not within a portion of the first coding polynucleotide or second coding polynucleotide that encodes a C2 domain.

In some embodiments of any of the foregoing aspects, the promoter is a Myo15 promoter.

In some embodiments of any of the foregoing aspects, the promoter is a long promoter (e.g., a promoter that is longer than 1 kb, e.g., 1.1 kb, 1.25 kb, 1.5 kb, 1.75 kb, 2 kb, 2.5 kb, 3 kb or longer). In some embodiments, the long promoter is a Myo15 promoter that is longer than 1 kb (e.g., a Myo15 promoter comprising or consisting of the sequence of SEQ ID NO: 36).

In some embodiments of any of the foregoing aspects, the exon boundary is selected such that the first coding polynucleotide encodes the entire C2C domain and the second coding polynucleotide encodes the entire C2D domain. In some embodiments of any of the foregoing aspects, the first coding polynucleotide contains exons 1-21 of a polynucleotide encoding the OTOF protein and 500 kb 3' of the exon 21/22 boundary; and the second coding polynucleotide contains 500 kb 5' of the exon 21/22 boundary and exons 22-48 of a polynucleotide encoding the OTOF protein. In some embodiments of any of the foregoing aspects, the first nucleic acid vector and the second nucleic acid vector do not contain OTOF untranslated regions (UTRs).

In some embodiments of any of the foregoing aspects, the promoter is a short promoter (e.g., a promoter that is 1 kb or shorter, e.g., approximately 1 kb, 950 bp, 900 bp, 850 bp, 800 bp, 750 bp, 700 bp, 650 bp, 600 bp, 550 bp 500 bp, 450 bp, 400 bp, 350 bp, 300 bp or shorter). In some embodiments, the short promoter is a CAG promoter. In some embodiments, the short promoter is a CMV promoter. In some embodiments, the short promoter is a Myo15 promoter that is 1 kb or shorter.

In some embodiments of any of the foregoing aspects, the exon boundary is within a portion of the first coding polynucleotide and the second coding polynucleotide that encodes the C2D domain. In some embodiments of any of the foregoing aspects, the first coding polynucleotide contains exons 1-24 of a polynucleotide encoding the OTOF protein and 500 kb 3' of the exon 24/25 boundary; and the second coding polynucleotide contains 500 kb 5' of the exon 24/25 boundary and exons 25-48 of a polynucleotide encoding the OTOF protein. In some embodiments of any of the foregoing aspects, the first and second nucleic acid vectors include OTOF UTRs (e.g., full-length 3' and 5' UTRs).

In some embodiments of any of the foregoing aspects, the exon boundary is selected such that the first coding polynucleotide encodes the entire C2D domain and the second coding polynucleotide encodes the entire C2E domain. In some embodiments of any of the foregoing aspects, the first coding polynucleotide contains exons 1-28 of a polynucleotide encoding the OTOF protein and 500 kb 3' of the exon 28/29 boundary; and the second coding polynucleotide contains 500 kb 5' of the exon 28/29 boundary and exons 29-48 of a polynucleotide encoding the OTOF protein. In some embodiments of any of the foregoing aspects, the second nucleic acid vector contains a full-length OTOF 3' UTR.

In another aspect, the invention provides a composition comprising: a first nucleic acid vector containing a promoter selected from the group consisting of a Myo15 promoter, a VGLUT3 promoter, and an FGF8 promoter operably linked to a first coding polynucleotide that encodes an N-terminal portion of an OTOF protein, and a splice donor signal sequence positioned at the 3' end of the first coding polynucleotide; and a second nucleic acid vector containing a splice acceptor signal sequence, a second coding polynucleotide that encodes a C-terminal portion of an OTOF protein positioned at the 3' end of the splice acceptor signal sequence, and a poly(A) sequence at the 3' end of the second coding polynucleotide; wherein the first coding polynucleotide and the second coding polynucleotide do not overlap, and wherein neither the first nor second nucleic acid vector encodes a full-length OTOF protein.

In another aspect, the invention provides a dual vector system comprising: a first nucleic acid vector containing a promoter selected from the group consisting of a Myo15 promoter, a VGLUT3 promoter, and an FGF8 promoter operably linked to a first coding polynucleotide that encodes an N-terminal portion of an OTOF protein, and a splice donor signal sequence positioned at the 3' end of the first coding polynucleotide; and a second nucleic acid vector containing a splice acceptor signal sequence, a second coding polynucleotide that encodes a C-terminal portion of an OTOF protein positioned at the 3' end of the splice acceptor signal sequence, and a poly(A) sequence at the 3' end of the second coding polynucleotide; wherein the first coding polynucleotide and the second coding polynucleotide do not overlap, and wherein neither the first nor second nucleic acid vector encodes a full-length OTOF protein.

In another aspect, the invention provides a composition comprising: a first nucleic acid vector containing a promoter selected from the group consisting of a Myo15 promoter, a VGLUT3 promoter, and an FGF8 promoter operably linked to a first coding polynucleotide that encodes an N-terminal portion of an OTOF protein, a splice donor signal sequence positioned at the 3' end of the first coding polynucleotide, and a recombinogenic region positioned 3' of the splice donor signal sequence; and a second nucleic acid vector containing a second recombinogenic region, a splice acceptor signal sequence positioned 3' of the second recombinogenic region, a second coding polynucleotide that encodes a C-terminal portion of an OTOF protein positioned at the 3' end of the splice acceptor signal sequence, and a poly(A) sequence positioned at the 3' end of the second coding polynucleotide; wherein the first coding polynucleotide and the second coding polynucleotide do not overlap, and wherein neither the first nor second nucleic acid vector encodes a full-length OTOF protein.

In another aspect, the invention provides a dual vector system comprising: a first nucleic acid vector containing a promoter selected from the group consisting of a Myo15 promoter, a VGLUT3 promoter, and an FGF8 promoter operably linked to a first coding polynucleotide that encodes an N-terminal portion of an OTOF protein, a splice donor signal sequence positioned at the 3' end of the first coding polynucleotide, and a recombinogenic region positioned 3' of the splice donor signal sequence; and a second nucleic acid vector containing a second recombinogenic region, a splice acceptor signal sequence positioned 3' of the second recombinogenic region, a second coding polynucleotide that encodes a C-terminal portion of an OTOF protein positioned at the 3' end of the splice acceptor signal sequence, and a poly(A) sequence positioned at the 3' end of the second coding polynucleotide; wherein the first coding polynucleotide and the second coding polynucleotide do not overlap, and wherein neither the first nor second nucleic acid vector encodes a full-length OTOF protein.

In another aspect, the invention provides a composition comprising: a first nucleic acid vector containing a promoter selected from the group consisting of a CAG promoter, a CMV promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of a human OTOF protein, and a splice donor signal sequence positioned at the 3' end of the first coding polynucleotide; and a second nucleic acid vector containing a splice acceptor signal sequence, a second coding polynucleotide that encodes a C-terminal portion of a human OTOF protein positioned at the 3' end of the splice acceptor signal sequence, and a poly(A) sequence at the 3' end of the second coding polynucleotide; wherein the first coding polynucleotide and the second coding polynucleotide do not overlap, and wherein neither the first nor second nucleic acid vector encodes a full-length OTOF protein.

In another aspect, the invention provides a dual vector system comprising: a first nucleic acid vector containing a promoter selected from the group consisting of a CAG promoter, a CMV promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of a human OTOF protein, and a splice donor signal sequence positioned at the 3' end of the first coding polynucleotide; and a second nucleic acid vector containing a splice acceptor signal sequence, a second coding polynucleotide that encodes a C-terminal portion of a human OTOF protein positioned at the 3' end of the splice acceptor signal sequence, and a poly(A) sequence at the 3' end of the second coding polynucleotide; wherein the first coding polynucleotide and the second coding polynucleotide do not overlap, and wherein neither the first nor second nucleic acid vector encodes a full-length OTOF protein.

In some embodiments of any of the foregoing aspects, the first and second nucleic acid vectors are adeno-associated virus (AAV) vectors. In some embodiments of any of the foregoing aspects, the serotype of the AAV vectors is selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a composition comprising: a first nucleic acid vector containing a promoter selected from the group consisting of a CAG promoter, a CMV promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of an OTOF protein, and a splice donor signal sequence positioned at the 3' end of the first coding polynucleotide; and a second nucleic acid vector containing a splice acceptor signal sequence, a second coding polynucleotide that encodes a C-terminal portion of an OTOF protein positioned at the 3' end of the splice acceptor signal sequence, and a poly(A) sequence at the 3' end of the second coding polynucleotide; wherein the first coding polynucleotide and the second coding polynucleotide do not overlap, wherein neither the first nor second nucleic acid vector encodes a full-length OTOF protein, and wherein the first and second nucleic acid vectors are AAV vectors having a serotype selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a dual vector system comprising: a first nucleic acid vector containing a promoter selected from the group consisting of a CAG promoter, a CMV promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of an OTOF protein, and a splice donor signal sequence positioned at the 3' end of the first coding polynucleotide; and a second nucleic acid vector containing a splice acceptor signal sequence, a second coding polynucleotide that encodes a C-terminal portion of an OTOF protein positioned at the 3' end of the splice acceptor signal sequence, and a poly(A) sequence at the 3' end of the second coding polynucleotide; wherein the first coding polynucleotide and the second coding polynucleotide do not overlap, wherein neither the first nor second nucleic acid vector encodes a full-length OTOF protein, and wherein the first and second nucleic acid vectors are AAV vectors having a serotype selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a composition comprising: a first nucleic acid vector containing a promoter operably linked to a first coding polynucleotide that encodes an N-terminal portion of a human OTOF protein, and a splice donor signal sequence positioned at the 3' end of the first coding polynucleotide; and a second nucleic acid vector containing a splice acceptor signal sequence, a second coding polynucleotide that encodes a C-terminal portion of a human OTOF protein positioned at the 3' end of the splice acceptor signal sequence, and a poly(A) sequence at the 3' end of the second coding polynucleotide; wherein the first coding polynucleotide and the second coding polynucleotide do not overlap, wherein neither the first nor second nucleic acid vector encodes a full-length OTOF protein, and wherein the first and second nucleic acid vectors are AAV vectors having a serotype selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a dual vector system comprising: a first nucleic acid vector containing a promoter operably linked to a first coding polynucleotide that encodes an N-terminal portion of a human OTOF protein, and a splice donor signal sequence positioned at the 3' end of the first coding polynucleotide; and a second nucleic acid vector containing a splice acceptor signal sequence, a second coding polynucleotide that encodes a C-terminal portion of a human OTOF protein positioned at the 3' end of the splice acceptor signal sequence, and a poly(A) sequence at the 3' end of the second coding polynucleotide; wherein the first coding polynucleotide and the second coding polynucleotide do not overlap, wherein neither the first nor second nucleic acid vector encodes a full-length OTOF protein, and wherein the first and second nucleic acid vectors are AAV vectors having a serotype selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a composition comprising: a first nucleic acid vector containing a promoter selected from the group consisting of a CAG promoter, a CMV promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of a human OTOF protein, a splice donor signal sequence positioned at the 3' end of the first coding polynucleotide, and a recombinogenic region positioned 3' of the splice donor signal sequence; and a second nucleic acid vector containing a second recombinogenic region, a splice acceptor signal sequence positioned 3' of the second recombinogenic region, a second coding polynucleotide that encodes a C-terminal portion of a human OTOF protein positioned at the 3' end of the splice acceptor signal sequence, and a poly(A) sequence positioned at the 3' end of the second coding polynucleotide; wherein the first coding polynucleotide and the second coding polynucleotide do not overlap, and wherein neither the first nor second nucleic acid vector encodes a full-length OTOF protein.

In another aspect, the invention provides a dual vector system comprising: a first nucleic acid vector containing a promoter selected from the group consisting of a CAG promoter, a CMV promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of a human OTOF protein, a splice donor signal sequence positioned at the 3' end of the first coding polynucleotide, and a recombinogenic region positioned 3' of the splice donor signal sequence; and a second nucleic acid vector containing a second recombinogenic region, a splice acceptor signal sequence positioned 3' of the second recombinogenic region, a second coding polynucleotide that encodes a C-terminal portion of a human OTOF protein positioned at the 3' end of the splice acceptor signal sequence, and a poly(A) sequence positioned at the 3' end of the second coding polynucleotide; wherein the first coding polynucleotide and the second coding polynucleotide do not overlap, and wherein neither the first nor second nucleic acid vector encodes a full-length OTOF protein.

In some embodiments of any of the foregoing aspects, the first and second nucleic acid vectors are AAV vectors. In some embodiments of any of the foregoing aspects, the serotype of the AAV vectors is selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a composition comprising: a first nucleic acid vector containing a promoter selected from the group consisting of a CAG promoter, a CMV promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of an OTOF protein, a splice donor signal sequence positioned at the 3' end of the first coding polynucleotide, and a recombinogenic region positioned 3' of the splice donor signal sequence; and a second nucleic acid vector containing a second recombinogenic region, a splice acceptor signal sequence positioned 3' of the second recombinogenic region, a second coding polynucleotide that encodes a C-terminal portion of an OTOF protein positioned at the 3' end of the splice acceptor signal sequence, and a poly(A) sequence positioned at the 3' end of the second coding polynucleotide; wherein the first coding polynucleotide and the second coding polynucleotide do not overlap, wherein neither the first nor second nucleic acid vector encodes a full-length OTOF protein, and wherein the first and second nucleic acid vectors are AAV vectors having a serotype selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a dual vector system comprising: a first nucleic acid vector containing a promoter selected from the group consisting of a CAG promoter, a CMV promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of an OTOF protein, a splice donor signal sequence positioned at the 3' end of the first coding polynucleotide, and a recombinogenic region positioned 3' of the splice donor signal sequence; and a second nucleic acid vector containing a second recombinogenic region, a splice acceptor signal sequence positioned 3' of the second recombinogenic region, a second coding polynucleotide that encodes a C-terminal portion of an OTOF protein positioned at the 3' end of the splice acceptor signal sequence, and a poly(A) sequence positioned at the 3' end of the second coding polynucleotide; wherein the first coding polynucleotide and the second coding polynucleotide do not overlap, wherein neither the first nor second nucleic acid vector encodes a full-length OTOF protein, and wherein the first and second nucleic acid vectors are AAV vectors having a serotype selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a composition comprising: a first nucleic acid vector containing a promoter operably linked to a first coding polynucleotide that encodes an N-terminal portion of a human OTOF protein, a splice donor signal sequence positioned at the 3' end of the first coding polynucleotide, and a recombinogenic region positioned 3' of the splice donor signal sequence; and a second nucleic acid vector containing a second recombinogenic region, a splice acceptor signal sequence positioned 3' of the second recombinogenic region, a second coding polynucleotide that encodes a C-terminal portion of a human OTOF protein positioned at the 3' end of the splice acceptor signal sequence, and a poly(A) sequence positioned at the 3' end of the second coding polynucleotide; wherein the first coding polynucleotide and the second coding polynucleotide do not overlap, wherein neither the first nor second nucleic acid vector encodes a full-length OTOF protein, and wherein the first and second nucleic acid vectors are AAV vectors having a serotype selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a dual vector system comprising: a first nucleic acid vector containing a promoter operably linked to a first coding polynucleotide that encodes an N-terminal portion of a human OTOF protein, a splice donor signal sequence positioned at the 3' end of the first coding polynucleotide, and a recombinogenic region positioned 3' of the splice donor signal sequence; and a second nucleic acid vector containing a second recombinogenic region, a splice acceptor signal sequence positioned 3' of the second recombinogenic region, a second coding polynucleotide that encodes a C-terminal portion of a human OTOF protein positioned at the 3' end of the splice acceptor signal sequence, and a poly(A) sequence positioned at the 3' end of the second coding polynucleotide; wherein the first coding polynucleotide and the second coding polynucleotide do not overlap, wherein neither the first nor second nucleic acid vector encodes a full-length OTOF protein, and wherein the first and second nucleic acid vectors are AAV vectors having a serotype selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In some embodiments of any of the foregoing aspects, the first and second coding polynucleotides that encode the OTOF protein (e.g., the human OTOF protein) do not contain introns.

In some embodiments of any of the foregoing aspects, the OTOF protein is a mammalian OTOF protein.

In some embodiments of any of the foregoing aspects, the OTOF protein is a murine OTOF protein. In some embodiments of any of the foregoing aspects, the murine OTOF protein has at least 85% sequence identity (e.g., 85%, 86%, 87%, 88%, 89%, 90%, 91%, 92%, 93%, 94%, 95%, 96%, 97%, 98%, 99%, or 100% identity) to the sequence of SEQ ID NO: 6, SEQ ID NO: 7, SEQ ID NO: 8, or SEQ ID NO: 9. In some embodiments of any of the foregoing aspects, the murine OTOF protein comprises or consists of the sequence of SEQ ID NO: 6.

In some embodiments of any of the foregoing aspects, the OTOF protein is a human OTOF protein. In some embodiments of any of the foregoing aspects, the human OTOF protein has at least 85% sequence identity (e.g., 85%, 86%, 87%, 88%, 89%, 90%, 91%, 92%, 93%, 94%, 95%, 96%, 97%, 98%, 99%, or 100% identity) to the sequence of SEQ ID NO: 1, SEQ ID NO: 2, SEQ ID NO:3, SEQ ID NO: 4, or SEQ ID NO: 5. In some embodiments of any of the foregoing aspects, the human OTOF protein comprises or consists of the sequence of SEQ ID NO: 1.

In some embodiments of any of the foregoing aspects, the serotype of the AAV vectors is AAV1. In some embodiments of any of the foregoing aspects, the serotype of the AAV vectors is AAV9. In some embodiments of any of the foregoing aspects, the serotype of the AAV vectors is AAV6. In some embodiments of any of the foregoing aspects, the serotype of the AAV vectors is Anc80. In some embodiments of any of the foregoing aspects, the serotype of the AAV vectors is Anc80L65. In some embodiments of any of the foregoing aspects, the serotype of the AAV vectors is DJ/9. In some embodiments of any of the foregoing aspects, the serotype of the AAV vectors is 7m8. In some embodiments of any of the foregoing aspects, the serotype of the AAV vectors is AAV2. In some embodiments of any of the foregoing aspects, the serotype of the AAV vectors is PHP.B. In some embodiments of any of the foregoing aspects, the serotype of the AAV vectors is AAV8. In some embodiments of any of the foregoing aspects, the first and second nucleic acid vectors have the same serotype (e.g., both the first and second nucleic acid vector are AAV vectors having an AAV1 serotype or an AAV9 serotype). In some embodiments of any of the foregoing aspects, the first and second nucleic acid vectors have different serotypes (e.g., the first nucleic acid vector is an AAV having an AAV1 serotype, and the second nucleic acid vector is an AAV having an AAV9 serotype).

In some embodiments, of any of the foregoing aspects, the first and second recombinogenic regions are the same. In some embodiments, of any of the foregoing aspects, the recombinogenic region is an AP gene fragment or an F1 phage AK gene. In some embodiments of any of the foregoing aspects, the recombinogenic region is an F1 phage AK gene. In some embodiments of any of the foregoing aspects, the F1 phage AK gene comprises or consists of the sequence of SEQ ID NO: 19. In some embodiments of any of the foregoing aspects, the recombinogenic region is an AP gene fragment. In some embodiments of any of the foregoing aspects, the AP gene fragment comprises or consists of the sequence of any one of SEQ ID NOs 39-44.

In some embodiments of any of the foregoing aspects, the first nucleic acid vector further includes a degradation signal sequence positioned 3' of the recombinogenic region; and the second nucleic acid vector further includes a degradation signal sequence positioned between the recombinogenic region and the splice acceptor signal sequence. In some embodiments of any of the foregoing aspects, the degradation signal sequence comprises or consists of the sequence of SEQ ID NO: 22.

In some embodiments of any of the foregoing aspects, each of the first and second coding polynucleotides encode about half of the OTOF protein sequence.

In some embodiments of any of the foregoing aspects, the division between the first and second coding polynucleotides is at an OTOF exon boundary.

In some embodiments of any of the foregoing aspects, the OTOF exon boundary is not within a portion of the first coding polynucleotide or second coding polynucleotide that encodes a C2 domain.

In some embodiments of any of the foregoing aspects, the promoter is a short promoter (e.g., a promoter that is 1 kb or shorter, e.g., approximately 1 kb, 950 bp, 900 bp, 850 bp, 800 bp, 750 bp, 700 bp, 650 bp, 600 bp, 550 bp 500 bp, 450 bp, 400 bp, 350 bp, 300 bp or shorter). In some embodiments, the short promoter is a CAG promoter. In some embodiments, the short promoter is a CMV promoter. In some embodiments, the short promoter is a Myo15 promoter that is 1 kb or shorter.

In some embodiments of any of the foregoing aspects, the exon boundary is selected such that the first coding polynucleotide encodes the entire C2D domain and the second coding polynucleotide encodes the entire C2E domain. In some embodiments of any of the foregoing aspects, the first coding polynucleotide encodes exons 1-26 of a polynucleotide encoding the OTOF protein and the second coding polynucleotide encodes exons 27-48 of a polynucleotide encoding the OTOF protein. In some embodiments of any of the foregoing aspects, the first coding polynucleotide encodes exons 1-28 of a polynucleotide encoding the OTOF protein and the second coding polynucleotide encodes exons 29-48 of a polynucleotide encoding the OTOF protein. In some embodiments of any of the foregoing aspects, the first and second nucleic acid vectors contain OTOF UTRs (e.g., full-length 3' and 5' UTRs).

In some embodiments of any of the foregoing aspects, the promoter is a Myo15 promoter.

In some embodiments of any of the foregoing aspects, the promoter is a long promoter (e.g., a promoter that is longer than 1 kb, e.g., 1.1 kb, 1.25 kb, 1.5 kb, 1.75 kb, 2 kb, 2.5 kb, 3 kb or longer). In some embodiments, the long promoter is a Myo15 promoter that is longer than 1 kb (e.g., a Myo15 promoter comprising or consisting of the sequence of SEQ ID NO: 36).

In some embodiments of any of the foregoing aspects, the OTOF exon boundary is not within a portion of the first coding polynucleotide or second coding polynucleotide that encodes a C2 domain.

In some embodiments of any of the foregoing aspects, the exon boundary is selected such that the first coding polynucleotide encodes the entire C2C domain and the second coding polynucleotide encodes the entire C2D domain. In some embodiments of any of the foregoing aspects, the first coding polynucleotide encodes exons 1-19 of a polynucleotide encoding the OTOF protein and the second coding polynucleotide encodes exons 20-48 of a polynucleotide encoding the OTOF protein. In some embodiments of any of the foregoing aspects, the first coding polynucleotide encodes exons 1-20 of a polynucleotide encoding the OTOF protein and the second coding polynucleotide encodes exons 21-48 of a polynucleotide encoding the OTOF protein. In some embodiments of any of the foregoing aspects, the first nucleic acid vector and the second nucleic acid vector do not contain OTOF UTRs.

In some embodiments of any of the foregoing aspects, the exon boundary is within a portion of the first coding polynucleotide and the second coding polynucleotide that encodes the C2D domain. In some embodiments of any of the foregoing aspects, the first coding polynucleotide encodes exons 1-25 of a polynucleotide encoding the OTOF protein and the second coding polynucleotide encodes exons 26-48 of a polynucleotide encoding the OTOF protein. In some embodiments of any of the foregoing aspects, the first coding polynucleotide encodes exons 1-24 of a polynucleotide encoding the OTOF protein and the second coding polynucleotide encodes exons 25-48 of a polynucleotide encoding the OTOF protein. In some embodiments of any of the foregoing aspects, the second nucleic acid vector contains a full-length OTOF 3' UTR.

In some embodiments of any of the foregoing aspects, the splice donor sequence comprises or consists of the sequence of SEQ ID NO: 20.

In some embodiments of any of the foregoing aspects, the splice acceptor sequence comprises or consists of the sequence of SEQ ID NO: 21.

In some embodiments, the first and second nucleic acid vectors contain inverted terminal repeats (ITRs). In some embodiments of any of the foregoing aspects, the ITRs are AAV2 ITRs.

In some embodiments of any of the foregoing aspects, the poly(A) sequence is a bovine growth hormone (bGH) poly (A) signal sequence.

In some embodiments of any of the foregoing aspects, the second nucleic acid vector contains a Woodchuck Hepatitis Virus Posttranscriptional Regulatory Element (WPRE). In some embodiments of any of the foregoing aspects, the WPRE comprises or consists of the sequence of SEQ ID NO: 23. In some embodiments of any of the foregoing aspects, the WPRE comprises or consists of the sequence of SEQ ID NO: 38.

In some embodiments of any of the foregoing aspects, the composition contains a pharmaceutically acceptable excipient.

In another aspect, the invention provides a kit containing a composition of the invention.

In another aspect, the invention provides a method of increasing OTOF expression in a subject in need thereof by administering to the subject a therapeutically effective amount of a composition of the invention.

In another aspect, the invention provides a method of treating a subject having or at risk of developing sensorineural hearing loss by administering to the subject a therapeutically effective amount of a composition of the invention.

In another aspect, the invention provides a method of treating a subject having or at risk of developing auditory neuropathy by administering to the subject a therapeutically effective amount of a composition of the invention.

In another aspect, the invention provides a method of increasing OTOF expression in a subject in need thereof by administering to the subject a therapeutically effective amount of a pair of nucleic acid vectors listed in Table 4.

In another aspect, the invention provides a method of treating a subject having or at risk of developing sensorineural hearing loss by administering to the subject a therapeutically effective amount of a pair of nucleic acid vectors listed in Table 4.

In another aspect, the invention provides a method of treating a subject having or at risk of developing auditory neuropathy by administering to the subject a therapeutically effective amount of a pair of nucleic acid vectors listed in Table 4.

In some embodiments of any of the foregoing aspects, the subject has a mutation in OTOF.

In some embodiments of any of the foregoing aspects, the subject has been identified as having a mutation in OTOF.

In some embodiments of any of the foregoing aspects, the method further includes the step of identifying the subject as having a mutation in OTOF prior to administering the composition or the pair of nucleic acid vectors.

In some embodiments of any of the foregoing aspects, the method further includes the step of evaluating the hearing of the subject prior to administering the composition or the pair of nucleic acid vectors.

In some embodiments of any of the foregoing aspects, the composition or the pair of nucleic acid vectors is administered locally to the ear. In some embodiments of any of the foregoing aspects, the nucleic acid vectors are administered concurrently. In some embodiments of any of the foregoing aspects, the nucleic acid vectors are administered sequentially.

In some embodiments of any of the foregoing aspects, the method increases OTOF expression in a cochlear hair cell. In some embodiments of any of the foregoing aspects, the cochlear hair cell is an inner hair cell.

In some embodiments of any of the foregoing aspects, the subject is a mammal. In some embodiments of any of the foregoing aspects, the subject is a human.

In some embodiments of any of the foregoing aspects, the method further includes the step of evaluating the hearing of the subject after administering the composition or the pair of nucleic acid vectors. In some embodiments of any of the foregoing aspects, the method further includes the step of evaluating OTOF expression after administering the composition or the pair of nucleic acid vectors.

In some embodiments of any of the foregoing aspects, the composition or the pair of nucleic acid vectors increases OTOF expression in a cell (e.g., a cochlear hair cell), improves hearing (e.g., as assessed by standard tests, such as audiometry, auditory brainstem response (ABR), electrocochleography (ECOG), and otoacoustic emissions), prevents or reduces hearing loss, delays the development of hearing loss, slows the progression of hearing loss, improves speech discrimination, or improves hair cell function.

In some embodiments of any of the foregoing aspects, the composition or the pair of nucleic acid vectors is administered in an amount sufficient to increase OTOF expression in a cochlear hair cell, prevent or reduce hearing loss, delay the development of hearing loss, slow the progression of hearing loss, improve hearing (e.g., as assessed by standard tests, such as audiometry, ABR, ECOG, and otoacoustic emissions), improve speech discrimination, or improve hair cell function.

In another aspect, the invention provides a method of increasing OTOF expression in a cell by introducing a composition of the invention into the cell.

In another aspect, the invention provides a method of increasing OTOF expression in a cell by introducing a pair of nucleic acid vectors listed in Table 4 into the cell.

In some embodiments of any of the foregoing aspects, the cell is a cochlear hair cell. In some embodiments of any of the foregoing aspects, the cell is an inner hair cell.

In some embodiments of any of the foregoing aspects, the cell is a mammalian cell. In some embodiments of any of the foregoing aspects, the cell is a human cell.

In some embodiments of any of the foregoing aspects, the OTOF protein encoded by the pair of nucleic acid vectors has at least 85% sequence identity (e.g., 85%, 86%, 87%, 88%, 89%, 90%, 91%, 92%, 93%, 94%, 95%, 96%, 97%, 98%, 99%, or 100% identity) to the sequence of SEQ ID NO: 1, SEQ ID NO: 2, SEQ ID NO:3, SEQ ID NO: 4, or SEQ ID NO: 5. In some embodiments of any of the foregoing aspects, the OTOF protein encoded by the pair of nucleic acid vectors comprises or consists of the sequence of SEQ ID NO: 1.

In some embodiments of any of the foregoing aspects, the nucleic acid vectors are AAV vectors. In some embodiments of any of the foregoing aspects, the serotype of the AAV vectors is selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, or 7m8. In some embodiments of any of the foregoing aspects, the serotype of the AAV vectors is AAV1. In some embodiments of any of the foregoing aspects, the serotype of the AAV vectors is AAV9. In some embodiments of any of the foregoing aspects, the serotype of the AAV vectors is AAV6. In some embodiments of any of the foregoing aspects, the serotype of the AAV vectors is Anc80. In some embodiments of any of the foregoing aspects, the serotype of the AAV vectors is Anc80L65. In some embodiments of any of the foregoing aspects, the serotype of the AAV vectors is DJ/9. In some embodiments of any of the foregoing aspects, the serotype of the AAV vectors is 7m8. In some embodiments of any of the foregoing aspects, the serotype of the AAV vectors is AAV2. In some embodiments of any of the foregoing aspects, the serotype of the AAV vectors is PHP.B. In some embodiments of any of the foregoing aspects, the serotype of the AAV vectors is AAV8. In some embodiments of any of the foregoing aspects, the first and second nucleic acid vectors have the same serotype (e.g., both the first and second nucleic acid vector are AAV vectors having an AAV1 serotype or an AAV9 serotype). In some embodiments of any of the foregoing aspects, the first and second nucleic acid vectors have different serotypes (e.g., the first nucleic acid vector is an AAV having an AAV1 serotype, and the second nucleic acid vector is an AAV having an AAV9 serotype).

In some embodiments of any of the foregoing aspects, the vectors contain AAV2 ITRs.

In some embodiments of any of the foregoing aspects, the second nucleic acid vector in the pair of nucleic acid vectors contains a WPRE. In some embodiments of any of the foregoing aspects, the WPRE comprises or consists of the sequence of SEQ ID NO: 23. In some embodiments of any of the foregoing aspects, the WPRE comprises or consists of the sequence of SEQ ID NO: 38.

In some embodiments of any of the foregoing aspects, the nucleic acid vectors are overlapping dual vectors.

In some embodiments of any of the foregoing aspects, the nucleic acid vectors are trans-splicing dual vectors.

In some embodiments of any of the foregoing aspects, the nucleic acid vectors are dual hybrid vectors.

In some embodiments of any of the foregoing aspects, the recombinogenic region in the dual hybrid vectors is an AP gene fragment or an F1 phage AK gene. In some embodiments of any of the foregoing aspects, the F1 phage AK gene comprises or consists of the sequence of SEQ ID NO: 19. In some embodiments of any of the foregoing aspects, the AP gene fragment comprises or consists of the sequence of any one of SEQ ID NOs 39-44. In some embodiments of any of the foregoing aspects, the first nucleic acid vector in the pair of nucleic acid vectors further contains a degradation signal sequence positioned 3' of the recombinogenic region; and the second nucleic acid vector in the pair of nucleic acid vectors further contains a degradation signal sequence positioned between the recombinogenic region and the splice acceptor sequence. In some embodiments of any of the foregoing aspects, the degradation signal sequence comprises or consists of the sequence of SEQ ID NO: 22.

In some embodiments of any of the foregoing aspects, the splice donor sequence in the first nucleic acid vector comprises or consists of the sequence of SEQ ID NO: 20.

In some embodiments of any of the foregoing aspects, the splice acceptor sequence in the second nucleic acid vector comprises or consists of the sequence of SEQ ID NO: 21.

In some embodiments of any of the foregoing aspects, the Myo15 promoter comprises or consists of a first region having at least 85% sequence identity (e.g., 85%, 90%, 95%, 96%, 97%, 98%, 99%, or more, sequence identity) to SEQ ID NO: 24 or a functional portion or derivative thereof including the sequence of SEQ ID NO: 26 and/or SEQ ID NO: 27, operably linked to a second region having at least 85% sequence identity (e.g., 85%, 90%, 95%, 96%, 97%, 98%, 99%, or more, sequence identity) to SEQ ID NO: 25 or a functional portion or derivative thereof including the sequence of SEQ ID NO: 31 and/or SEQ ID NO: 32, optionally containing a linker including one to one hundred nucleotides (e.g., 1-5, 1-10, 1-15, 1-20, 1-25, 1-30, 1-35, 1-40, 1-45, 1-50, 1-60, 1-70, 1-80, 1-90, 10-20, 10-30, 10-40, 10-50, 10-60, 10-70, 10-80, 10-90, 10-100, 20-30, 20-40, 20-50, 20-60, 20-70, 20-80, 20-90, or 20-100 nucleotides) between the first region and the second region. In some embodiments, the first region comprises or consists of the sequence of SEQ ID NO: 24. In some embodiments, the second region comprises or consists of the sequence of SEQ ID NO: 25.

In some embodiments of any of the foregoing aspects, the Myo15 promoter comprises or consists of the sequence of SEQ ID NO: 36.

In some embodiments of any of the foregoing aspects, the Myo15 promoter comprises or consists of a first region having at least 85% sequence identity (e.g., 85%, 90%, 95%, 96%, 97%, 98%, 99%, or more, sequence identity) to SEQ ID NO: 25 or a functional portion or derivative thereof including the sequence of SEQ ID NO: 31 and/or SEQ ID NO: 32, operably linked to a second region having at least 85% sequence identity (e.g., 85%, 90%, 95%, 96%, 97%, 98%, 99%, or more, sequence identity) to SEQ ID NO: 24 or a functional portion or derivative thereof including the sequence of SEQ ID NO: 26 and/or SEQ ID NO: 27, optionally containing a linker including one to one hundred nucleotides (e.g., 1-5, 1-10, 1-15, 1-20, 1-25, 1-30, 1-35, 1-40, 1-45, 1-50, 1-60, 1-70, 1-80, 1-90, 10-20, 10-30, 10-40, 10-50, 10-60, 10-70, 10-80, 10-90, 10-100, 20-30, 20-40, 20-50, 20-60, 20-70, 20-80, 20-90, or 20-100 nucleotides) between the first region and the second region. In some embodiments, the first region comprises or consists of the sequence of SEQ ID NO: 25. In some embodiments, the second region comprises or consists of the sequence of SEQ ID NO: 24.

In some embodiments of any of the foregoing aspects, the Myo15 promoter comprises or consists of the sequence of SEQ ID NO: 37.

In some embodiments of any of the foregoing aspects, the Myo15 promoter comprises or consists of a region having at least 85% sequence identity (e.g., 85%, 90%, 95%, 96%, 97%, 98%, 99%, or more, sequence identity) to SEQ ID NO: 24 or a functional portion or derivative thereof including the sequence of SEQ ID NO: 26 and/or SEQ ID NO: 27. In some embodiments, the region comprises or consists of the sequence of SEQ ID NO: 24.

In some embodiments of any of the foregoing aspects, the Myo15 promoter comprises or consists of a region having at least 85% sequence identity (e.g., 85%, 90%, 95%, 96%, 97%, 98%, 99%, or more, sequence identity) to SEQ ID NO: 25 or a functional portion or derivative thereof including the sequence of SEQ ID NO: 31 and/or SEQ ID NO: 32. In some embodiments, the region comprises or consists of the sequence of SEQ ID NO: 25.

In some embodiments of any of the foregoing aspects, the functional portion of SEQ ID NO: 24 contains the sequence of SEQ ID NO: 26. In some embodiments of any of the foregoing aspects, the functional portion of SEQ ID NO: 24 contains the sequence of SEQ ID NO: 27. In some embodiments of any of the foregoing aspects, the functional portion of SEQ ID NO: 24 contains the sequence of SEQ ID NO: 26 and the sequence of SEQ ID NO: 27. In some embodiments of any of the foregoing aspects, the functional portion of SEQ ID NO: 24 contains the sequence of SEQ ID NO: 28. In some embodiments of any of the foregoing aspects, the functional portion of SEQ ID NO: 24 contains the sequence of SEQ ID NO: 29. In some embodiments of any of the foregoing aspects, the functional portion of SEQ ID NO: 24 contains the sequence of SEQ ID NO: 30.

In some embodiments of any of the foregoing aspects, the functional portion of SEQ ID NO: 25 contains the sequence of SEQ ID NO: 31. In some embodiments of any of the foregoing aspects, the functional portion of SEQ ID NO: 25 contains the sequence of SEQ ID NO: 32. In some embodiments of any of the foregoing aspects, the functional portion of SEQ ID NO: 25 contains the sequence of SEQ ID NO: 31 and the sequence of SEQ ID NO: 32. In some embodiments of any of the foregoing aspects, the functional portion of SEQ ID NO: 25 contains the sequence of SEQ ID NO: 33. In some embodiments of any of the foregoing aspects, the functional portion of SEQ ID NO: 25 contains the sequence of SEQ ID NO: 34. In some embodiments of any of the foregoing aspects, the functional portion of SEQ ID NO: 25 contains the sequence of SEQ ID NO: 35.

In some embodiments of any of the foregoing aspects, the Myo15 promoter induces transgene expression when operably linked to a transgene and introduced into a hair cell.

Definitions

As used herein, the term "about" refers to a value that is within 10% above or below the value being described.

As used herein, "administration" refers to providing or giving a subject a therapeutic agent (e.g., a composition containing a first nucleic acid vector containing a polynucleotide that encodes an N-terminal portion of an otoferlin protein and a second nucleic acid vector containing a polynucleotide that encodes a C-terminal portion of an otoferlin protein), by any effective route. Exemplary routes of administration are described herein below.

As used herein, the term "cell type" refers to a group of cells sharing a phenotype that is statistically separable based on gene expression data. For instance, cells of a common cell type may share similar structural and/or functional characteristics, such as similar gene activation patterns and antigen presentation profiles. Cells of a common cell type may include those that are isolated from a common tissue (e.g., epithelial tissue, neural tissue, connective tissue, or muscle tissue) and/or those that are isolated from a common organ, tissue system, blood vessel, or other structure and/or region in an organism.

As used herein, the term "cochlear hair cell" refers to group of specialized cells in the inner ear that are involved in sensing sound. There are two types of cochlear hair cells: inner hair cells and outer hair cells. Damage to cochlear hair cells and genetic mutations that disrupt cochlear hair cell function are implicated in hearing loss and deafness.

As used herein, the terms "conservative mutation," "conservative substitution," and "conservative amino acid substitution" refer to a substitution of one or more amino acids for one or more different amino acids that exhibit similar physicochemical properties, such as polarity, electrostatic charge, and steric volume. These properties are summarized for each of the twenty naturally-occurring amino acids in table 1 below.

TABLE 1

Representative physicochemical properties of naturally-occurring amino acids

| Amino Acid | 3 Letter Code | 1 Letter Code | Side-chain Polarity | Electrostatic character at physiological pH (7.4) | Steric Volume† |
|---|---|---|---|---|---|
| Alanine | Ala | A | nonpolar | neutral | small |
| Arginine | Arg | R | polar | cationic | large |
| Asparagine | Asn | N | polar | neutral | intermediate |
| Aspartic acid | Asp | D | polar | anionic | intermediate |
| Cysteine | Cys | C | nonpolar | neutral | intermediate |
| Glutamic acid | Glu | E | polar | anionic | intermediate |
| Glutamine | Gln | Q | polar | neutral | intermediate |
| Glycine | Gly | G | nonpolar | neutral | small |
| Histidine | His | H | polar | Both neutral and cationic forms in equilibrium at pH 7.4 | large |
| Isoleucine | Ile | I | nonpolar | neutral | large |
| Leucine | Leu | L | nonpolar | neutral | large |
| Lysine | Lys | K | polar | cationic | large |
| Methionine | Met | M | nonpolar | neutral | large |
| Phenylalanine | Phe | F | nonpolar | neutral | large |
| Proline | Pro | P | non-polar | neutral | intermediate |
| Serine | Ser | S | polar | neutral | small |
| Threonine | Thr | T | polar | neutral | intermediate |
| Tryptophan | Trp | W | nonpolar | neutral | bulky |
| Tyrosine | Tyr | Y | polar | neutral | large |
| Valine | Val | V | nonpolar | neutral | intermediate |

†based on volume in $A^3$: 50-100 is small, 100-150 is intermediate, 150-200 is large, and >200 is bulky From this table it is appreciated that the conservative amino acid families include (i) G, A, V, L and I; (ii) D and E; (iii) C, S and T; (iv) H, K and R; (v) N and Q; and (vi) F, Y and W. A conservative mutation or substitution is therefore one that substitutes one amino acid for a member of the same amino acid family (e.g., a substitution of Ser for Thr or Lys for Arg).

As used herein, the term "degradation signal sequence" refers to a sequence (e.g., a nucleotide sequence that can be translated into an amino acid sequence) that mediates the degradation of a polypeptide in which it is contained. Degradation signal sequences can be included in the nucleic acid vectors of the invention to reduce or prevent the expression of portions of otoferlin proteins that have not undergone recombination and/or splicing. An exemplary degradation signal sequence for use in the invention is GCCTGCAAGAACTGGTTCAGCAGCCTGAGC-CACTTCGTGATCCACCTG (SEQ ID NO: 22).

As used herein, the terms "effective amount," "therapeutically effective amount," and a "sufficient amount" of a composition, vector construct, or viral vector described herein refer to a quantity sufficient to, when administered to the subject in need thereof, including a mammal, for example a human, effect beneficial or desired results, including clinical results, and, as such, an "effective amount" or synonym thereto depends upon the context in which it is being applied. For example, in the context of treating sensorineural hearing loss, it is an amount of the composition, vector construct, or viral vector sufficient to achieve a treatment response as compared to the response obtained without administration of the composition, vector construct, or viral vector. The amount of a given composition described herein that will correspond to such an amount will vary depending upon various factors, such as the given agent, the pharmaceutical formulation, the route of administration, the type of disease or disorder, the identity of the subject (e.g. age, sex, weight) or host being treated, and the like, but can nevertheless be routinely determined by one skilled in the art. Also, as used herein, a "therapeutically effective amount" of a composition, vector construct, or viral vector of the present disclosure is an amount which results in a beneficial or desired result in a subject as compared to a control. Note that when a combination of active ingredients is administered, the effective amount of the combination may or may not include amounts of each ingredient that would have been effective if administered individually. As defined herein, a therapeutically effective amount of a composition, vector construct, viral vector or cell of the present disclosure may be readily determined by one of ordinary skill by routine methods known in the art. Dosage regime may be adjusted to provide the optimum therapeutic response.

As used herein, the term "endogenous" describes a molecule (e.g., a polypeptide, nucleic acid, or cofactor) that is found naturally in a particular organism (e.g., a human) or in a particular location within an organism (e.g., an organ, a tissue, or a cell, such as a human cell, e.g., a human cochlear hair cell).

As used herein, the term "express" refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

As used herein, the term "exogenous" describes a molecule (e.g., a polypeptide, nucleic acid, or cofactor) that is not found naturally in a particular organism (e.g., a human) or in a particular location within an organism (e.g., an organ, a tissue, or a cell, such as a human cell, e.g., a human cochlear hair cell). Exogenous materials include those that are provided from an external source to an organism or to cultured matter extracted there from.

As used herein, the term "hair cell-specific expression" refers to production of an RNA transcript or polypeptide primarily within hair cells (e.g., cochlear hair cells) as compared to other cell types of the inner ear (e.g., spiral ganglion neurons, glia, or other inner ear cell types). Hair cell-specific expression of a transgene can be confirmed by comparing transgene expression (e.g., RNA or protein expression) between various cell types of the inner ear (e.g., hair cells vs. non-hair cells) using any standard technique (e.g., quantitative RT PCR, immunohistochemistry, Western Blot analysis, or measurement of the fluorescence of a reporter (e.g., GFP) operably linked to a promoter). A hair cell-specific promoter induces expression (e.g., RNA or protein expression) of a transgene to which it is operably linked that is at least 50% greater (e.g., 50%, 75%, 100%, 125%, 150%, 175%, 200% greater or more) in hair cells (e.g., cochlear hair cells) compared to at least 3 (e.g., 3, 4, 5, 6, 7, 8, 9, 10, or more) of the following inner ear cell types: Border cells, inner phalangeal cells, inner pillar cells, outer pillar cells, first row Deiter cells, second row Deiter cells, third row Deiter cells, Hensen's cells, Claudius cells, inner sulcus cells, outer sulcus cells, spiral prominence cells, root cells, interdental cells, basal cells of the stria vascularis, intermediate cells of the stria vascularis, marginal cells of the stria vascularis, spiral ganglion neurons, Schwann cells.

As used herein, the terms "increasing" and "decreasing" refer to modulating resulting in, respectively, greater or lesser amounts, of function, expression, or activity of a metric relative to a reference. For example, subsequent to administration of a composition in a method described herein, the amount of a marker of a metric (e.g., OTOF expression) as described herein may be increased or decreased in a subject by at least 5%, 10%, 15%, 20%, 25%, 30%, 35%, 40%, 45%, 50%, 55%, 60%, 65%, 70%, 75%, 80%, 85%, 90%, 95% or 98% or more relative to the amount of the marker prior to administration. Generally, the metric is measured subsequent to administration at a time that the administration has had the recited effect, e.g., at least one week, one month, 3 months, or 6 months, after a treatment regimen has begun.

As used herein, the term "intron" refers to a region within the coding region of a gene, the nucleotide sequence of which is not translated into the amino acid sequence of the corresponding protein. The term intron also refers to the corresponding region of the RNA transcribed from a gene. Introns are transcribed into pre-mRNA, but are removed during processing, and are not included in the mature mRNA.

As used herein, "locally" or "local administration" means administration at a particular site of the body intended for a local effect and not a systemic effect. Examples of local administration are epicutaneous, inhalational, intra-articular, intrathecal, intravaginal, intravitreal, intrauterine, intra-lesional administration, lymph node administration, intratumoral administration, administration to the inner ear, and administration to a mucous membrane of the subject, wherein the administration is intended to have a local and not a systemic effect.

As used herein, the term "operably linked" refers to a first molecule that can be joined to a second molecule, wherein the molecules are so arranged that the first molecule affects the function of the second molecule. The term "operably linked" includes the juxtaposition of two or more components (e.g., a promoter and another sequence element) such that both components function normally and allow for the possibility that at least one of the components can mediate a function that is exerted upon at least one of the other components. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell. In additional embodiments, two portions of a transcription regulatory element are operably linked to one another if they are joined such that the transcription-activating functionality of one portion is not adversely affected by the presence of the other portion. Two transcription regulatory elements may be operably linked to one another by way of a linker nucleic acid (e.g., an intervening non-coding nucleic acid) or may be operably linked to one another with no intervening nucleotides present.

As used herein, the terms "otoferlin" and "OTOF" refer to the gene associated with nonsyndromic recessive deafness DNFB9. The terms "otoferlin" and "OTOF" also refer to variants of wild-type OTOF protein and nucleic acids encoding the same, such as variant proteins having at least 85% sequence identity (e.g., 85%, 86%, 87%, 88%, 89%, 90%, 91%, 92%, 93%, 94%, 95%, 96%, 97%, 98%, 99%, or 99.9% identity, or more) to the amino acid sequence of a wild-type OTOF protein (e.g., SEQ ID NO: 1) or polynucleotides having at least 85% sequence identity (e.g., 85%, 86%, 87%, 88%, 89%, 90%, 91%, 92%, 93%, 94%, 95%, 96%, 97%, 98%, 99%, or 99.9% identity, or more) to the nucleic acid sequence of a wild-type OTOF gene, provided that the OTOF analog encoded retains the therapeutic function of wild-type OTOF. As used herein, OTOF may refer to the protein localized to inner hair cells or to the gene encoding this protein, depending upon the context, as will be appreciated by one of skill in the art.

As used herein, the term "plasmid" refers to a to an extrachromosomal circular double stranded DNA molecule into which additional DNA segments may be ligated. A plasmid is a type of vector, a nucleic acid molecule capable of transporting another nucleic acid to which it has been linked. Certain plasmids are capable of autonomous replication in a host cell into which they are introduced (e.g., bacterial plasmids having a bacterial origin of replication and episomal mammalian plasmids). Other vectors (e.g., non-episomal mammalian vectors) can be integrated into the genome of a host cell upon introduction into the host cell, and thereby are replicated along with the host genome. Certain plasmids are capable of directing the expression of genes to which they are operably linked.

As used herein, the terms "nucleic acid" and "polynucleotide," used interchangeably herein, refer to a polymeric form of nucleosides in any length. Typically a polynucleotide is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However the term encompasses molecules containing nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. "Polynucleotide sequence" as used herein can refer to the polynucleotide material itself and/or to the sequence information (i.e., the succession of letters used as abbreviations for bases) that biochemically characterizes a specific nucleic acid. A polynucleotide sequence presented herein is presented in a 5' to 3' direction unless otherwise indicated.

As used herein, the terms "complementarity" or "complementary" of nucleic acids means that a nucleotide sequence in one strand of nucleic acid, due to orientation of its nucleobase groups, forms hydrogen bonds with another sequence on an opposing nucleic acid strand. The complementary bases in DNA are typically A with T and C with G. In RNA, they are typically C with G and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm (melting temperature) of hybridized strands, or by empirical determination of Tm by using routine methods. Tm includes the temperature at which a population of hybridization complexes formed between two nucleic acid strands are 50% denatured (i.e., a population of double-stranded nucleic acid molecules becomes half dissociated into single strands). At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+0.41 (% G+C), although other known Tm computations take into account nucleic acid structural characteristics.

As used herein, the term "promoter" refers to a recognition site on DNA that is bound by an RNA polymerase. The polymerase drives transcription of the transgene. Exemplary promoters suitable for use with the compositions and methods described herein include constitutive promoters (e.g., the CAG promoter and cytomegalovirus (CMV) promoter), cochlear hair cell-specific promoters (e.g., the Myosin 15 (Myo15) promoter, the Myosin 7A (Myo7A) promoter, the Myosin 6 (Myo6) promoter, the POU Class 4 Homeobox 3 (POU4F3) promoter), and inner hair cell-specific promoters (e.g., the Fibroblast growth factor 8 (FGF8) promoter, the vesicular glutamate transporter 3 (VGLUT3) promoter, and the OTOF promoter).

"Percent (%) sequence identity" with respect to a reference polynucleotide or polypeptide sequence is defined as the percentage of nucleic acids or amino acids in a candidate sequence that are identical to the nucleic acids or amino acids in the reference polynucleotide or polypeptide sequence, after aligning the sequences and introducing gaps, if necessary, to achieve the maximum percent sequence identity. Alignment for purposes of determining percent nucleic acid or amino acid sequence identity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal alignment over the full-length of the sequences being compared. For example, percent sequence identity values may be generated using the sequence comparison computer program BLAST. As an illustration, the percent sequence identity of a given nucleic acid or amino acid sequence, A, to, with, or against a given nucleic acid or amino acid sequence, B, (which can alternatively be phrased as a given nucleic acid or amino acid sequence, A that has a certain percent sequence identity to, with, or against a given nucleic acid or amino acid sequence, B) is calculated as follows:

100 multiplied by (the fraction $X/Y$)

where X is the number of nucleotides or amino acids scored as identical matches by a sequence alignment program (e.g., BLAST) in that program's alignment of A and B, and where Y is the total number of nucleic acids in B. It will be appreciated that where the length of nucleic acid or amino acid sequence A is not equal to the length of nucleic acid or amino acid sequence B, the percent sequence identity of A to B will not equal the percent sequence identity of B to A.

The term "derivative" as used herein refers to a nucleic acid, peptide, or protein or a variant or analog thereof comprising one or more mutations and/or chemical modifications as compared to a corresponding full-length wild-type nucleic acid, peptide, or protein. Non-limiting examples of chemical modifications involving nucleic acids include, for example, modifications to the base moiety, sugar moiety, phosphate moiety, phosphate-sugar backbone, or a combination thereof.

As used herein, the term "pharmaceutical composition" refers to a mixture containing a therapeutic agent, optionally in combination with one or more pharmaceutically acceptable excipients, diluents, and/or carriers, to be administered to a subject, such as a mammal, e.g., a human, in order to prevent, treat or control a particular disease or condition affecting or that may affect the subject.

As used herein, the term "pharmaceutically acceptable" refers to those compounds, materials, compositions and/or dosage forms, which are suitable for contact with the tissues of a subject, such as a mammal (e.g., a human) without excessive toxicity, irritation, allergic response and other problem complications commensurate with a reasonable benefit/risk ratio. Preferably, the term "pharmaceutically acceptable" means approved by a regulatory agency of the Federal or a state government or listed in the U.S. Pharmacopeia or other generally recognized pharmacopeia for use in mammals, and more particularly in humans.

As used herein, the term "recombinogenic region" refers to a region of homology that mediates recombination between two different sequences.

As used herein, the term "regulatory sequence" includes promoters, enhancers and other expression control elements (e.g., polyadenylation signals) that control the transcription or translation of the polynucleotides that encode OTOF. Such regulatory sequences are described, for example, in Goeddel, Gene Expression Technology: Methods in Enzymology 185 (Academic Press, San Diego, CA, 1990); incorporated herein by reference.

As used herein, the term "sample" refers to a specimen (e.g., blood, blood component (e.g., serum or plasma), urine, saliva, amniotic fluid, cerebrospinal fluid, tissue (e.g., placental or dermal), pancreatic fluid, chorionic villus sample, and cells) isolated from a subject.

As used herein, the term "transfection" refers to any of a wide variety of techniques commonly used for the introduction of exogenous DNA into a prokaryotic or eukaryotic host cell, e.g., electroporation, lipofection, calcium-phosphate precipitation, DEAE-dextran transfection, Nucleofection, squeeze-poration, sonoporation, optical transfection, Magnetofection, impalefection and the like.

As used herein, the terms "subject" and "patient" refer to an animal (e.g., a mammal, such as a human), veterinary animals (e.g., cats, dogs, cows, horses, sheep, pigs, etc.) and experimental animal models of diseases (e.g., mice, rats). A subject to be treated according to the methods described herein may be one who has been diagnosed with hearing loss (e.g., hearing loss associated with a mutation in OTOF), or one at risk of developing these conditions. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

As used herein, the terms "transduction" and "transduce" refer to a method of introducing a vector construct or a part thereof into a cell. Wherein the vector construct is contained in a viral vector such as for example an AAV vector, transduction refers to viral infection of the cell and subsequent transfer and integration of the vector construct or part thereof into the cell genome.

As used herein, "treatment" and "treating" of a state, disorder or condition can include: (1) preventing, delaying, or reducing the incidence and/or likelihood of the appearance of at least one clinical or sub-clinical symptom of the state, disorder or condition developing in a subject that may be afflicted with or predisposed to the state, disorder or condition, but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

As used herein, the term "vector" includes a nucleic acid vector, e.g., a DNA vector, such as a plasmid, a RNA vector, virus or other suitable replicon (e.g., viral vector). A variety of vectors have been developed for the delivery of polynucleotides encoding exogenous proteins into a prokaryotic or eukaryotic cell. Examples of such expression vectors are disclosed in, e.g., WO94/11026; incorporated herein by reference as it pertains to vectors suitable for the expression of a gene of interest. Expression vectors suitable for use with the compositions and methods described herein contain a polynucleotide sequence as well as, e.g., additional sequence elements used for the expression of proteins and/or the integration of these polynucleotide sequences into the genome of a mammalian cell. Certain vectors that can be used for the expression of OTOF as described herein include vectors that contain regulatory sequences, such as promoter and enhancer regions, which direct gene transcription. Other useful vectors for expression of OTOF contain polynucleotide sequences that enhance the rate of translation of these genes or improve the stability or nuclear export of the mRNA that results from gene transcription. These sequence elements include, e.g., 5' and 3' untranslated regions and a polyadenylation signal site in order to direct efficient transcription of the gene carried on the expression vector. The expression vectors suitable for use with the compositions and methods described herein may also contain a polynucleotide encoding a marker for selection of cells that contain such a vector. Examples of a suitable marker include genes that encode resistance to antibiotics, such as ampicillin, chloramphenicol, kanamycin, or nourseothricin.

As used herein, the term "wild-type" refers to a genotype with the highest frequency for a particular gene in a given organism.

DETAILED DESCRIPTION

Figure 1A:
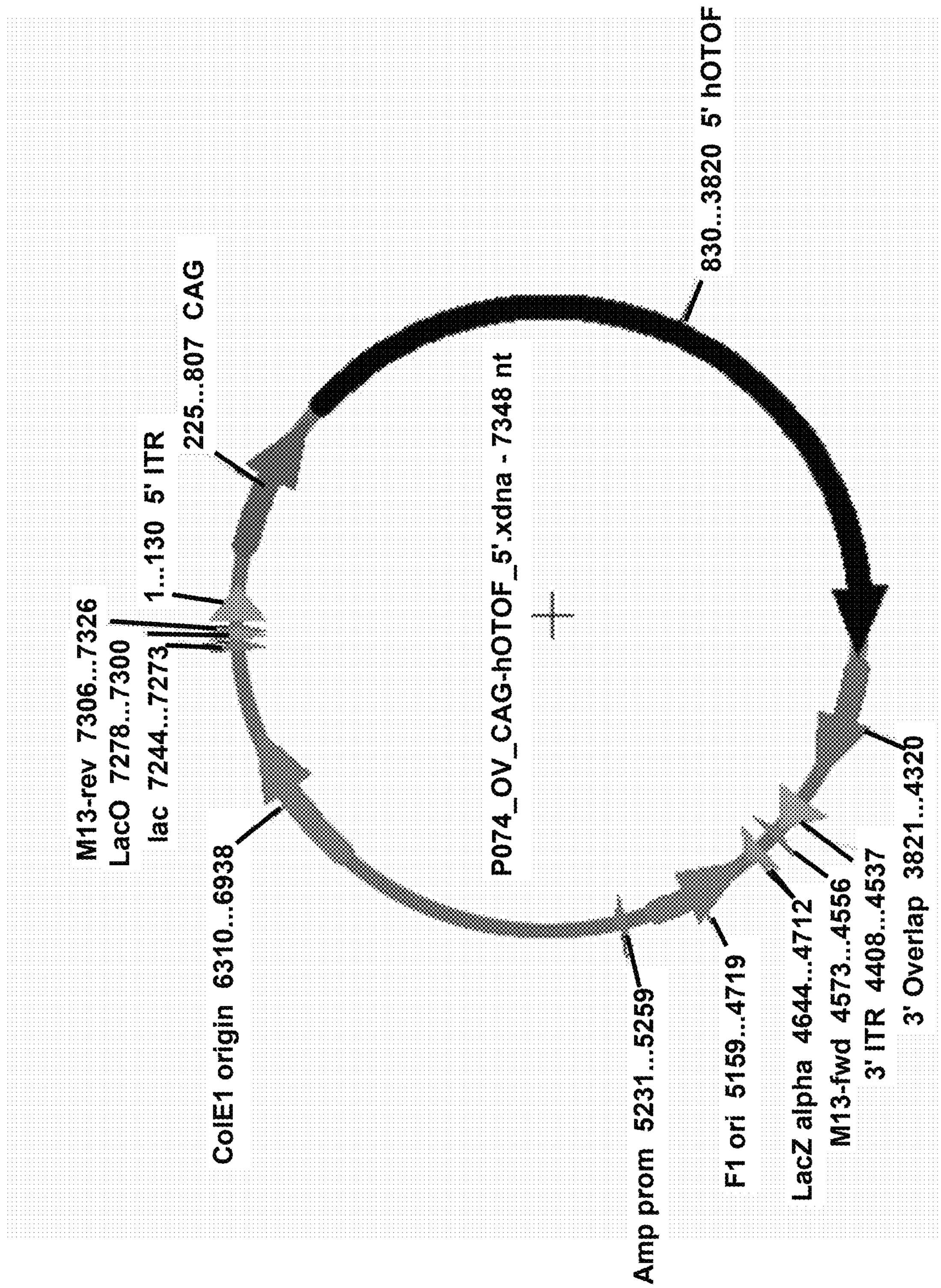
FIGS. 1A and 1B are maps of the 5' and 3' vectors in an overlapping dual vector system. The 5' vector contains AAV2 ITRs, and a CAG promoter operably linked to exons 1-24 of a polynucleotide encoding the human OTOF protein of SEQ ID NO: 1 and the 500 kb immediately 3' of the exon 24/25 boundary (FIG. 1A). The 3' vector contains AAV2 ITRs, the 500 kb immediately 5' of the exon 24/25 boundary and exons 25-48 of a polynucleotide encoding the human OTOF protein of SEQ ID NO: 1, and a WPRE sequence (SEQ ID NO: 23) (FIG. 1B).
Figure 1B:
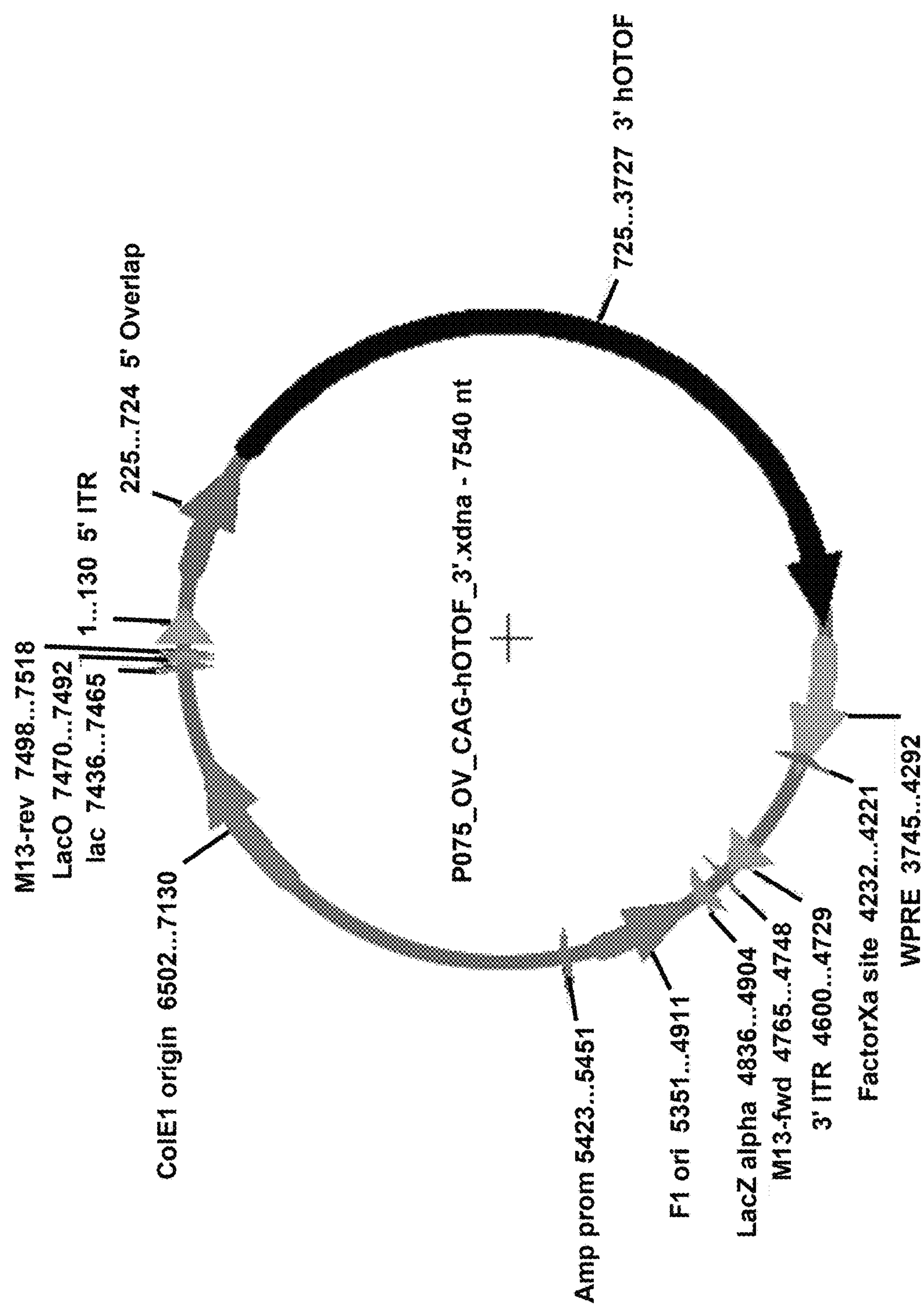
Figure 2A:
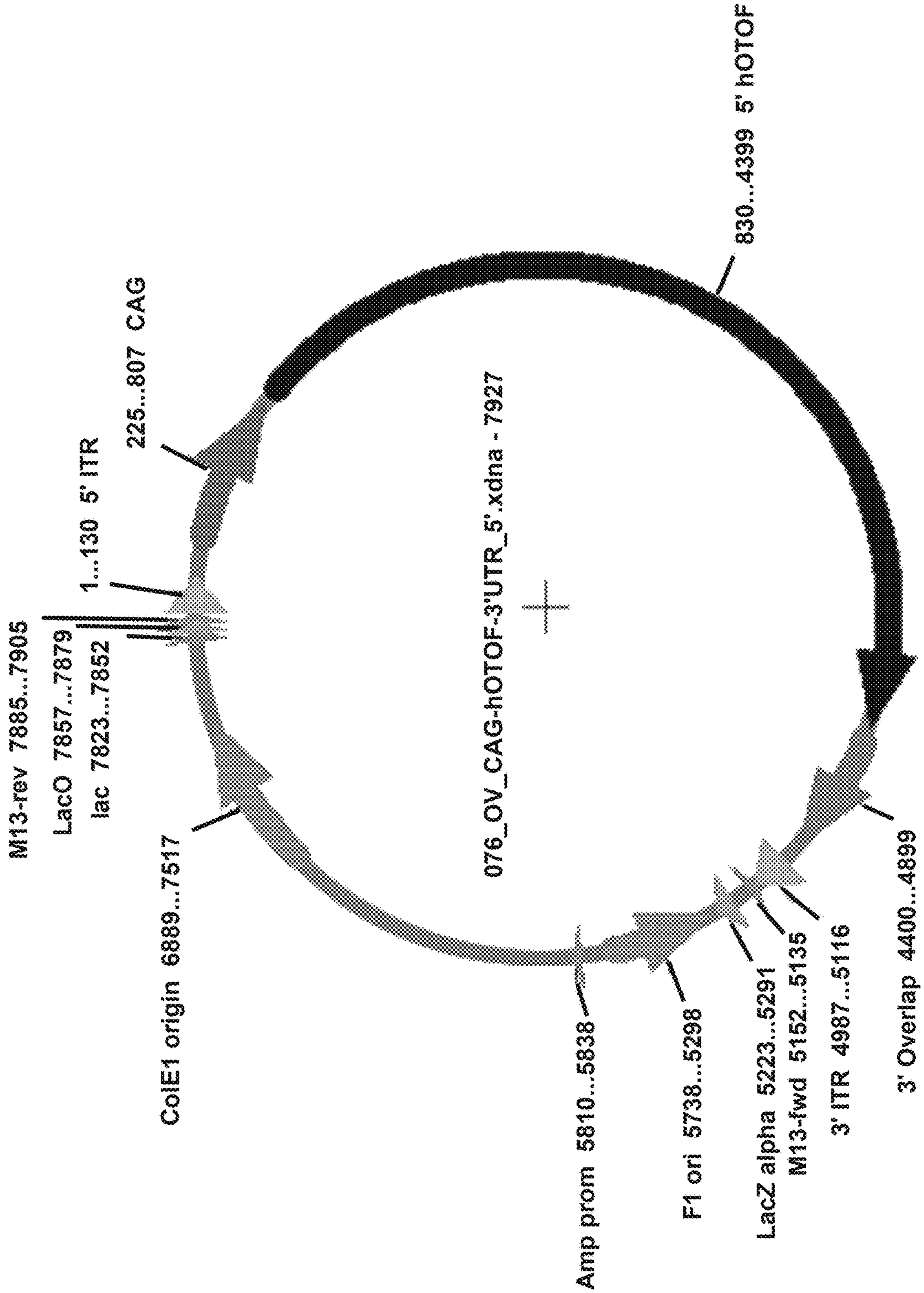
FIGS. 2A and 2B are maps of the 5' and 3' vectors in an overlapping dual vector system. The 5' vector contains AAV2 ITRs, and a CAG promoter operably linked to exons 1-28 of a polynucleotide encoding the human OTOF protein of SEQ ID NO: 1 and the 500 kb immediately 3' of the exon 28/29 boundary (FIG. 2A). The 3' vector contains AAV2 ITRs, the 500 kb immediately 5' of the exon 28/29 boundary and exons 29-48 of a polynucleotide encoding the human OTOF protein of SEQ ID NO: 1, the full-length human OTOF 3' UTR, and a WPRE sequence (SEQ ID NO: 23) (FIG. 2B).
Figure 2B:
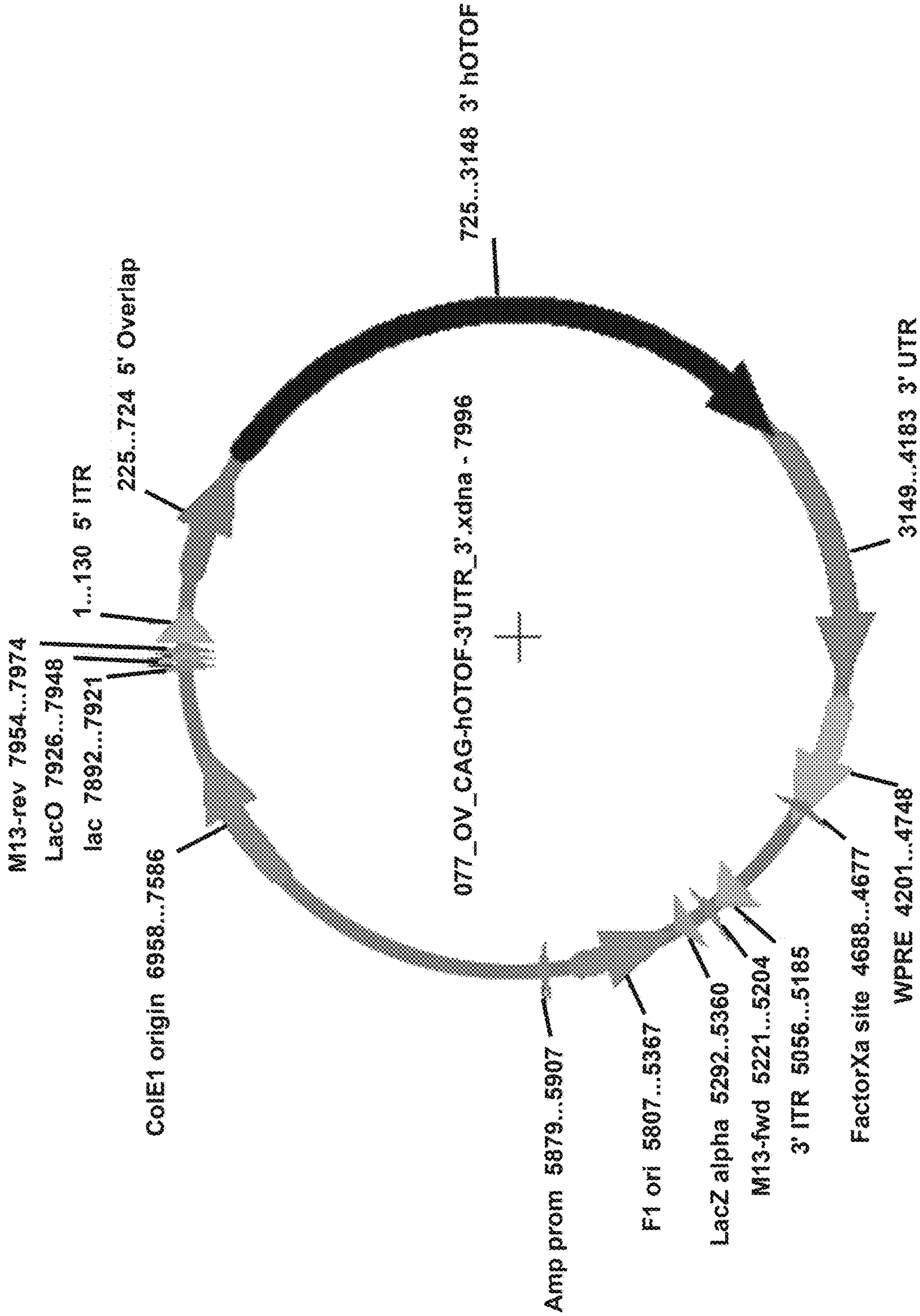
Figure 3A:
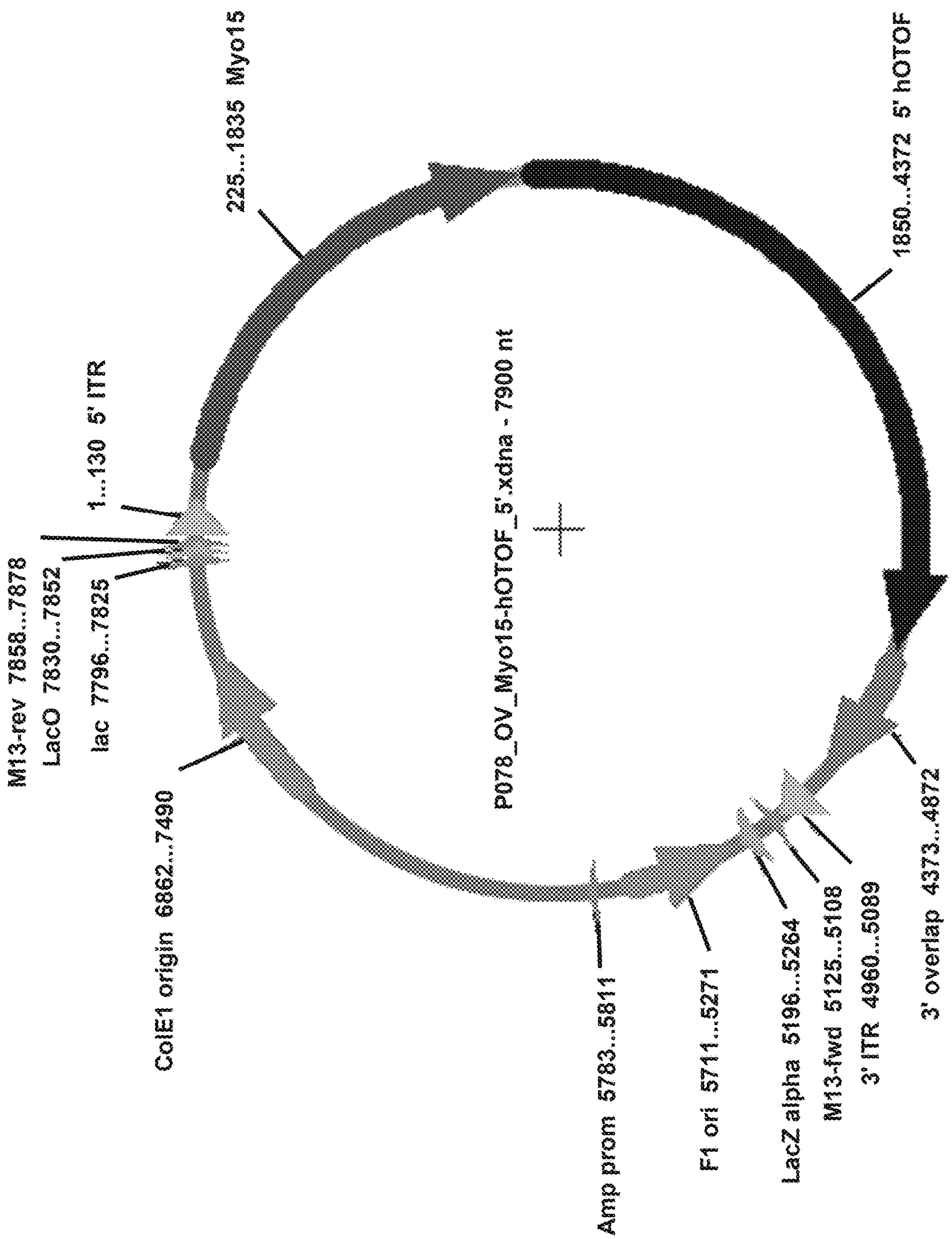
FIGS. 3A and 3B are maps of the 5' and 3' vectors in an overlapping dual vector system. The 5' vector contains AAV2 ITRs, and a Myo15 promoter (SEQ ID NO: 36) operably linked to exons 1-21 of a polynucleotide encoding the human OTOF protein of SEQ ID NO: 1 and the 500 kb immediately 3' of the exon 21/22 boundary (FIG. 3A). The 3' vector contains AAV2 ITRs, the 500 kb immediately 5' of the exon 21/22 boundary and exons 22-48 of a polynucleotide encoding the human OTOF protein of SEQ ID NO: 1, and a WPRE sequence (SEQ ID NO: 23) (FIG. 3B).
Figure 3B:
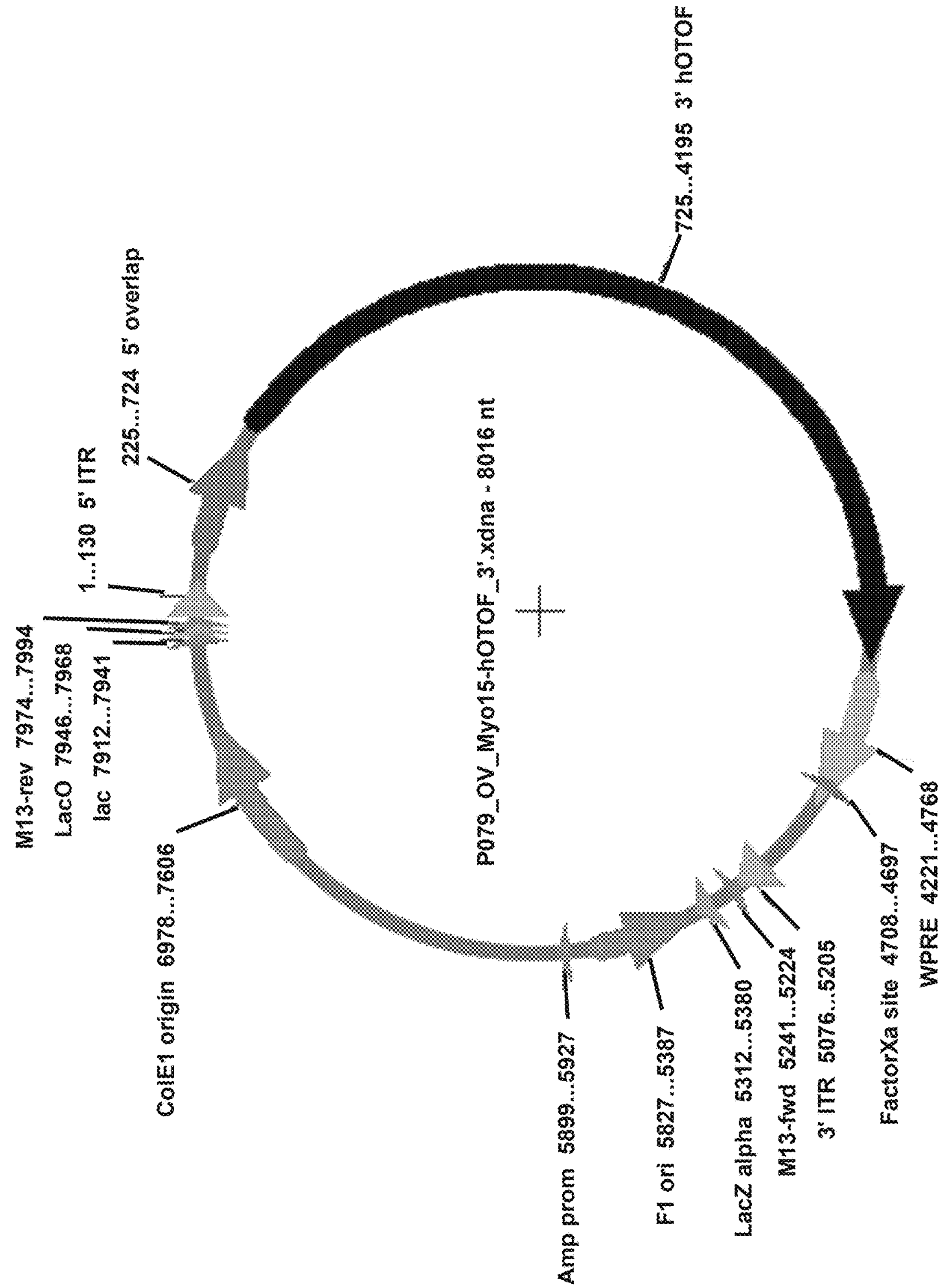
Figure 4A:
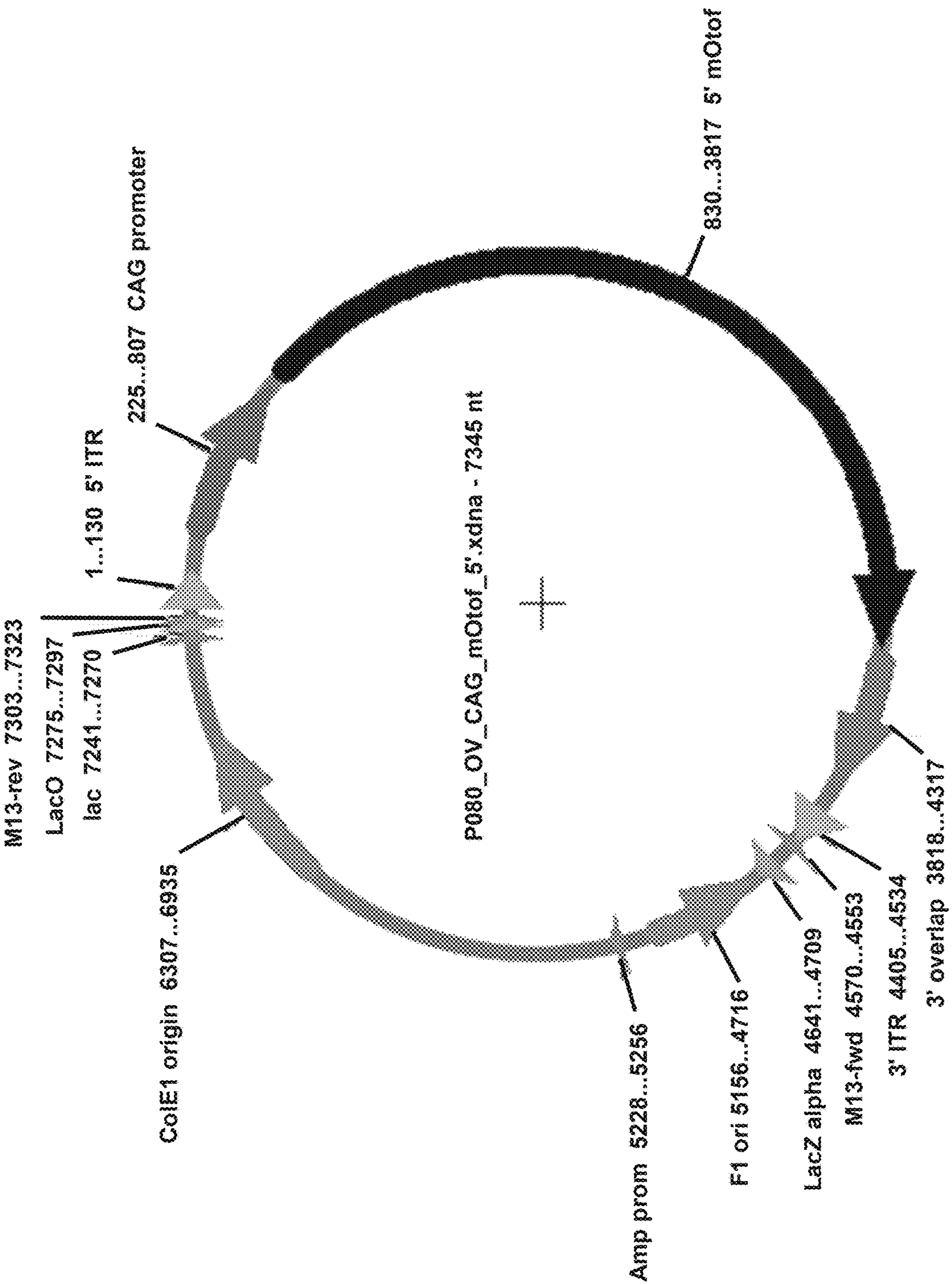
FIGS. 4A and 4B are maps of the 5' and 3' vectors in an overlapping dual vector system. The 5' vector contains AAV2 ITRs, and a CAG promoter operably linked to exons 1-24 of a polynucleotide encoding the mouse OTOF protein of SEQ ID NO: 6 and the 500 kb immediately 3' of the exon 24/25 boundary (FIG. 4A). The 3' vector contains AAV2 ITRs, the 500 kb immediately 5' of the exon 24/25 boundary and exons 25-48 of a polynucleotide encoding the mouse OTOF protein of SEQ ID NO: 6, and a WPRE sequence (SEQ ID NO: 23) (FIG. 4B).
Figure 4B:
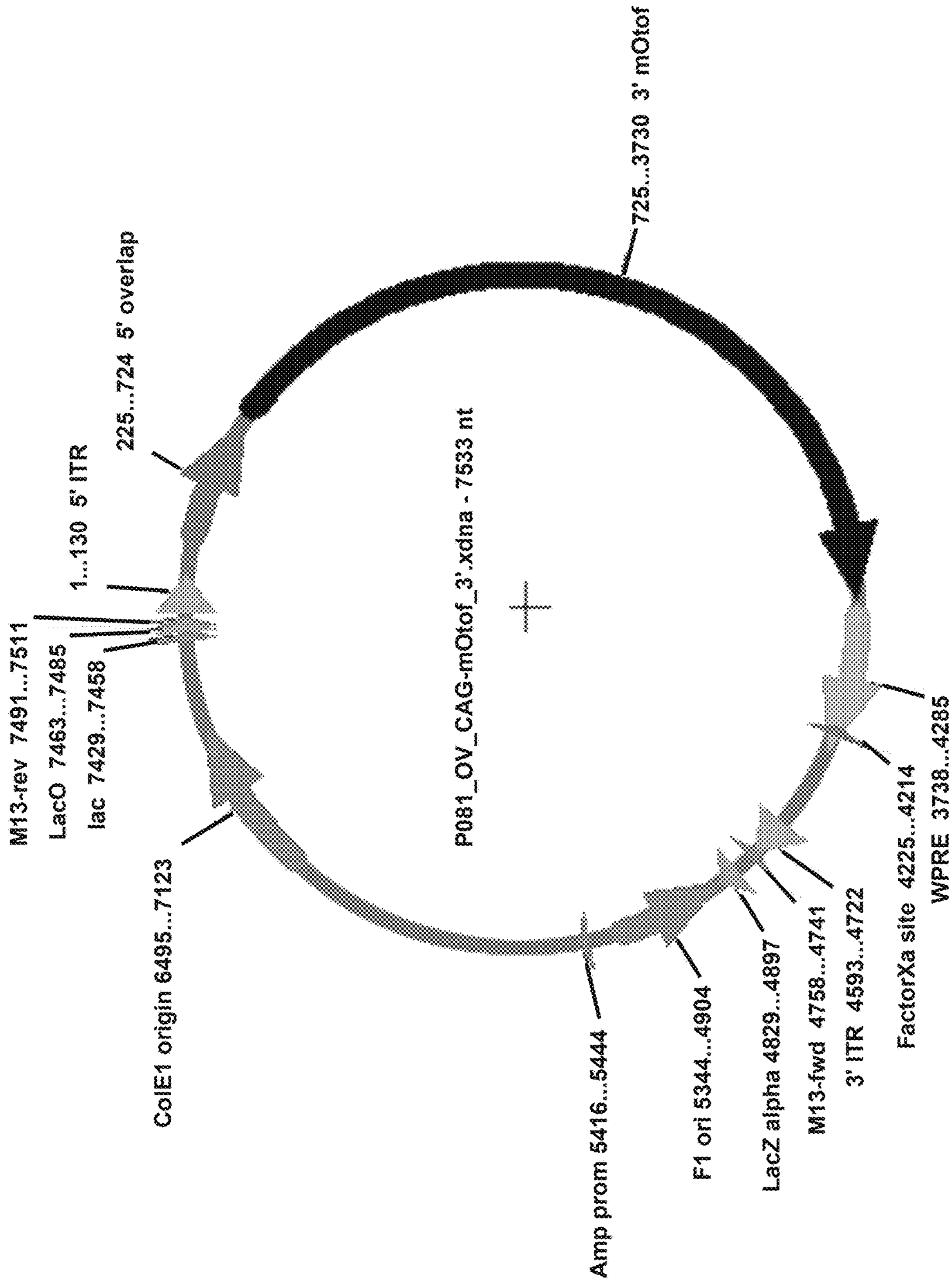
Figure 5A:
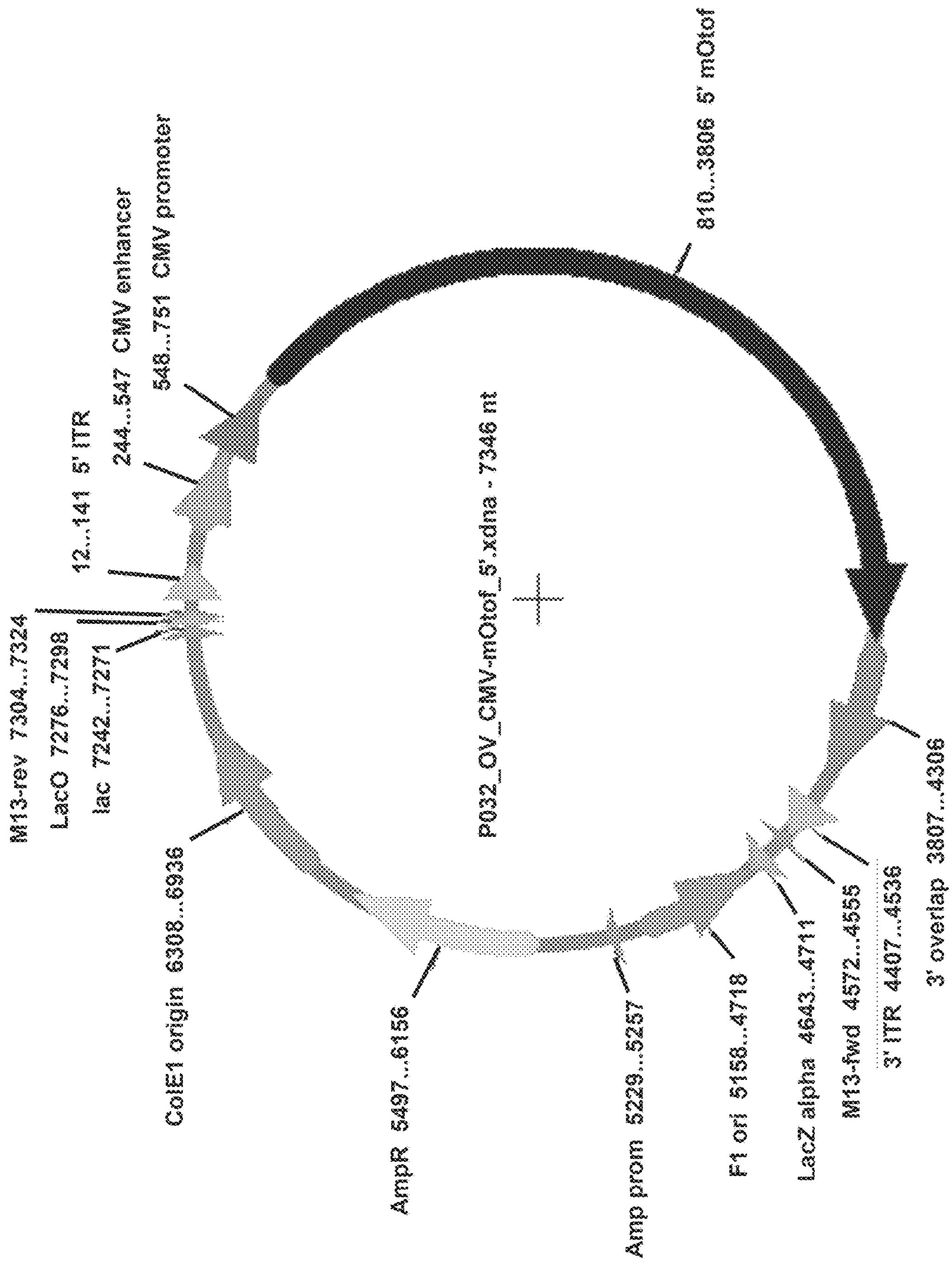
FIGS. 5A and 5B are maps of the 5' and 3' vectors in an overlapping dual vector system. The 5' vector contains AAV2 ITRs, a CMV enhancer, and a CMV promoter operably linked to exons 1-24 of a polynucleotide encoding the mouse OTOF protein of SEQ ID NO: 6 and the 500 kb immediately 3' of the exon 24/25 boundary (FIG. 5A). The 3' vector contains AAV2 ITRs, the 500 kb immediately 5' of the exon 24/25 boundary and exons 25-48 of a polynucleotide encoding the mouse OTOF protein of SEQ ID NO: 6, and a WPRE sequence (SEQ ID NO: 23) (FIG. 5B).
Figure 5B:
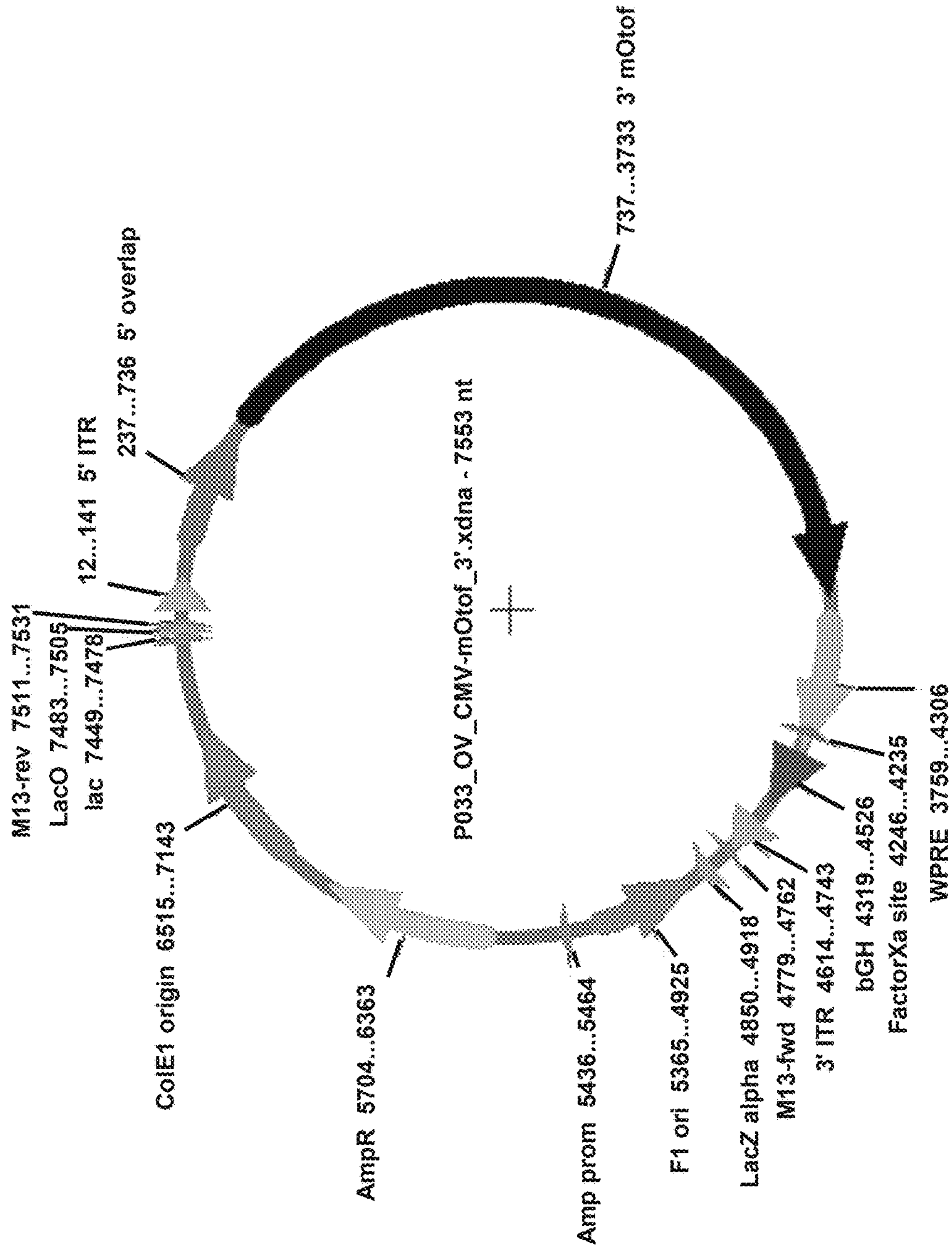
Figure 6A:
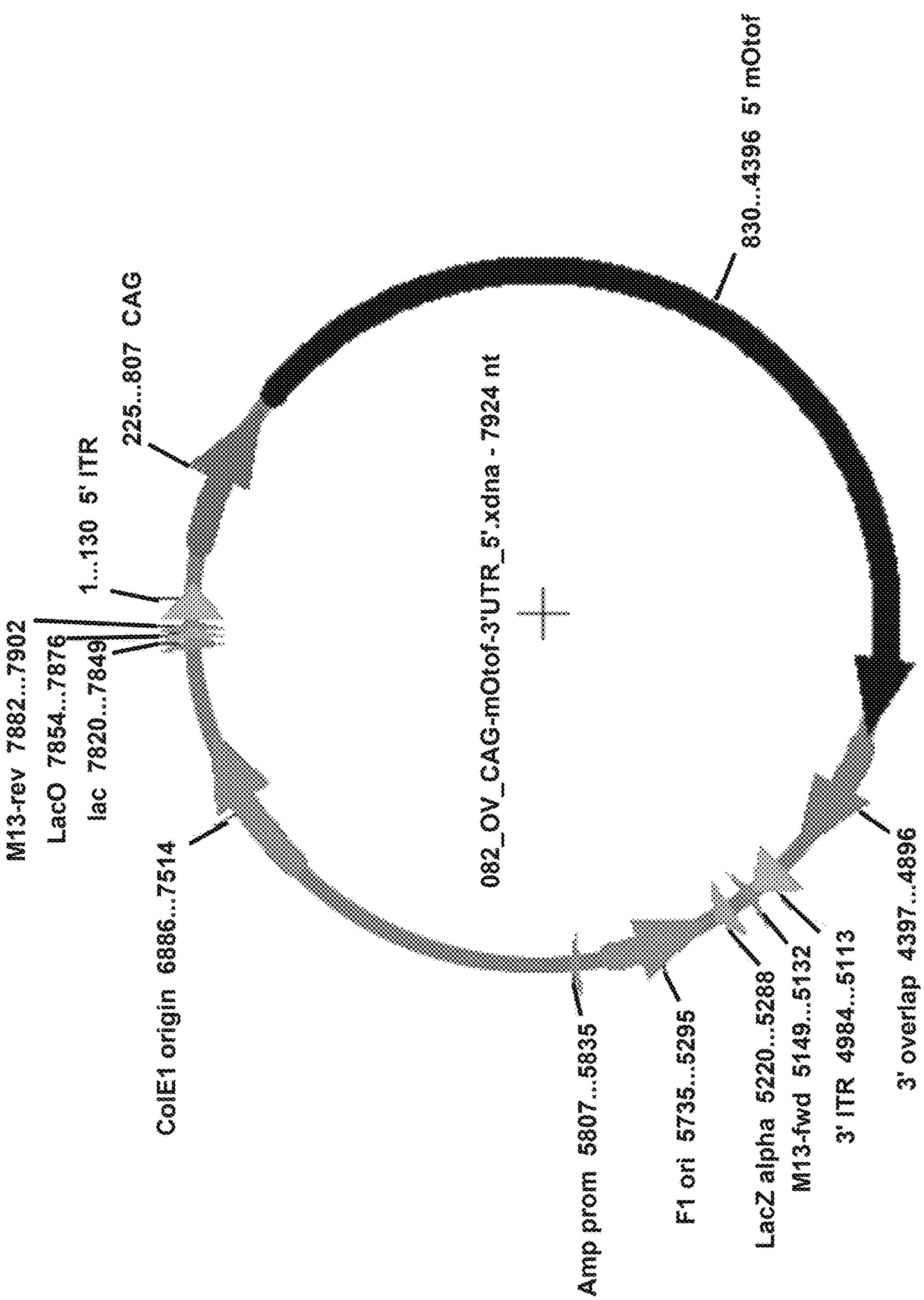
FIGS. 6A and 6B are maps of the 5' and 3' vectors in an overlapping dual vector system. The 5' vector contains AAV2 ITRs, and a CAG promoter operably linked to exons 1-28 of a polynucleotide encoding the mouse OTOF protein of SEQ ID NO: 6 and the 500 kb immediately 3' of the exon 28/29 boundary (FIG. 6A). The 3' vector contains AAV2 ITRs, the 500 kb immediately 5' of the exon 28/29 boundary and exons 29-48 of a polynucleotide encoding the mouse OTOF protein of SEQ ID NO: 6, the full-length mouse OTOF 3' UTR, and a WPRE sequence (SEQ ID NO: 23) (FIG. 6B).
Figure 6B:
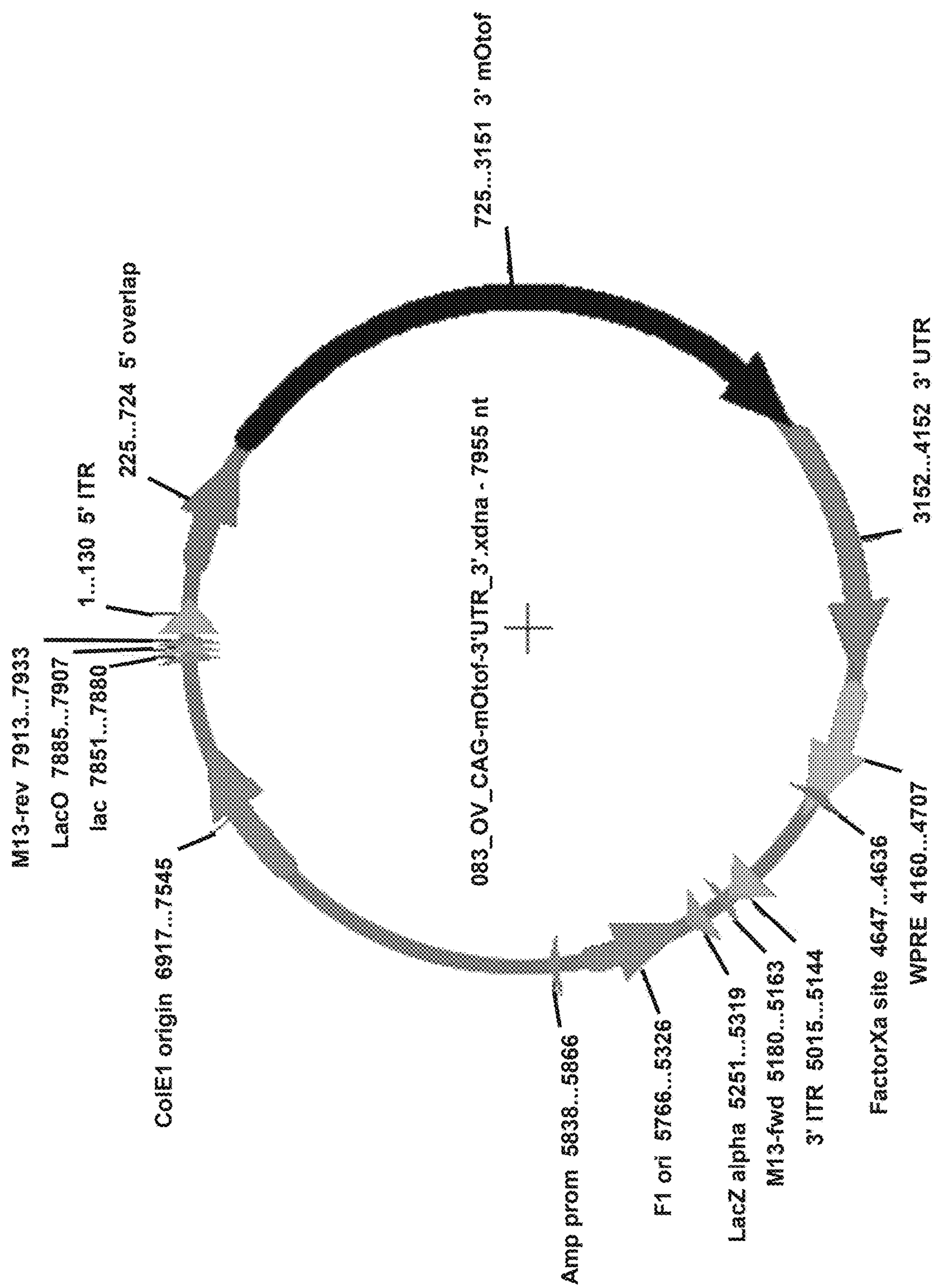
Figure 7A:
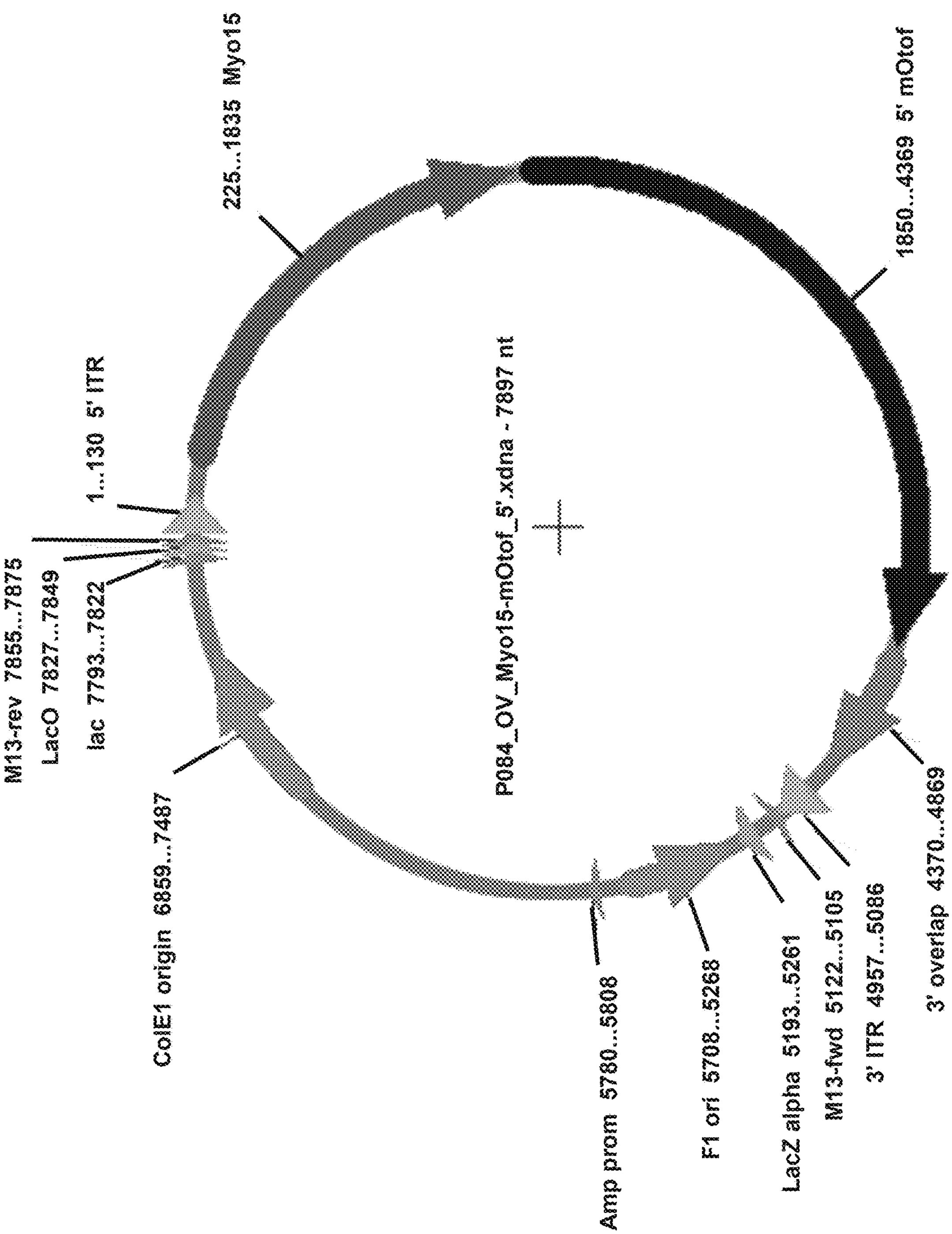
FIGS. 7A and 7B are maps of the 5' and 3' vectors in an overlapping dual vector system. The 5' vector contains AAV2 ITRs, and a Myo15 promoter (SEQ ID NO: 36) operably linked to exons 1-21 of a polynucleotide encoding the mouse OTOF protein of SEQ ID NO: 6 and the 500 kb immediately 3' of the exon 21/22 boundary (FIG. 7A). The 3' vector contains AAV2 ITRs, the 500 kb immediately 5' of the exon 21/22 boundary and exons 22-48 of a polynucleotide encoding the mouse OTOF protein of SEQ ID NO: 6, and a WPRE sequence (SEQ ID NO: 23) (FIG. 7B).
Figure 7B:
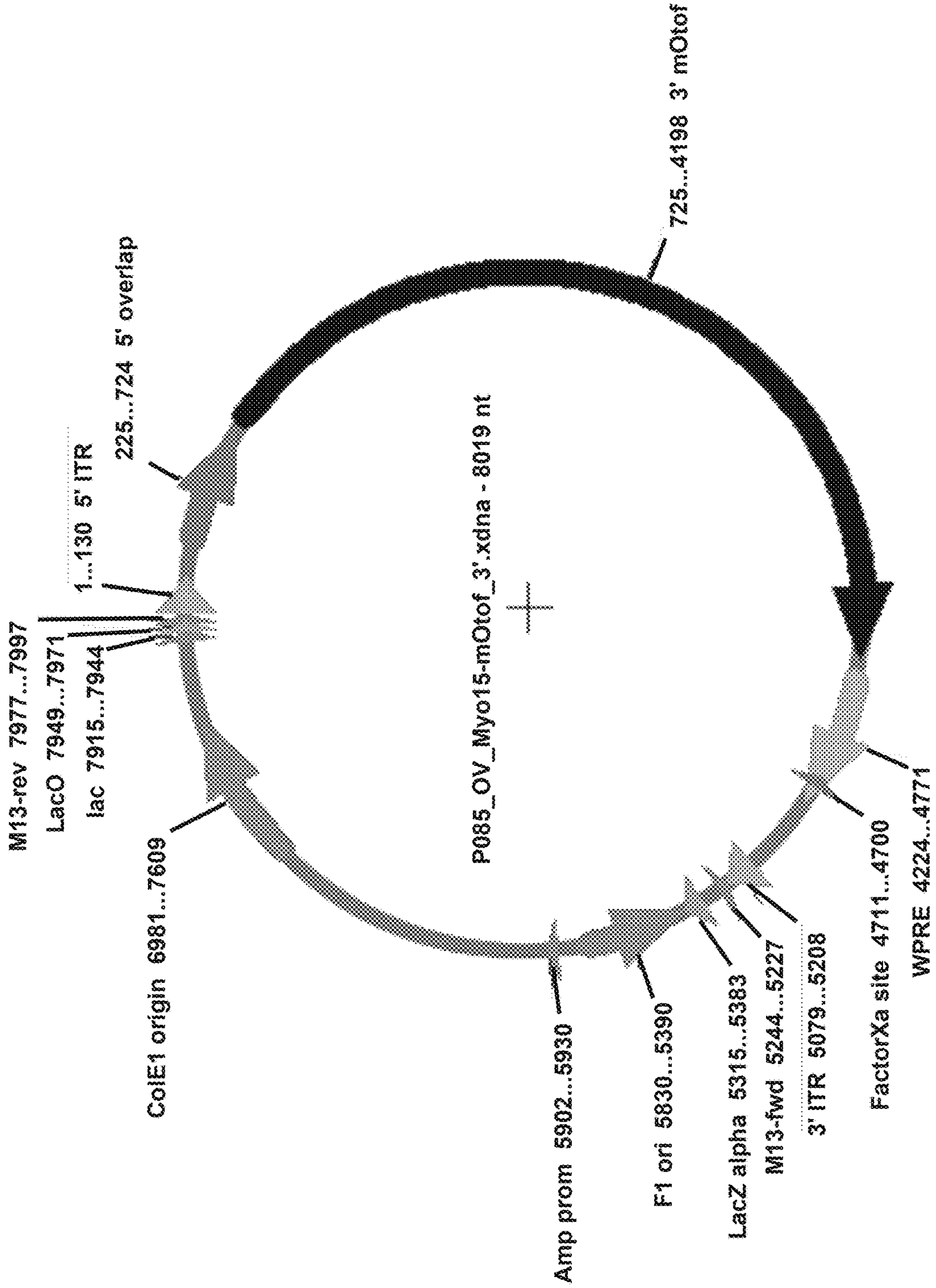
Figure 8A:
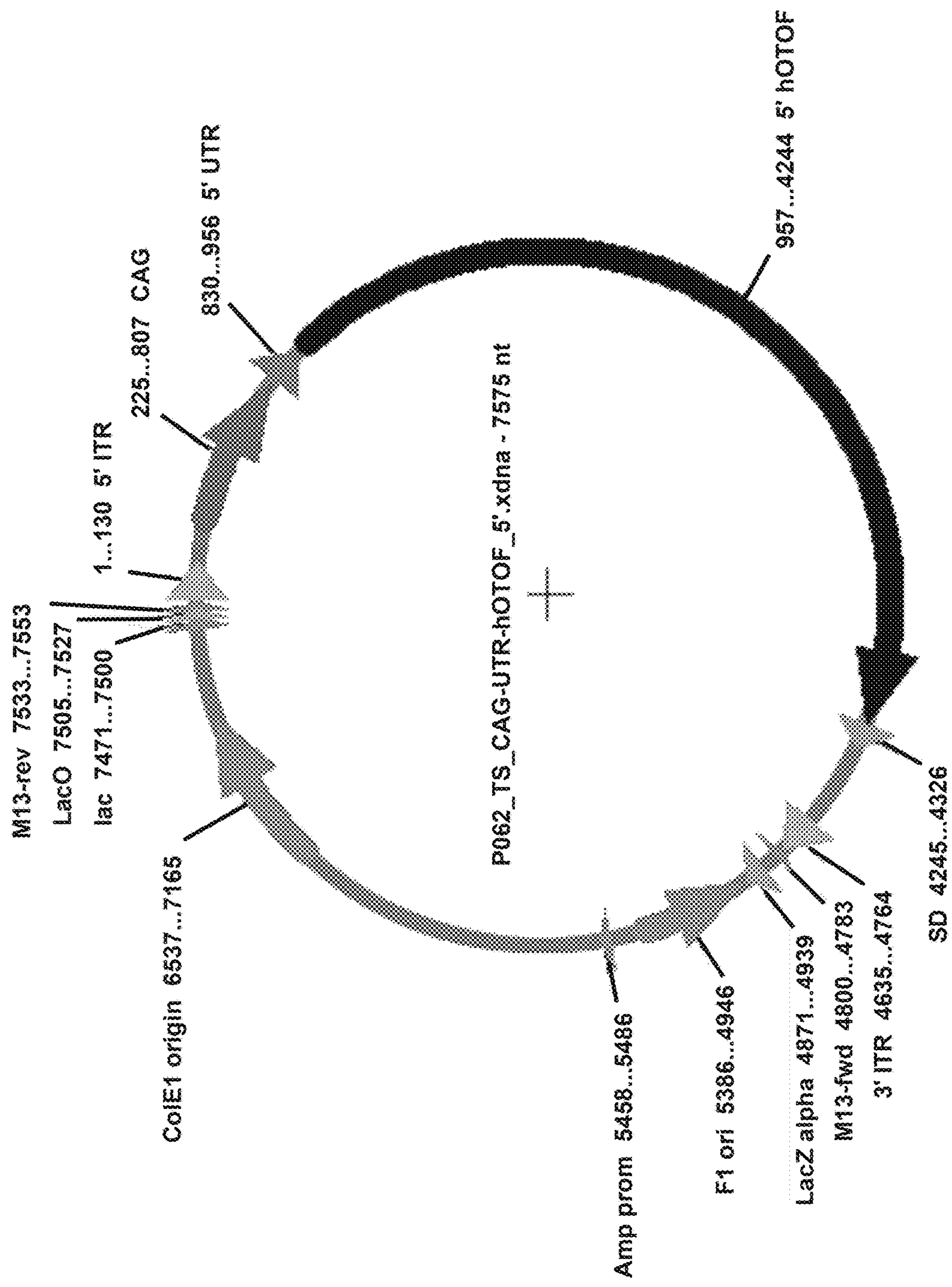
FIGS. 8A and 8B are maps of the 5' and 3' vectors in a trans-splicing dual vector system. The 5' vector contains AAV2 ITRs, a CAG promoter operably linked to the full-length human OTOF 5' UTR and exons 1-26 of a polynucleotide encoding the human OTOF protein of SEQ ID NO: 1, and a splice donor sequence (SD) (FIG. 8A). The 3' vector contains AAV2 ITRs, a splice acceptor sequence (SA), exons 27-48 of a polynucleotide encoding the human OTOF protein of SEQ ID NO: 1, the full-length human OTOF 3' UTR, and a WPRE sequence (SEQ ID NO: 23) (FIG. 8B).
Figure 8B:
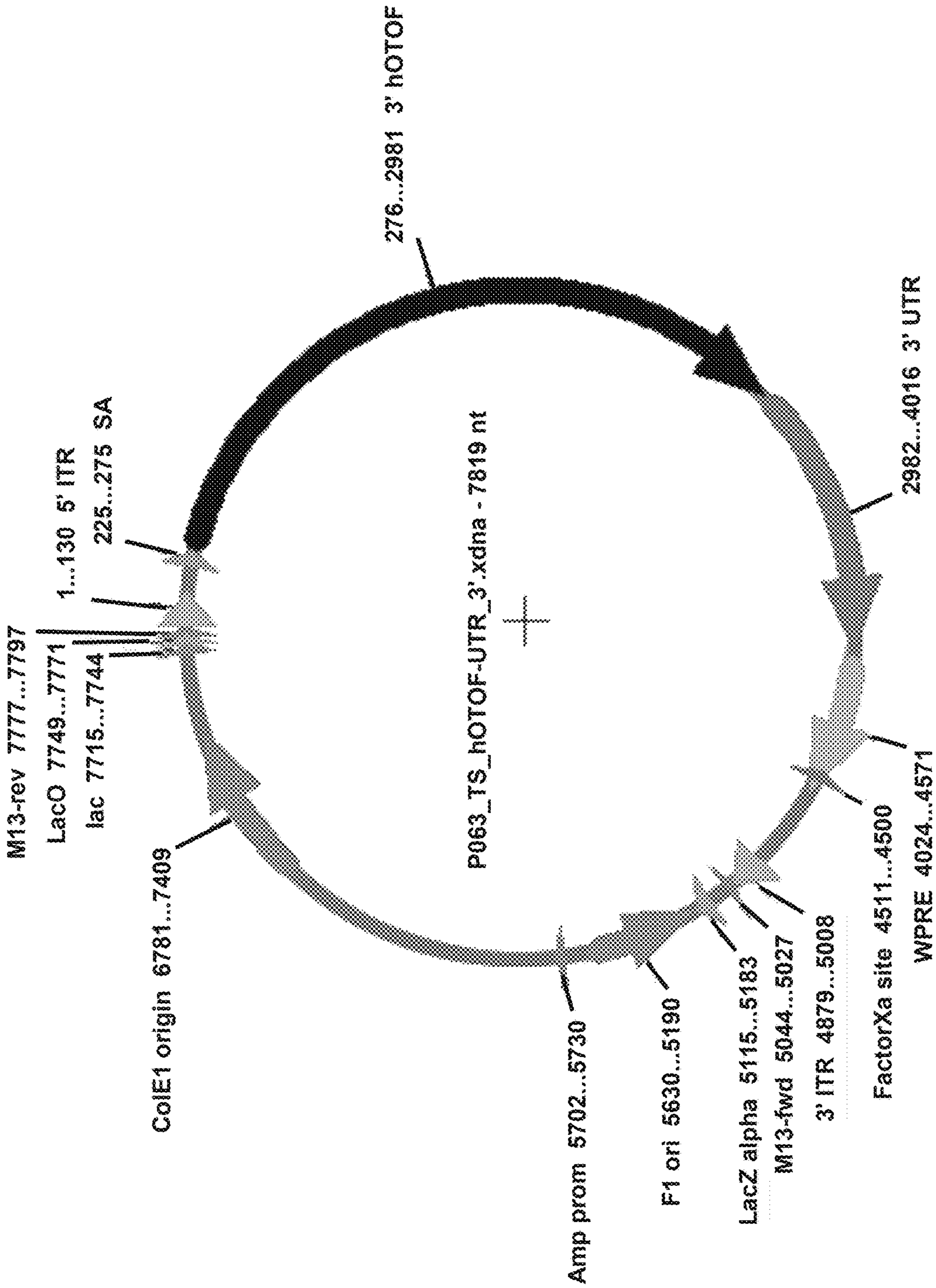
Figure 9A:
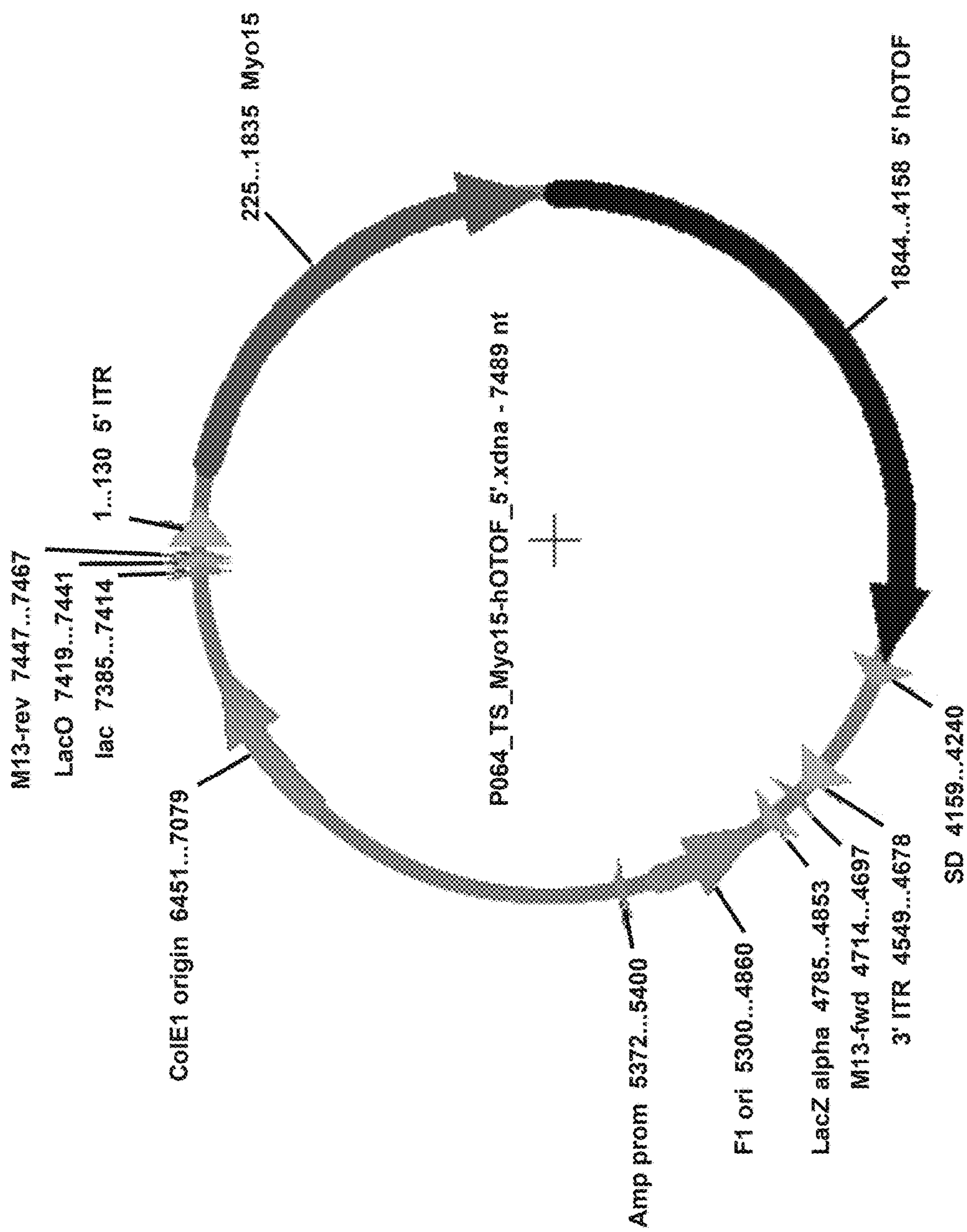
FIGS. 9A and 9B are maps of the 5' and 3' vectors in a trans-splicing dual vector system. The 5' vector contains AAV2 ITRs, a Myo15 promoter (SEQ ID NO: 36) operably linked to exons 1-19 of a polynucleotide encoding the human OTOF protein of SEQ ID NO: 1, and a splice donor sequence (SD) (FIG. 9A). The 3' vector contains AAV2 ITRs, a splice acceptor sequence (SA), exons 20-48 of a polynucleotide encoding the human OTOF protein of SEQ ID NO: 1, and a WPRE sequence (SEQ ID NO: 23) (FIG. 9B).
Figure 9B:
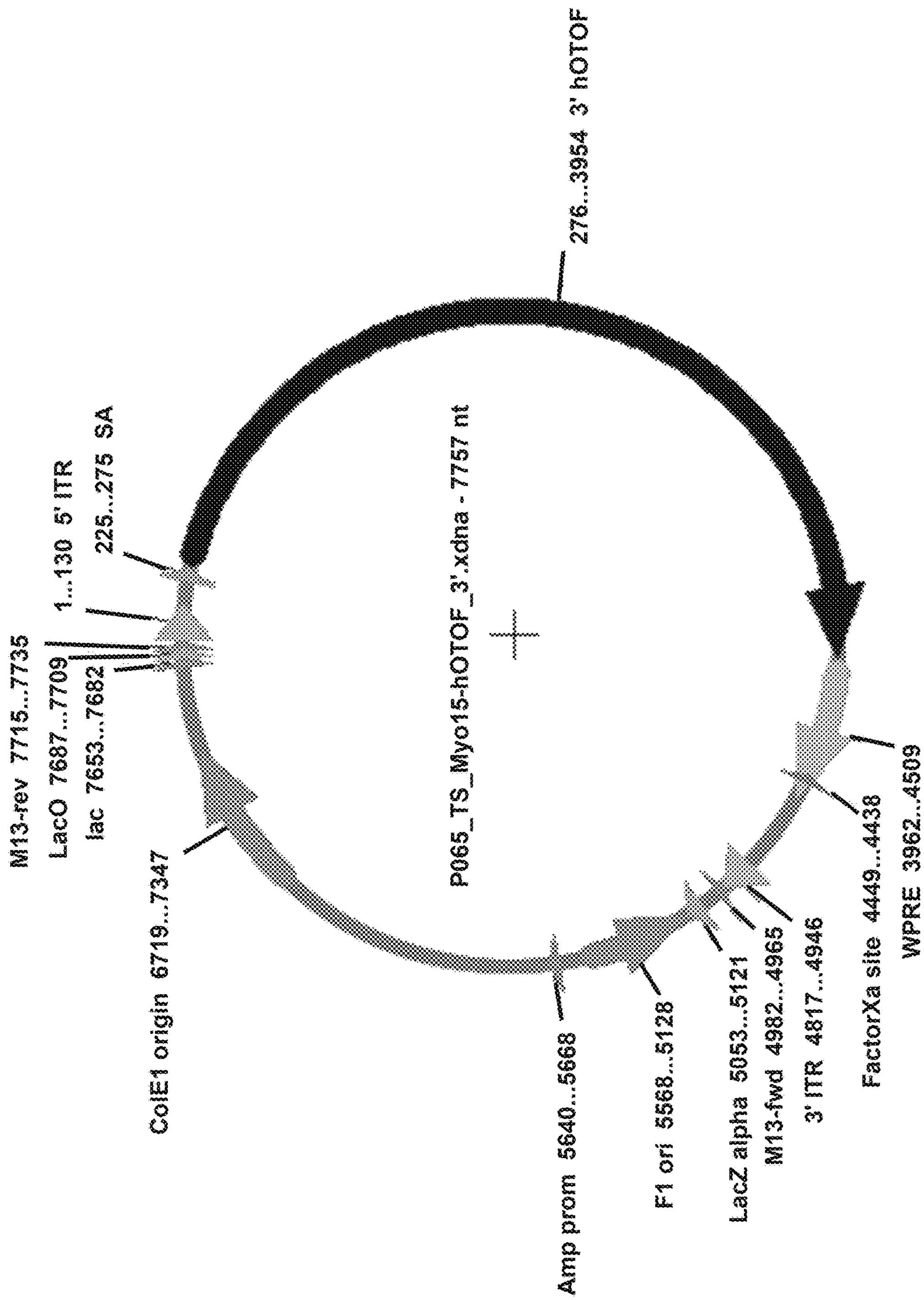
Figure 10A:
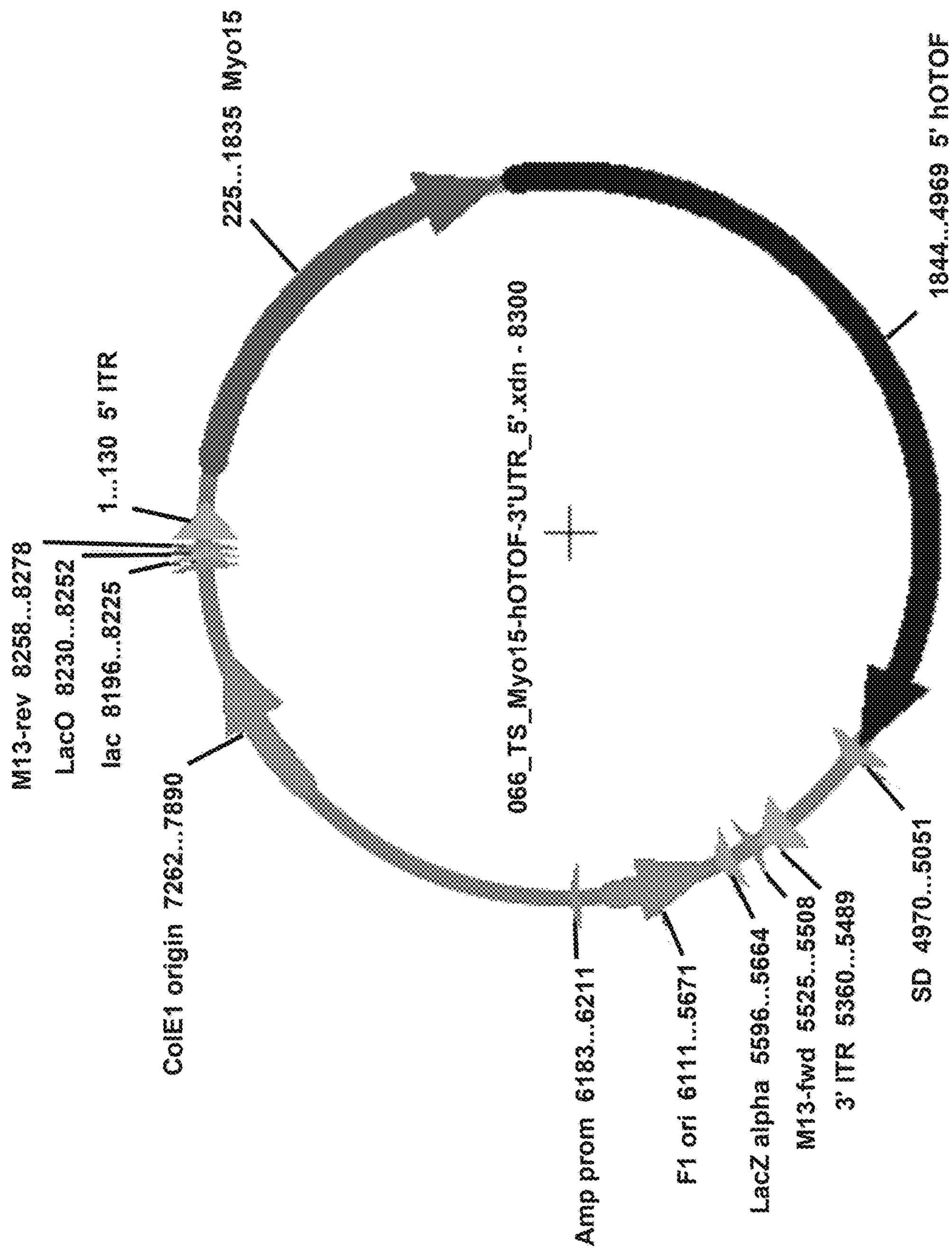
FIGS. 10A and 10B are maps of the 5' and 3' vectors in a trans-splicing dual vector system. The 5' vector contains AAV2 ITRs, a Myo15 promoter (SEQ ID NO: 36) operably linked to exons 1-25 of a polynucleotide encoding the human OTOF protein of SEQ ID NO: 1, and a splice donor sequence (SD) (FIG. 10A). The 3' vector contains AAV2 ITRs, a splice acceptor sequence (SA), exons 26-48 of a polynucleotide encoding the human OTOF protein of SEQ ID NO: 1, the full-length human OTOF 3' UTR, and a WPRE sequence (SEQ ID NO: 23) (FIG. 10B).
Figure 10B:
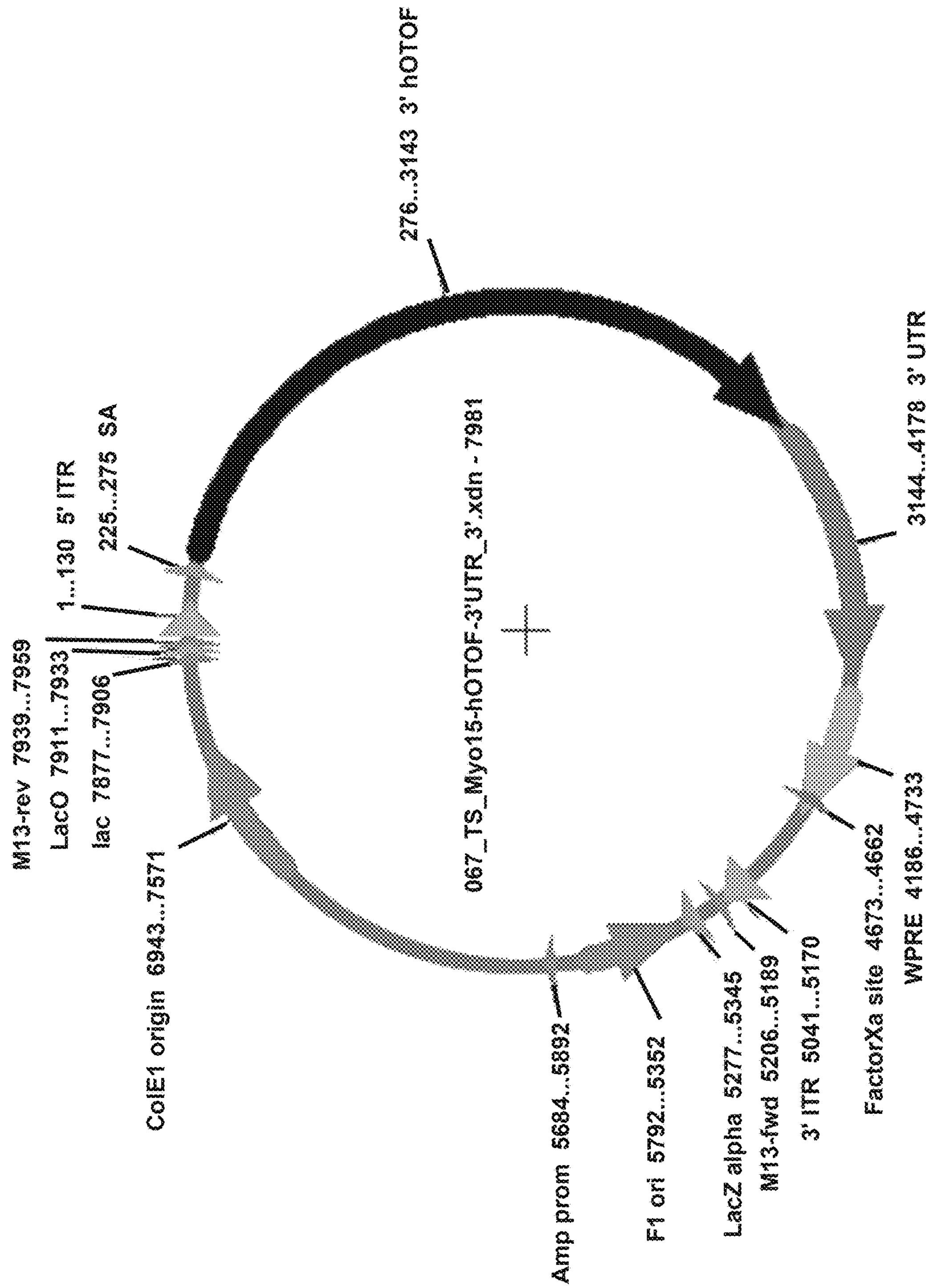
Figure 11A:
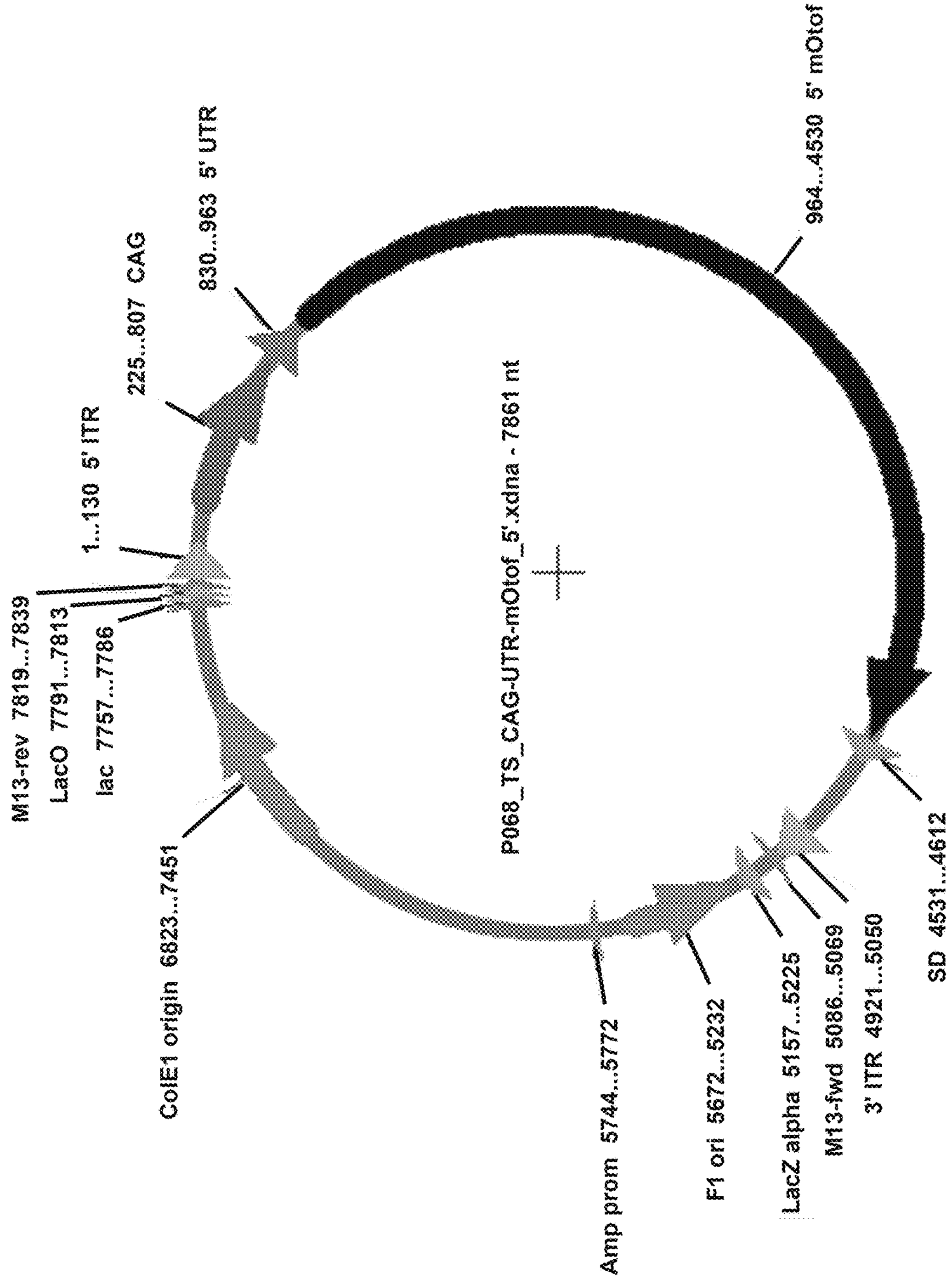
FIGS. 11A and 11B are maps of the 5' and 3' vectors in a trans-splicing dual vector system. The 5' vector contains AAV2 ITRs, a CAG promoter operably linked to the full-length mouse OTOF 5' UTR and exons 1-28 of a polynucleotide encoding the mouse OTOF protein of SEQ ID NO: 6, and a splice donor sequence (SD) (FIG. 11A). The 3' vector contains AAV2 ITRs, a splice acceptor sequence (SA), exons 29-48 of a polynucleotide encoding the mouse OTOF protein of SEQ ID NO: 6, the full-length mouse OTOF 3' UTR, and a WPRE sequence (SEQ ID NO: 23) (FIG. 11B).
Figure 11B:
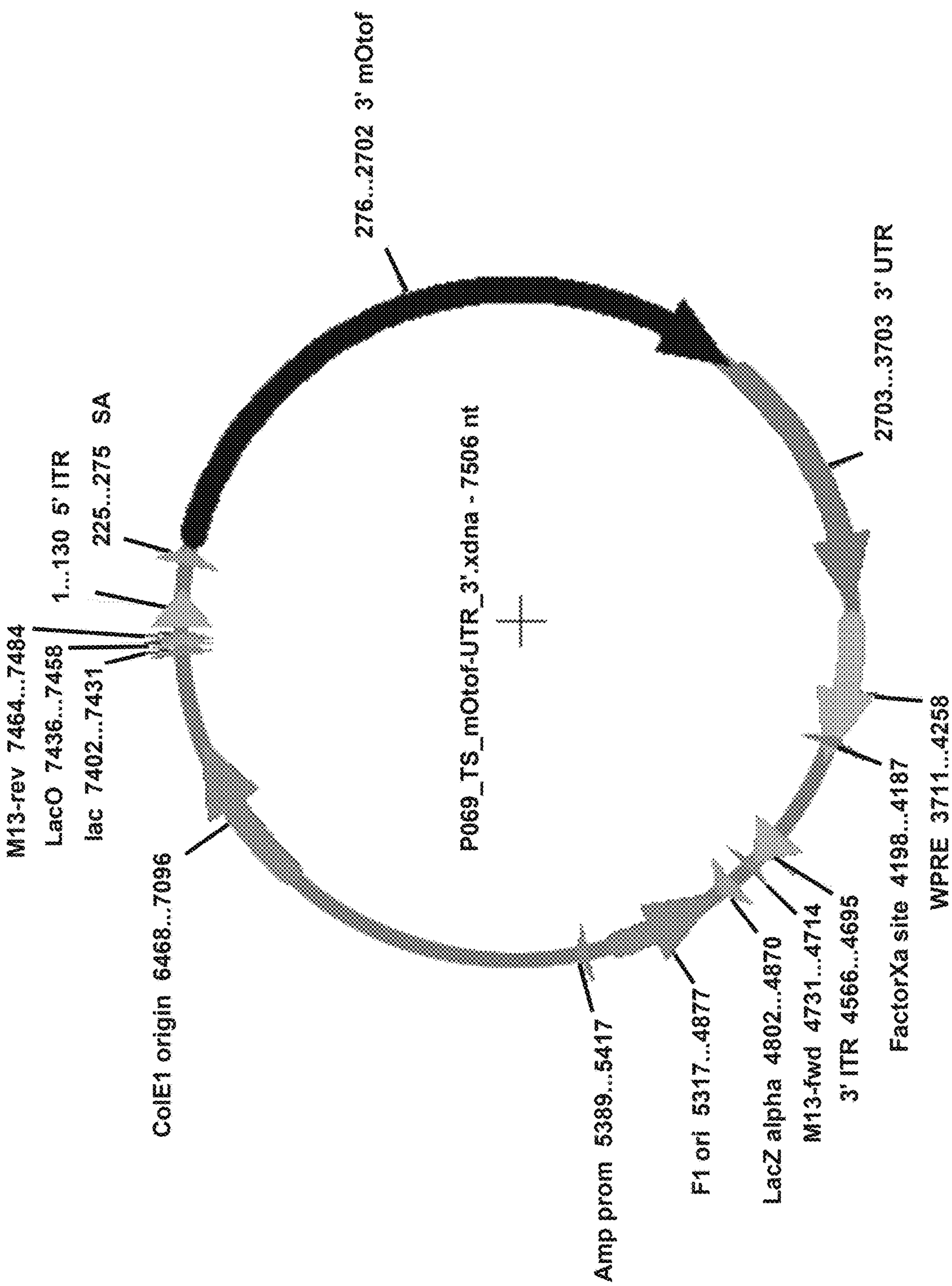
Figure 12A:
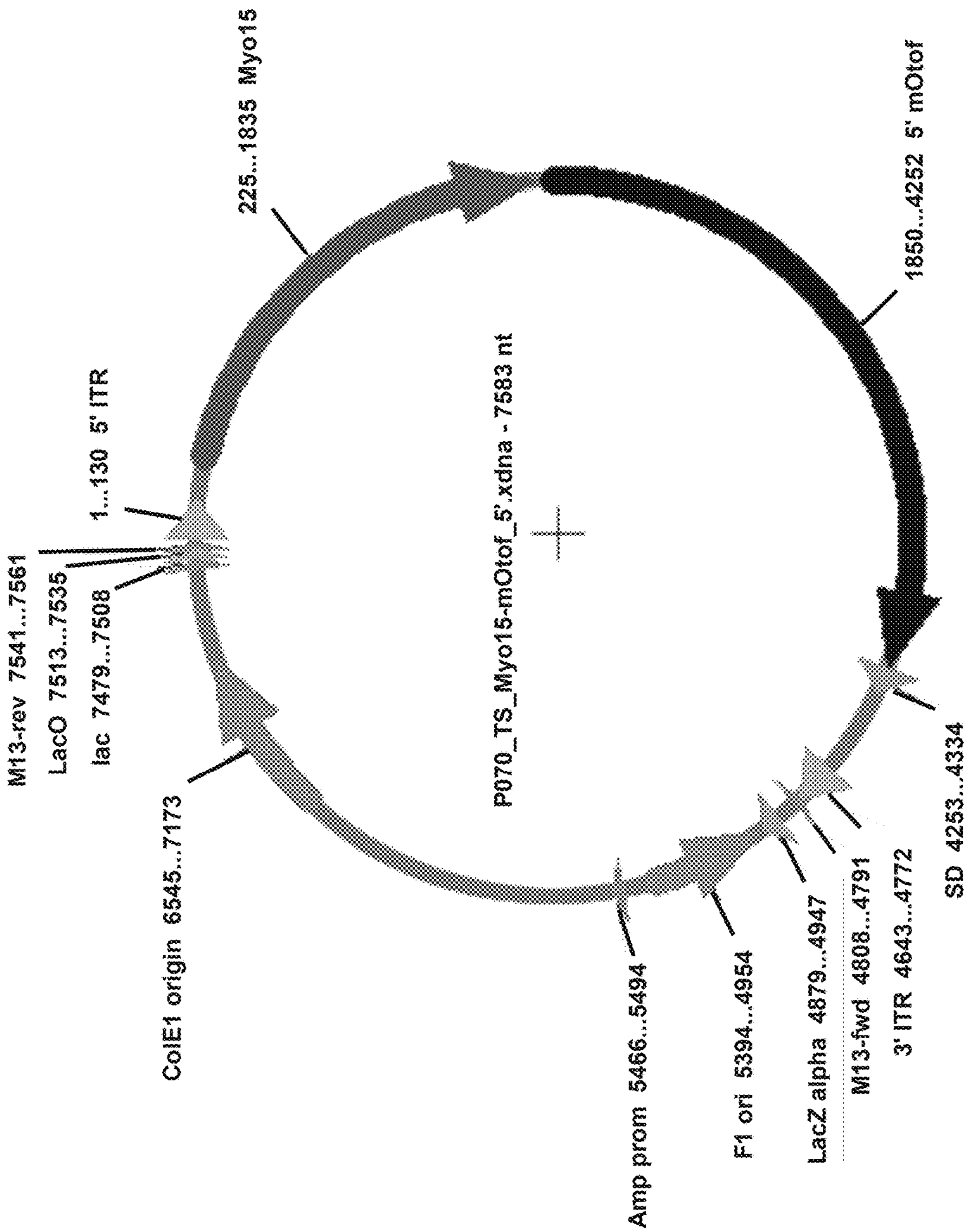
FIGS. 12A and 12B are maps of the 5' and 3' vectors in a trans-splicing dual vector system. The 5' vector contains AAV2 ITRs, a Myo15 promoter (SEQ ID NO: 36) operably linked to exons 1-20 of a polynucleotide encoding the mouse OTOF protein of SEQ ID NO: 6, and a splice donor sequence (SD) (FIG. 12A). The 3' vector contains AAV2 ITRs, a splice acceptor sequence (SA), exons 21-48 of a polynucleotide encoding the mouse OTOF protein of SEQ ID NO: 6, and a WPRE sequence (SEQ ID NO: 23) (FIG. 12B).
Figure 12B:
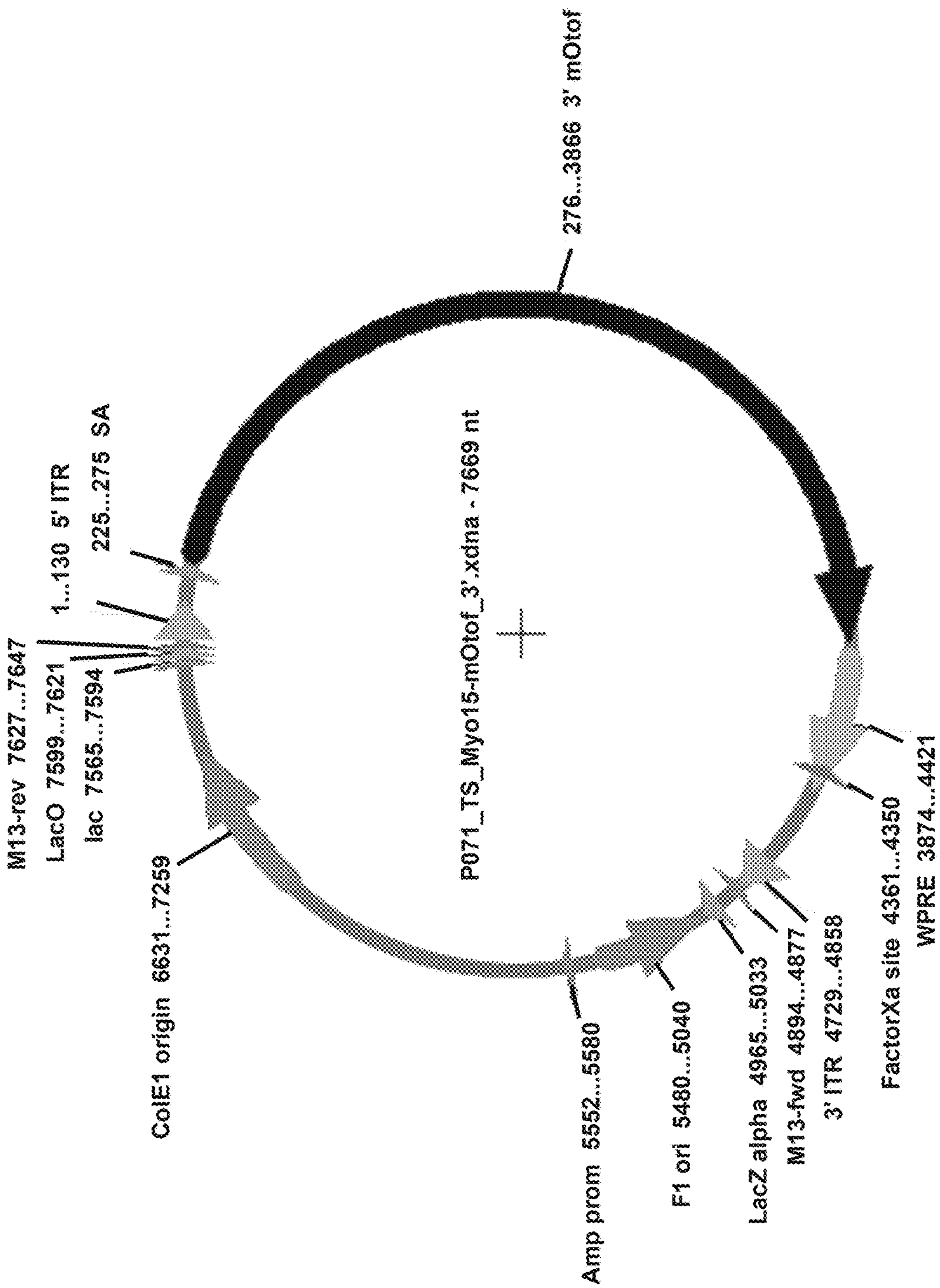
Figure 13A:
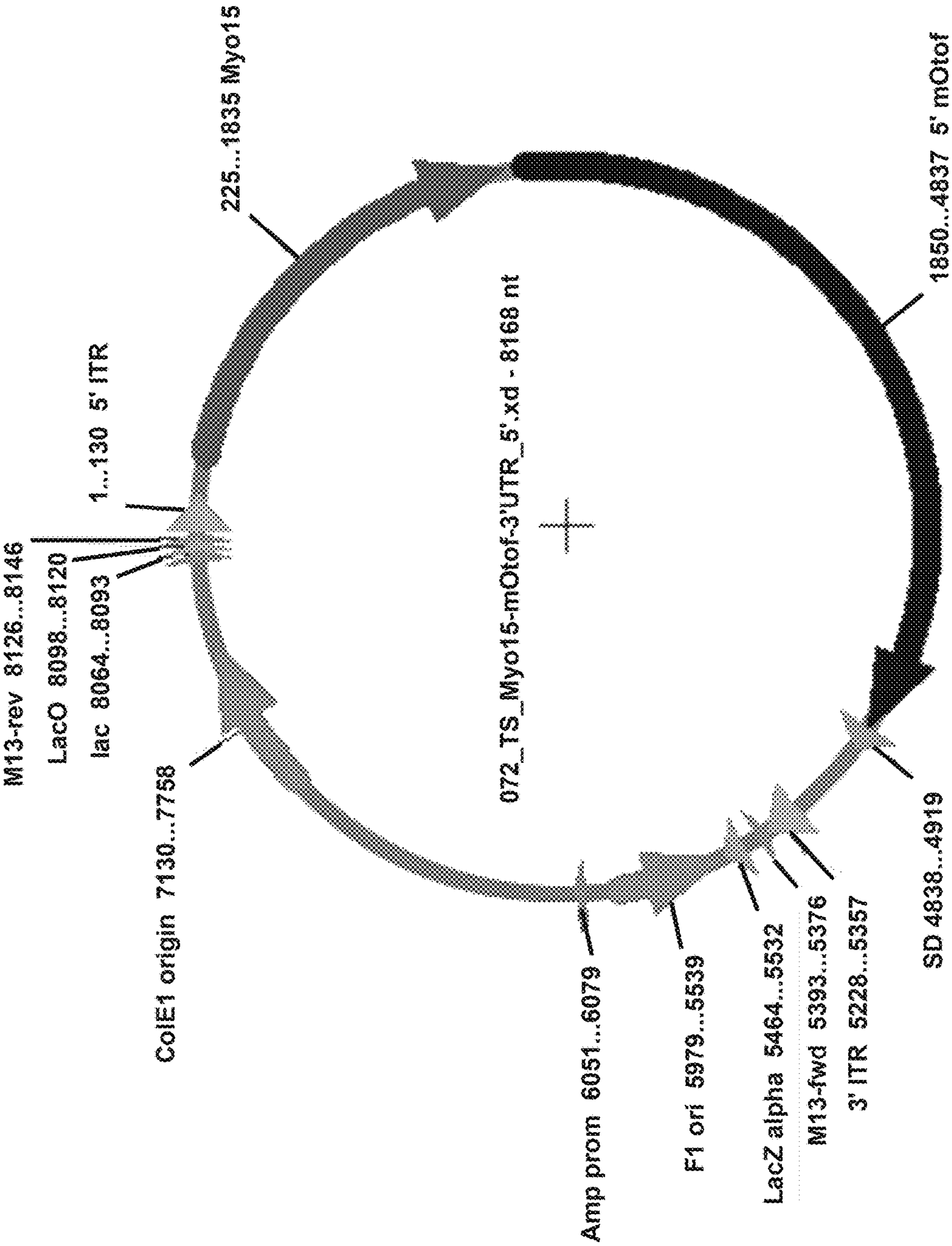
FIGS. 13A and 13B are maps of the 5' and 3' vectors in a trans-splicing dual vector system. The 5' vector contains AAV2 ITRs, a Myo15 promoter (SEQ ID NO: 36) operably linked to exons 1-24 of a polynucleotide encoding the mouse OTOF protein of SEQ ID NO: 6, and a splice donor sequence (SD) (FIG. 13A). The 3' vector contains AAV2 ITRs, a splice acceptor sequence (SA), exons 25-48 of a polynucleotide encoding the mouse OTOF protein of SEQ ID NO: 6, the full-length mouse OTOF 3' UTR, and a WPRE sequence (SEQ ID NO: 23) (FIG. 13B).
Figure 13B:
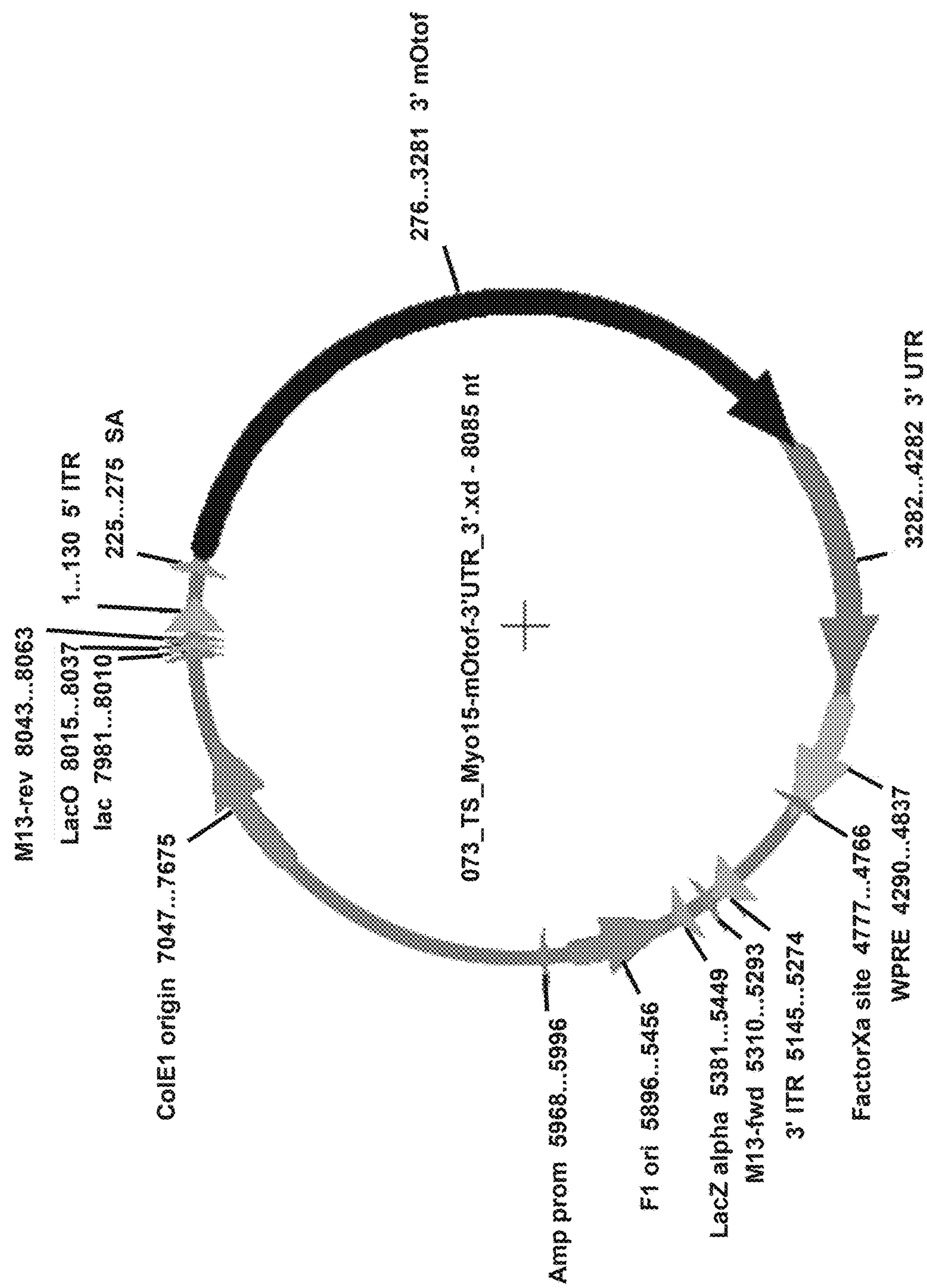
Figure 14A:
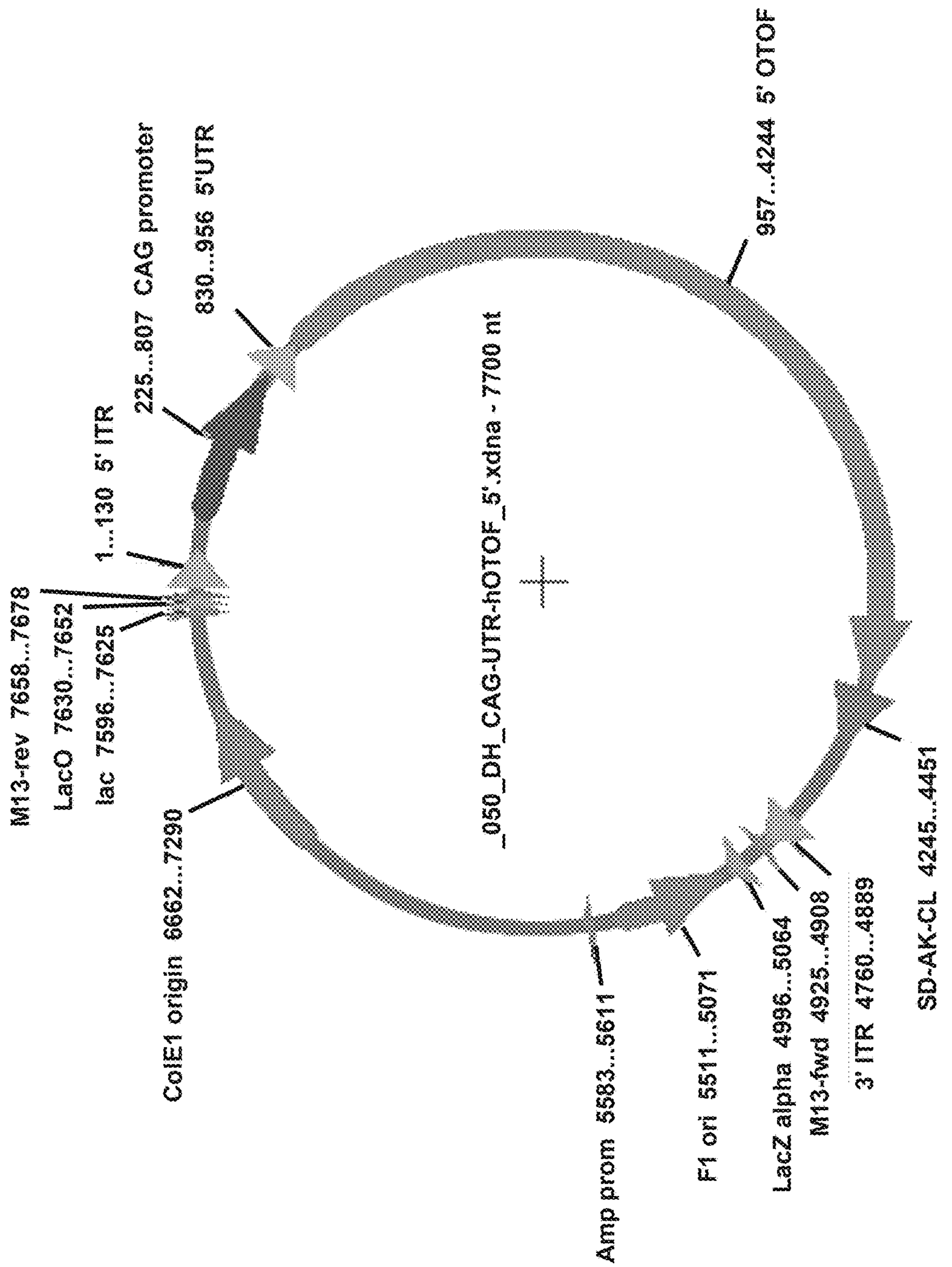
FIGS. 14A and 14B are maps of the 5' and 3' vectors in a dual hybrid vector system. The 5' vector contains AAV2 ITRs, a CAG promoter operably linked to the full-length human OTOF 5' UTR and exons 1-26 of a polynucleotide encoding the human OTOF protein of SEQ ID NO: 1, a splice donor sequence (SD), a recombinogenic region (AK), and a degradation signal sequence (CL1) (FIG. 14A). The 3' vector contains AAV2 ITRs, a recombinogenic region (AK), a degradation signal sequence (CL1), a splice acceptor sequence (SA), exons 27-48 of a polynucleotide encoding the human OTOF protein of SEQ ID NO: 1, the full-length human OTOF 3' UTR, and a WPRE sequence (SEQ ID NO: 23) (FIG. 14B).
Figure 14B:
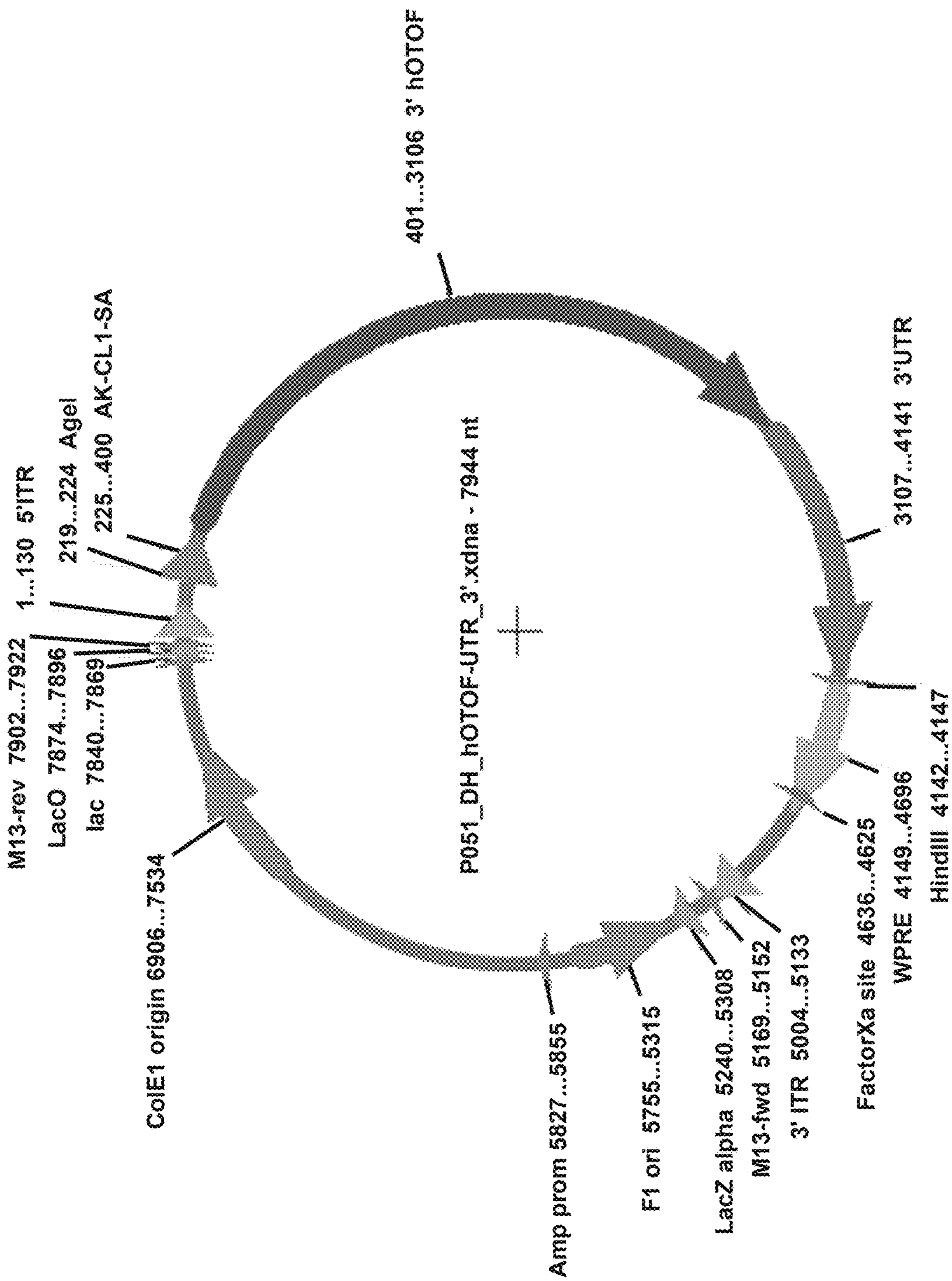
Figure 15A:
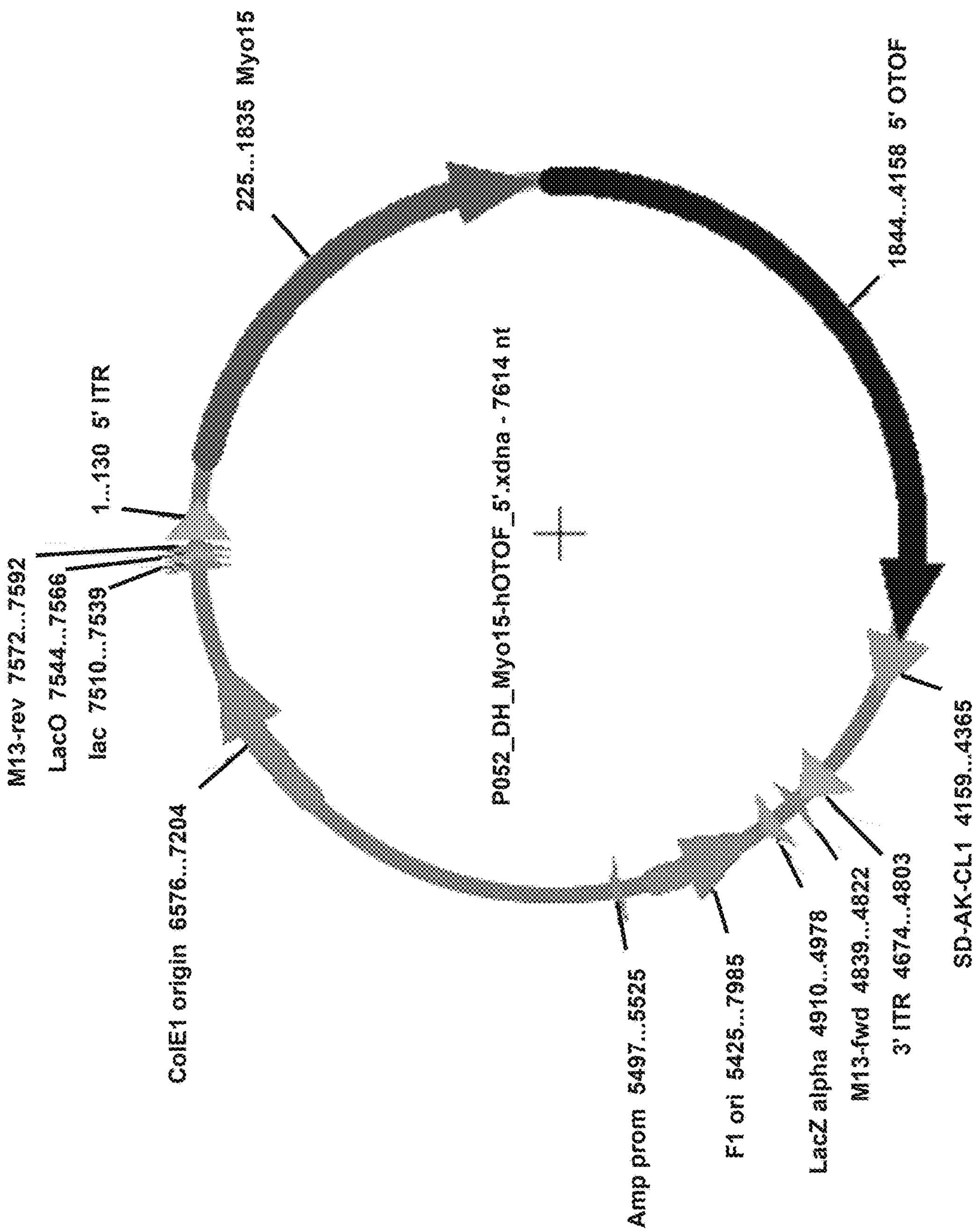
FIGS. 15A and 15B are maps of the 5' and 3' vectors in a dual hybrid vector system. The 5' vector contains AAV2 ITRs, a Myo15 promoter (SEQ ID NO: 36) operably linked to exons 1-19 of a polynucleotide encoding the human OTOF protein of SEQ ID NO: 1, a splice donor sequence (SD), a recombinogenic region (AK), and a degradation signal sequence (CL1) (FIG. 15A). The 3' vector contains AAV2 ITRs, a recombinogenic region (AK), a degradation signal sequence (CL1), a splice acceptor sequence (SA), exons 20-48 of a polynucleotide encoding the human OTOF protein of SEQ ID NO: 1, and a WPRE sequence (SEQ ID NO: 23) (FIG. 15B).
Figure 15B:
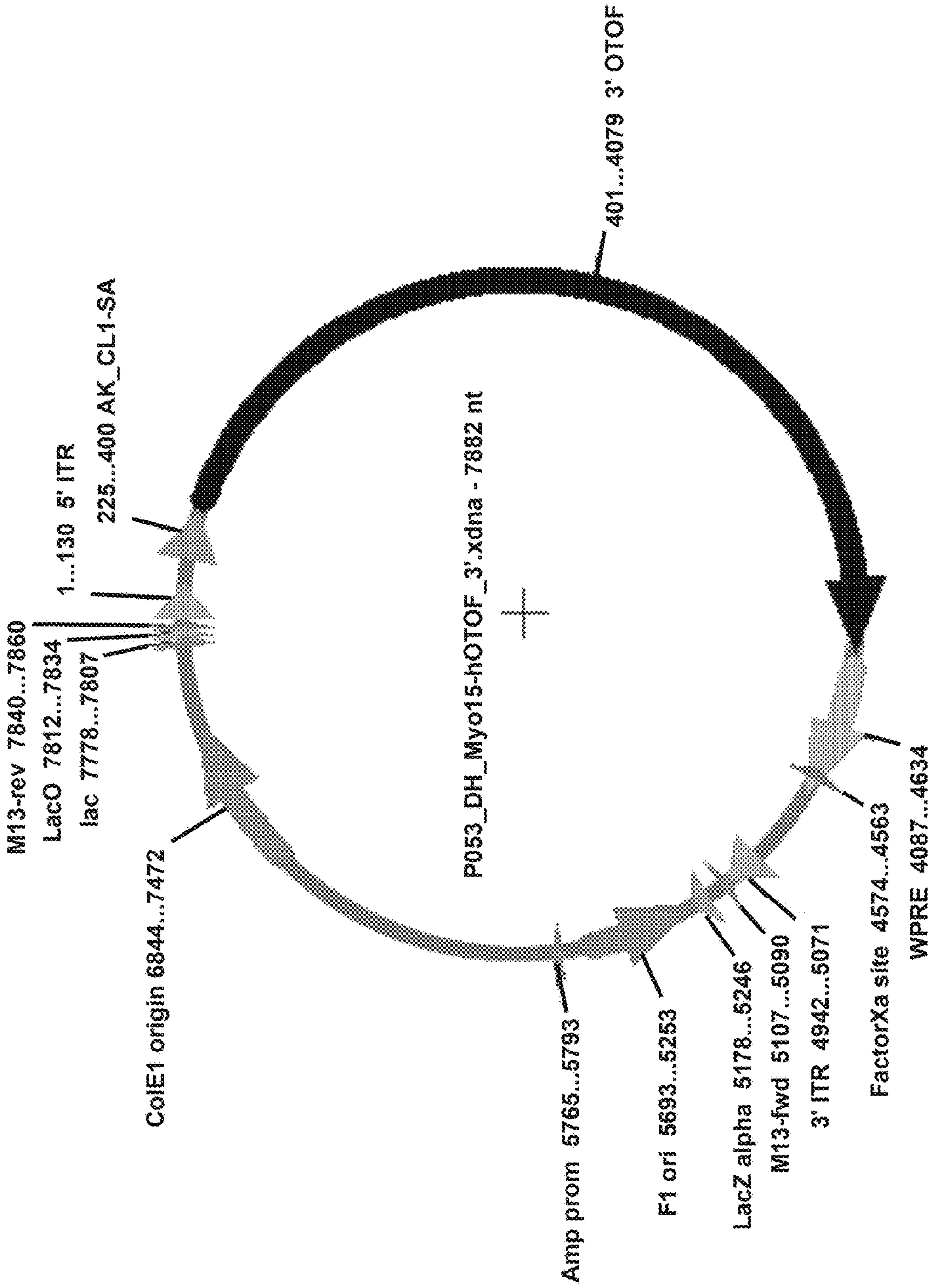
Figure 16A:
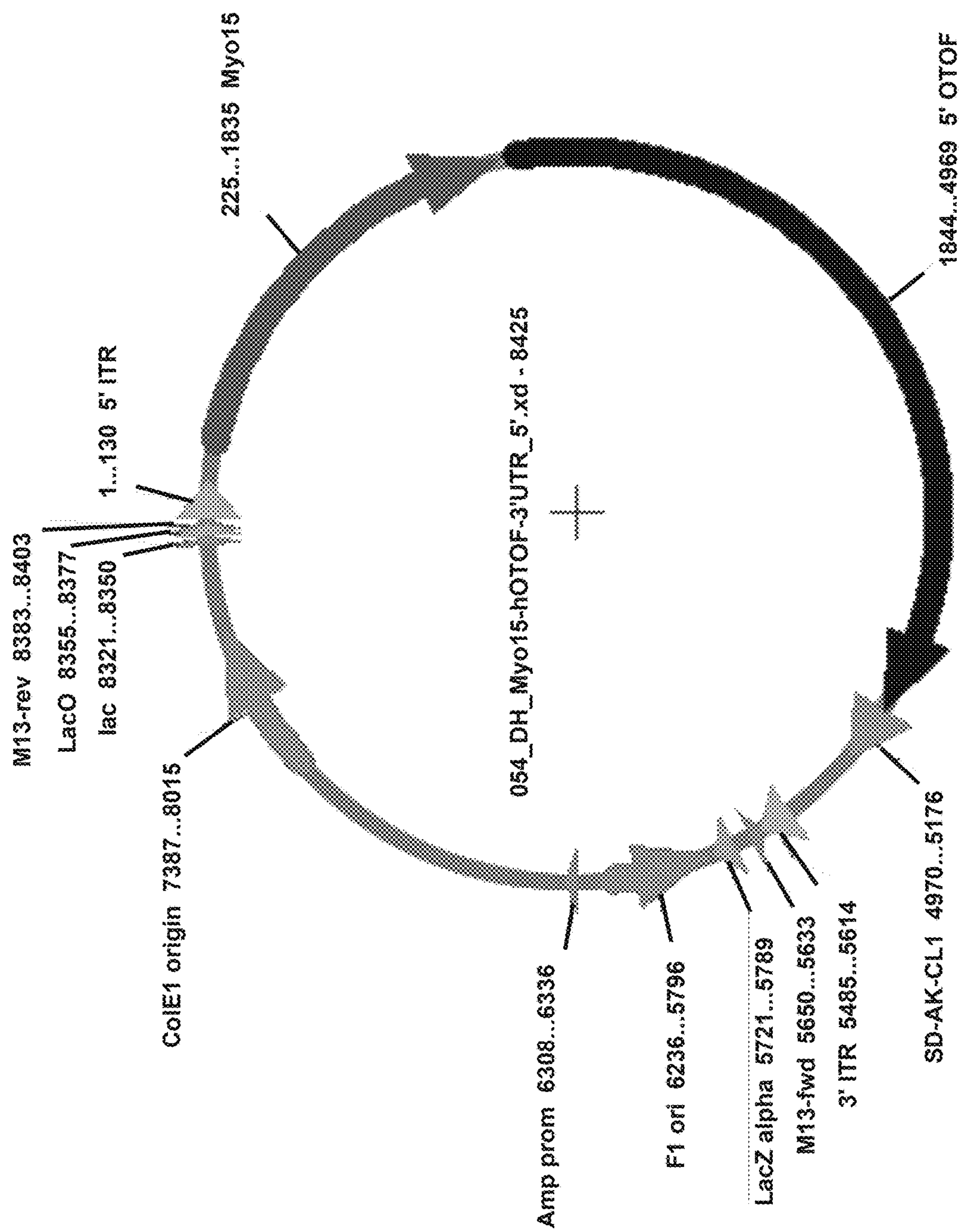
FIGS. 16A and 16B are maps of the 5' and 3' vectors in a dual hybrid vector system. The 5' vector contains AAV2 ITRs, a Myo15 promoter (SEQ ID NO: 36) operably linked to exons 1-25 of a polynucleotide encoding the human OTOF protein of SEQ ID NO: 1, a splice donor sequence (SD), a recombinogenic region (AK), and a degradation signal sequence (CL1) (FIG. 16A). The 3' vector contains AAV2 ITRs, a recombinogenic region (AK), a degradation signal sequence (CL1), a splice acceptor sequence (SA), exons 26-48 of a polynucleotide encoding the human OTOF protein of SEQ ID NO: 1, the full-length human OTOF 3' UTR, and a WPRE sequence (SEQ ID NO: 23) (FIG. 16B).
Figure 16B:
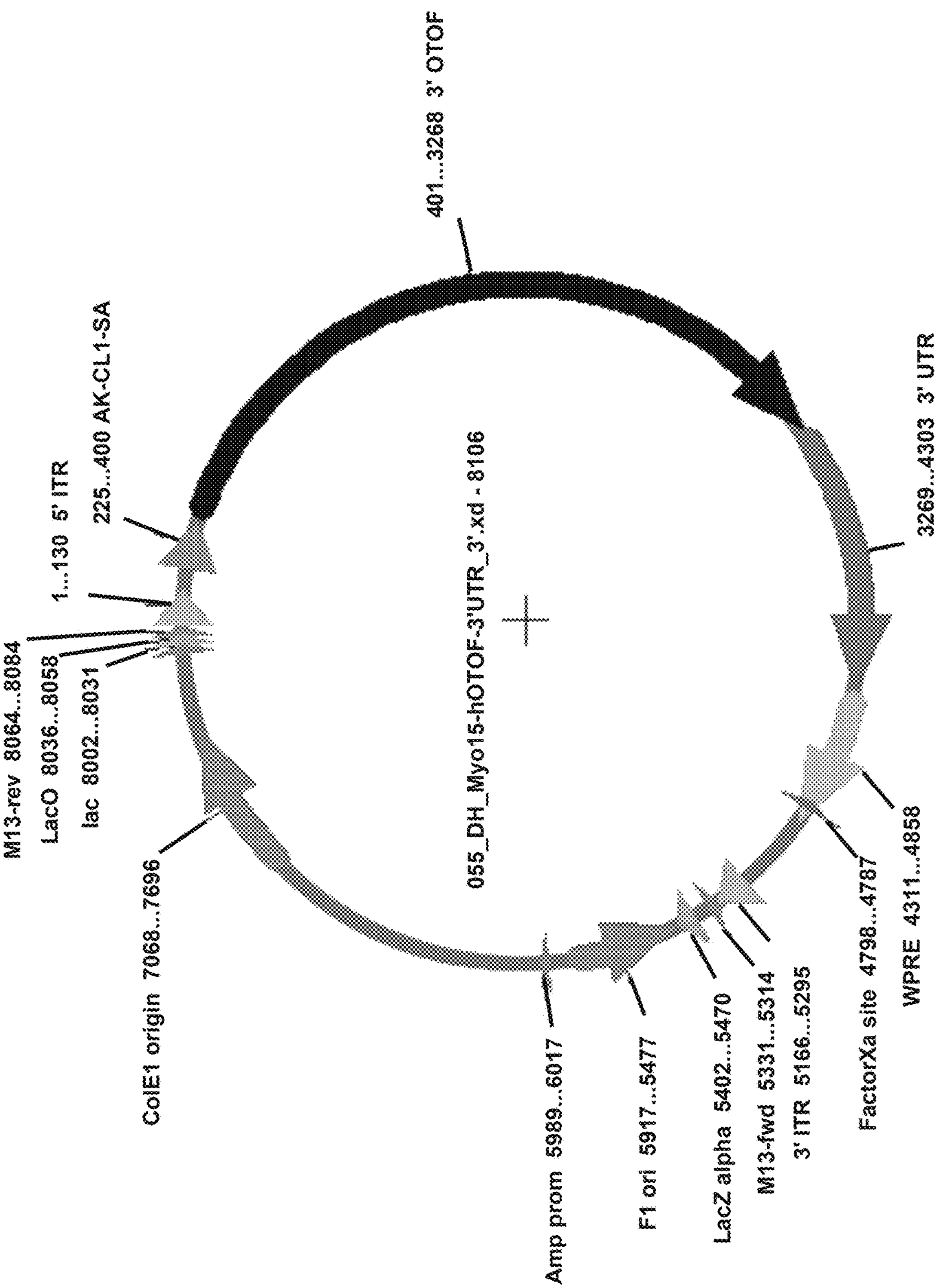
Figure 17A:
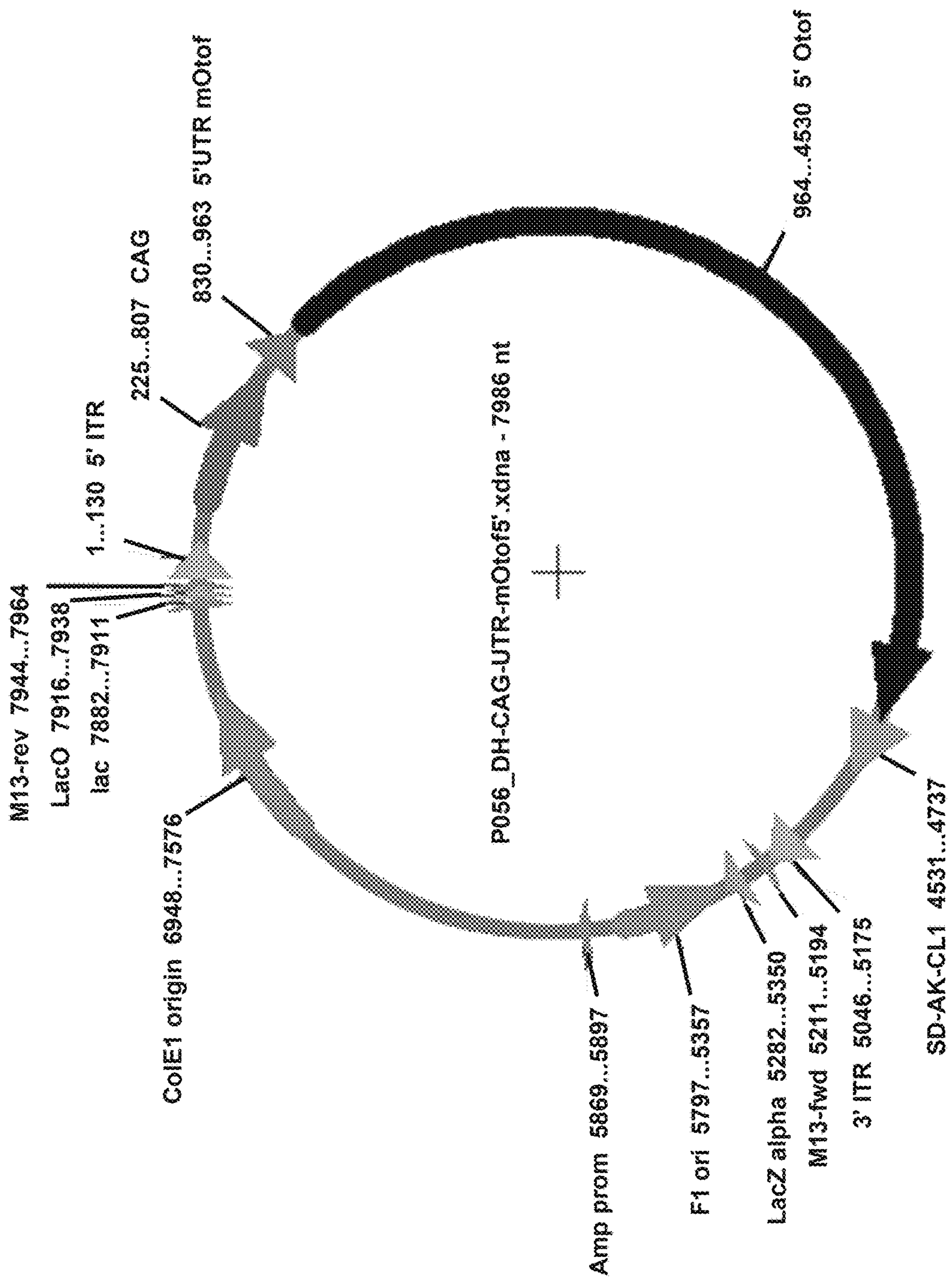
FIGS. 17A and 17B are maps of the 5' and 3' vectors in a dual hybrid vector system. The 5' vector contains AAV2 ITRs, a CAG promoter operably linked to the full-length mouse OTOF 5' UTR and exons 1-28 of a polynucleotide encoding the mouse OTOF protein of SEQ ID NO: 6, a splice donor sequence (SD), a recombinogenic region (AK), and a degradation signal sequence (CL1) (FIG. 17A). The 3' vector contains AAV2 ITRs, a recombinogenic region (AK), a degradation signal sequence (CL1), a splice acceptor sequence (SA), exons 29-48 of a polynucleotide encoding the mouse OTOF protein of SEQ ID NO: 6, the full-length mouse OTOF 3' UTR, and a WPRE sequence (SEQ ID NO: 23) (FIG. 17B).
Figure 17B:
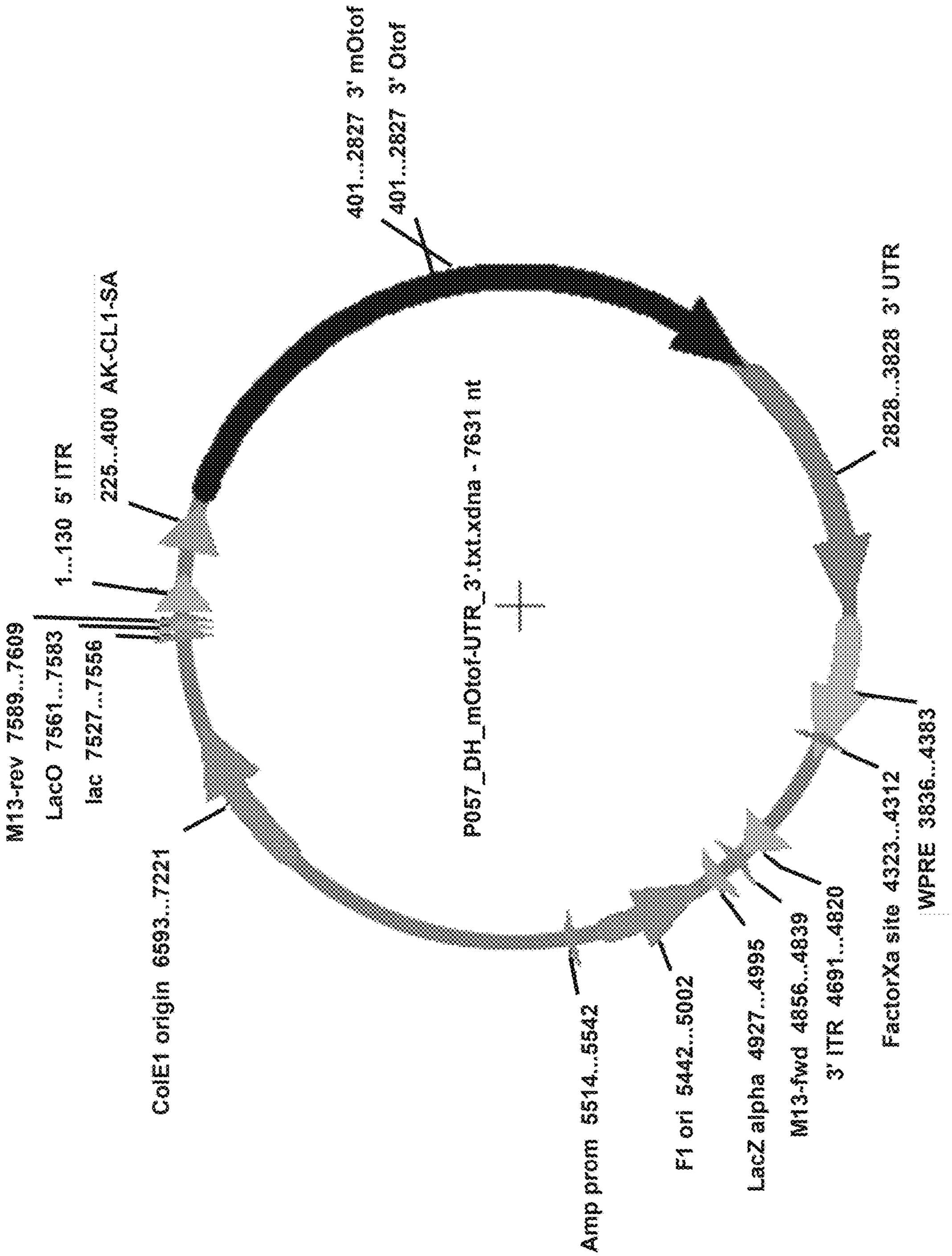
Figure 18A:
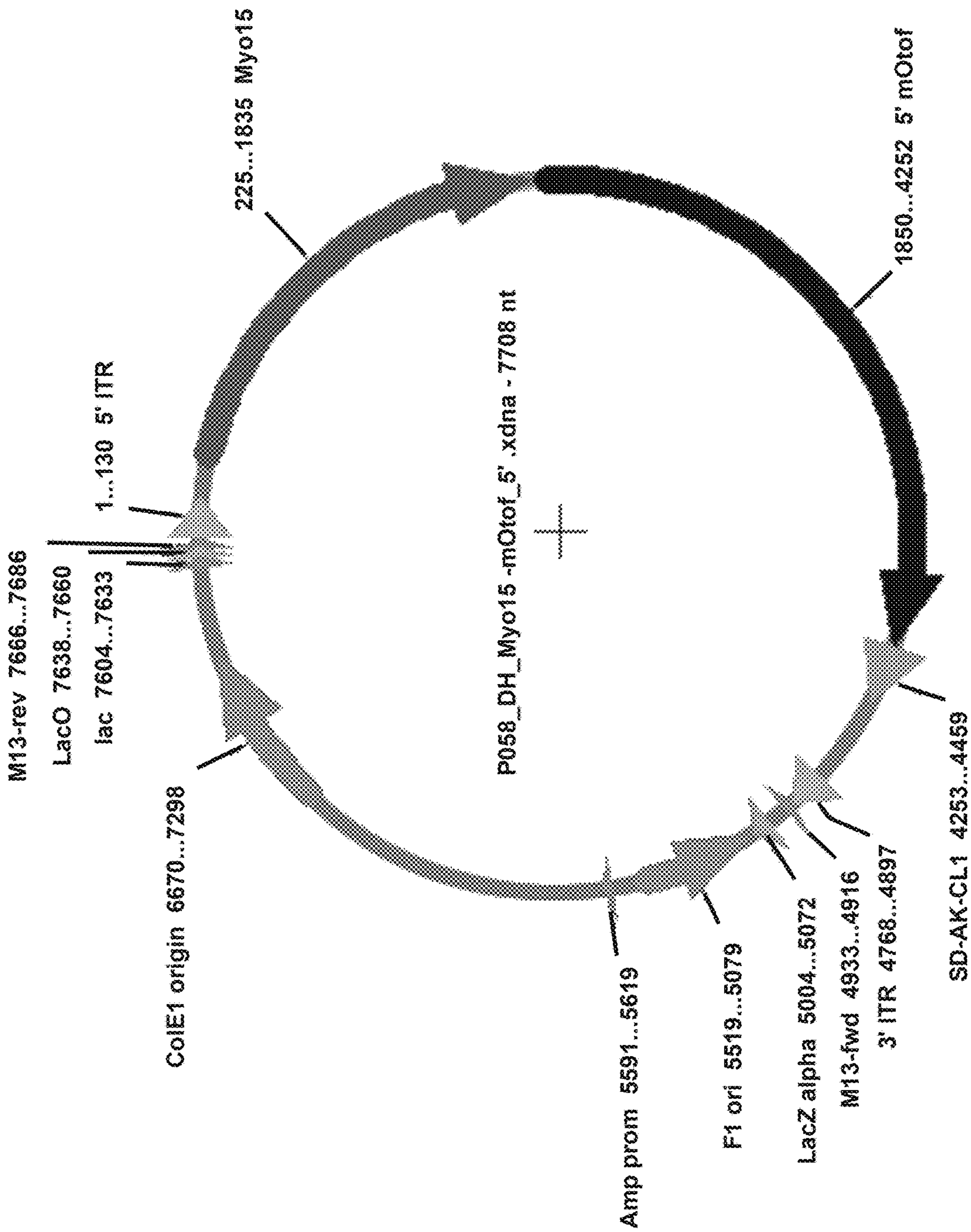
FIGS. 18A and 18B are maps of the 5' and 3' vectors in a dual hybrid vector system. The 5' vector contains AAV2 ITRs, a Myo15 promoter (SEQ ID NO: 36) operably linked to exons 1-20 of a polynucleotide encoding the mouse OTOF protein of SEQ ID NO: 6, a splice donor sequence (SD), a recombinogenic region (AK), and a degradation signal sequence (CL1) (FIG. 18A). The 3' vector contains AAV2 ITRs, a recombinogenic region (AK), a degradation signal sequence (CL1), a splice acceptor sequence (SA), exons 21-48 of a polynucleotide encoding the mouse OTOF protein of SEQ ID NO: 6, and a WPRE sequence (SEQ ID NO: 23) (FIG. 18B).
Figure 18B:
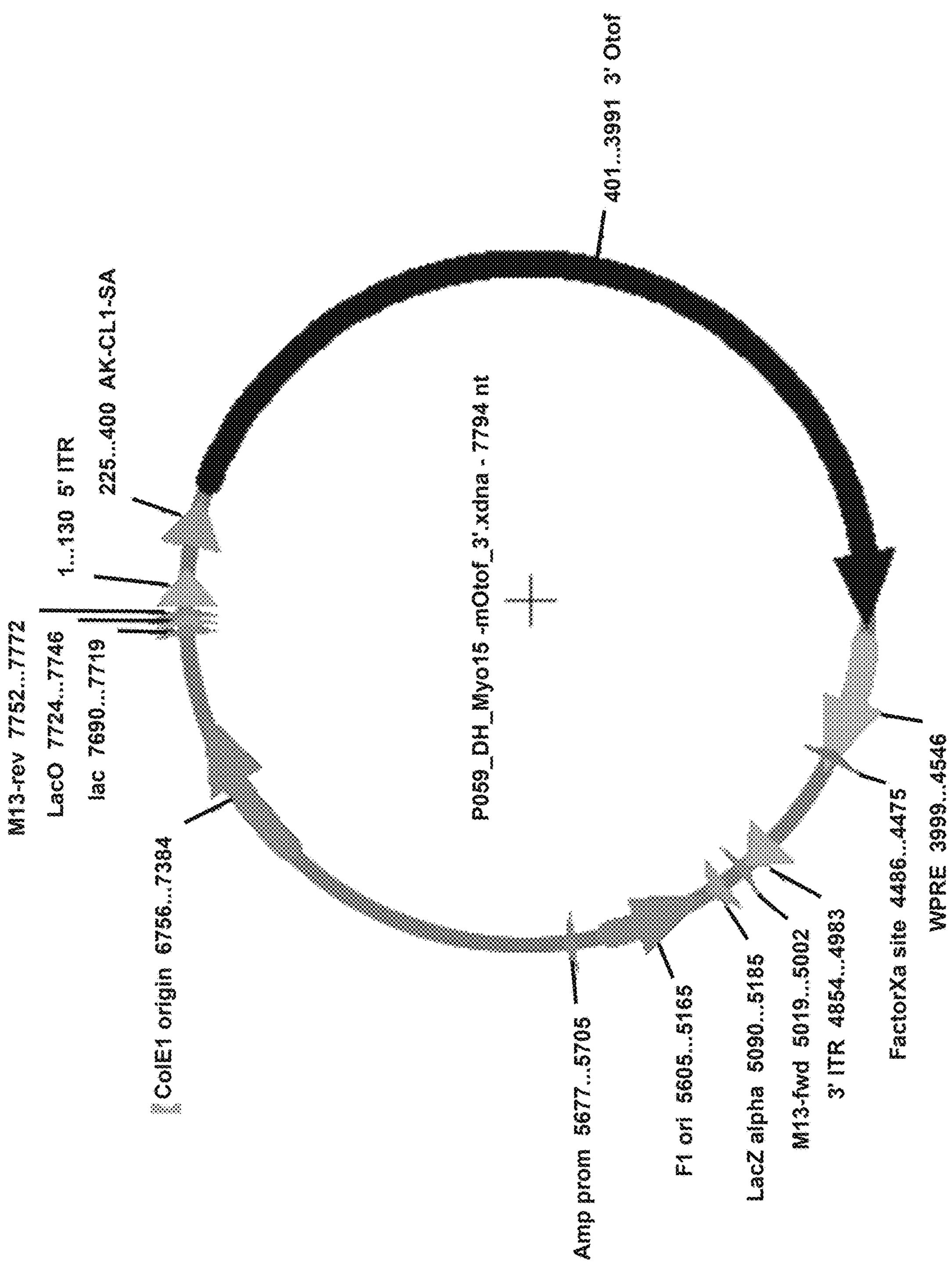
Figure 19A:
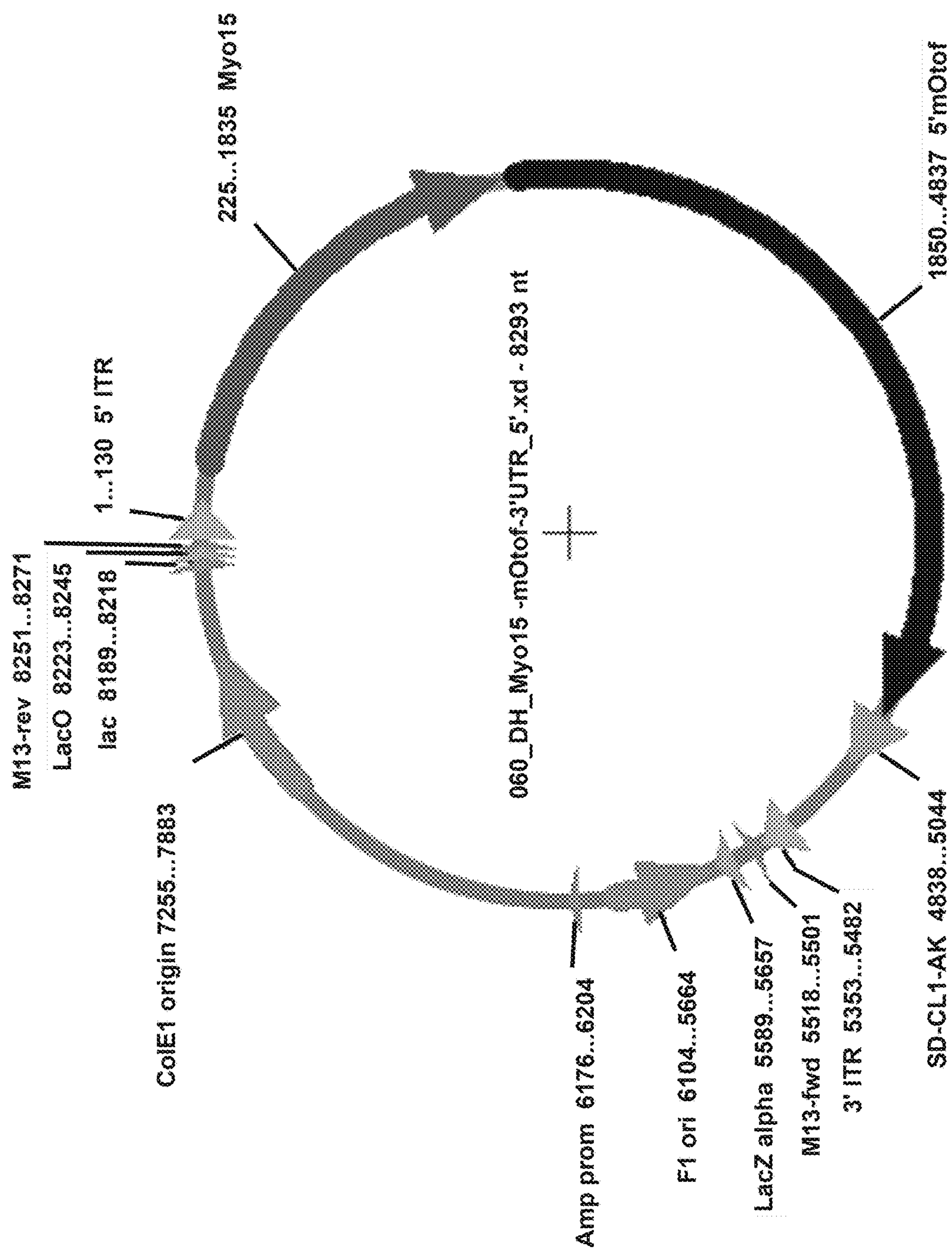
FIGS. 19A and 19B are maps of the 5' and 3' vectors in a dual hybrid vector system. The 5' vector contains AAV2 ITRs, a Myo15 promoter (SEQ ID NO: 36) operably linked to exons 1-24 of a polynucleotide encoding the mouse OTOF protein of SEQ ID NO: 6, a splice donor sequence (SD), a recombinogenic region (AK), and a degradation signal sequence (CL1) (FIG. 19A). The 3' vector contains AAV2 ITRs, a recombinogenic region (AK), a degradation signal sequence (CL1), a splice acceptor sequence (SA), exons 25-48 of a polynucleotide encoding the mouse OTOF protein of SEQ ID NO: 6, the full-length mouse OTOF 3' UTR, and a WPRE sequence (SEQ ID NO: 23) (FIG. 19B).
Figure 19B:
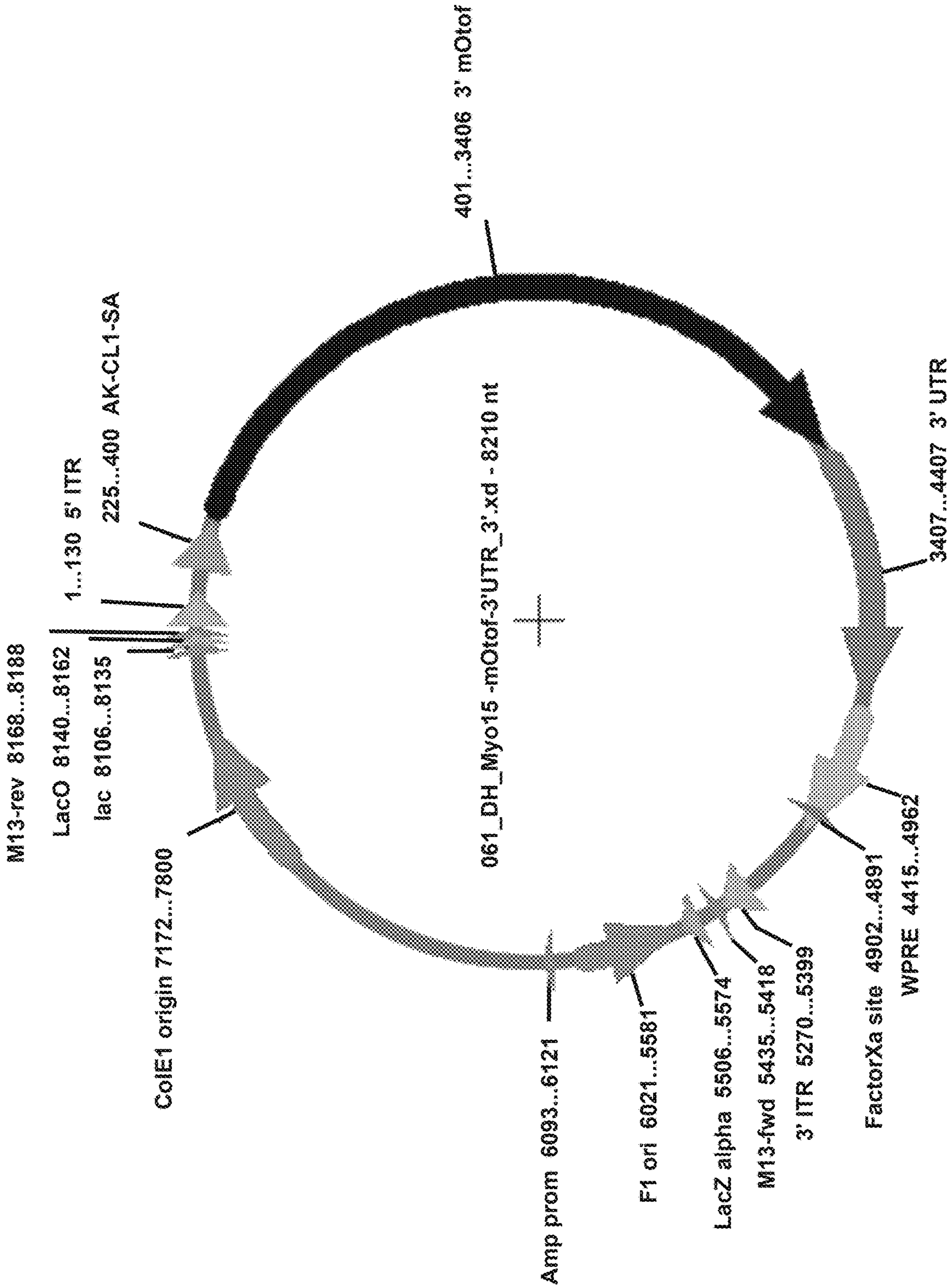

Described herein are compositions and methods for the treatment of sensorineural hearing loss or auditory neuropathy in a subject (such as a mammalian subject, for instance, a human) by administering a first nucleic acid vector containing a promoter and a polynucleotide encoding an N-terminal portion of an otoferlin (OTOF) protein (e.g., a wild-type (WT) OTOF protein) and a second nucleic acid vector containing a polynucleotide encoding a C-terminal portion of an OTOF protein and a polyadenylation (poly(A)) sequence. When introduced into a mammalian cell, such as a cochlear hair cell, the polynucleotides encoded by the two nucleic acid vectors can combine to form a nucleic acid molecule that encodes the full-length OTOF protein. The compositions and methods described herein can, therefore, be used to induce or increase expression of WT OTOF in cochlear hair cells of a subject who has an OTOF deficiency (e.g., low OTOF expression or an OTOF mutation that impairs OTOF expression or function).

Otoferlin

OTOF is a 230 kDa membrane protein that contains at least six C2 domains implicated in calcium, phospholipid, and protein binding. It is encoded by a gene that contains 48 exons, and the full-length protein is made up of 1,997 amino acids. OTOF is located at ribbon synapses in inner hair cells, where it is believed to function as a calcium sensor in synaptic vesicle fusion, triggering the fusion of neurotransmitter-containing vesicles with the plasma membrane. It has also been implicated in vesicle replenishment and clathrin-mediated endocytosis, and has been shown to interact with Myosin VI, Rab8b, SNARE proteins, calcium channel Cav1.3, Ergic2, and AP-2. The mechanism by which OTOF mediates exocytosis and the physiological significance of its interactions with its binding partners remain to be determined.

OTOF-Associated Hearing Loss

OTOF was first identified by a study investigating the genetics of a non-syndromic form of deafness, autosomal recessive deafness-9 (DFNB9). Mutations in OTOF have since been found to cause sensorineural hearing loss in patients throughout the world, with many patients carrying OTOF mutations having auditory neuropathy, a disorder in which the inner ear detects sound, but is unable to properly transmit sound from the ear to the brain. These patients have an abnormal auditory brainstem response (ABR) and impaired speech discrimination with initially normal otoacoustic emissions. Patients carrying homozygous or compound heterozygous mutations often develop hearing loss in early childhood, and the severity of hearing impairment has been found to vary with the location and type of mutation in OTOF.

The compositions and methods described herein can be used to treat sensorineural hearing loss or auditory neuropathy by administering a first nucleic acid vector containing a polynucleotide encoding an N-terminal portion of an OTOF protein and a second nucleic acid vector containing a polynucleotide encoding a C-terminal portion of an OTOF protein. The full-length OTOF coding sequence is too large to include in the type of vector that is commonly used for gene therapy (e.g., an adeno-associated virus (AAV) vector, which is thought to have a packaging limit of 5 kb). The compositions and methods described herein overcome this problem by dividing the OTOF coding sequence between two different nucleic acid vectors that can recombine in a cell to reconstitute the full-length OTOF sequence. These compositions and methods can be used to treat subjects having one or more mutations in the OTOF gene, e.g., an OTOF mutation that reduces OTOF expression, reduces OTOF function, or is associated with hearing loss. When the first and second nucleic acid vectors are administered in a composition, the polynucleotides encoding the N-terminal and C-terminal portions of OTOF can combine within a cell (e.g., a human cell, e.g., a cochlear hair cell) to form a single nucleic acid molecule that contains the full-length OTOF coding sequence (e.g., through homologous recombination and/or splicing).

The nucleic acid vectors used in the compositions and methods described herein include nucleic acid sequences that encode wild-type OTOF, or a variant thereof, such as a nucleic acid sequences that, when combined, encode a protein having at least 85% sequence identity (e.g., 85%, 90%, 95%, 96%, 97%, 98%, 99%, or more, sequence identity) to the amino acid sequence of wild-type human or mouse OTOF. The polynucleotides used in the nucleic acid vectors described herein encode an N-terminal portion and a C-terminal portion of an OTOF amino acid sequence in Table 2 below (e.g., two portions that, when combined, encode a full-length OTOF amino acid sequence listed in Table 2, e.g., SEQ ID NO: 1).

According to the methods described herein, a subject can be administered a composition containing a first nucleic acid vector and a second nucleic acid vector that encode an N-terminal and C-terminal portion, respectively, of a nucleic acid sequence encoding the amino acid sequence of SEQ ID NO: 1, or a nucleic acid sequence encoding an amino acid sequence having at least 85% sequence identity (e.g., 85%, 90%, 95%, 96%, 97%, 98%, 99%, or more, sequence identity) to the amino acid sequence of SEQ ID NO: 1, or a nucleic acid sequence encoding an amino acid sequence that contains one or more conservative amino acid substitutions relative to SEQ ID NO: 1 (e.g., 1, 2, 3, 4, 5, 6, 7, 8, 9, or 10 or more conservative amino acid substitutions), provided that the OTOF analog encoded retains the therapeutic function of wild-type OTOF (e.g., the ability to regulate exocytosis at ribbon synapses).

TABLE 2

OTOF Sequences

| SEQ ID NO. | Sequence Name | Sequence |
|---|---|---|
| 1 | OTOF-201 protein<br>(NP_919224.1),<br>human otoferlin<br>isoform a, 1997 aa | MALLIHLKTVSELRGRGDRIAKVTFRGQSFYSRVLENCEDVADFDE<br>TFRWPVASSIDRNEMLEIQVFNYSKVFSNKLIGTFRMVLQKVVEES<br>HVEVTDTLIDDNNAIIKTSLCVEVRYQATDGTVGSWDDGDFLGDES<br>LQEEEKDSQETDGLLPGSRPSSRPPGEKSFRRAGRSVFSAMKLGK<br>NRSHKEEPQRPDEPAVLEMEDLDHLAIRLGDGLDPDSVSLASVTAL<br>TTNVSNKRSKPDIKMEPSAGRPMDYQVSITVIEARQLVGLNMDPVV<br>CVEVGDDKKYTSMKESTNCPYYNEYFVFDFHVSPDVMFDKIIKISVI<br>HSKNLLRSGTLVGSFKMDVGTVYSQPEHQFHHKWAILSDPDDISS<br>GLKGYVKCDVAVVGKGDNIKTPHKANETDEDDIEGNLLLPEGVPPE<br>RQWARFYVKIYRAEGLPRMNTSLMANVKKAFIGENKDLVDPYVQV<br>FFAGQKGKTSVQKSSYEPLWNEQVVFTDLFPPLCKRMKVQIRDSD<br>KVNDVAIGTHFIDLRKISNDGDKGFLPTLGPAWVNMYGSTRNYTLL<br>DEHQDLNEGLGEGVSFRARLLLGLAVEIVDTSNPELTSSTEVQVEQ<br>ATPISESCAGKMEEFFLFGAFLEASMIDRRNGDKPITFEVTIGNYGN<br>EVDGLSRPQRPRPRKEPGDEEEVDLIQNASDDEAGDAGDLASVSS<br>TPPMRPQVTDRNYFHLPYLERKPCIYIKSWWPDQRRRLYNANIMD<br>HIADKLEEGLNDIQEMIKTEKSYPERRLRGVLEELSCGCCRFLSLAD<br>KDQGHSSRTRLDRERLKSCMRELENMGQQARMLRAQVKRHTVRD<br>KLRLCONFLQKLRFLADEPQHSIPDIFIWMMSNNKRVAYARVPSKD<br>LLFSIVEEETGKDCAKVKTLFLKLPGKRGFGSAGWTVQAKVELYLW<br>LGLSKQRKEFLCGLPCGFQEVKAAQGLGLHAFPPVSLVYTKKQAF<br>QLRAHMYQARSLFAADSSGLSDPFARVFFINQSQCTEVLNETLCPT<br>WDQMLVFDNLELYGEAHELRDDPPIIVIEIYDQDSMGKADFMGRTF<br>AKPLVKMADEAYCPPRFPPQLEYYQIYRGNATAGDLLAAFELLQIG<br>PAGKADLPPINGPVDVDRGPIMPVPMGIRPVLSKYRVEVLFWGLRD<br>LKRVNLAQVDRPRVDIECAGKGVQSSLIHNYKKNPNFNTLVKWFEV<br>DLPENELLHPPLNIRVVDCRAFGRYTLVGSHAVSSLRRFIYRPPDRS<br>APSWNTTVRLLRRCRVLCNGGSSSHSTGEVVVTMEPEVPIKKLET<br>MVKLDATSEAVVKVDVAEEEKEKKKKKKGTAEEPEEEEPDESMLD<br>WWSKYFASIDTMKEQLRQQEPSGIDLEEKEEVDNTEGLKGSMKGK<br>EKARAAKEEKKKKTQSSGSGQGSEAPEKKKPKIDELKVYPKELESE<br>FDNFEDWLHTFNLLRGKTGDDEDGSTEEERIVGRFKGSLCVYKVPL<br>PEDVSREAGYDSTYGMFQGIPSNDPINVLVRVYVVRATDLHPADIN<br>GKADPYIAIRLGKTDIRDKENYISKQLNPVFGKSFDIEASFPMESMLT<br>VAVYDWDLVGTDDLIGETKIDLENRFYSKHRATCGIAQTYSTHGYNI<br>WRDPMKPSQILTRLCKDGKVDGPHFGPPGRVKVANRVFTGPSEIE<br>DENGQRKPTDEHVALLALRHWEDIPRAGCRLVPEHVETRPLLNPD<br>KPGIEQGRLELWVDMFPMDMPAPGTPLDISPRKPKKYELRVIIWNT<br>DEVVLEDDDFFTGEKSSDIFVRGWLKGQQEDKQDTDVHYHSLTGE<br>GNFNWRYLFPFDYLAAEEKIVISKKESMFSWDETEYKIPARLTLQIW<br>DADHFSADDFLGAIELDLNRFPRGAKTAKQCTMEMATGEVDVPLV<br>SIFKQKRVKGWWPLLARNENDEFELTGKVEAELHLLTAEEAEKNPV<br>GLARNEPDPLEKPNRPDTSFIWFLNPLKSARYFLWHTYRWLLLKLL<br>LLLLLLLLLALFLYSVPGYLVKKILGA |
| 2 | OTOF-202 protein<br>(NP_004793.2),<br>human otoferlin<br>isoform b, 1230 aa | MIKTEKSYPERRLRGVLEELSCGCCRFLSLADKDQGHSSRTRLDRE<br>RLKSCMRELENMGQQARMLRAQVKRHTVRDKLRLCQNFLQKLRF<br>LADEPQHSIPDIFIWMMSNNKRVAYARVPSKDLLFSIVEEETGKDCA<br>KVKTLFLKLPGKRGFGSAGWTVQAKVELYLWLGLSKQRKEFLCGL<br>PCGFQEVKAAQGLGLHAFPPVSLVYTKKQAFQLRAHMYQARSLFA<br>ADSSGLSDPFARVFFINQSQCTEVLNETLCPTWDQMLVFDNLELYG<br>EAHELRDDPPIIVIEIYDQDSMGKADFMGRTFAKPLVKMADEAYCPP |

TABLE 2-continued

| OTOF Sequences | | |
|---|---|---|
| SEQ ID NO. | Sequence Name | Sequence |
| | | RFPPQLEYYQIYRGNATAGDLLAAFELLQIGPAGKADLPPINGPVDV DRGPIMPVPMGIRPVLSKYRVEVLFWGLRDLKRVNLAQVDRPRVDI ECAGKGVQSSLIHNYKKNPNFNTLVKWFEVDLPENELLHPPLNIRV VDCRAFGRYTLVGSHAVSSLRRFIYRPPDRSAPSWNTTGEVVVTM EPEVPIKKLETMVKLDATSEAVVKVDVAEEEKEKKKKKGTAEEPE EEEPDESMLDWWSKYFASIDTMKEQLRQQEPSGIDLEEKEEVDNT EGLKGSMKGKEKARAAKEEKKKKTQSSGSGQGSEAPEKKKPKIDE LKVYPKELESEFDNFEDWLHTFNLLRGKTGDDEDGSTEEERIVGRF KGSLCVYKVPLPEDVSREAGYDSTYGMFQGIPSNDPINVLVRVYVV RATDLHPADINGKADPYIAIRLGKTDIRDKENYISKQLNPVFGKSFDI EASFPMESMLTVAVYDWDLVGTDDLIGETKIDLENRFYSKHRATCG IAQTYSTHGYNIWRDPMKPSQILTRLCKDGKVDGPHFGPPGRVKVA NRVFTGPSEIEDENGQRKPTDEHVALLALRHWEDIPRAGCRLVPEH VETRPLLNPDKPGIEQGRLELWVDMFPMDMPAPGTPLDISPRKPKK YELRVIIWNTDEVVLEDDDFFTGEKSSDIFVRGWLKGQQEDKQDTD VHYHSLTGEGNFNWRYLFPFDYLAAEEKIVISKKESMFSWDETEYKI PARLTLQIWDADHFSADDFLGAIELDLNRFPRGAKTAKQCTMEMAT GEVDVPLVSIFKQKRVKGWWPLLARNENDEFELTGKVEAELHLLTA EEAEKNPVGLARNEPDPLEKPNRPDTSFIWFLNPLKSARYFLWHTY RWLLLKLLLLLLLLLLALFLYSVPGYLVKKILGA |
| 3 | OTOF-203 protein (NP_919304.1), human otoferlin isoform d, 1230 aa | MIKTEKSYPERRLRGVLEELSCGCCRFLSLADKDQGHSSRTRLDRE RLKSCMRELENMGQQARMLRAQVKRHTVRDKLRLCQNFLQKLRF LADEPQHSIPDIFIWMMSNNKRVAYARVPSKDLLFSIVEEETGKDCA KVKTLFLKLPGKRGFGSAGWTVQAKVELYLWLGLSKQRKEFLCGL PCGFQEVKAAQGLGLHAFPPVSLVYTKKQAFQLRAHMYQARSLFA ADSSGLSDPFARVFFINQSQCTEVLNETLCPTWDQMLVFDNLELYG EAHELRDDPPIIVIEIYDQDSMGKADFMGRTFAKPLVKMADEAYCPP RFPPQLEYYQIYRGNATAGDLLAAFELLQIGPAGKADLPPINGPVDV DRGPIMPVPMGIRPVLSKYRVEVLFWGLRDLKRVNLAQVDRPRVDI ECAGKGVQSSLIHNYKKNPNFNTLVKWFEVDLPENELLHPPLNIRV VDCRAFGRYTLVGSHAVSSLRRFIYRPPDRSAPSWNTTGEVVVTM EPEVPIKKLETMVKLDATSEAVVKVDVAEEEKEKKKKKGTAEEPE EEEPDESMLDWWSKYFASIDTMKEQLRQQEPSGIDLEEKEEVDNT EGLKGSMKGKEKARAAKEEKKKKTQSSGSGQGSEAPEKKKPKIDE LKVYPKELESEFDNFEDWLHTFNLLRGKTGDDEDGSTEEERIVGRF KGSLCVYKVPLPEDVSREAGYDSTYGMFQGIPSNDPINVLVRVYVV RATDLHPADINGKADPYIAIRLGKTDIRDKENYISKQLNPVFGKSFDI EASFPMESMLTVAVYDWDLVGTDDLIGETKIDLENRFYSKHRATCG IAQTYSTHGYNIWRDPMKPSQILTRLCKDGKVDGPHFGPPGRVKVA NRVFTGPSEIEDENGQRKPTDEHVALLALRHWEDIPRAGCRLVPEH VETRPLLNPDKPGIEQGRLELWVDMFPMDMPAPGTPLDISPRKPKK YELRVIIWNTDEVVLEDDDFFTGEKSSDIFVRGWLKGQQEDKQDTD VHYHSLTGEGNFNWRYLFPFDYLAAEEKIVISKKESMFSWDETEYKI PARLTLQIWDADHFSADDFLGAIELDLNRFPRGAKTAKQCTMEMAT GEVDVPLVSIFKQKRVKGWWPLLARNENDEFELTGKVEAELHLLTA EEAEKNPVGLARNEPDPLEKPNRPDTAFVWFLNPLKSIKYLICTRYK WLIIKIVLALLGLLMLGLFLYSLPGYMVKKLLGA |
| 4 | OTOF-208 protein (NP_919303.1), human otoferlin isoform c, 1307 aa | MMTDTQDGPSESSQIMRSLTPLINREEAFGEAGEAGLWPSITHTPD SQEEGLNDIQEMIKTEKSYPERRLRGVLEELSCGCCRFLSLADKDQ GHSSRTRLDRERLKSCMRELENMGQQARMLRAQVKRHTVRDKLR LCQNFLQKLRFLADEPQHSIPDIFIWMMSNNKRVAYARVPSKDLLFS IVEEETGKDCAKVKTLFLKLPGKRGFGSAGWTVQAKVELYLWLGLS KQRKEFLCGLPCGFQEVKAAQGLGLHAFPPVSLVYTKKQAFQLRA HMYQARSLFAADSSGLSDPFARVFFINQSQCTEVLNETLCPTWDQ MLVFDNLELYGEAHELRDDPPIIVIEIYDQDSMGKADFMGRTFAKPL VKMADEAYCPPRFPPQLEYYQIYRGNATAGDLLAAFELLQIGPAGK ADLPPINGPVDVDRGPIMPVPMGIRPVLSKYRVEVLFWGLRDLKRV NLAQVDRPRVDIECAGKGVQSSLIHNYKKNPNFNTLVKWFEVDLPE NELLHPPLNIRVVDCRAFGRYTLVGSHAVSSLRRFIYRPPDRSAPS WNTTVRLLRRCRVLCNGGSSSHSTGEVVVTMEPEVPIKKLETMVK LDATSEAVVKVDVAEEEKEKKKKKGTAEEPEEEEPDESMLDWWS KYFASIDTMKEQLRQQEPSGIDLEEKEEVDNTEGLKGSMKGKEKAR AAKEEKKKKTQSSGSGQGSEAPEKKKPKIDELKVYPKELESEFDNF EDWLHTFNLLRGKTGDDEDGSTEEERIVGRFKGSLCVYKVPLPED VSREAGYDSTYGMFQGIPSNDPINVLVRVYVVRATDLHPADINGKA DPYIAIRLGKTDIRDKENYISKQLNPVFGKSFDIEASFPMESMLTVAV YDWDLVGTDDLIGETKIDLENRFYSKHRATCGIAQTYSTHGYNIWR DPMKPSQILTRLCKDGKVDGPHFGPPGRVKVANRVFTGPSEIEDE NGQRKPTDEHVALLALRHWEDIPRAGCRLVPEHVETRPLLNPDKP GIEQGRLELWVDMFPMDMPAPGTPLDISPRKPKKYELRVIIWNTDE VVLEDDDFFTGEKSSDIFVRGWLKGQQEDKQDTDVHYHSLTGEGN FNWRYLFPFDYLAAEEKIVISKKESMFSWDETEYKIPARLTLQIWDA DHFSADDFLGAIELDLNRFPRGAKTAKQCTMEMATGEVDVPLVSIF |

TABLE 2-continued

| OTOF Sequences | | |
|---|---|---|
| SEQ ID NO. | Sequence Name | Sequence |
| | | KQKRVKGWWPLLARNENDEFELTGKVEAELHLLTAEEAEKNPVGL<br>ARNEPDPLEKPNRPDTSFIWFLNPLKSARYFLWHTYRWLLLKLLLLL<br>LLLLLLALFLYSVPGYLVKKILGA |
| 5 | OTOF-205 protein (NP_001274418.1), human otoferlin isoform e, 1997 aa | MALLIHLKTVSELRGRGDRIAKVTFRGQSFYSRVLENCEDVADFDE<br>TFRWPVASSIDRNEMLEIQVFNYSKVFSNKLIGTFRMVLQKVVEES<br>HVEVTDTLIDDNNAIIKTSLCVEVRYQATDGTVGSWDDGDFLGDES<br>LQEEEKDSQETDGLLPGSRPSSRPPGEKSFRRAGRSVFSAMKLGK<br>NRSHKEEPQRPDEPAVLEMEDLDHLAIRLGDGLDPDSVSLASVTAL<br>TTNVSNKRSKPDIKMEPSAGRPMDYQVSITVIEARQLVGLNMDPVV<br>CVEVGDDKKYTSMKESTNCPYYNEYFVFDFHVSPDVMFDKIIKISVI<br>HSKNLLRSGTLVGSFKMDVGTVYSQPEHQFHHKWAILSDPDDISS<br>GLKGYVKCDVAVVGKGDNIKTPHKANETDEDDIEGNLLLPEGVPPE<br>RQWARFYVKIYRAEGLPRMNTSLMANVKKAFIGENKDLVDPYVQV<br>FFAGQKGKTSVQKSSYEPLWNEQVVFTDLFPPLCKRMKVQIRDSD<br>KVNDVAIGTHFIDLRKISNDGDKGFLPTLGPAWVNMYGSTRNYTLL<br>DEHQDLNEGLGEGVSFRARLLLGLAVEIVDTSNPELTSSTEVQVEQ<br>ATPISESCAGKMEEFFLFGAFLEASMIDRRNGDKPITFEVTIGNYGN<br>EVDGLSRPQRPRPRKEPGDEEEVDLIQNASDDEAGDAGDLASVSS<br>TPPMRPQVTDRNYFHLPYLERKPCIYIKSWWPDQRRRLYNANIMD<br>HIADKLEEGLNDIQEMIKTEKSYPERRLRGVLEELSCGCCRFLSLAD<br>KDQGHSSRTRLDRERLKSCMRELENMGQQARMLRAQVKRHTVRD<br>KLRLCQNFLQKLRFLADEPQHSIPDIFIWMMSNNKRVAYARVPSKD<br>LLFSIVEEETGKDCAKVKTLFLKLPGKRGFGSAGWTVQAKVELYLW<br>LGLSKQRKEFLCGLPCGFQEVKAAQGLGLHAFPPVSLVYTKKQAF<br>QLRAHMYQARSLFAADSSGLSDPFARVFFINQSQCTEVLNETLCPT<br>WDQMLVFDNLELYGEAHELRDDPPIIVIEIYDQDSMGKADFMGRTF<br>AKPLVKMADEAYCPPRFPPQLEYYQIYRGNATAGDLLAAFELLQIG<br>PAGKADLPPINGPVDVDRGPIMPVPMGIRPVLSKYRVEVLFWGLRD<br>LKRVNLAQVDRPRVDIECAGKGVQSSLIHNYKKNPNFNTLVKWFEV<br>DLPENELLHPPLNIRVVDCRAFGRYTLVGSHAVSSLRRFIYRPPDRS<br>APSWNTTVRLLRRCRVLCNGGSSSHSTGEVVVTMEPEVPIKKLET<br>MVKLDATSEAVVKVDVAEEEKEKKKKKKGTAEEPEEEEPDESMLD<br>WWSKYFASIDTMKEQLRQQEPSGIDLEEKEEVDNTEGLKGSMKGK<br>EKARAAKEEKKKKTQSSGSGQGSEAPEKKKPKIDELKVYPKELESE<br>FDNFEDWLHTFNLLRGKTGDDEDGSTEEERIVGRFKGSLCVYKVPL<br>PEDVSREAGYDSTYGMFQGIPSNDPINVLVRVYVVRATDLHPADIN<br>GKADPYIAIRLGKTDIRDKENYISKQLNPVFGKSFDIEASFPMESMLT<br>VAVYDWDLVGTDDLIGETKIDLENRFYSKHRATCGIAQTYSTHGYNI<br>WRDPMKPSQILTRLCKDGKVDGPHFGPPGRVKVANRVFTGPSEIE<br>DENGQRKPTDEHVALLALRHWEDIPRAGCRLVPEHVETRPLLNPD<br>KPGIEQGRLELWVDMFPMDMPAPGTPLDISPRKPKKYELRVIIWNT<br>DEVVLEDDDFFTGEKSSDIFVRGWLKGQQEDKQDTDVHYHSLTGE<br>GNFNWRYLFPFDYLAAEEKIVISKKESMFSWDETEYKIPARLTLQIW<br>DADHFSADDFLGAIELDLNRFPRGAKTAKQCTMEMATGEVDVPLV<br>SIFKQKRVKGWWPLLARNENDEFELTGKVEAELHLLTAEEAEKNPV<br>GLARNEPDPLEKPNRPDTAFVWFLNPLKSIKYLICTRYKWLIIKIVLAL<br>LGLLMLGLFLYSLPGYMVKKLLGA |
| 6 | mOTOF-201_1 protein (NP_114081.2), mouse otoferlin isoform 2, 1997 aa | MALIVHLKTVSELRGKGDRIAKVTFRGQSFYSRVLENCEGVADFDE<br>TFRWPVASSIDRNEVLEIQIFNYSKVFSNKLIGTFCMVLQKVVEENR<br>VEVTDTLMDDSNAIIKTSLSMEVRYQATDGTVGPWDDGDFLGDESL<br>QEEKDSQETDGLLPGSRPSTRISGEKSFRRAGRSVFSAMKLGKTR<br>SHKEEPQRQDEPAVLEMEDLDHLAIQLGDGLDPDSVSLASVTALTS<br>NVSNKRSKPDIKMEPSAGRPMDYQVSITVIEARQLVGLNMDPVVCV<br>EVGDDKKYTSMKESTNCPYYNEYFVFDFHVSPDVMFDKIIKISVIHS<br>KNLLRSGTLVGSFKMDVGTVYSQPEHQFHHKWAILSDPDDISAGLK<br>GYVKCDVAVVGKGDNIKTPHKANETDEDDIEGNLLLPEGVPPERQ<br>WARFYVKIYRAEGLPRMNTSLMANVKKAFIGENKDLVDPYVQVFFA<br>GQKGKTSVQKSSYEPLWNEQVVFTDLFPPLCKRMKVQIRDSDKVN<br>DVAIGTHFIDLRKISNDGDKGFLPTLGPAWVNMYGSTRNYTLLDEH<br>QDLNEGLGEGVSFRARLMLGLAVEILDTSNPELTSSTEVQVEQATP<br>VSESCTGRMEEFFLFGAFLEASMIDRKNGDKPITFEVTIGNYGNEV<br>DGMSRPLRPRPRKEPGDEEEVDLIQNSSDDEGDEAGDLASVSSTP<br>PMRPQITDRNYFHLPYLERKPCIYIKSWWPDQRRRLYNANIMDHIA<br>DKLEEGLNDVQEMIKTEKSYPERRLRGVLEELSCGCHRFLSLSDKD<br>QGRSSRTRLDRERLKSCMRELESMGQQAKSLRAQVKRHTVRDKL<br>RSCQNFLQKLRFLADEPQHSIPDVFIWMMSNNKRIAYARVPSKDLL<br>FSIVEEELGKDCAKVKTLFLKLPGKRGFGSAGWTVQAKLELYLWLG<br>LSKQRKDFLCGLPCGFEEVKAAQGLGLHSFPPISLVYTKKQAFQLR<br>AHMYQARSLFAADSSGLSDPFARVFFINQSQCTEVLNETLCPTWD<br>QMLVFDNLELYGEAHELRDDPPIIVIEIYDQDSMGKADFMGRTFAKP<br>LVKMADEAYCPPRFPPQLEYYQIYRGSATAGDLLAAFELLQIGPSG<br>KADLPPINGPVDMDRGPIMPVPVGIRPVLSKYRVEVLFWGLRDLKR<br>VNLAQVDRPRVDIECAGKGVQSSLIHNYKKNPNFNTLVKWFEVDLP |

TABLE 2-continued

| SEQ ID NO. | Sequence Name | Sequence |
|---|---|---|
| | OTOF Sequences | |
| | | ENELLHPPLNIRVVDCRAFGRYTLVGSHAVSSLRRFIYRPPDRSAP NWNTTVRLLRGCHRLRNGGPSSRPTGEVVVSMEPEEPVKKLETM VKLDATSDAVVKVDVAEDEKERKKKKKGPSEEPEEEEPDESMLD WWSKYFASIDTMKEQLRQHETSGTDLEEKEEMESAEGLKGPMKS KEKSRAAKEEKKKKNQSPGPGQGSEAPEKKKAKIDELKVYPKELES EFDSFEDWLHTFNLLRGKTGDDEDGSTEEERIVGRFKGSLCVYKV PLPEDVSREAGYDPTYGMFQGIPSNDPINVLVRIYVVRATDLHPADI NGKADPYIAIKLGKTDIRDKENYISKQLNPVFGKSFDIEASFPMESML TVAVYDWDLVGTDDLIGETKIDLENRFYSKHRATCGIAQTYSIHGYN IWRDPMKPSQILTRLCKEGKVDGPHFGPHGRVRVANRVFTGPSEIE DENGQRKPTDEHVALSALRHWEDIPRVGCRLVPEHVETRPLLNPD KPGIEQGRLELWVDMFPMDMPAPGTPLDISPRKPKKYELRVIVWNT DEVVLEDDDFFTGEKSSDIFVRGWLKGQQEDKQDTDVHYHSLTGE GNFNWRYLFPFDYLAAEEKIVMSKKESMFSWDETEYKIPARLTLQI WDADHFSADDFLGAIELDLNRFPRGAKTAKQCTMEMATGEVDVPL VSIFKQKRVKGWWPLLARNENDEFELTGKVEAELHLLTAEEAEKNP VGLARNEPDPLEKPNRPDTSFIWFLNPLKSARYFLWHTYRWLLLKF LLLFLLLLLFALFLYSLPGYLAKKILGA |
| 7 | mOTOF-201_2 protein (NP_001273350.1), mouse otoferlin isoform 3, 1977 aa | MALIVHLKTVSELRGKGDRIAKVTFRGQSFYSRVLENCEGVADFDE TFRWPVASSIDRNEVLEIQIFNYSKVFSNKLIGTFCMVLQKVVEENR VEVTDTLMDDSNAIIKTSLSMEVRYQATDGTVGPWDDGDFLGDESL QEEKDSQETDGLLPGSRPSTRISGEKSFRRAGRSVFSAMKLGKTR SHKEEPQRQDEPAVLEMEDLDHLAIQLGDGLDPDSVSLASVTALTS NVSNKRSKPDIKMEPSAGRPMDYQVSITVIEARQLVGLNMDPVVCV EVGDDKKYTSMKESTNCPYYNEYFVFDFHVSPDVMFDKIIKISVIHS KNLLRSGTLVGSFKMDVGTVYSQPEHQFHHKWAILSDPDDISAGLK GYVKCDVAVVGKGDNIKTPHKANETDEDDIEGNLLLPEGVPPERQ WARFYVKIYRAEGLPRMNTSLMANVKKAFIGENKDLVDPYVQVFFA GQKGKTSVQKSSYEPLWNEQVVFTDLFPPLCKRMKVQIRDSDKVN DVAIGTHFIDLRKISNDGDKGFLPTLGPAWVNMYGSTRNYTLLDEH QDLNEGLGEGVSFRARLMLGLAVEILDTSNPELTSSTEVQVEQATP VSESCTGRMEEFFLFGAFLEASMIDRKNGDKPITFEVTIGNYGNEV DGMSRPLRPRPRKEPGDEEEVDLIQNSSDDEGDEAGDLASVSSTP PMRPQITDRNYFHLPYLERKPCIYIKSWWPDQRRRLYNANIMDHIA DKLEEGLNDVQEMIKTEKSYPERRLRGVLEELSCGCHRFLSLSDKD QGRSSRTRLDRERLKSCMRELESMGQQAKSLRAQVKRHTVRDKL RSCQNFLQKLRFLADEPQHSIPDVFIWMMSNNKRIAYARVPSKDLL FSIVEEELGKDCAKVKTLFLKLPGKRGFGSAGWTVQAKLELYLWLG LSKQRKDFLCGLPCGFEEVKAAQGLGLHSFPPISLVYTKKQAFQLR AHMYQARSLFAADSSGLSDPFARVFFINQSQCTEVLNETLCPTWD QMLVFDNLELYGEAHELRDDPPIIVIEIYDQDSMGKADFMGRTFAKP LVKMADEAYCPPRFPPQLEYYQIYRGSATAGDLLAAFELLQIGPSG KADLPPINGPVDMDRGPIMPVPVGIRPVLSKYRVEVLFWGLRDLKR VNLAQVDRPRVDIECAGKGVQSSLIHNYKKNPNFNTLVKWFEVDLP ENELLHPPLNIRVVDCRAFGRYTLVGSHAVSSLRRFIYRPPDRSAP NWNTTGEVVVSMEPEEPVKKLETMVKLDATSDAVVKVDVAEDEKE RKKKKKGPSEEPEEEEPDESMLDWWSKYFASIDTMKEQLRQHET SGTDLEEKEEMESAEGLKGPMKSKEKSRAAKEEKKKKNQSPGPG QGSEAPEKKKAKIDELKVYPKELESEFDSFEDWLHTFNLLRGKTGD DEDGSTEEERIVGRFKGSLCVYKVPLPEDVSREAGYDPTYGMFQGI PSNDPINVLVRIYVVRATDLHPADINGKADPYIAIKLGKTDIRDKENYI SKQLNPVFGKSFDIEASFPMESMLTVAVYDWDLVGTDDLIGETKIDL ENRFYSKHRATCGIAQTYSIHGYNIWRDPMKPSQILTRLCKEGKVD GPHFGPHGRVRVANRVFTGPSEIEDENGQRKPTDEHVALSALRHW EDIPRVGCRLVPEHVETRPLLNPDKPGIEQGRLELWVDMFPMDMP APGTPLDISPRKPKKYELRVIVWNTDEVVLEDDDFFTGEKSSDIFVR GWLKGQQEDKQDTDVHYHSLTGEGNFNWRYLFPFDYLAAEEKIV MSKKESMFSWDETEYKIPARLTLQIWDADHFSADDFLGAIELDLNR FPRGAKTAKQCTMEMATGEVDVPLVSIFKQKRVKGWWPLLARNEN DEFELTGKVEAELHLLTAEEAEKNPVGLARNEPDPLEKPNRPDTSFI WFLNPLKSARYFLWHTYRWLLLKFLLLFLLLLLFALFLYSLPGYLAKK ILGA |
| 8 | mOTOF-202_1 protein (NP_001093865.1), mouse otoferlin isoform 1, 1992 aa | MALIVHLKTVSELRGKGDRIAKVTFRGQSFYSRVLENCEGVADFDE TFRWPVASSIDRNEVLEIQIFNYSKVFSNKLIGTFCMVLQKVVEENR VEVTDTLMDDSNAIIKTSLSMEVRYQATDGTVGPWDDGDFLGDESL QEEKDSQETDGLLPGSRPSTRISGEKSFRSKGREKTKGGRDGEHK AGRSVFSAMKLGKTRSHKEEPQRQDEPAVLEMEDLDHLAIQLGDG LDPDSVSLASVTALTSNVSNKRSKPDIKMEPSAGRPMDYQVSITVIE ARQLVGLNMDPVVCVEVGDDKKYTSMKESTNCPYYNEYFVFDFHV SPDVMFDKIIKISVIHSKNLLRSGTLVGSFKMDVGTVYSQPEHQFHH KWAILSDPDDISAGLKGYVKCDVAVVGKGDNIKTPHKANETDEDDIE GNLLLPEGVPPERQWARFYVKIYRAEGLPRMNTSLMANVKKAFIGE NKDLVDPYVQVFFAGQKGKTSVQKSSYEPLWNEQVVFTDLFPPLC |

TABLE 2-continued

| OTOF Sequences | | |
|---|---|---|
| SEQ ID NO. | Sequence Name | Sequence |
| | | KRMKVQIRDSDKVNDVAIGTHFIDLRKISNDGDKGFLPTLGPAWVN<br>MYGSTRNYTLLDEHQDLNEGLGEGVSFRARLMLGLAVEILDTSNPE<br>LTSSTEVQVEQATPVSESCTGRMEEFFLFGAFLEASMIDRKNGDKP<br>ITFEVTIGNYGNEVDGMSRPLRPRPRKEPGDEEEVDLIQNSSDDEG<br>DEAGDLASVSSTPPMRPQITDRNYFHLPYLERKPCIYIKSWWPDQR<br>RRLYNANIMDHIADKLEEGLNDVQEMIKTEKSYPERRLRGVLEELSC<br>GCHRFLSLSDKDQGRSSRTRLDRERLKSCMRELESMGQQAKSLR<br>AQVKRHTVRDKLRSCQNFLQKLRFLADEPQHSIPDVFIWMMSNNK<br>RIAYARVPSKDLLFSIVEEELGKDCAKVKTLFLKLPGKRGFGSAGWT<br>VQAKLELYLWLGLSKQRKDFLCGLPCGFEEVKAAQGLGLHSFPPIS<br>LVYTKKQAFQLRAHMYQARSLFAADSSGLSDPFARVFFINQSQCTE<br>VLNETLCPTWDQMLVFDNLELYGEAHELRDDPPIIVIEIYDQDSMGK<br>ADFMGRTFAKPLVKMADEAYCPPRFPPQLEYYQIYRGSATAGDLLA<br>AFELLQIGPSGKADLPPINGPVDMDRGPIMPVPVGIRPVLSKYRVEV<br>LFWGLRDLKRVNLAQVDRPRVDIECAGKGVQSSLIHNYKKNPNFNT<br>LVKWFEVDLPENELLHPPLNIRVVDCRAFGRYTLVGSHAVSSLRRFI<br>YRPPDRSAPNWNTTGEVVVSMEPEEPVKKLETMVKLDATSDAVVK<br>VDVAEDEKERKKKKKGPSEEPEEEEPDESMLDWWSKYFASIDTM<br>KEQLRQHETSGTDLEEKEEMESAEGLKGPMKSKEKSRAAKEEKKK<br>KNQSPGPGQGSEAPEKKKAKIDELKVYPKELESEFDSFEDWLHTF<br>NLLRGKTGDDEDGSTEEERIVGRFKGSLCVYKVPLPEDVSREAGY<br>DPTYGMFQGIPSNDPINVLVRIYVVRATDLHPADINGKADPYIAIKLG<br>KTDIRDKENYISKQLNPVFGKSFDIEASFPMESMLTVAVYDWDLVG<br>TDDLIGETKIDLENRFYSKHRATCGIAQTYSIFIGYNIWRDPMKPSQIL<br>TRLCKEGKVDGPHFGPHGRVRVANRVFTGPSEIEDENGQRKPTDE<br>HVALSALRHWEDIPRVGCRLVPEHVETRPLLNPDKPGIEQGRLELW<br>VDMFPMDMPAPGTPLDISPRKPKKYELRVIVWNTDEVVLEDDDFFT<br>GEKSSDIFVRGWLKGQQEDKQDTDVHYHSLTGEGNFNWRYLFPF<br>DYLAAEEKIVMSKKESMFSWDETEYKIPARLTLQIWDADHFSADDF<br>LGAIELDLNRFPRGAKTAKQCTMEMATGEVDVPLVSIFKQKRVKGW<br>WPLLARNENDEFELTGKVEAELHLLTAEEAEKNPVGLARNEPDPLE<br>KPNRPDTAFVWFLNPLKSIKYLICTRYKWLIIKIVLALLGLLMLALFLY<br>SLPGYMVKKLLGA |
| 9 | mOTOF-202_2 protein (NP_001300696.1), mouse otoferlin isoform 4, 1977 aa | MALIVHLKTVSELRGKGDRIAKVTFRGQSFYSRVLENCEGVADFDE<br>TFRWPVASSIDRNEVLEIQIFNYSKVFSNKLIGTFCMVLQKVVEENR<br>VEVTDTLMDDSNAIIKTSLSMEVRYQATDGTVGPWDDGDFLGDESL<br>QEEKDSQETDGLLPGSRPSTRISGEKSFRRAGRSVFSAMKLGKTR<br>SHKEEPQRQDEPAVLEMEDLDHLAIQLGDGLDPDSVSLASVTALTS<br>NVSNKRSKPDIKMEPSAGRPMDYQVSITVIEARQLVGLNMDPVVCV<br>EVGDDKKYTSMKESTNCPYYNEYFVFDFHVSPDVMFDKIIKISVIHS<br>KNLLRSGTLVGSFKMDVGTVYSQPEHQFHHKWAILSDPDDISAGLK<br>GYVKCDVAVVGKGDNIKTPHKANETDEDDIEGNLLLPEGVPPERQ<br>WARFYVKIYRAEGLPRMNTSLMANVKKAFIGENKDLVDPYVQVFFA<br>GQKGKTSVQKSSYEPLWNEQVVFTDLFPPLCKRMKVQIRDSDKVN<br>DVAIGTHFIDLRKISNDGDKGFLPTLGPAWVNMYGSTRNYTLLDEH<br>QDLNEGLGEGVSFRARLMLGLAVEILDTSNPELTSSTEVQVEQATP<br>VSESCTGRMEEFFLFGAFLEASMIDRKNGDKPITFEVTIGNYGNEV<br>DGMSRPLRPRPRKEPGDEEEVDLIQNSSDDEGDEAGDLASVSSTP<br>PMRPQITDRNYFHLPYLERKPCIYIKSWWPDQRRRLYNANIMDHIA<br>DKLEEGLNDVQEMIKTEKSYPERRLRGVLEELSCGCHRFLSLSDKD<br>QGRSSRTRLDRERLKSCMRELESMGQQAKSLRAQVKRHTVRDKL<br>RSCQNFLQKLRFLADEPQHSIPDVFIWMMSNNKRIAYARVPSKDLL<br>FSIVEEELGKDCAKVKTLFLKLPGKRGFGSAGWTVQAKLELYLWLG<br>LSKQRKDFLCGLPCGFEEVKAAQGLGLHSFPPISLVYTKKQAFQLR<br>AHMYQARSLFAADSSGLSDPFARVFFINQSQCTEVLNETLCPTWD<br>QMLVFDNLELYGEAHELRDDPPIIVIEIYDQDSMGKADFMGRTFAKP<br>LVKMADEAYCPPRFPPQLEYYQIYRGSATAGDLLAAFELLQIGPSG<br>KADLPPINGPVDMDRGPIMPVPVGIRPVLSKYRVEVLFWGLRDLKR<br>VNLAQVDRPRVDIECAGKGVQSSLIHNYKKNPNFNTLVKWFEVDLP<br>ENELLHPPLNIRVVDCRAFGRYTLVGSHAVSSLRRFIYRPPDRSAP<br>NWNTTGEVVVSMEPEEPVKKLETMVKLDATSDAVVKVDVAEDEKE<br>RKKKKKKGPSEEPEEEEPDESMLDWWSKYFASIDTMKEQLRQHET<br>SGTDLEEKEEMESAEGLKGPMKSKEKSRAAKEEKKKKNQSPGPG<br>QGSEAPEKKKAKIDELKVYPKELESEFDSFEDWLHTFNLLRGKTGD<br>DEDGSTEEERIVGRFKGSLCVYKVPLPEDVSREAGYDPTYGMFQGI<br>PSNDPINVLVRIYVVRATDLHPADINGKADPYIAIKLGKTDIRDKENYI<br>SKQLNPVFGKSFDIEASFPMESMLTVAVYDWDLVGTDDLIGETKIDL<br>ENRFYSKHRATCGIAQTYSIHGYNIWRDPMKPSQILTRLCKEGKVD<br>GPHFGPHGRVRVANRVFTGPSEIEDENGQRKPTDEHVALSALRHW<br>EDIPRVGCRLVPEHVETRPLLNPDKPGIEQGRLELWVDMFPMDMP<br>APGTPLDISPRKPKKYELRVIVWNTDEVVLEDDDFFTGEKSSDIFVR<br>GWLKGQQEDKQDTDVHYHSLTGEGNFNWRYLFPFDYLAAEEKIV<br>MSKKESMFSWDETEYKIPARLTLQIWDADHFSADDFLGAIELDLNR<br>FPRGAKTAKQCTMEMATGEVDVPLVSIFKQKRVKGWWPLLARNEN |

TABLE 2-continued

OTOF Sequences

| SEQ ID NO. | Sequence Name | Sequence |
|---|---|---|
| | | DEFELTGKVEAELHLLTAEEAEKNPVGLARNEPDPLEKPNRPDTAF<br>VWFLNPLKSIKYLICTRYKWLIIKIVLALLGLLMLALFLYSLPGYMVKK<br>LLGA |
| 10 | OTOF-201 transcript (NM_194248.1), human otoferlin transcript variant 1, 7156 bp, encodes the protein of SEQ ID NO: 1 | ATCGGAGGGGGGTCGGGAGGAGGAGGAGGAGGCAGCGGCAG<br>AGAAGAGAGAGGCGTGTGAGCCGTGCTCCACCGGCTAGCTCCT<br>TCCCGCTGCTCCTGCCTGGCAGTGCCAGGCAGCCCACACCAGC<br>ATGGCCTTGCTCATCCACCTCAAGACAGTCTCGGAGCTGCGGG<br>GCAGGGGCGACCGGATCGCCAAAGTGACTTTCCGAGGGCAATC<br>CTTCTACTCTCGGGTCCTGGAGAACTGTGAGGATGTGGCTGACT<br>TTGATGAGACATTTCGGTGGCCGGTGGCCAGCAGCATCGACAG<br>AAATGAGATGCTGGAGATTCAGGTTTTCAACTACAGCAAAGTCTT<br>CAGCAACAAGCTCATCGGGACCTTCCGCATGGTGCTGCAGAAG<br>GTGGTAGAGGAGAGCCATGTGGAGGTGACTGACACGCTGATTG<br>ATGACAACAATGCTATCATCAAGACCAGCCTGTGCGTGGAGGTC<br>CGGTATCAGGCCACTGACGGCACAGTGGGCTCCTGGGACGATG<br>GGGACTTCCTGGGAGATGAGTCTCTTCAAGAGGAAGAGAAGGA<br>CAGCCAAGAGACGGATGGACTGCTCCCAGGCTCCCGGCCCAGC<br>TCCCGGCCCCCAGGAGAGAAGAGCTTCCGGAGAGCCGGGAGG<br>AGCGTGTTCTCCGCCATGAAGCTCGGCAAAAACCGGTCTCACAA<br>GGAGGAGCCCCAAAGACCAGATGAACCGGCGGTGCTGGAGAT<br>GGAAGACCTTGACCATCTGGCCATTCGGCTAGGAGATGGACTG<br>GATCCCGACTCGGTGTCTCTAGCCTCAGTCACAGCTCTCACCAC<br>TAATGTCTCCAACAAGCGATCTAAGCCAGACATTAAGATGGAGC<br>CAAGTGCTGGGCGGCCCATGGATTACCAGGTCAGCATCACGGT<br>GATCGAGGCCCGGCAGCTGGTGGGCTTGAACATGGACCCTGTG<br>GTGTGCGTGGAGGTGGGTGACGACAAGAAGTACACATCCATGA<br>AGGAGTCCACTAACTGCCCCTATTACAACGAGTACTTCGTCTTC<br>GACTTCCATGTCTCTCCGGATGTCATGTTTGACAAGATCATCAAG<br>ATTTCGGTGATTCACTCCAAGAACCTGCTGCGCAGTGGCACCCT<br>GGTGGGCTCCTTCAAAATGGACGTGGGAACCGTGTACTCGCAG<br>CCAGAGCACCAGTTCCATCACAAGTGGGCCATCCTGTCTGACCC<br>CGATGACATCTCCTCGGGGCTGAAGGGCTACGTGAAGTGTGAC<br>GTTGCCGTGGTGGGCAAAGGGGACAACATCAAGACGCCCCACA<br>AGGCCAATGAGACCGACGAAGATGACATTGAGGGGAACTTGCT<br>GCTCCCCGAGGGGGTGCCCCCCGAACGCCAGTGGGCCCGGTT<br>CTATGTGAAAATTTACCGAGCAGAGGGGCTGCCCCGTATGAACA<br>CAAGCCTCATGGCCAATGTAAAGAAGGCTTTCATCGGTGAAAAC<br>AAGGACCTCGTGGACCCCTACGTGCAAGTCTTCTTTGCTGGCCA<br>GAAGGGCAAGACTTCAGTGCAGAAGAGCAGCTATGAGCCCCTG<br>TGGAATGAGCAGGTCGTCTTTACAGACCTCTTCCCCCCACTCTG<br>CAAACGCATGAAGGTGCAGATCCGAGACTCGGACAAGGTCAAC<br>GACGTGGCCATCGGCACCCACTTCATTGACCTGCGCAAGATTTC<br>TAATGACGGAGACAAAGGCTTCCTGCCCACACTGGGCCCAGCC<br>TGGGTGAACATGTACGGCTCCACACGTAACTACACGCTGCTGGA<br>TGAGCATCAGGACCTGAACGAGGGCCTGGGGGAGGGTGTGTC<br>CTTCCGGGCCCGGCTCCTGCTGGGCCTGGCTGTGGAGATCGTA<br>GACACCTCCAACCCTGAGCTCACCAGCTCCACAGAGGTGCAGG<br>TGGAGCAGGCCACGCCCATCTCGGAGAGCTGTGCAGGTAAAAT<br>GGAAGAATTCTTTCTCTTTGGAGCCTTCCTGGAGGCCTCAATGA<br>TCGACCGGAGAAACGGAGACAAGCCCATCACCTTTGAGGTCAC<br>CATAGGCAACTATGGGAACGAAGTTGATGGCCTGTCCCGGCCC<br>CAGCGGCCTCGGCCCCGGAAGGAGCCGGGGGATGAGGAAGAA<br>GTAGACCTGATTCAGAACGCAAGTGATGACGAGGCCGGTGATG<br>CCGGGGACCTGGCCTCAGTCTCCTCCACTCCACCAATGCGGCC<br>CCAGGTCACCGACAGGAACTACTTCCATCTGCCCTACCTGGAGC<br>GAAAGCCCTGCATCTACATCAAGAGCTGGTGGCCGGACCAGCG<br>CCGCCGCCTCTACAATGCCAACATCATGGACCACATTGCCGACA<br>AGCTGGAAGAAGGCCTGAACGACATACAGGAGATGATCAAAAC<br>GGAGAAGTCCTACCCTGAGCGTCGCCTGCGGGGCGTCCTGGA<br>GGAGCTGAGCTGTGGCTGCTGCCGCTTCCTCTCCCTCGCTGAC<br>AAGGACCAGGGCCACTCATCCCGCACCAGGCTTGACCGGGAGC<br>GCCTCAAGTCCTGCATGAGGGAGCTGGAAAACATGGGGCAGCA<br>GGCCAGGATGCTGCGGGCCCAGGTGAAGCGGCACACGGTGCG<br>GGACAAGCTGAGGCTGTGCCAGAACTTCCTGCAGAAGCTGCGC<br>TTCCTGGCGGACGAGCCCCAGCACAGCATTCCCGACATCTTCAT<br>CTGGATGATGAGCAACAACAAGCGTGTCGCCTATGCCCGTGTG<br>CCCTCCAAGGACCTGCTCTTCTCCATCGTGGAGGAGGAGACTG<br>GCAAGGACTGCGCCAAGGTCAAGACGCTCTTCCTTAAGCTGCC<br>AGGGAAGCGGGGCTTCGGCTCGGCAGGCTGGACAGTGCAGGC<br>CAAGGTGGAGCTGTACCTGTGGCTGGGCCTCAGCAAACAGCGC<br>AAGGAGTTCCTGTGCGGCCTGCCCTGTGGCTTCCAGGAGGTCA<br>AGGCAGCCCAGGGCCTGGGCCTGCATGCCTTCCCACCCGTCAG<br>CCTGGTCTACACCAAGAAGCAGGCGTTCCAGCTCCGAGCGCAC<br>ATGTACCAGGCCCGCAGCCTCTTTGCCGCCGACAGCAGCGGAC |

TABLE 2-continued

OTOF Sequences

| SEQ ID NO. | Sequence Name | Sequence |
|---|---|---|
| | | TCTCAGACCCCTTTGCCCGCGTCTTCTTCATCAATCAGAGTCAG |
| | | TGCACAGAGGTGCTGAATGAGACCCTGTGTCCCACCTGGGACC |
| | | AGATGCTGGTGTTCGACAACCTGGAGCTCTATGGTGAAGCTCAT |
| | | GAGCTGAGGGACGATCCGCCCATCATTGTCATTGAAATCTATGA |
| | | CCAGGATTCCATGGGCAAAGCTGACTTCATGGGCCGGACCTTC |
| | | GCCAAACCCCTGGTGAAGATGGCAGACGAGGCGTACTGCCCAC |
| | | CCCGCTTCCCACCTCAGCTCGAGTACTACCAGATCTACCGTGGC |
| | | AACGCCACAGCTGGAGACCTGCTGGCGGCCTTCGAGCTGCTGC |
| | | AGATTGGACCAGCAGGGAAGGCTGACCTGCCCCCCATCAATGG |
| | | CCCGGTGGACGTGGACCGAGGTCCCATCATGCCCGTGCCCATG |
| | | GGCATCCGGCCCGTGCTCAGCAAGTACCGAGTGGAGGTGCTGT |
| | | TCTGGGGCCTACGGGACCTAAAGCGGGTGAACCTGGCCCAGGT |
| | | GGACCGGCCACGGGTGGACATCGAGTGTGCAGGGAAGGGGGT |
| | | GCAGTCGTCCCTGATCCACAATTATAAGAAGAACCCCAACTTCA |
| | | ACACCCTCGTCAAGTGGTTTGAAGTGGACCTCCCAGAGAACGA |
| | | GCTGCTGCACCCGCCCTTGAACATCCGTGTGGTGGACTGCCGG |
| | | GCCTTCGGTCGCTACACACTGGTGGGCTCCCATGCCGTCAGCT |
| | | CCCTGCGACGCTTCATCTACCGGCCCCCAGACCGCTCGGCCCC |
| | | CAGCTGGAACACCACGGTCAGGCTTCTCCGGCGCTGCCGTGTG |
| | | CTGTGCAATGGGGGCTCCTCCTCTCACTCCACAGGGGAGGTTG |
| | | TGGTGACTATGGAGCCAGAGGTACCCATCAAGAAACTGGAGAC |
| | | CATGGTGAAGCTGGACGCGACTTCTGAAGCTGTTGTCAAGGTG |
| | | GATGTGGCTGAGGAGGAGAAGGAGAAGAAGAAGAAGAAGAAGG |
| | | GCACTGCGGAGGAGCCAGAGGAGGAGGAGCCAGACGAGAGCA |
| | | TGCTGGACTGGTGGTCCAAGTACTTTGCCTCCATTGACACCATG |
| | | AAGGAGCAACTTCGACAACAAGAGCCCTCTGGAATTGACTTGGA |
| | | GGAGAAGGAGGAAGTGGACAATACCGAGGGCCTGAAGGGGTC |
| | | AATGAAGGGCAAGGAGAAGGCAAGGGCTGCCAAAGAGGAGAAG |
| | | AAGAAGAAAACTCAGAGCTCTGGCTCTGGCCAGGGGTCCGAGG |
| | | CCCCCGAGAAGAAGAAACCCAAGATTGATGAGCTTAAGGTATAC |
| | | CCCAAAGAGCTGGAGTCCGAGTTTGATAACTTTGAGGACTGGCT |
| | | GCACACTTTCAACTTGCTTCGGGGCAAGACCGGGGATGATGAG |
| | | GATGGCTCCACCGAGGAGGAGCGCATTGTGGGACGCTTCAAGG |
| | | GCTCCCTCTGCGTGTACAAAGTGCCACTCCCAGAGGACGTGTC |
| | | CCGGGAAGCCGGCTACGACTCCACCTACGGCATGTTCCAGGGC |
| | | ATCCCGAGCAATGACCCCATCAATGTGCTGGTCCGAGTCTATGT |
| | | GGTCCGGGCCACGGACCTGCACCCTGCTGACATCAACGGCAAA |
| | | GCTGACCCCTACATCGCCATCCGGCTAGGCAAGACTGACATCC |
| | | GCGACAAGGAGAACTACATCTCCAAGCAGCTCAACCCTGTCTTT |
| | | GGGAAGTCCTTTGACATCGAGGCCTCCTTCCCCATGGAATCCAT |
| | | GCTGACGGTGGCTGTGTATGACTGGGACCTGGTGGGCACTGAT |
| | | GACCTCATTGGGGAAACCAAGATCGACCTGGAGAACCGCTTCTA |
| | | CAGCAAGCACCGCGCCACCTGCGGCATCGCCCAGACCTACTCC |
| | | ACACATGGCTACAATATCTGGCGGGACCCCATGAAGCCCAGCC |
| | | AGATCCTGACCCGCCTCTGCAAAGACGGCAAAGTGGACGGCCC |
| | | CCACTTTGGGCCCCCTGGGAGAGTGAAGGTGGCCAACCGCGTC |
| | | TTCACTGGGCCCTCTGAGATTGAGGACGAGAACGGTCAGAGGA |
| | | AGCCCACAGACGAGCATGTGGCGCTGTTGGCCCTGAGGCACTG |
| | | GGAGGACATCCCCCGCGCAGGCTGCCGCCTGGTGCCAGAGCA |
| | | TGTGGAGACGAGGCCGCTGCTCAACCCCGACAAGCCGGGCATC |
| | | GAGCAGGGCCGCCTGGAGCTGTGGGTGGACATGTTCCCCATGG |
| | | ACATGCCAGCCCCTGGGACGCCTCTGGACATCTCACCTCGGAA |
| | | GCCCAAGAAGTACGAGCTGCGGGTCATCATCTGGAACACAGAT |
| | | GAGGTGGTCTTGGAGGACGACGACTTCTTCACAGGGGAGAAGT |
| | | CCAGTGACATCTTCGTGAGGGGGTGGCTGAAGGGCCAGCAGGA |
| | | GGACAAGCAGGACACAGACGTCCACTACCACTCCCTCACTGGC |
| | | GAGGGCAACTTCAACTGGCGCTACCTGTTCCCCTTCGACTACCT |
| | | GGCGGCGGAGGAGAAGATCGTCATCTCCAAGAAGGAGTCCATG |
| | | TTCTCCTGGGACGAGACCGAGTACAAGATCCCCGCGCGGCTCA |
| | | CCCTGCAGATCTGGGATGCGGACCACTTCTCCGCTGACGACTT |
| | | CCTGGGGGCCATCGAGCTGGACCTGAACCGGTTCCCGCGGGG |
| | | CGCAAAGACAGCCAAGCAGTGCACCATGGAGATGGCCACCGGG |
| | | GAGGTGGACGTGCCCCTCGTGTCCATCTTCAAGCAAAAGCGCG |
| | | TCAAAGGCTGGTGGCCCCTCCTGGCCCGCAATGAGAACGATGA |
| | | GTTTGAGCTCACGGGCAAGGTGGAGGCTGAGCTGCATTTACTG |
| | | ACAGCAGAGGAGGCAGAGAAGAACCCAGTGGGCCTGGCCCGC |
| | | AATGAACCTGACCCCCTAGAGAAACCCAACCGGCCCGACACGA |
| | | GCTTCATCTGGTTCCTGAACCCTCTCAAGTCGGCTCGCTACTTC |
| | | TTGTGGCACACGTATCGCTGGCTGCTCCTCAAACTGTTGCTGCT |
| | | CCTGCTGCTGCTCCTCCTCCTCGCCCTGTTCCTCTACTCTGTGC |
| | | CTGGCTACCTGGTCAAGAAAATCCTCGGGGCCTGAGCCCAGTG |
| | | GCCTCCTGGCCGGCCCGACACGGCCTTCGTCTGGTTCCTCAAC |
| | | CCTCTCAAGTCCATCAAGTACCTCATCTGCACCCGGTACAAGTG |
| | | GCTCATCATCAAGATCGTGCTGGCGCTGTTGGGGCTGCTCATGT |
| | | TGGGGCTCTTCCTCTACAGCCTCCCTGGCTACATGGTCAAAAAG |

TABLE 2-continued

OTOF Sequences

| SEQ ID NO. | Sequence Name | Sequence |
|---|---|---|
| | | CTCCTTGGGGCATGAAGGCCGCCAGCTCCCGCCAGCCGCTCCC<br>CAGCCCTGCCGCATTTCCTTTCAGTGGCTTGGACTCTTTCCCAT<br>CTCCCCTGGGGAGCCTGAGGAGCCCAGCGTCCACTCTTCATGC<br>CTTGGGCCGAGCCTGCCTCCTGCTTGCGGGGGCCGCCTGTCCT<br>CACTGCCCCAGGCTGCGGCTTGCCCAGTCCCGCCCCTCTGACC<br>CCTGCCTGTGGGCTGGGGAGCCTTGGATGGGGTGGGGACCTG<br>GAATGGGTCTCTCTTGCCCCACCTGGCTGAGGCGCCACCCTTC<br>TTCAGGCCCAGGCTCCAGAGGAAGACTCCTGAAACCCTCCCCA<br>GGTCTTCCAAGTACAGGATTGAAGCTTTAGTGAAATTAACCAAG<br>GACCATGGGTCAGTGCCCAGGGCTTTAAAAAGAATGAACGAGC<br>AAAAGGTATCCCCGCCGTGACCCCTGCAGATAGCACCGGTCTTT<br>GATCCGCAGCAGGGGCCAGACCCTGCCCACAAGTCCCAGCGC<br>GGCTGCTTCTGCCACTGCTGGGCTCCACTTGGCTCCTCTCACTT<br>CCCAGGGGGTCGCCTGTCCTGCCTGTGGGTTTCCATGGCTTCC<br>CAGAGCTCCCTCTGCCCCAGCCAGCGCCTCCAGGCCCAGCTGA<br>GGAGCTGTGAGAAGCAGCAGAGGGGACTCCCCATCCCGGGCA<br>CACCCTGTCCTCCCACCCCTGCCCCCTTGCCCTTCCAGCCCTTT<br>CAGCTGCAGCTGGGAGCTGGCCCGTCAAGTGCTGCCCCTGCCT<br>GTGTCTGGGTTTCTGTTGGCTGTTTTTCTTTTCTTGAGTGGTGAT<br>TTTTCTCTAAATAAAAGAAGTCAAGCACTGAAAAAAAAAAAAAAA<br>A |
| 11 | OTOF-202 transcript (NM_004802.3), human otoferlin transcript variant 2, 4954 bp, encodes the protein of SEQ ID NO: 2 | CCGTGAGTTCTGCCCAGGCCCTGTGAGCTCACCAGAGCCACAG<br>ACTCACAGCCCAGAGGTGGCTTCTTCCTTCAGGAACTGAAGAAC<br>CCCCATGAACACCAACATCTCCAGGTTCTGAGAACAGAACCTGG<br>GAAATTGATGACTTCCTCATGATGACCGATACTCAGGATGGCCC<br>TAGCGAGAGCTCCCAGATCATGAGGAAGAAGGCCTGAACGACA<br>TACAGGAGATGATCAAAACGGAGAAGTCCTACCCTGAGCGTCG<br>CCTGCGGGGCGTCCTGGAGGAGCTGAGCTGTGGCTGCTGCCG<br>CTTCCTCTCCCTCGCTGACAAGGACCAGGGCCACTCATCCCGC<br>ACCAGGCTTGACCGGGAGCGCCTCAAGTCCTGCATGAGGGAGC<br>TGGAAAACATGGGGCAGCAGGCCAGGATGCTGCGGGCCCAGG<br>TGAAGCGGCACACGGTGCGGGACAAGCTGAGGCTGTGCCAGAA<br>CTTCCTGCAGAAGCTGCGCTTCCTGGCGGACGAGCCCCAGCAC<br>AGCATTCCCGACATCTTCATCTGGATGATGAGCAACAACAAGCG<br>TGTCGCCTATGCCCGTGTGCCCTCCAAGGACCTGCTCTTCTCCA<br>TCGTGGAGGAGGAGACTGGCAAGGACTGCGCCAAGGTCAAGAC<br>GCTCTTCCTTAAGCTGCCAGGGAAGCGGGGCTTCGGCTCGGCA<br>GGCTGGACAGTGCAGGCCAAGGTGGAGCTGTACCTGTGGCTGG<br>GCCTCAGCAAACAGCGCAAGGAGTTCCTGTGCGGCCTGCCCTG<br>TGGCTTCCAGGAGGTCAAGGCAGCCCAGGGCCTGGGCCTGCAT<br>GCCTTCCCACCCGTCAGCCTGGTCTACACCAAGAAGCAGGCGT<br>TCCAGCTCCGAGCGCACATGTACCAGGCCCGCAGCCTCTTTGC<br>CGCCGACAGCAGCGGACTCTCAGACCCCTTTGCCCGCGTCTTC<br>TTCATCAATCAGAGTCAGTGCACAGAGGTGCTGAATGAGACCCT<br>GTGTCCCACCTGGGACCAGATGCTGGTGTTCGACAACCTGGAG<br>CTCTATGGTGAAGCTCATGAGCTGAGGGACGATCCGCCCATCAT<br>TGTCATTGAAATCTATGACCAGGATTCCATGGGCAAAGCTGACT<br>TCATGGGCCGGACCTTCGCCAAACCCCTGGTGAAGATGGCAGA<br>CGAGGCGTACTGCCCACCCCGCTTCCCACCTCAGCTCGAGTAC<br>TACCAGATCTACCGTGGCAACGCCACAGCTGGAGACCTGCTGG<br>CGGCCTTCGAGCTGCTGCAGATTGGACCAGCAGGGAAGGCTGA<br>CCTGCCCCCCATCAATGGCCCGGTGGACGTGGACCGAGGTCCC<br>ATCATGCCCGTGCCCATGGGCATCCGGCCCGTGCTCAGCAAGT<br>ACCGAGTGGAGGTGCTGTTCTGGGGCCTACGGGACCTAAAGCG<br>GGTGAACCTGGCCCAGGTGGACCGGCCACGGGTGGACATCGA<br>GTGTGCAGGGAAGGGGGTGCAGTCGTCCCTGATCCACAATTAT<br>AAGAAGAACCCCAACTTCAACACCCTCGTCAAGTGGTTTGAAGT<br>GGACCTCCCAGAGAACGAGCTGCTGCACCCGCCCTTGAACATC<br>CGTGTGGTGGACTGCCGGGCCTTCGGTCGCTACACACTGGTGG<br>GCTCCCATGCCGTCAGCTCCCTGCGACGCTTCATCTACCGGCC<br>CCCAGACCGCTCGGCCCCCAGCTGGAACACCACGGGGGAGGT<br>TGTGGTGACTATGGAGCCAGAGGTACCCATCAAGAAACTGGAG<br>ACCATGGTGAAGCTGGACGCGACTTCTGAAGCTGTTGTCAAGGT<br>GGATGTGGCTGAGGAGGAGAAGGAGAAGAAGAAGAAGAAGAAG<br>GGCACTGCGGAGGAGCCAGAGGAGGAGGAGCCAGACGAGAGC<br>ATGCTGGACTGGTGGTCCAAGTACTTTGCCTCCATTGACACCAT<br>GAAGGAGCAACTTCGACAACAAGAGCCCTCTGGAATTGACTTGG<br>AGGAGAAGGAGGAAGTGGACAATACCGAGGGCCTGAAGGGGT<br>CAATGAAGGGCAAGGAGAAGGCAAGGGCTGCCAAAGAGGAGAA<br>GAAGAAGAAAACTCAGAGCTCTGGCTCTGGCCAGGGGTCCGAG<br>GCCCCCGAGAAGAAGAAACCCAAGATTGATGAGCTTAAGGTATA<br>CCCCAAAGAGCTGGAGTCCGAGTTTGATAACTTTGAGGACTGGC<br>TGCACACTTTCAACTTGCTTCGGGGCAAGACCGGGGATGATGA<br>GGATGGCTCCACCGAGGAGGAGCGCATTGTGGGACGCTTCAAG |

TABLE 2-continued

OTOF Sequences

| SEQ ID NO. | Sequence Name | Sequence |
|---|---|---|
| | | GGCTCCCTCTGCGTGTACAAAGTGCCACTCCCAGAGGACGTGT<br>CCCGGGAAGCCGGCTACGACTCCACCTACGGCATGTTCCAGGG<br>CATCCCGAGCAATGACCCCATCAATGTGCTGGTCCGAGTCTATG<br>TGGTCCGGGCCACGGACCTGCACCCTGCTGACATCAACGGCAA<br>AGCTGACCCCTACATCGCCATCCGGCTAGGCAAGACTGACATC<br>CGCGACAAGGAGAACTACATCTCCAAGCAGCTCAACCCTGTCTT<br>TGGGAAGTCCTTTGACATCGAGGCCTCCTTCCCCATGGAATCCA<br>TGCTGACGGTGGCTGTGTATGACTGGGACCTGGTGGGCACTGA<br>TGACCTCATTGGGGAAACCAAGATCGACCTGGAGAACCGCTTCT<br>ACAGCAAGCACCGCGCCACCTGCGGCATCGCCCAGACCTACTC<br>CACACATGGCTACAATATCTGGCGGGACCCCATGAAGCCCAGC<br>CAGATCCTGACCCGCCTCTGCAAAGACGGCAAAGTGGACGGCC<br>CCCACTTTGGGCCCCCTGGGAGAGTGAAGGTGGCCAACCGCGT<br>CTTCACTGGGCCCTCTGAGATTGAGGACGAGAACGGTCAGAGG<br>AAGCCCACAGACGAGCATGTGGCGCTGTTGGCCCTGAGGCACT<br>GGGAGGACATCCCCCGCGCAGGCTGCCGCCTGGTGCCAGAGC<br>ATGTGGAGACGAGGCCGCTGCTCAACCCCGACAAGCCGGGCAT<br>CGAGCAGGGCCGCCTGGAGCTGTGGGTGGACATGTTCCCCATG<br>GACATGCCAGCCCCTGGGACGCCTCTGGACATCTCACCTCGGA<br>AGCCCAAGAAGTACGAGCTGCGGGTCATCATCTGGAACACAGA<br>TGAGGTGGTCTTGGAGGACGACGACTTCTTCACAGGGGAGAAG<br>TCCAGTGACATCTTCGTGAGGGGGTGGCTGAAGGGCCAGCAGG<br>AGGACAAGCAGGACACAGACGTCCACTACCACTCCCTCACTGG<br>CGAGGGCAACTTCAACTGGCGCTACCTGTTCCCCTTCGACTACC<br>TGGCGGCGGAGGAGAAGATCGTCATCTCCAAGAAGGAGTCCAT<br>GTTCTCCTGGGACGAGACCGAGTACAAGATCCCCGCGCGGCTC<br>ACCCTGCAGATCTGGGATGCGGACCACTTCTCCGCTGACGACTT<br>CCTGGGGGCCATCGAGCTGGACCTGAACCGGTTCCCGCGGGG<br>CGCAAAGACAGCCAAGCAGTGCACCATGGAGATGGCCACCGGG<br>GAGGTGGACGTGCCCCTCGTGTCCATCTTCAAGCAAAAGCGCG<br>TCAAAGGCTGGTGGCCCCTCCTGGCCCGCAATGAGAACGATGA<br>GTTTGAGCTCACGGGCAAGGTGGAGGCTGAGCTGCATTTACTG<br>ACAGCAGAGGAGGCAGAGAAGAACCCAGTGGGCCTGGCCCGC<br>AATGAACCTGACCCCCTAGAGAAACCCAACCGGCCCGACACGA<br>GCTTCATCTGGTTCCTGAACCCTCTCAAGTCGGCTCGCTACTTC<br>TTGTGGCACACGTATCGCTGGCTGCTCCTCAAACTGTTGCTGCT<br>CCTGCTGCTGCTCCTCCTCCTCGCCCTGTTCCTCTACTCTGTGC<br>CTGGCTACCTGGTCAAGAAAATCCTCGGGGCCTGAGCCCAGTG<br>GCCTCCTGGCCGGCCCGACACGGCCTTCGTCTGGTTCCTCAAC<br>CCTCTCAAGTCCATCAAGTACCTCATCTGCACCCGGTACAAGTG<br>GCTCATCATCAAGATCGTGCTGGCGCTGTTGGGGCTGCTCATGT<br>TGGGGCTCTTCCTCTACAGCCTCCCTGGCTACATGGTCAAAAAG<br>CTCCTTGGGGCATGAAGGCCGCCAGCTCCCGCCAGCCGCTCCC<br>CAGCCCTGCCGCATTTCCTTTCAGTGGCTTGGACTCTTTCCCAT<br>CTCCCCTGGGGAGCCTGAGGAGCCCAGCGTCCACTCTTCATGC<br>CTTGGGCCGAGCCTGCCTCCTGCTTGCGGGGGCCGCCTGTCCT<br>CACTGCCCCAGGCTGCGGCTTGCCCAGTCCCGCCCCTCTGACC<br>CCTGCCTGTGGGCTGGGGAGCCTTGGATGGGGTGGGGACCTG<br>GAATGGGTCTCTCTTGCCCCACCTGGCTGAGGCGCCACCCTTC<br>TTCAGGCCCAGGCTCCAGAGGAAGACTCCTGAAACCCTCCCCA<br>GGTCTTCCAAGTACAGGATTGAAGCTTTAGTGAAATTAACCAAG<br>GACCATGGGTCAGTGCCCAGGGCTTTAAAAAGAATGAACGAGC<br>AAAAGGTATCCCCGCCGTGACCCCTGCAGATAGCACCGGTCTTT<br>GATCCGCAGCAGGGGCCAGACCCTGCCCACAAGTCCCAGCGC<br>GGCTGCTTCTGCCACTGCTGGGCTCCACTTGGCTCCTCTCACTT<br>CCCAGGGGGTCGCCTGTCCTGCCTGTGGGTTTCCATGGCTTCC<br>CAGAGCTCCCTCTGCCCCAGCCAGCGCCTCCAGGCCCAGCTGA<br>GGAGCTGTGAGAAGCAGCAGAGGGGACTCCCCATCCCGGGCA<br>CACCCTGTCCTCCCACCCCTGCCCCCTTGCCCTTCCAGCCCTTT<br>CAGCTGCAGCTGGGAGCTGGCCCGTCAAGTGCTGCCCCTGCCT<br>GTGTCTGGGTTTCTGTTGGCTGTTTTTCTTTTCTTGAGTGGTGAT<br>TTTTCTCTAAATAAAAGAAGTCAAGCACTGAAAAAAAAAAAAAAA<br>A |
| 12 | OTOF-203 transcript (NM_194323.2), human otoferlin transcript variant 4, 4756 bp, encodes the protein of SEQ ID NO: 3 | CCGTGAGTTCTGCCCAGGCCCTGTGAGCTCACCAGAGCCACAG<br>ACTCACAGCCCAGAGGTGGCTTCTTCCTTCAGGAACTGAAGAAC<br>CCCCATGAACACCAACATCTCCAGGTTCTGAGAACAGAACCTGG<br>GAAATTGATGACTTCCTCATGATGACCGATACTCAGGATGGCCC<br>TAGCGAGAGCTCCCAGATCATGAGGAAGAAGGCCTGAACGACA<br>TACAGGAGATGATCAAAACGGAGAAGTCCTACCCTGAGCGTCG<br>CCTGCGGGGCGTCCTGGAGGAGCTGAGCTGTGGCTGCTGCCG<br>CTTCCTCTCCCTCGCTGACAAGGACCAGGGCCACTCATCCCGC<br>ACCAGGCTTGACCGGGAGCGCCTCAAGTCCTGCATGAGGGAGC<br>TGGAAAACATGGGGCAGCAGGCCAGGATGCTGCGGGCCCAGG<br>TGAAGCGGCACACGGTGCGGGACAAGCTGAGGCTGTGCCAGAA |

TABLE 2-continued

| OTOF Sequences | | |
|---|---|---|
| SEQ ID NO. | Sequence Name | Sequence |
| | | CTTCCTGCAGAAGCTGCGCTTCCTGGCGGACGAGCCCCAGCAC |
| | | AGCATTCCCGACATCTTCATCTGGATGATGAGCAACAACAAGCG |
| | | TGTCGCCTATGCCCGTGTGCCCTCCAAGGACCTGCTCTTCTCCA |
| | | TCGTGGAGGAGGAGACTGGCAAGGACTGCGCCAAGGTCAAGAC |
| | | GCTCTTCCTTAAGCTGCCAGGGAAGCGGGGCTTCGGCTCGGCA |
| | | GGCTGGACAGTGCAGGCCAAGGTGGAGCTGTACCTGTGGCTGG |
| | | GCCTCAGCAAACAGCGCAAGGAGTTCCTGTGCGGCCTGCCCTG |
| | | TGGCTTCCAGGAGGTCAAGGCAGCCCAGGGCCTGGGCCTGCAT |
| | | GCCTTCCCACCCGTCAGCCTGGTCTACACCAAGAAGCAGGCGT |
| | | TCCAGCTCCGAGCGCACATGTACCAGGCCCGCAGCCTCTTTGC |
| | | CGCCGACAGCAGCGGACTCTCAGACCCCTTTGCCCGCGTCTTC |
| | | TTCATCAATCAGAGTCAGTGCACAGAGGTGCTGAATGAGACCCT |
| | | GTGTCCCACCTGGGACCAGATGCTGGTGTTCGACAACCTGGAG |
| | | CTCTATGGTGAAGCTCATGAGCTGAGGGACGATCCGCCCATCAT |
| | | TGTCATTGAAATCTATGACCAGGATTCCATGGGCAAAGCTGACT |
| | | TCATGGGCCGGACCTTCGCCAAACCCCTGGTGAAGATGGCAGA |
| | | CGAGGCGTACTGCCCACCCCGCTTCCCACCTCAGCTCGAGTAC |
| | | TACCAGATCTACCGTGGCAACGCCACAGCTGGAGACCTGCTGG |
| | | CGGCCTTCGAGCTGCTGCAGATTGGACCAGCAGGGAAGGCTGA |
| | | CCTGCCCCCCATCAATGGCCCGGTGGACGTGGACCGAGGTCCC |
| | | ATCATGCCCGTGCCCATGGGCATCCGGCCCGTGCTCAGCAAGT |
| | | ACCGAGTGGAGGTGCTGTTCTGGGGCCTACGGGACCTAAAGCG |
| | | GGTGAACCTGGCCCAGGTGGACCGGCCACGGGTGGACATCGA |
| | | GTGTGCAGGGAAGGGGGTGCAGTCGTCCCTGATCCACAATTAT |
| | | AAGAAGAACCCCAACTTCAACACCCTCGTCAAGTGGTTTGAAGT |
| | | GGACCTCCCAGAGAACGAGCTGCTGCACCCGCCCTTGAACATC |
| | | CGTGTGGTGGACTGCCGGGCCTTCGGTCGCTACACACTGGTGG |
| | | GCTCCCATGCCGTCAGCTCCCTGCGACGCTTCATCTACCGGCC |
| | | CCCAGACCGCTCGGCCCCCAGCTGGAACACCACGGGGGAGGT |
| | | TGTGGTGACTATGGAGCCAGAGGTACCCATCAAGAAACTGGAG |
| | | ACCATGGTGAAGCTGGACGCGACTTCTGAAGCTGTTGTCAAGGT |
| | | GGATGTGGCTGAGGAGGAGAAGGAGAAGAAGAAGAAGAAGAAG |
| | | GGCACTGCGGAGGAGCCAGAGGAGGAGGAGCCAGACGAGAGC |
| | | ATGCTGGACTGGTGGTCCAAGTACTTTGCCTCCATTGACACCAT |
| | | GAAGGAGCAACTTCGACAACAAGAGCCCTCTGGAATTGACTTGG |
| | | AGGAGAAGGAGGAAGTGGACAATACCGAGGGCCTGAAGGGGT |
| | | CAATGAAGGGCAAGGAGAAGGCAAGGGCTGCCAAAGAGGAGAA |
| | | GAAGAAGAAAACTCAGAGCTCTGGCTCTGGCCAGGGGTCCGAG |
| | | GCCCCCGAGAAGAAGAAACCCAAGATTGATGAGCTTAAGGTATA |
| | | CCCCAAAGAGCTGGAGTCCGAGTTTGATAACTTTGAGGACTGGC |
| | | TGCACACTTTCAACTTGCTTCGGGGCAAGACCGGGGATGATGA |
| | | GGATGGCTCCACCGAGGAGGAGCGCATTGTGGGACGCTTCAAG |
| | | GGCTCCCTCTGCGTGTACAAAGTGCCACTCCCAGAGGACGTGT |
| | | CCCGGGAAGCCGGCTACGACTCCACCTACGGCATGTTCCAGGG |
| | | CATCCCGAGCAATGACCCCATCAATGTGCTGGTCCGAGTCTATG |
| | | TGGTCCGGGCCACGGACCTGCACCCTGCTGACATCAACGGCAA |
| | | AGCTGACCCCTACATCGCCATCCGGCTAGGCAAGACTGACATC |
| | | CGCGACAAGGAGAACTACATCTCCAAGCAGCTCAACCCTGTCTT |
| | | TGGGAAGTCCTTTGACATCGAGGCCTCCTTCCCCATGGAATCCA |
| | | TGCTGACGGTGGCTGTGTATGACTGGGACCTGGTGGGCACTGA |
| | | TGACCTCATTGGGGAAACCAAGATCGACCTGGAGAACCGCTTCT |
| | | ACAGCAAGCACCGCGCCACCTGCGGCATCGCCCAGACCTACTC |
| | | CACACATGGCTACAATATCTGGCGGGACCCCATGAAGCCCAGC |
| | | CAGATCCTGACCCGCCTCTGCAAAGACGGCAAAGTGGACGGCC |
| | | CCCACTTTGGGCCCCCTGGGAGAGTGAAGGTGGCCAACCGCGT |
| | | CTTCACTGGGCCCTCTGAGATTGAGGACGAGAACGGTCAGAGG |
| | | AAGCCCACAGACGAGCATGTGGCGCTGTTGGCCCTGAGGCACT |
| | | GGGAGGACATCCCCCGCGCAGGCTGCCGCCTGGTGCCAGAGC |
| | | ATGTGGAGACGAGGCCGCTGCTCAACCCCGACAAGCCGGGCAT |
| | | CGAGCAGGGCCGCCTGGAGCTGTGGGTGGACATGTTCCCCATG |
| | | GACATGCCAGCCCCTGGGACGCCTCTGGACATCTCACCTCGGA |
| | | AGCCCAAGAAGTACGAGCTGCGGGTCATCATCTGGAACACAGA |
| | | TGAGGTGGTCTTGGAGGACGACGACTTCTTCACAGGGGAGAAG |
| | | TCCAGTGACATCTTCGTGAGGGGGTGGCTGAAGGGCCAGCAGG |
| | | AGGACAAGCAGGACACAGACGTCCACTACCACTCCCTCACTGG |
| | | CGAGGGCAACTTCAACTGGCGCTACCTGTTCCCCTTCGACTACC |
| | | TGGCGGCGGAGGAGAAGATCGTCATCTCCAAGAAGGAGTCCAT |
| | | GTTCTCCTGGGACGAGACCGAGTACAAGATCCCCGCGCGGCTC |
| | | ACCCTGCAGATCTGGGATGCGGACCACTTCTCCGCTGACGACTT |
| | | CCTGGGGGCCATCGAGCTGGACCTGAACCGGTTCCCGCGGGG |
| | | CGCAAAGACAGCCAAGCAGTGCACCATGGAGATGGCCACCGGG |
| | | GAGGTGGACGTGCCCCTCGTGTCCATCTTCAAGCAAAAGCGCG |
| | | TCAAAGGCTGGTGGCCCCTCCTGGCCCGCAATGAGAACGATGA |
| | | GTTTGAGCTCACGGGCAAGGTGGAGGCTGAGCTGCATTTACTG |
| | | ACAGCAGAGGAGGCAGAGAAGAACCCAGTGGGCCTGGCCCGC |

TABLE 2-continued

OTOF Sequences

| SEQ ID NO. | Sequence Name | Sequence |
|---|---|---|
| | | AATGAACCTGACCCCCTAGAGAAACCCAACCGGCCCGACACGG<br>CCTTCGTCTGGTTCCTCAACCCTCTCAAGTCCATCAAGTACCTCA<br>TCTGCACCCGGTACAAGTGGCTCATCATCAAGATCGTGCTGGCG<br>CTGTTGGGGCTGCTCATGTTGGGGCTCTTCCTCTACAGCCTCCC<br>TGGCTACATGGTCAAAAAGCTCCTTGGGGCATGAAGGCCGCCA<br>GCTCCCGCCAGCCGCTCCCCAGCCCTGCCGCATTTCCTTTCAG<br>TGGCTTGGACTCTTTCCCATCTCCCCTGGGGAGCCTGAGGAGC<br>CCAGCGTCCACTCTTCATGCCTTGGGCCGAGCCTGCCTCCTGC<br>TTGCGGGGGCCGCCTGTCCTCACTGCCCCAGGCTGCGGCTTGC<br>CCAGTCCCGCCCCTCTGACCCCTGCCTGTGGGCTGGGGAGCCT<br>TGGATGGGGTGGGGACCTGGAATGGGTCTCTCTTGCCCCACCT<br>GGCTGAGGCGCCACCCTTCTTCAGGCCCAGGCTCCAGAGGAAG<br>ACTCCTGAAACCCTCCCCAGGTCTTCCAAGTACAGGATTGAAGC<br>TTTAGTGAAATTAACCAAGGACCATGGGTCAGTGCCCAGGGCTT<br>TAAAAAGAATGAACGAGCAAAAGGTATCCCCGCCGTGACCCCTG<br>CAGATAGCACCGGTCTTTGATCCGCAGCAGGGGCCAGACCCTG<br>CCCACAAGTCCCAGCGCGGCTGCTTCTGCCACTGCTGGGCTCC<br>ACTTGGCTCCTCTCACTTCCCAGGGGGTCGCCTGTCCTGCCTGT<br>GGGTTTCCATGGCTTCCCAGAGCTCCCTCTGCCCCAGCCAGCG<br>CCTCCAGGCCCAGCTGAGGAGCTGTGAGAAGCAGCAGAGGGG<br>ACTCCCCATCCCGGGCACACCCTGTCCTCCCACCCCTGCCCCC<br>TTGCCCTTCCAGCCCTTTCAGCTGCAGCTGGGAGCTGGCCCGT<br>CAAGTGCTGCCCCTGCCTGTGTCTGGGTTTCTGTTGGCTGTTTT<br>TCTTTTCTTGAGTGGTGATTTTTCTCTAAATAAAAGAAGTCAAGC<br>ACTGAAAAAAAAAAAAAAAA |
| 13 | OTOF-208 transcript (NM_194322.2), human otoferlin transcript variant 3, 3924 bp, encodes the protein of SEQ ID NO: 4 | CCGTGAGTTCTGCCCAGGCCCTGTGAGCTCACCAGAGCCACAG<br>ACTCACAGCCCAGAGGTGGCTTCTTCCTTCAGGAACTGAAGAAC<br>CCCCATGAACACCAACATCTCCAGGTTCTGAGAACAGAACCTGG<br>GAAATTGATGACTTCCTCATGATGACCGATACTCAGGATGGCCC<br>TAGCGAGAGCTCCCAGATCATGAGGTCCCTCACTCCCCTGATCA<br>ACAGGGAGGAGGCATTTGGGGAGGCTGGGGAGGCGGGGCTGT<br>GGCCCAGCATCACCCACACTCCTGATTCACAGGAAGAAGGCCT<br>GAACGACATACAGGAGATGATCAAAACGGAGAAGTCCTACCCTG<br>AGCGTCGCCTGCGGGGCGTCCTGGAGGAGCTGAGCTGTGGCT<br>GCTGCCGCTTCCTCTCCCTCGCTGACAAGGACCAGGGCCACTC<br>ATCCCGCACCAGGCTTGACCGGGAGCGCCTCAAGTCCTGCATG<br>AGGGAGCTGGAAAACATGGGGCAGCAGGCCAGGATGCTGCGG<br>GCCCAGGTGAAGCGGCACACGGTGCGGGACAAGCTGAGGCTG<br>TGCCAGAACTTCCTGCAGAAGCTGCGCTTCCTGGCGGACGAGC<br>CCCAGCACAGCATTCCCGACATCTTCATCTGGATGATGAGCAAC<br>AACAAGCGTGTCGCCTATGCCCGTGTGCCCTCCAAGGACCTGC<br>TCTTCTCCATCGTGGAGGAGGAGACTGGCAAGGACTGCGCCAA<br>GGTCAAGACGCTCTTCCTTAAGCTGCCAGGGAAGCGGGGCTTC<br>GGCTCGGCAGGCTGGACAGTGCAGGCCAAGGTGGAGCTGTAC<br>CTGTGGCTGGGCCTCAGCAAACAGCGCAAGGAGTTCCTGTGCG<br>GCCTGCCCTGTGGCTTCCAGGAGGTCAAGGCAGCCCAGGGCCT<br>GGGCCTGCATGCCTTCCCACCCGTCAGCCTGGTCTACACCAAG<br>AAGCAGGCGTTCCAGCTCCGAGCGCACATGTACCAGGCCCGCA<br>GCCTCTTTGCCGCCGACAGCAGCGGACTCTCAGACCCCTTTGC<br>CCGCGTCTTCTTCATCAATCAGAGTCAGTGCACAGAGGTGCTGA<br>ATGAGACCCTGTGTCCCACCTGGGACCAGATGCTGGTGTTCGA<br>CAACCTGGAGCTCTATGGTGAAGCTCATGAGCTGAGGGACGAT<br>CCGCCCATCATTGTCATTGAAATCTATGACCAGGATTCCATGGG<br>CAAAGCTGACTTCATGGGCCGGACCTTCGCCAAACCCCTGGTG<br>AAGATGGCAGACGAGGCGTACTGCCCACCCCGCTTCCCACCTC<br>AGCTCGAGTACTACCAGATCTACCGTGGCAACGCCACAGCTGG<br>AGACCTGCTGGCGGCCTTCGAGCTGCTGCAGATTGGACCAGCA<br>GGGAAGGCTGACCTGCCCCCCATCAATGGCCCGGTGGACGTG<br>GACCGAGGTCCCATCATGCCCGTGCCCATGGGCATCCGGCCCG<br>TGCTCAGCAAGTACCGAGTGGAGGTGCTGTTCTGGGGCCTACG<br>GGACCTAAAGCGGGTGAACCTGGCCCAGGTGGACCGGCCACG<br>GGTGGACATCGAGTGTGCAGGGAAGGGGGTGCAGTCGTCCCT<br>GATCCACAATTATAAGAAGAACCCCAACTTCAACACCCTCGTCAA<br>GTGGTTTGAAGTGGACCTCCCAGAGAACGAGCTGCTGCACCCG<br>CCCTTGAACATCCGTGTGGTGGACTGCCGGGCCTTCGGTCGCT<br>ACACACTGGTGGGCTCCCATGCCGTCAGCTCCCTGCGACGCTT<br>CATCTACCGGCCCCCAGACCGCTCGGCCCCCAGCTGGAACACC<br>ACGGTCAGGCTTCTCCGGCGCTGCCGTGTGCTGTGCAATGGGG<br>GCTCCTCCTCTCACTCCACAGGGGAGGTTGTGGTGACTATGGA<br>GCCAGAGGTACCCATCAAGAAACTGGAGACCATGGTGAAGCTG<br>GACGCGACTTCTGAAGCTGTTGTCAAGGTGGATGTGGCTGAGG<br>AGGAGAAGGAGAAGAAGAAGAAGAAGAAGGGCACTGCGGAGG<br>AGCCAGAGGAGGAGGAGCCAGACGAGAGCATGCTGGACTGGT<br>GGTCCAAGTACTTTGCCTCCATTGACACCATGAAGGAGCAACTT |

TABLE 2-continued

| OTOF Sequences | | |
|---|---|---|
| SEQ ID NO. | Sequence Name | Sequence |
| | | CGACAACAAGAGCCCTCTGGAATTGACTTGGAGGAGAAGGAGG<br>AAGTGGACAATACCGAGGGCCTGAAGGGGTCAATGAAGGGCAA<br>GGAGAAGGCAAGGGCTGCCAAAGAGGAGAAGAAGAAGAAAACT<br>CAGAGCTCTGGCTCTGGCCAGGGGTCCGAGGCCCCCGAGAAG<br>AAGAAACCCAAGATTGATGAGCTTAAGGTATACCCCAAAGAGCT<br>GGAGTCCGAGTTTGATAACTTTGAGGACTGGCTGCACACTTTCA<br>ACTTGCTTCGGGGCAAGACCGGGGATGATGAGGATGGCTCCAC<br>CGAGGAGGAGCGCATTGTGGGACGCTTCAAGGGCTCCCTCTGC<br>GTGTACAAAGTGCCACTCCCAGAGGACGTGTCCCGGGAAGCCG<br>GCTACGACTCCACCTACGGCATGTTCCAGGGCATCCCGAGCAA<br>TGACCCCATCAATGTGCTGGTCCGAGTCTATGTGGTCCGGGCC<br>ACGGACCTGCACCCTGCTGACATCAACGGCAAAGCTGACCCCT<br>ACATCGCCATCCGGCTAGGCAAGACTGACATCCGCGACAAGGA<br>GAACTACATCTCCAAGCAGCTCAACCCTGTCTTTGGGAAGTCCT<br>TTGACATCGAGGCCTCCTTCCCCATGGAATCCATGCTGACGGTG<br>GCTGTGTATGACTGGGACCTGGTGGGCACTGATGACCTCATTG<br>GGGAAACCAAGATCGACCTGGAGAACCGCTTCTACAGCAAGCA<br>CCGCGCCACCTGCGGCATCGCCCAGACCTACTCCACACATGGC<br>TACAATATCTGGCGGGACCCCATGAAGCCCAGCCAGATCCTGA<br>CCCGCCTCTGCAAAGACGGCAAAGTGGACGGCCCCCACTTTGG<br>GCCCCCTGGGAGAGTGAAGGTGGCCAACCGCGTCTTCACTGGG<br>CCCTCTGAGATTGAGGACGAGAACGGTCAGAGGAAGCCCACAG<br>ACGAGCATGTGGCGCTGTTGGCCCTGAGGCACTGGGAGGACAT<br>CCCCCGCGCAGGCTGCCGCCTGGTGCCAGAGCATGTGGAGAC<br>GAGGCCGCTGCTCAACCCCGACAAGCCGGGCATCGAGCAGGG<br>CCGCCTGGAGCTGTGGGTGGACATGTTCCCCATGGACATGCCA<br>GCCCCTGGGACGCCTCTGGACATCTCACCTCGGAAGCCCAAGA<br>AGTACGAGCTGCGGGTCATCATCTGGAACACAGATGAGGTGGT<br>CTTGGAGGACGACGACTTCTTCACAGGGGAGAAGTCCAGTGAC<br>ATCTTCGTGAGGGGGTGGCTGAAGGGCCAGCAGGAGGACAAG<br>CAGGACACAGACGTCCACTACCACTCCCTCACTGGCGAGGGCA<br>ACTTCAACTGGCGCTACCTGTTCCCCTTCGACTACCTGGCGGCG<br>GAGGAGAAGATCGTCATCTCCAAGAAGGAGTCCATGTTCTCCTG<br>GGACGAGACCGAGTACAAGATCCCCGCGCGGCTCACCCTGCAG<br>ATCTGGGATGCGGACCACTTCTCCGCTGACGACTTCCTGGGGG<br>CCATCGAGCTGGACCTGAACCGGTTCCCGCGGGGCGCAAAGAC<br>AGCCAAGCAGTGCACCATGGAGATGGCCACCGGGGAGGTGGA<br>CGTGCCCCTCGTGTCCATCTTCAAGCAAAAGCGCGTCAAAGGCT<br>GGTGGCCCCTCCTGGCCCGCAATGAGAACGATGAGTTTGAGCT<br>CACGGGCAAGGTGGAGGCTGAGCTGCATTTACTGACAGCAGAG<br>GAGGCAGAGAAGAACCCAGTGGGCCTGGCCCGCAATGAACCTG<br>ACCCCCTAGAGAAACCCAACCGGCCCGACACGAGCTTCATCTG<br>GTTCCTGAACCCTCTCAAGTCGGCTCGCTACTTCTTGTGGCACA<br>CGTATCGCTGGCTGCTCCTCAAACTGTTGCTGCTCCTGCTGCTG<br>CTCCTCCTCCTCGCCCTGTTCCTCTACTCTGTGCCTGGCTACCT<br>GGTCAAGAAAATCCTCGGGGCCTGAGCCCAGTGGCCTCCTGGC<br>CGGCCCGACACGGCCTTCGTCTGGTTCCTCAACCCTCTCAAGTC<br>CATCAAGTACCTCATCTGCACCCGGTACAAGTGGCTCATCATCA<br>AGATCGTGCTGGCGCTGTTGGGGCTGCTCATGTTGGGGCTCTT<br>CCTCTACAGCCTCCCTGGCTACATGGTCAAAAAGCTCCTTGGGG<br>CATGAAGGCCGCCAGCTCCCGCCAGCCGCTCCCCAGCCCTGCC<br>GCATTTCCTTTCAGTGGCTTGGACTCTTTCCCATCTCCCCTGGG<br>GAGCCTGAGGAGCCCAGCGTCCACTCTTCATGCCTTGGGCCGA<br>GCCTGCCTCCTGCTTGCGGGGGCCGCCTGTCCTCACTGCCCCA<br>GGCTGCGGCTTGCCCAGTCCCGCCCCTCTGACCCCTGCCTGTG<br>GGCTGGGGAGCCTTGGATGGGGTGGGGACCTGGAATGGGTCT<br>CTCTTGCCCCACCTGGCTGAGGCGCCACCCTTCTTCAGGCCCA<br>GGCTCCAGAGGAAGACTCCTGAAACCCTCCCCAGGTCTTCCAA<br>GTACAGGATTGAAGCTTTAGTGAAATTAACCAAGGACCATGGGT<br>CAGTGCCCAGGGCTTTAAAAAGAATGAACGAGCAAAAGGTATCC<br>CCGCCGTGACCCCTGCAGATAGCACCGGTCTTTGATCCGCAGC<br>AGGGGCCAGACCCTGCCCACAAGTCCCAGCGCGGCTGCTTCTG<br>CCACTGCTGGGCTCCACTTGGCTCCTCTCACTTCCCAGGGGGT<br>CGCCTGTCCTGCCTGTGGGTTTCCATGGCTTCCCAGAGCTCCCT<br>CTGCCCCAGCCAGCGCCTCCAGGCCCAGCTGAGGAGCTGTGA<br>GAAGCAGCAGAGGGGACTCCCCATCCCGGGCACACCCTGTCCT<br>CCCACCCCTGCCCCCTTGCCCTTCCAGCCCTTTCAGCTGCAGCT<br>GGGAGCTGGCCCGTCAAGTGCTGCCCCTGCCTGTGTCTGGGTT<br>TCTGTTGGCTGTTTTTCTTTTCTTGAGTGGTGATTTTTCTCTAAAT<br>AAAAGAAGTCAAGCACTGAAAAAAAAAAAAAAAA |
| 14 | OTOF-205 transcript (NM_001287489.1), human otoferlin transcript variant 5, | ATCGGAGGGGGGTCGGGAGGAGGAGGAGGAGGCAGCGGCAG<br>AGAAGAGAGAGGCGTGTGAGCCGTGCTCCACCGGCTAGCTCCT<br>TCCCGCTGCTCCTGCCTGGCAGTGCCAGGCAGCCCACACCAGC<br>ATGGCCTTGCTCATCCACCTCAAGACAGTCTCGGAGCTGCGGG |

TABLE 2-continued

OTOF Sequences

| SEQ ID NO. | Sequence Name | Sequence |
|---|---|---|
| | 6937 bp, encodes the protein of SEQ ID NO: 5 | GCAGGGGCGACCGGATCGCCAAAGTGACTTTCCGAGGGCAATC<br>CTTCTACTCTCGGGTCCTGGAGAACTGTGAGGATGTGGCTGACT<br>TTGATGAGACATTTCGGTGGCCGGTGGCCAGCAGCATCGACAG<br>AAATGAGATGCTGGAGATTCAGGTTTTCAACTACAGCAAAGTCTT<br>CAGCAACAAGCTCATCGGGACCTTCCGCATGGTGCTGCAGAAG<br>GTGGTAGAGGAGAGCCATGTGGAGGTGACTGACACGCTGATTG<br>ATGACAACAATGCTATCATCAAGACCAGCCTGTGCGTGGAGGTC<br>CGGTATCAGGCCACTGACGGCACAGTGGGCTCCTGGGACGATG<br>GGGACTTCCTGGGAGATGAGTCTCTTCAAGAGGAAGAGAAGGA<br>CAGCCAAGAGACGGATGGACTGCTCCCAGGCTCCCGGCCCAGC<br>TCCCGGCCCCCAGGAGAGAAGAGCTTCCGGAGAGCCGGGAGG<br>AGCGTGTTCTCCGCCATGAAGCTCGGCAAAAACCGGTCTCACAA<br>GGAGGAGCCCCAAAGACCAGATGAACCGGCGGTGCTGGAGAT<br>GGAAGACCTTGACCATCTGGCCATTCGGCTAGGAGATGGACTG<br>GATCCCGACTCGGTGTCTCTAGCCTCAGTCACAGCTCTCACCAC<br>TAATGTCTCCAACAAGCGATCTAAGCCAGACATTAAGATGGAGC<br>CAAGTGCTGGGCGGCCCATGGATTACCAGGTCAGCATCACGGT<br>GATCGAGGCCCGGCAGCTGGTGGGCTTGAACATGGACCCTGTG<br>GTGTGCGTGGAGGTGGGTGACGACAAGAAGTACACATCCATGA<br>AGGAGTCCACTAACTGCCCCTATTACAACGAGTACTTCGTCTTC<br>GACTTCCATGTCTCTCCGGATGTCATGTTTGACAAGATCATCAAG<br>ATTTCGGTGATTCACTCCAAGAACCTGCTGCGCAGTGGCACCCT<br>GGTGGGCTCCTTCAAAATGGACGTGGGAACCGTGTACTCGCAG<br>CCAGAGCACCAGTTCCATCACAAGTGGGCCATCCTGTCTGACCC<br>CGATGACATCTCCTCGGGGCTGAAGGGCTACGTGAAGTGTGAC<br>GTTGCCGTGGTGGGCAAAGGGGACAACATCAAGACGCCCCACA<br>AGGCCAATGAGACCGACGAAGATGACATTGAGGGGAACTTGCT<br>GCTCCCCGAGGGGGTGCCCCCCGAACGCCAGTGGGCCCGGTT<br>CTATGTGAAAATTTACCGAGCAGAGGGGCTGCCCCGTATGAACA<br>CAAGCCTCATGGCCAATGTAAAGAAGGCTTTCATCGGTGAAAAC<br>AAGGACCTCGTGGACCCCTACGTGCAAGTCTTCTTTGCTGGCCA<br>GAAGGGCAAGACTTCAGTGCAGAAGAGCAGCTATGAGCCCCTG<br>TGGAATGAGCAGGTCGTCTTTACAGACCTCTTCCCCCCACTCTG<br>CAAACGCATGAAGGTGCAGATCCGAGACTCGGACAAGGTCAAC<br>GACGTGGCCATCGGCACCCACTTCATTGACCTGCGCAAGATTTC<br>TAATGACGGAGACAAAGGCTTCCTGCCCACACTGGGCCCAGCC<br>TGGGTGAACATGTACGGCTCCACACGTAACTACACGCTGCTGGA<br>TGAGCATCAGGACCTGAACGAGGGCCTGGGGGAGGGTGTGTC<br>CTTCCGGGCCCGGCTCCTGCTGGGCCTGGCTGTGGAGATCGTA<br>GACACCTCCAACCCTGAGCTCACCAGCTCCACAGAGGTGCAGG<br>TGGAGCAGGCCACGCCCATCTCGGAGAGCTGTGCAGGTAAAAT<br>GGAAGAATTCTTTCTCTTTGGAGCCTTCCTGGAGGCCTCAATGA<br>TCGACCGGAGAAACGGAGACAAGCCCATCACCTTTGAGGTCAC<br>CATAGGCAACTATGGGAACGAAGTTGATGGCCTGTCCCGGCCC<br>CAGCGGCCTCGGCCCCGGAAGGAGCCGGGGGATGAGGAAGAA<br>GTAGACCTGATTCAGAACGCAAGTGATGACGAGGCCGGTGATG<br>CCGGGGACCTGGCCTCAGTCTCCTCCACTCCACCAATGCGGCC<br>CCAGGTCACCGACAGGAACTACTTCCATCTGCCCTACCTGGAGC<br>GAAAGCCCTGCATCTACATCAAGAGCTGGTGGCCGGACCAGCG<br>CCGCCGCCTCTACAATGCCAACATCATGGACCACATTGCCGACA<br>AGCTGGAAGAAGGCCTGAACGACATACAGGAGATGATCAAAAC<br>GGAGAAGTCCTACCCTGAGCGTCGCCTGCGGGGCGTCCTGGA<br>GGAGCTGAGCTGTGGCTGCTGCCGCTTCCTCTCCCTCGCTGAC<br>AAGGACCAGGGCCACTCATCCCGCACCAGGCTTGACCGGGAGC<br>GCCTCAAGTCCTGCATGAGGGAGCTGGAAAACATGGGGCAGCA<br>GGCCAGGATGCTGCGGGCCCAGGTGAAGCGGCACACGGTGCG<br>GGACAAGCTGAGGCTGTGCCAGAACTTCCTGCAGAAGCTGCGC<br>TTCCTGGCGGACGAGCCCCAGCACAGCATTCCCGACATCTTCAT<br>CTGGATGATGAGCAACAACAAGCGTGTCGCCTATGCCCGTGTG<br>CCCTCCAAGGACCTGCTCTTCTCCATCGTGGAGGAGGAGACTG<br>GCAAGGACTGCGCCAAGGTCAAGACGCTCTTCCTTAAGCTGCC<br>AGGGAAGCGGGGCTTCGGCTCGGCAGGCTGGACAGTGCAGGC<br>CAAGGTGGAGCTGTACCTGTGGCTGGGCCTCAGCAAACAGCGC<br>AAGGAGTTCCTGTGCGGCCTGCCCTGTGGCTTCCAGGAGGTCA<br>AGGCAGCCCAGGGCCTGGGCCTGCATGCCTTCCCACCCGTCAG<br>CCTGGTCTACACCAAGAAGCAGGCGTTCCAGCTCCGAGCGCAC<br>ATGTACCAGGCCCGCAGCCTCTTTGCCGCCGACAGCAGCGGAC<br>TCTCAGACCCCTTTGCCCGCGTCTTCTTCATCAATCAGAGTCAG<br>TGCACAGAGGTGCTGAATGAGACCCTGTGTCCCACCTGGGACC<br>AGATGCTGGTGTTCGACAACCTGGAGCTCTATGGTGAAGCTCAT<br>GAGCTGAGGGACGATCCGCCCATCATTGTCATTGAAATCTATGA<br>CCAGGATTCCATGGGCAAAGCTGACTTCATGGGCCGGACCTTC<br>GCCAAACCCCTGGTGAAGATGGCAGACGAGGCGTACTGCCCAC<br>CCCGCTTCCCACCTCAGCTCGAGTACTACCAGATCTACCGTGGC<br>AACGCCACAGCTGGAGACCTGCTGGCGGCCTTCGAGCTGCTGC |

TABLE 2-continued

OTOF Sequences

| SEQ ID NO. | Sequence Name | Sequence |
|---|---|---|
| | | AGATTGGACCAGCAGGGAAGGCTGACCTGCCCCCCATCAATGG |
| | | CCCGGTGGACGTGGACCGAGGTCCCATCATGCCCGTGCCCATG |
| | | GGCATCCGGCCCGTGCTCAGCAAGTACCGAGTGGAGGTGCTGT |
| | | TCTGGGGCCTACGGGACCTAAAGCGGGTGAACCTGGCCCAGGT |
| | | GGACCGGCCACGGGTGGACATCGAGTGTGCAGGGAAGGGGGT |
| | | GCAGTCGTCCCTGATCCACAATTATAAGAAGAACCCCAACTTCA |
| | | ACACCCTCGTCAAGTGGTTTGAAGTGGACCTCCCAGAGAACGA |
| | | GCTGCTGCACCCGCCCTTGAACATCCGTGTGGTGGACTGCCGG |
| | | GCCTTCGGTCGCTACACACTGGTGGGCTCCCATGCCGTCAGCT |
| | | CCCTGCGACGCTTCATCTACCGGCCCCCAGACCGCTCGGCCCC |
| | | CAGCTGGAACACCACGGTCAGGCTTCTCCGGCGCTGCCGTGTG |
| | | CTGTGCAATGGGGGCTCCTCCTCTCACTCCACAGGGGAGGTTG |
| | | TGGTGACTATGGAGCCAGAGGTACCCATCAAGAAACTGGAGAC |
| | | CATGGTGAAGCTGGACGCGACTTCTGAAGCTGTTGTCAAGGTG |
| | | GATGTGGCTGAGGAGGAGAAGGAGAAGAAGAAGAAGAAGAAGG |
| | | GCACTGCGGAGGAGCCAGAGGAGGAGGAGCCAGACGAGAGCA |
| | | TGCTGGACTGGTGGTCCAAGTACTTTGCCTCCATTGACACCATG |
| | | AAGGAGCAACTTCGACAACAAGAGCCCTCTGGAATTGACTTGGA |
| | | GGAGAAGGAGGAAGTGGACAATACCGAGGGCCTGAAGGGGTC |
| | | AATGAAGGGCAAGGAGAAGGCAAGGGCTGCCAAAGAGGAGAAG |
| | | AAGAAGAAAACTCAGAGCTCTGGCTCTGGCCAGGGGTCCGAGG |
| | | CCCCCGAGAAGAAGAAACCCAAGATTGATGAGCTTAAGGTATAC |
| | | CCCAAAGAGCTGGAGTCCGAGTTTGATAACTTTGAGGACTGGCT |
| | | GCACACTTTCAACTTGCTTCGGGGCAAGACCGGGGATGATGAG |
| | | GATGGCTCCACCGAGGAGGAGCGCATTGTGGGACGCTTCAAGG |
| | | GCTCCCTCTGCGTGTACAAAGTGCCACTCCCAGAGGACGTGTC |
| | | CCGGGAAGCCGGCTACGACTCCACCTACGGCATGTTCCAGGGC |
| | | ATCCCGAGCAATGACCCCATCAATGTGCTGGTCCGAGTCTATGT |
| | | GGTCCGGGCCACGGACCTGCACCCTGCTGACATCAACGGCAAA |
| | | GCTGACCCCTACATCGCCATCCGGCTAGGCAAGACTGACATCC |
| | | GCGACAAGGAGAACTACATCTCCAAGCAGCTCAACCCTGTCTTT |
| | | GGGAAGTCCTTTGACATCGAGGCCTCCTTCCCCATGGAATCCAT |
| | | GCTGACGGTGGCTGTGTATGACTGGGACCTGGTGGGCACTGAT |
| | | GACCTCATTGGGGAAACCAAGATCGACCTGGAGAACCGCTTCTA |
| | | CAGCAAGCACCGCGCCACCTGCGGCATCGCCCAGACCTACTCC |
| | | ACACATGGCTACAATATCTGGCGGGACCCCATGAAGCCCAGCC |
| | | AGATCCTGACCCGCCTCTGCAAAGACGGCAAAGTGGACGGCCC |
| | | CCACTTTGGGCCCCCTGGGAGAGTGAAGGTGGCCAACCGCGTC |
| | | TTCACTGGGCCCTCTGAGATTGAGGACGAGAACGGTCAGAGGA |
| | | AGCCCACAGACGAGCATGTGGCGCTGTTGGCCCTGAGGCACTG |
| | | GGAGGACATCCCCCGCGCAGGCTGCCGCCTGGTGCCAGAGCA |
| | | TGTGGAGACGAGGCCGCTGCTCAACCCCGACAAGCCGGGCATC |
| | | GAGCAGGGCCGCCTGGAGCTGTGGGTGGACATGTTCCCCATGG |
| | | ACATGCCAGCCCCTGGGACGCCTCTGGACATCTCACCTCGGAA |
| | | GCCCAAGAAGTACGAGCTGCGGGTCATCATCTGGAACACAGAT |
| | | GAGGTGGTCTTGGAGGACGACGACTTCTTCACAGGGGAGAAGT |
| | | CCAGTGACATCTTCGTGAGGGGGTGGCTGAAGGGCCAGCAGGA |
| | | GGACAAGCAGGACACAGACGTCCACTACCACTCCCTCACTGGC |
| | | GAGGGCAACTTCAACTGGCGCTACCTGTTCCCCTTCGACTACCT |
| | | GGCGGCGGAGGAGAAGATCGTCATCTCCAAGAAGGAGTCCATG |
| | | TTCTCCTGGGACGAGACCGAGTACAAGATCCCCGCGCGGCTCA |
| | | CCCTGCAGATCTGGGATGCGGACCACTTCTCCGCTGACGACTT |
| | | CCTGGGGGCCATCGAGCTGGACCTGAACCGGTTCCCGCGGGG |
| | | CGCAAAGACAGCCAAGCAGTGCACCATGGAGATGGCCACCGGG |
| | | GAGGTGGACGTGCCCCTCGTGTCCATCTTCAAGCAAAAGCGCG |
| | | TCAAAGGCTGGTGGCCCCTCCTGGCCCGCAATGAGAACGATGA |
| | | GTTTGAGCTCACGGGCAAGGTGGAGGCTGAGCTGCATTTACTG |
| | | ACAGCAGAGGAGGCAGAGAAGAACCCAGTGGGCCTGGCCCGC |
| | | AATGAACCTGACCCCCTAGAGAAACCCAACCGGCCCGACACGG |
| | | CCTTCGTCTGGTTCCTCAACCCTCTCAAGTCCATCAAGTACCTCA |
| | | TCTGCACCCGGTACAAGTGGCTCATCATCAAGATCGTGCTGGCG |
| | | CTGTTGGGGCTGCTCATGTTGGGGCTCTTCCTCTACAGCCTCCC |
| | | TGGCTACATGGTCAAAAAGCTCCTTGGGGCATGAAGGCCGCCA |
| | | GCTCCCGCCAGCCGCTCCCCAGCCCTGCCGCATTTCCTTTCAG |
| | | TGGCTTGGACTCTTTCCCATCTCCCCTGGGGAGCCTGAGGAGC |
| | | CCAGCGTCCACTCTTCATGCCTTGGGCCGAGCCTGCCTCCTGC |
| | | TTGCGGGGGCCGCCTGTCCTCACTGCCCCAGGCTGCGGCTTGC |
| | | CCAGTCCCGCCCCTCTGACCCCTGCCTGTGGGCTGGGGAGCCT |
| | | TGGATGGGGTGGGGACCTGGAATGGGTCTCTCTTGCCCCACCT |
| | | GGCTGAGGCGCCACCCTTCTTCAGGCCCAGGCTCCAGAGGAAG |
| | | ACTCCTGAAACCCTCCCCAGGTCTTCCAAGTACAGGATTGAAGC |
| | | TTTAGTGAAATTAACCAAGGACCATGGGTCAGTGCCCAGGGCTT |
| | | TAAAAAGAATGAACGAGCAAAAGGTATCCCCGCCGTGACCCCTG |
| | | CAGATAGCACCGGTCTTTGATCCGCAGCAGGGGCCAGACCCTG |
| | | CCCACAAGTCCCAGCGCGGCTGCTTCTGCCACTGCTGGGCTCC |

TABLE 2-continued

OTOF Sequences

| SEQ ID NO. | Sequence Name | Sequence |
|---|---|---|
| | | ACTTGGCTCCTCTCACTTCCCAGGGGGTCGCCTGTCCTGCCTGT<br>GGGTTTCCATGGCTTCCCAGAGCTCCCTCTGCCCCAGCCAGCG<br>CCTCCAGGCCCAGCTGAGGAGCTGTGAGAAGCAGCAGAGGGG<br>ACTCCCCATCCCGGGCACACCCTGTCCTCCCACCCCTGCCCCC<br>TTGCCCTTCCAGCCCTTTCAGCTGCAGCTGGGAGCTGGCCCGT<br>CAAGTGCTGCCCCTGCCTGTGTCTGGGTTTCTGTTGGCTGTTTT<br>TCTTTTCTTGAGTGGTGATTTTTCTCTAAATAAAAGAAGTCAAGC<br>ACTGAAAAAAAAAAAAAAAA |
| 15 | mOTOF-201_1 transcript (NM_031875.2), mouse otoferlin transcript variant 2, 7129 bp, encodes the protein of SEQ ID NO: 6 | TTGGTTGCCTTGGTCTCTGTGGGCAGCAGCAGGAGGAGGCGGC<br>AGCAGCCAGAGAAGAGGGAGGCGTGTGAGCCACACTCCACCAG<br>CGAGCTTCTTCCCGCTGCTCTGGAACTGCCCAGGCTCTCCCCA<br>CCAGCATGGCCCTGATTGTTCACCTCAAGACTGTCTCAGAGCTC<br>CGAGGCAAAGGTGACCGGATTGCCAAAGTCACTTTCCGAGGGC<br>AGTCTTTCTACTCCCGGGTCCTGGAGAACTGCGAGGGTGTGGC<br>TGACTTTGATGAGACGTTCCGGTGGCCAGTGGCCAGCAGCATC<br>GACCGGAATGAAGTGTTGGAGATTCAGATTTTCAACTACAGCAA<br>AGTCTTCAGCAACAAGCTGATAGGGACCTTCTGCATGGTGCTGC<br>AGAAAGTGGTGGAGGAGAATCGGGTAGAGGTGACCGACACGCT<br>GATGGATGACAGCAATGCTATCATCAAGACCAGCCTGAGCATGG<br>AGGTCCGGTATCAGGCCACAGATGGCACTGTGGGCCCCTGGGA<br>TGATGGAGACTTCCTGGGAGATGAATCCCTCCAGGAGGAGAAG<br>GACAGCCAGGAGACAGATGGGCTGCTACCTGGTTCCCGACCCA<br>GCACCCGGATATCTGGCGAGAAGAGCTTTCGCAGAGCGGGAAG<br>GAGTGTGTTCTCGGCCATGAAACTCGGCAAAACTCGGTCCCACA<br>AAGAGGAGCCCCAAAGACAAGATGAGCCAGCAGTGCTGGAGAT<br>GGAGGACCTGGACCACCTAGCCATTCAGCTGGGGGATGGGCTG<br>GATCCTGACTCCGTGTCTCTAGCCTCGGTCACCGCTCTCACCAG<br>CAATGTCTCCAACAAACGGTCTAAGCCAGATATTAAGATGGAGC<br>CCAGTGCTGGAAGGCCCATGGATTACCAGGTCAGCATCACAGT<br>GATTGAGGCTCGGCAGCTGGTGGGCTTGAACATGGACCCTGTG<br>GTGTGTGTGGAGGTGGGTGATGACAAGAAATACACGTCAATGAA<br>GGAGTCCACAAACTGCCCTTACTACAACGAGTACTTTGTCTTCG<br>ACTTCCATGTCTCTCCTGATGTCATGTTTGACAAGATCATCAAGA<br>TCTCGGTTATCCATTCTAAGAACCTGCTTCGGAGCGGCACCCTG<br>GTGGGTTCCTTCAAAATGGATGTGGGGACTGTGTATTCCCAGCC<br>TGAACACCAGTTCCATCACAAATGGGCCATCCTGTCAGACCCCG<br>ATGACATCTCTGCTGGGTTGAAGGGTTATGTAAAGTGTGATGTC<br>GCTGTGGTGGGCAAGGGAGACAACATCAAGACACCCCACAAGG<br>CCAACGAGACGGATGAGGACGACATTGAAGGGAACTTGCTGCT<br>CCCCGAGGGCGTGCCCCCCGAACGGCAGTGGGCACGGTTCTA<br>TGTGAAAATTTACCGAGCAGAGGGACTGCCCCGGATGAACACAA<br>GCCTCATGGCCAACGTGAAGAAGGCGTTCATCGGTGAGAACAA<br>GGACCTCGTCGACCCCTATGTGCAAGTCTTCTTTGCTGGACAAA<br>AGGGCAAAACATCAGTGCAGAAGAGCAGCTATGAGCCGCTATG<br>GAATGAGCAGGTCGTCTTCACAGACTTGTTCCCCCCACTCTGCA<br>AACGCATGAAGGTGCAGATCCGGGACTCTGACAAGGTCAATGAT<br>GTGGCCATCGGCACCCACTTCATCGACCTGCGCAAGATTTCCAA<br>CGATGGAGACAAAGGCTTCCTGCCTACCCTCGGTCCAGCCTGG<br>GTGAACATGTACGGCTCCACGCGCAACTACACACTGCTGGACG<br>AGCACCAGGACTTGAATGAAGGCCTGGGGGAGGGTGTGTCCTT<br>CCGGGCCCGCCTCATGTTGGGACTAGCTGTGGAGATCCTGGAC<br>ACCTCCAACCCAGAGCTCACCAGCTCCACGGAGGTGCAGGTGG<br>AGCAGGCCACGCCTGTCTCGGAGAGCTGCACAGGGAGAATGGA<br>AGAATTTTTCTATTTGGAGCCTTCTTGGAAGCCTCAATGATTGA<br>CCGGAAAAATGGGGACAAGCCAATTACCTTTGAGGTGACCATAG<br>GAAACTACGGCAATGAAGTCGATGGTATGTCCCGGCCCCTGAG<br>GCCTCGGCCCCGGAAAGAGCCTGGGGATGAAGAAGAGGTAGA<br>CCTGATTCAGAACTCCAGTGACGATGAAGGTGACGAAGCCGGG<br>GACCTGGCCTCGGTGTCCTCCACCCCACCTATGCGGCCCCAGA<br>TCACGGACAGGAACTATTTCCACCTGCCCTACCTGGAGCGCAAG<br>CCCTGCATCTATATCAAGAGCTGGTGGCCTGACCAGAGGCGGC<br>GCCTCTACAATGCCAACATCATGGATCACATTGCTGACAAGCTG<br>GAAGAAGGCCTGAATGATGTACAGGAGATGATCAAAACGGAGAA<br>GTCCTACCCGGAGCGCCGCCTGCGGGGTGTGCTAGAGGAACTC<br>AGCTGTGGCTGCCACCGCTTCCTCTCCCTCTCGGACAAGGACC<br>AGGGCCGCTCGTCCCGCACCAGGCTGGATCGAGAGCGTCTTAA<br>GTCCTGTATGAGGGAGTTGGAGAGCATGGGACAGCAGGCCAAG<br>AGCCTGAGGGCTCAGGTGAAGCGGCACACTGTTCGGGACAAGC<br>TGAGGTCATGCCAGAACTTTCTGCAGAAGCTACGCTTCCTGGCG<br>GATGAGCCCCAGCACAGCATTCCTGATGTGTTCATTTGGATGAT<br>GAGCAACAACAAACGTATCGCCTATGCCCGCGTGCCTTCCAAAG<br>ACCTGCTCTTCTCCATCGTGGAGGAGGAACTGGGCAAGGACTG<br>CGCCAAAGTCAAGACCCTCTTCCTGAAGCTGCCAGGGAAGAGG<br>GGCTTCGGCTCGGCAGGCTGGACAGTACAGGCCAAGCTGGAG |

TABLE 2-continued

| OTOF Sequences | | |
|---|---|---|
| SEQ ID NO. | Sequence Name | Sequence |
| | | CTCTACCTGTGGCTGGGCCTCAGCAAGCAGCGAAAGGACTTCC<br>TGTGTGGTCTGCCCTGTGGCTTCGAGGAGGTCAAGGCAGCCCA<br>AGGCCTGGGCCTGCATTCCTTTCCGCCCATCAGCCTAGTCTACA<br>CCAAGAAGCAAGCCTTCCAGCTCCGAGCACACATGTATCAGGC<br>CCGAAGCCTCTTTGCTGCTGACAGCAGTGGGCTCTCTGATCCCT<br>TTGCCCGTGTCTTCTTCATCAACCAGAGCCAATGCACTGAGGTT<br>CTAAACGAGACACTGTGTCCCACCTGGGACCAGATGCTGGTATT<br>TGACAACCTGGAGCTGTACGGTGAAGCTCACGAGTTACGAGAT<br>GATCCCCCCATCATTGTCATTGAAATCTACGACCAGGACAGCAT<br>GGGCAAAGCCGACTTCATGGGCCGGACCTTCGCCAAGCCCCTG<br>GTGAAGATGGCAGATGAAGCATACTGCCCACCTCGCTTCCCGC<br>CGCAGCTTGAGTACTACCAGATCTACCGAGGCAGTGCCACTGC<br>CGGAGACCTACTGGCTGCCTTCGAGCTGCTGCAGATTGGGCCA<br>TCAGGGAAGGCTGACCTGCCACCCATCAATGGCCCAGTGGACA<br>TGGACAGAGGGCCCATCATGCCTGTGCCCGTGGGAATCCGGCC<br>AGTGCTCAGCAAGTACCGAGTGGAGGTGCTGTTCTGGGGCCTG<br>AGGGACCTAAAGAGGGTGAACCTGGCCCAGGTGGACCGACCAC<br>GGGTGGACATCGAGTGTGCAGGAAAGGGGGTACAATCCTCCCT<br>GATTCACAATTATAAGAAGAACCCCAACTTCAACACGCTGGTCAA<br>GTGGTTTGAAGTGGACCTCCCGGAGAATGAGCTCCTGCACCCA<br>CCCTTGAACATCCGAGTGGTAGATTGCCGGGCCTTTGGACGATA<br>CACCCTGGTGGGTTCCCACGCAGTCAGCTCACTGAGGCGCTTC<br>ATCTACCGACCTCCAGACCGCTCAGCCCCCAACTGGAACACCA<br>CAGTCAGGCTGCTCCGGGGCTGCCACAGGCTGCGCAATGGGG<br>GCCCCTCTTCTCGCCCCACAGGGGAGGTTGTAGTAAGCATGGA<br>GCCTGAGGAGCCAGTTAAGAAGCTGGAGACCATGGTGAAACTG<br>GATGCGACTTCTGATGCTGTGGTCAAGGTGGATGTGGCTGAAG<br>ATGAGAAGGAAAGGAAGAAGAAGAAAAAGAAAGGCCCGTCAGA<br>GGAGCCAGAGGAGGAAGAGCCCGATGAGAGCATGCTGGATTG<br>GTGGTCCAAGTACTTCGCCTCCATCGACACAATGAAGGAGCAAC<br>TTCGACAACATGAGACCTCTGGAACTGACTTGGAAGAGAAGGAA<br>GAGATGGAAAGCGCTGAGGGCCTGAAGGGACCAATGAAGAGCA<br>AGGAGAAGTCCAGAGCTGCAAAGGAGGAGAAAAAGAAGAAAAA<br>CCAGAGCCCTGGCCCTGGCCAGGGATCGGAGGCTCCTGAGAA<br>GAAGAAAGCCAAGATCGATGAGCTTAAGGTGTACCCCAAGGAG<br>CTGGAATCGGAGTTTGACAGCTTTGAGGACTGGCTGCACACCTT<br>CAACCTGTTGAGGGGCAAGACGGGAGATGATGAGGATGGCTCC<br>ACAGAGGAGGAGCGCATAGTAGGCCGATTCAAGGGCTCCCTCT<br>GTGTGTACAAAGTGCCACTCCCAGAAGATGTATCTCGAGAAGCT<br>GGCTATGATCCCACCTATGGAATGTTCCAGGGCATCCCAAGCAA<br>TGACCCCATCAATGTGCTGGTCCGAATCTATGTGGTCCGGGCCA<br>CAGACCTGCACCCGGCCGACATCAATGGCAAAGCTGACCCCTA<br>TATTGCCATCAAGTTAGGCAAGACCGACATCCGAGACAAGGAGA<br>ACTACATCTCCAAGCAGCTCAACCCTGTGTTTGGGAAGTCCTTT<br>GACATTGAGGCCTCCTTCCCCATGGAGTCCATGTTGACAGTGGC<br>CGTGTACGACTGGGATCTGGTGGGCACTGATGACCTCATCGGA<br>GAAACCAAGATTGACCTGGAAAACCGCTTCTACAGCAAGCATCG<br>CGCCACCTGCGGCATCGCACAGACCTATTCCATACATGGCTACA<br>ATATCTGGAGGGACCCCATGAAGCCCAGCCAGATCCTGACACG<br>CCTCTGTAAAGAGGGCAAAGTGGACGGCCCCCACTTTGGTCCC<br>CATGGGAGAGTGAGGGTTGCCAACCGTGTCTTCACGGGGCCTT<br>CAGAAATAGAGGATGAGAATGGTCAGAGGAAGCCCACAGATGA<br>GCACGTGGCACTGTCTGCTCTGAGACACTGGGAGGACATCCCC<br>CGGGTGGGCTGCCGCCTTGTGCCGGAACACGTGGAGACCAGG<br>CCGCTGCTCAACCCTGACAAGCCAGGCATTGAGCAGGGCCGCC<br>TGGAGCTGTGGGTGGACATGTTCCCCATGGACATGCCAGCCCC<br>TGGGACACCTCTGGATATATCCCCCAGGAAACCCAAGAAGTACG<br>AGCTGCGGGTCATCGTGTGGAACACAGACGAGGTGGTCCTGGA<br>AGACGATGATTTCTTCACGGGAGAGAAGTCCAGTGACATTTTTG<br>TGAGGGGGTGGCTGAAGGGCCAGCAGGAGGACAAACAGGACA<br>CAGATGTCCACTATCACTCCCTCACGGGGGAGGGCAACTTCAAC<br>TGGAGATACCTCTTCCCCTTCGACTACCTAGCGGCCGAAGAGAA<br>GATCGTTATGTCCAAAAAGGAGTCTATGTTCTCCTGGGATGAGA<br>CGGAGTACAAGATCCCTGCGCGGCTCACCCTGCAGATCTGGGA<br>CGCTGACCACTTCTCGGCTGACGACTTCCTGGGGGCTATCGAG<br>CTGGACCTGAACCGGTTCCCGAGGGGCGCTAAGACAGCCAAGC<br>AGTGCACCATGGAGATGGCCACCGGGGAGGTGGACGTACCCCT<br>GGTTTCCATCTTTAAACAGAAACGTGTCAAAGGCTGGTGGCCCC<br>TCCTGGCCCGCAATGAGAATGATGAGTTTGAGCTCACAGGCAAA<br>GTGGAGGCGGAGCTACACCTACTCACGGCAGAGGAGGCAGAG<br>AAGAACCCTGTGGGCCTGGCTCGCAATGAACCTGATCCCCTAG<br>AAAAACCCAATCGGCCGGACACAAGCTTCATCTGGTTCTTGAAC<br>CCTCTCAAGTCTGCCCGCTACTTCCTGTGGCATACCTACCGCTG<br>GCTACTCCTCAAATTCCTGCTGCTCTTCCTCCTGCTGCTGCTCTT<br>CGCCCTGTTTCTCTACTCTCTGCCTGGCTACCTGGCCAAGAAGA |

TABLE 2-continued

OTOF Sequences

| SEQ ID NO. | Sequence Name | Sequence |
|---|---|---|
| | | TCCTTGGGGCCTGAGCCCTGCAGTCGCCTAGGCCTGCCGGCCT |
| | | GACACGGCATTCGTCTGGTTCCTGAACCCACTCAAATCTATCAA |
| | | GTACCTCATCTGCACCCGGTACAAGTGGCTGATCATCAAGATCG |
| | | TGCTGGCGCTGCTGGGGCTGCTCATGCTGGCCCTCTTCCTTTAC |
| | | AGCCTCCCAGGCTACATGGTCAAGAAGCTCCTAGGGGCCTGAA |
| | | GTGTGCCCCACCCCAGCCCGCTCCAGCATCCCTCCAGGGGCTG |
| | | CTGCGTATTTTGCCTTCCCTCACCTGGACTCTCTCCCAACTCCCT |
| | | GAGGAGCCCTCCCACGCCTGCCAGCCTTGAGCAAGACACCTGC |
| | | TTGCTGGACTTCATCCCCACCCCACACCCAAACTGTTGCTTGCC |
| | | TGATCTTGTCCCAGGCCTGCCTGGGGTTTGGGGCACAGTTGGC |
| | | CTCCAAAACCAGATACCCTCTTGTCTAAAGTACCAGGTTCCTCTG |
| | | CCCAACCCCAAGAGTGGTAGTGGCCCAACCCTCCCTGTGCTTTC |
| | | CAAATCTTGTCTTAAGGCACCAGTGAAATTAACCAAGAAACGCG |
| | | GAGCAATGCCCAAGGCTCTGATGAGTAGGAACACGTGGAAAGC |
| | | ACCAGGAATGCCAGCAGAGGCGAGGCGGCACACCTCTCTGCAG |
| | | AGCATCCAGGCCGAGCGGCGGGCAGCGGCCAGCTGCTTCTGC |
| | | GCATGCTCTCCTCTTGGCTCTGCTTCTTTCTCACAGTCACAGTCA |
| | | CTTCACAGCTTAGCCTTGGGCTTCCCATCACTTCCAGGGGTGCC |
| | | TCTGCCTTGGCCAGTGTGTGTCAGCTAGTACACAAGCTCCAAGT |
| | | GTGAATCAGGTGTACTGGCCGTCCTGAAGACTGACTGCCCTGTC |
| | | CTTCCTGCCGACAGCCACACCCGAGTGTACACTTAAAGCGGTG |
| | | CCCTTCTGCCTCTGTGGGCCTGCTGGCTGCTGTTCCTTTCTTGA |
| | | GTGTGATTTTTTTTTCTCTCCCTCAATAAAATAAATCAAACTCTG |
| | | AGAC |
| 16 | mOTOF-201_2 | TTGGTTGCCTTGGTCTCTGTGGGCAGCAGCAGGAGGAGGCGGC |
| | transcript | AGCAGCCAGAGAAGAGGGAGGCGTGTGAGCCACACTCCACCAG |
| | (NM_001286421.1), | CGAGCTTCTTCCCGCTGCTCTGGAACTGCCCAGGCTCTCCCCA |
| | mouse otoferlin | CCAGCATGGCCCTGATTGTTCACCTCAAGACTGTCTCAGAGCTC |
| | transcript variant 3, | CGAGGCAAAGGTGACCGGATTGCCAAAGTCACTTTCCGAGGGC |
| | 7129 bp, encodes | AGTCTTTCTACTCCCGGGTCCTGGAGAACTGCGAGGGTGTGGC |
| | the protein of SEQ | TGACTTTGATGAGACGTTCCGGTGGCCAGTGGCCAGCAGCATC |
| | ID NO: 7 | GACCGGAATGAAGTGTTGGAGATTCAGATTTTCAACTACAGCAA |
| | | AGTCTTCAGCAACAAGCTGATAGGGACCTTCTGCATGGTGCTGC |
| | | AGAAAGTGGTGGAGGAGAATCGGGTAGAGGTGACCGACACGCT |
| | | GATGGATGACAGCAATGCTATCATCAAGACCAGCCTGAGCATGG |
| | | AGGTCCGGTATCAGGCCACAGATGGCACTGTGGGCCCCTGGGA |
| | | TGATGGAGACTTCCTGGGAGATGAATCCCTCCAGGAGGAGAAG |
| | | GACAGCCAGGAGACAGATGGGCTGCTACCTGGTTCCCGACCCA |
| | | GCACCCGGATATCTGGCGAGAAGAGCTTTCGCAGAGCGGGAAG |
| | | GAGTGTGTTCTCGGCCATGAAACTCGGCAAAACTCGGTCCCACA |
| | | AAGAGGAGCCCCAAAGACAAGATGAGCCAGCAGTGCTGGAGAT |
| | | GGAGGACCTGGACCACCTAGCCATTCAGCTGGGGGATGGGCTG |
| | | GATCCTGACTCCGTGTCTCTAGCCTCGGTCACCGCTCTCACCAG |
| | | CAATGTCTCCAACAAACGGTCTAAGCCAGATATTAAGATGGAGC |
| | | CCAGTGCTGGAAGGCCCATGGATTACCAGGTCAGCATCACAGT |
| | | GATTGAGGCTCGGCAGCTGGTGGGCTTGAACATGGACCCTGTG |
| | | GTGTGTGTGGAGGTGGGTGATGACAAGAAATACACGTCAATGAA |
| | | GGAGTCCACAAACTGCCCTTACTACAACGAGTACTTTGTCTTCG |
| | | ACTTCCATGTCTCTCCTGATGTCATGTTTGACAAGATCATCAAGA |
| | | TCTCGGTTATCCATTCTAAGAACCTGCTTCGGAGCGGCACCCTG |
| | | GTGGGTTCCTTCAAAATGGATGTGGGGACTGTGTATTCCCAGCC |
| | | TGAACACCAGTTCCATCACAAATGGGCCATCCTGTCAGACCCCG |
| | | ATGACATCTCTGCTGGGTTGAAGGGTTATGTAAAGTGTGATGTC |
| | | GCTGTGGTGGGCAAGGGAGACAACATCAAGACACCCCACAAGG |
| | | CCAACGAGACGGATGAGGACGACATTGAAGGGAACTTGCTGCT |
| | | CCCCGAGGGCGTGCCCCCCGAACGGCAGTGGGCACGGTTCTA |
| | | TGTGAAAATTTACCGAGCAGAGGGACTGCCCCGGATGAACACAA |
| | | GCCTCATGGCCAACGTGAAGAAGGCGTTCATCGGTGAGAACAA |
| | | GGACCTCGTCGACCCCTATGTGCAAGTCTTCTTTGCTGGACAAA |
| | | AGGGCAAAACATCAGTGCAGAAGAGCAGCTATGAGCCGCTATG |
| | | GAATGAGCAGGTCGTCTTCACAGACTTGTTCCCCCCACTCTGCA |
| | | AACGCATGAAGGTGCAGATCCGGGACTCTGACAAGGTCAATGAT |
| | | GTGGCCATCGGCACCCACTTCATCGACCTGCGCAAGATTTCCAA |
| | | CGATGGAGACAAAGGCTTCCTGCCTACCCTCGGTCCAGCCTGG |
| | | GTGAACATGTACGGCTCCACGCGCAACTACACACTGCTGGACG |
| | | AGCACCAGGACTTGAATGAAGGCCTGGGGGAGGGTGTGTCCTT |
| | | CCGGGCCCGCCTCATGTTGGGACTAGCTGTGGAGATCCTGGAC |
| | | ACCTCCAACCCAGAGCTCACCAGCTCCACGGAGGTGCAGGTGG |
| | | AGCAGGCCACGCCTGTCTCGGAGAGCTGCACAGGGAGAATGGA |
| | | AGAATTTTTTCTATTTGGAGCCTTCTTGGAAGCCTCAATGATTGA |
| | | CCGGAAAAATGGGGACAAGCCAATTACCTTTGAGGTGACCATAG |
| | | GAAACTACGGCAATGAAGTCGATGGTATGTCCCGGCCCCTGAG |
| | | GCCTCGGCCCCGGAAAGAGCCTGGGGATGAAGAAGAGGTAGA |
| | | CCTGATTCAGAACTCCAGTGACGATGAAGGTGACGAAGCCGGG |

TABLE 2-continued

OTOF Sequences

| SEQ ID NO. | Sequence Name | Sequence |
|---|---|---|
| | | GACCTGGCCTCGGTGTCCTCCACCCCACCTATGCGGCCCCAGA<br>TCACGGACAGGAACTATTTCCACCTGCCCTACCTGGAGCGCAAG<br>CCCTGCATCTATATCAAGAGCTGGTGGCCTGACCAGAGGCGGC<br>GCCTCTACAATGCCAACATCATGGATCACATTGCTGACAAGCTG<br>GAAGAAGGCCTGAATGATGTACAGGAGATGATCAAAACGGAGAA<br>GTCCTACCCGGAGCGCCGCCTGCGGGGTGTGCTAGAGGAACTC<br>AGCTGTGGCTGCCACCGCTTCCTCTCCCTCTCGGACAAGGACC<br>AGGGCCGCTCGTCCCGCACCAGGCTGGATCGAGAGCGTCTTAA<br>GTCCTGTATGAGGGAGTTGGAGAGCATGGGACAGCAGGCCAAG<br>AGCCTGAGGGCTCAGGTGAAGCGGCACACTGTTCGGGACAAGC<br>TGAGGTCATGCCAGAACTTTCTGCAGAAGCTACGCTTCCTGGCG<br>GATGAGCCCCAGCACAGCATTCCTGATGTGTTCATTTGGATGAT<br>GAGCAACAACAAACGTATCGCCTATGCCCGCGTGCCTTCCAAAG<br>ACCTGCTCTTCTCCATCGTGGAGGAGGAACTGGGCAAGGACTG<br>CGCCAAAGTCAAGACCCTCTTCCTGAAGCTGCCAGGGAAGAGG<br>GGCTTCGGCTCGGCAGGCTGGACAGTACAGGCCAAGCTGGAG<br>CTCTACCTGTGGCTGGGCCTCAGCAAGCAGCGAAAGGACTTCC<br>TGTGTGGTCTGCCCTGTGGCTTCGAGGAGGTCAAGGCAGCCCA<br>AGGCCTGGGCCTGCATTCCTTTCCGCCCATCAGCCTAGTCTACA<br>CCAAGAAGCAAGCCTTCCAGCTCCGAGCACACATGTATCAGGC<br>CCGAAGCCTCTTTGCTGCTGACAGCAGTGGGCTCTCTGATCCCT<br>TTGCCCGTGTCTTCTTCATCAACCAGAGCCAATGCACTGAGGTT<br>CTAAACGAGACACTGTGTCCCACCTGGGACCAGATGCTGGTATT<br>TGACAACCTGGAGCTGTACGGTGAAGCTCACGAGTTACGAGAT<br>GATCCCCCCATCATTGTCATTGAAATCTACGACCAGGACAGCAT<br>GGGCAAAGCCGACTTCATGGGCCGGACCTTCGCCAAGCCCCTG<br>GTGAAGATGGCAGATGAAGCATACTGCCCACCTCGCTTCCCGC<br>CGCAGCTTGAGTACTACCAGATCTACCGAGGCAGTGCCACTGC<br>CGGAGACCTACTGGCTGCCTTCGAGCTGCTGCAGATTGGGCCA<br>TCAGGGAAGGCTGACCTGCCACCCATCAATGGCCCAGTGGACA<br>TGGACAGAGGGCCCATCATGCCTGTGCCCGTGGGAATCCGGCC<br>AGTGCTCAGCAAGTACCGAGTGGAGGTGCTGTTCTGGGGCCTG<br>AGGGACCTAAAGAGGGTGAACCTGGCCCAGGTGGACCGACCAC<br>GGGTGGACATCGAGTGTGCAGGAAAGGGGGTACAATCCTCCCT<br>GATTCACAATTATAAGAAGAACCCCAACTTCAACACGCTGGTCAA<br>GTGGTTTGAAGTGGACCTCCCGGAGAATGAGCTCCTGCACCCA<br>CCCTTGAACATCCGAGTGGTAGATTGCCGGGCCTTTGGACGATA<br>CACCCTGGTGGGTTCCCACGCAGTCAGCTCACTGAGGCGCTTC<br>ATCTACCGACCTCCAGACCGCTCAGCCCCCAACTGGAACACCA<br>CAGGGGAGGTTGTAGTAAGCATGGAGCCTGAGGAGCCAGTTAA<br>GAAGCTGGAGACCATGGTGAAACTGGATGCGACTTCTGATGCT<br>GTGGTCAAGGTGGATGTGGCTGAAGATGAGAAGGAAAGGAAGA<br>AGAAGAAAAAGAAAGGCCCGTCAGAGGAGCCAGAGGAGGAAGA<br>GCCCGATGAGAGCATGCTGGATTGGTGGTCCAAGTACTTCGCC<br>TCCATCGACACAATGAAGGAGCAACTTCGACAACATGAGACCTC<br>TGGAACTGACTTGGAAGAGAAGGAAGAGATGGAAAGCGCTGAG<br>GGCCTGAAGGGACCAATGAAGAGCAAGGAGAAGTCCAGAGCTG<br>CAAAGGAGGAGAAAAAGAAGAAAAACCAGAGCCCTGGCCCTGG<br>CCAGGGATCGGAGGCTCCTGAGAAGAAGAAAGCCAAGATCGAT<br>GAGCTTAAGGTGTACCCCAAGGAGCTGGAATCGGAGTTTGACA<br>GCTTTGAGGACTGGCTGCACACCTTCAACCTGTTGAGGGGCAA<br>GACGGGAGATGATGAGGATGGCTCCACAGAGGAGGAGCGCATA<br>GTAGGCCGATTCAAGGGCTCCCTCTGTGTGTACAAAGTGCCACT<br>CCCAGAAGATGTATCTCGAGAAGCTGGCTATGATCCCACCTATG<br>GAATGTTCCAGGGCATCCCAAGCAATGACCCCATCAATGTGCTG<br>GTCCGAATCTATGTGGTCCGGGCCACAGACCTGCACCCGGCCG<br>ACATCAATGGCAAAGCTGACCCCTATATTGCCATCAAGTTAGGC<br>AAGACCGACATCCGAGACAAGGAGAACTACATCTCCAAGCAGCT<br>CAACCCTGTGTTTGGGAAGTCCTTTGACATTGAGGCCTCCTTCC<br>CCATGGAGTCCATGTTGACAGTGGCCGTGTACGACTGGGATCT<br>GGTGGGCACTGATGACCTCATCGGAGAAACCAAGATTGACCTG<br>GAAAACCGCTTCTACAGCAAGCATCGCGCCACCTGCGGCATCG<br>CACAGACCTATTCCATACATGGCTACAATATCTGGAGGGACCCC<br>ATGAAGCCCAGCCAGATCCTGACACGCCTCTGTAAAGAGGGCA<br>AAGTGGACGGCCCCCACTTTGGTCCCCATGGGAGAGTGAGGGT<br>TGCCAACCGTGTCTTCACGGGGCCTTCAGAAATAGAGGATGAGA<br>ATGGTCAGAGGAAGCCCACAGATGAGCACGTGGCACTGTCTGC<br>TCTGAGACACTGGGAGGACATCCCCCGGGTGGGCTGCCGCCTT<br>GTGCCGGAACACGTGGAGACCAGGCCGCTGCTCAACCCTGACA<br>AGCCAGGCATTGAGCAGGGCCGCCTGGAGCTGTGGGTGGACAT<br>GTTCCCCATGGACATGCCAGCCCCTGGGACACCTCTGGATATAT<br>CCCCCAGGAAACCCAAGAAGTACGAGCTGCGGGTCATCGTGTG<br>GAACACAGACGAGGTGGTCCTGGAAGACGATGATTTCTTCACG<br>GGAGAGAAGTCCAGTGACATTTTTGTGAGGGGGTGGCTGAAGG<br>GCCAGCAGGAGGACAAACAGGACACAGATGTCCACTATCACTC |

TABLE 2-continued

OTOF Sequences

| SEQ ID NO. | Sequence Name | Sequence |
|---|---|---|
| | | CCTCACGGGGGAGGGCAACTTCAACTGGAGATACCTCTTCCCC<br>TTCGACTACCTAGCGGCCGAAGAGAAGATCGTTATGTCCAAAAA<br>GGAGTCTATGTTCTCCTGGGATGAGACGGAGTACAAGATCCCTG<br>CGCGGCTCACCCTGCAGATCTGGGACGCTGACCACTTCTCGGC<br>TGACGACTTCCTGGGGGCTATCGAGCTGGACCTGAACCGGTTC<br>CCGAGGGGCGCTAAGACAGCCAAGCAGTGCACCATGGAGATGG<br>CCACCGGGGAGGTGGACGTACCCCTGGTTTCCATCTTTAAACAG<br>AAACGTGTCAAAGGCTGGTGGCCCCTCCTGGCCCGCAATGAGA<br>ATGATGAGTTTGAGCTCACAGGCAAAGTGGAGGCGGAGCTACA<br>CCTACTCACGGCAGAGGAGGCAGAGAAGAACCCTGTGGGCCTG<br>GCTCGCAATGAACCTGATCCCCTAGAAAAACCCAATCGGCCGGA<br>CACAAGCTTCATCTGGTTCTTGAACCCTCTCAAGTCTGCCCGCT<br>ACTTCCTGTGGCATACCTACCGCTGGCTACTCCTCAAATTCCTG<br>CTGCTCTTCCTCCTGCTGCTGCTCTTCGCCCTGTTTCTCTACTCT<br>CTGCCTGGCTACCTGGCCAAGAAGATCCTTGGGGCCTGAGCCC<br>TGCAGTCGCCTAGGCCTGCCGGCCTGACACGGCATTCGTCTGG<br>TTCCTGAACCCACTCAAATCTATCAAGTACCTCATCTGCACCCG<br>GTACAAGTGGCTGATCATCAAGATCGTGCTGGCGCTGCTGGGG<br>CTGCTCATGCTGGCCCTCTTCCTTTACAGCCTCCCAGGCTACAT<br>GGTCAAGAAGCTCCTAGGGGCCTGAAGTGTGCCCCACCCCAGC<br>CCGCTCCAGCATCCCTCCAGGGGCTGCTGCGTATTTTGCCTTCC<br>CTCACCTGGACTCTCTCCCAACTCCCTGAGGAGCCCTCCCACG<br>CCTGCCAGCCTTGAGCAAGACACCTGCTTGCTGGACTTCATCCC<br>CACCCCACACCCAAACTGTTGCTTGCCTGATCTTGTCCCAGGCC<br>TGCCTGGGGTTTGGGGCACAGTTGGCCTCCAAAACCAGATACC<br>CTCTTGTCTAAAGTACCAGGTTCCTCTGCCCAACCCCAAGAGTG<br>GTAGTGGCCCAACCCTCCCTGTGCTTTCCAAATCTTGTCTTAAG<br>GCACCAGTGAAATTAACCAAGAAACGCGGAGCAATGCCCAAGG<br>CTCTGATGAGTAGGAACACGTGGAAAGCACCAGGAATGCCAGC<br>AGAGGCGAGGCGGCACACCTCTCTGCAGAGCATCCAGGCCGA<br>GCGGCGGGCAGCGGCCAGCTGCTTCTGCGCATGCTCTCCTCTT<br>GGCTCTGCTTCTTTCTCACAGTCACAGTCACTTCACAGCTTAGC<br>CTTGGGCTTCCCATCACTTCCAGGGGTGCCTCTGCCTTGGCCA<br>GTGTGTGTCAGCTAGTACACAAGCTCCAAGTGTGAATCAGGTGT<br>ACTGGCCGTCCTGAAGACTGACTGCCCTGTCCTTCCTGCCGACA<br>GCCACACCCGAGTGTACACTTAAAGCGGTGCCCTTCTGCCTCTG<br>TGGGCCTGCTGGCTGCTGTTCCTTTCTTGAGTGTGATTTTTTTTT<br>TCTCTCCCTCAATAAAATAAATCAAACTCTGAGAC |
| 17 | mOTOF-202_1 transcript (NM_001100395.1), mouse otoferlin transcript variant 1, 6881 bp, encodes the protein of SEQ ID NO: 8 | TTGGTTGCCTTGGTCTCTGTGGGCAGCAGCAGGAGGAGGCGGC<br>AGCAGCCAGAGAAGAGGGAGGCGTGTGAGCCACACTCCACCAG<br>CGAGCTTCTTCCCGCTGCTCTGGAACTGCCCAGGCTCTCCCCA<br>CCAGCATGGCCCTGATTGTTCACCTCAAGACTGTCTCAGAGCTC<br>CGAGGCAAAGGTGACCGGATTGCCAAAGTCACTTTCCGAGGGC<br>AGTCTTTCTACTCCCGGGTCCTGGAGAACTGCGAGGGTGTGGC<br>TGACTTTGATGAGACGTTCCGGTGGCCAGTGGCCAGCAGCATC<br>GACCGGAATGAAGTGTTGGAGATTCAGATTTTCAACTACAGCAA<br>AGTCTTCAGCAACAAGCTGATAGGGACCTTCTGCATGGTGCTGC<br>AGAAAGTGGTGGAGGAGAATCGGGTAGAGGTGACCGACACGCT<br>GATGGATGACAGCAATGCTATCATCAAGACCAGCCTGAGCATGG<br>AGGTCCGGTATCAGGCCACAGATGGCACTGTGGGCCCCTGGGA<br>TGATGGAGACTTCCTGGGAGATGAATCCCTCCAGGAGGAGAAG<br>GACAGCCAGGAGACAGATGGGCTGCTACCTGGTTCCCGACCCA<br>GCACCCGGATATCTGGCGAGAAGAGCTTTCGCAGCAAAGGCAG<br>AGAGAAGACCAAGGGAGGCAGAGATGGCGAGCACAAAGCGGG<br>AAGGAGTGTGTTCTCGGCCATGAAACTCGGCAAAACTCGGTCCC<br>ACAAAGAGGAGCCCCAAAGACAAGATGAGCCAGCAGTGCTGGA<br>GATGGAGGACCTGGACCACCTAGCCATTCAGCTGGGGGATGGG<br>CTGGATCCTGACTCCGTGTCTCTAGCCTCGGTCACCGCTCTCAC<br>CAGCAATGTCTCCAACAAACGGTCTAAGCCAGATATTAAGATGG<br>AGCCCAGTGCTGGAAGGCCCATGGATTACCAGGTCAGCATCAC<br>AGTGATTGAGGCTCGGCAGCTGGTGGGCTTGAACATGGACCCT<br>GTGGTGTGTGTGGAGGTGGGTGATGACAAGAAATACACGTCAAT<br>GAAGGAGTCCACAAACTGCCCTTACTACAACGAGTACTTTGTCT<br>TCGACTTCCATGTCTCTCCTGATGTCATGTTTGACAAGATCATCA<br>AGATCTCGGTTATCCATTCTAAGAACCTGCTTCGGAGCGGCACC<br>CTGGTGGGTTCCTTCAAAATGGATGTGGGGACTGTGTATTCCCA<br>GCCTGAACACCAGTTCCATCACAAATGGGCCATCCTGTCAGACC<br>CCGATGACATCTCTGCTGGGTTGAAGGGTTATGTAAAGTGTGAT<br>GTCGCTGTGGTGGGCAAGGGAGACAACATCAAGACACCCCACA<br>AGGCCAACGAGACGGATGAGGACGACATTGAAGGGAACTTGCT<br>GCTCCCCGAGGGCGTGCCCCCCGAACGGCAGTGGGCACGGTT<br>CTATGTGAAAATTTACCGAGCAGAGGGACTGCCCCGGATGAACA<br>CAAGCCTCATGGCCAACGTGAAGAAGGCGTTCATCGGTGAGAA<br>CAAGGACCTCGTCGACCCCTATGTGCAAGTCTTCTTTGCTGGAC |

TABLE 2-continued

OTOF Sequences

| SEQ ID NO. | Sequence Name | Sequence |
|---|---|---|
| | | AAAAGGGCAAAACATCAGTGCAGAAGAGCAGCTATGAGCCGCT<br>ATGGAATGAGCAGGTCGTCTTCACAGACTTGTTCCCCCCACTCT<br>GCAAACGCATGAAGGTGCAGATCCGGGACTCTGACAAGGTCAA<br>TGATGTGGCCATCGGCACCCACTTCATCGACCTGCGCAAGATTT<br>CCAACGATGGAGACAAAGGCTTCCTGCCTACCCTCGGTCCAGC<br>CTGGGTGAACATGTACGGCTCCACGCGCAACTACACACTGCTG<br>GACGAGCACCAGGACTTGAATGAAGGCCTGGGGGAGGGTGTGT<br>CCTTCCGGGCCCGCCTCATGTTGGGACTAGCTGTGGAGATCCT<br>GGACACCTCCAACCCAGAGCTCACCAGCTCCACGGAGGTGCAG<br>GTGGAGCAGGCCACGCCTGTCTCGGAGAGCTGCACAGGGAGA<br>ATGGAAGAATTTTTTCTATTTGGAGCCTTCTTGGAAGCCTCAATG<br>ATTGACCGGAAAAATGGGGACAAGCCAATTACCTTTGAGGTGAC<br>CATAGGAAACTACGGCAATGAAGTCGATGGTATGTCCCGGCCC<br>CTGAGGCCTCGGCCCCGGAAAGAGCCTGGGGATGAAGAAGAG<br>GTAGACCTGATTCAGAACTCCAGTGACGATGAAGGTGACGAAGC<br>CGGGGACCTGGCCTCGGTGTCCTCCACCCCACCTATGCGGCCC<br>CAGATCACGGACAGGAACTATTTCCACCTGCCCTACCTGGAGCG<br>CAAGCCCTGCATCTATATCAAGAGCTGGTGGCCTGACCAGAGG<br>CGGCGCCTCTACAATGCCAACATCATGGATCACATTGCTGACAA<br>GCTGGAAGAAGGCCTGAATGATGTACAGGAGATGATCAAAACG<br>GAGAAGTCCTACCCGGAGCGCCGCCTGCGGGGTGTGCTAGAG<br>GAACTCAGCTGTGGCTGCCACCGCTTCCTCTCCCTCTCGGACAA<br>GGACCAGGGCCGCTCGTCCCGCACCAGGCTGGATCGAGAGCG<br>TCTTAAGTCCTGTATGAGGGAGTTGGAGAGCATGGGACAGCAG<br>GCCAAGAGCCTGAGGGCTCAGGTGAAGCGGCACACTGTTCGGG<br>ACAAGCTGAGGTCATGCCAGAACTTTCTGCAGAAGCTACGCTTC<br>CTGGCGGATGAGCCCCAGCACAGCATTCCTGATGTGTTCATTTG<br>GATGATGAGCAACAACAAACGTATCGCCTATGCCCGCGTGCCTT<br>CCAAAGACCTGCTCTTCTCCATCGTGGAGGAGGAACTGGGCAA<br>GGACTGCGCCAAAGTCAAGACCCTCTTCCTGAAGCTGCCAGGG<br>AAGAGGGGCTTCGGCTCGGCAGGCTGGACAGTACAGGCCAAG<br>CTGGAGCTCTACCTGTGGCTGGGCCTCAGCAAGCAGCGAAAGG<br>ACTTCCTGTGTGGTCTGCCCTGTGGCTTCGAGGAGGTCAAGGC<br>AGCCCAAGGCCTGGGCCTGCATTCCTTTCCGCCCATCAGCCTA<br>GTCTACACCAAGAAGCAAGCCTTCCAGCTCCGAGCACACATGTA<br>TCAGGCCCGAAGCCTCTTTGCTGCTGACAGCAGTGGGCTCTCT<br>GATCCCTTTGCCCGTGTCTTCTTCATCAACCAGAGCCAATGCAC<br>TGAGGTTCTAAACGAGACACTGTGTCCCACCTGGGACCAGATGC<br>TGGTATTTGACAACCTGGAGCTGTACGGTGAAGCTCACGAGTTA<br>CGAGATGATCCCCCCATCATTGTCATTGAAATCTACGACCAGGA<br>CAGCATGGGCAAAGCCGACTTCATGGGCCGGACCTTCGCCAAG<br>CCCCTGGTGAAGATGGCAGATGAAGCATACTGCCCACCTCGCTT<br>CCCGCCGCAGCTTGAGTACTACCAGATCTACCGAGGCAGTGCC<br>ACTGCCGGAGACCTACTGGCTGCCTTCGAGCTGCTGCAGATTG<br>GGCCATCAGGGAAGGCTGACCTGCCACCCATCAATGGCCCAGT<br>GGACATGGACAGAGGGCCCATCATGCCTGTGCCCGTGGGAATC<br>CGGCCAGTGCTCAGCAAGTACCGAGTGGAGGTGCTGTTCTGGG<br>GCCTGAGGGACCTAAAGAGGGTGAACCTGGCCCAGGTGGACC<br>GACCACGGGTGGACATCGAGTGTGCAGGAAAGGGGGTACAATC<br>CTCCCTGATTCACAATTATAAGAAGAACCCCAACTTCAACACGCT<br>GGTCAAGTGGTTTGAAGTGGACCTCCCGGAGAATGAGCTCCTG<br>CACCCACCCTTGAACATCCGAGTGGTAGATTGCCGGGCCTTTG<br>GACGATACACCCTGGTGGGTTCCCACGCAGTCAGCTCACTGAG<br>GCGCTTCATCTACCGACCTCCAGACCGCTCAGCCCCCAACTGG<br>AACACCACAGGGGAGGTTGTAGTAAGCATGGAGCCTGAGGAGC<br>CAGTTAAGAAGCTGGAGACCATGGTGAAACTGGATGCGACTTCT<br>GATGCTGTGGTCAAGGTGGATGTGGCTGAAGATGAGAAGGAAA<br>GGAAGAAGAAGAAAAAGAAAGGCCCGTCAGAGGAGCCAGAGGA<br>GGAAGAGCCCGATGAGAGCATGCTGGATTGGTGGTCCAAGTAC<br>TTCGCCTCCATCGACACAATGAAGGAGCAACTTCGACAACATGA<br>GACCTCTGGAACTGACTTGGAAGAGAAGGAAGAGATGGAAAGC<br>GCTGAGGGCCTGAAGGGACCAATGAAGAGCAAGGAGAAGTCCA<br>GAGCTGCAAAGGAGGAGAAAAAGAAGAAAAACCAGAGCCCTGG<br>CCCTGGCCAGGGATCGGAGGCTCCTGAGAAGAAGAAAGCCAAG<br>ATCGATGAGCTTAAGGTGTACCCCAAGGAGCTGGAATCGGAGTT<br>TGACAGCTTTGAGGACTGGCTGCACACCTTCAACCTGTTGAGGG<br>GCAAGACGGGAGATGATGAGGATGGCTCCACAGAGGAGGAGC<br>GCATAGTAGGCCGATTCAAGGGCTCCCTCTGTGTGTACAAAGTG<br>CCACTCCCAGAAGATGTATCTCGAGAAGCTGGCTATGATCCCAC<br>CTATGGAATGTTCCAGGGCATCCCAAGCAATGACCCCATCAATG<br>TGCTGGTCCGAATCTATGTGGTCCGGGCCACAGACCTGCACCC<br>GGCCGACATCAATGGCAAAGCTGACCCCTATATTGCCATCAAGT<br>TAGGCAAGACCGACATCCGAGACAAGGAGAACTACATCTCCAAG<br>CAGCTCAACCCTGTGTTTGGGAAGTCCTTTGACATTGAGGCCTC<br>CTTCCCCATGGAGTCCATGTTGACAGTGGCCGTGTACGACTGG |

TABLE 2-continued

OTOF Sequences

| SEQ ID NO. | Sequence Name | Sequence |
|---|---|---|
| | | GATCTGGTGGGCACTGATGACCTCATCGGAGAAACCAAGATTGA<br>CCTGGAAAACCGCTTCTACAGCAAGCATCGCGCCACCTGCGGC<br>ATCGCACAGACCTATTCCATACATGGCTACAATATCTGGAGGGA<br>CCCCATGAAGCCCAGCCAGATCCTGACACGCCTCTGTAAAGAG<br>GGCAAAGTGGACGGCCCCCACTTTGGTCCCCATGGGAGAGTGA<br>GGGTTGCCAACCGTGTCTTCACGGGGCCTTCAGAAATAGAGGA<br>TGAGAATGGTCAGAGGAAGCCCACAGATGAGCACGTGGCACTG<br>TCTGCTCTGAGACACTGGGAGGACATCCCCCGGGTGGGCTGCC<br>GCCTTGTGCCGGAACACGTGGAGACCAGGCCGCTGCTCAACCC<br>TGACAAGCCAGGCATTGAGCAGGGCCGCCTGGAGCTGTGGGTG<br>GACATGTTCCCCATGGACATGCCAGCCCCTGGGACACCTCTGG<br>ATATATCCCCCAGGAAACCCAAGAAGTACGAGCTGCGGGTCATC<br>GTGTGGAACACAGACGAGGTGGTCCTGGAAGACGATGATTTCTT<br>CACGGGAGAGAAGTCCAGTGACATTTTTGTGAGGGGGTGGCTG<br>AAGGGCCAGCAGGAGGACAAACAGGACACAGATGTCCACTATC<br>ACTCCCTCACGGGGGAGGGCAACTTCAACTGGAGATACCTCTTC<br>CCCTTCGACTACCTAGCGGCCGAAGAGAAGATCGTTATGTCCAA<br>AAAGGAGTCTATGTTCTCCTGGGATGAGACGGAGTACAAGATCC<br>CTGCGCGGCTCACCCTGCAGATCTGGGACGCTGACCACTTCTC<br>GGCTGACGACTTCCTGGGGGCTATCGAGCTGGACCTGAACCGG<br>TTCCCGAGGGGCGCTAAGACAGCCAAGCAGTGCACCATGGAGA<br>TGGCCACCGGGGAGGTGGACGTACCCCTGGTTTCCATCTTTAAA<br>CAGAAACGTGTCAAAGGCTGGTGGCCCCTCCTGGCCCGCAATG<br>AGAATGATGAGTTTGAGCTCACAGGCAAAGTGGAGGCGGAGCT<br>ACACCTACTCACGGCAGAGGAGGCAGAGAAGAACCCTGTGGGC<br>CTGGCTCGCAATGAACCTGATCCCCTAGAAAAACCCAACCGGCC<br>TGACACGGCATTCGTCTGGTTCCTGAACCCACTCAAATCTATCA<br>AGTACCTCATCTGCACCCGGTACAAGTGGCTGATCATCAAGATC<br>GTGCTGGCGCTGCTGGGGCTGCTCATGCTGGCCCTCTTCCTTT<br>ACAGCCTCCCAGGCTACATGGTCAAGAAGCTCCTAGGGGCCTG<br>AAGTGTGCCCCACCCCAGCCCGCTCCAGCATCCCTCCAGGGGC<br>TGCTGCGTATTTTGCCTTCCCTCACCTGGACTCTCTCCCAACTC<br>CCTGAGGAGCCCTCCCACGCCTGCCAGCCTTGAGCAAGACACC<br>TGCTTGCTGGACTTCATCCCCACCCCACACCCAAACTGTTGCTT<br>GCCTGATCTTGTCCCAGGCCTGCCTGGGGTTTGGGGCACAGTT<br>GGCCTCCAAAACCAGATACCCTCTTGTCTAAAGTACCAGGTTCC<br>TCTGCCCAACCCCAAGAGTGGTAGTGGCCCAACCCTCCCTGTG<br>CTTTCCAAATCTTGTCTTAAGGCACCAGTGAAATTAACCAAGAAA<br>CGCGGAGCAATGCCCAAGGCTCTGATGAGTAGGAACACGTGGA<br>AAGCACCAGGAATGCCAGCAGAGGCGAGGCGGCACACCTCTCT<br>GCAGAGCATCCAGGCCGAGCGGCGGGCAGCGGCCAGCTGCTT<br>CTGCGCATGCTCTCCTCTTGGCTCTGCTTCTTTCTCACAGTCACA<br>GTCACTTCACAGCTTAGCCTTGGGCTTCCCATCACTTCCAGGGG<br>TGCCTCTGCCTTGGCCAGTGTGTGTCAGCTAGTACACAAGCT<br>CCAAGTGTGAATCAGGTGTACTGGCCGTCCTGAAGACTGACTGC<br>CCTGTCCTTCCTGCCGACAGCCACACCCGAGTGTACACTTAAAG<br>CGGTGCCCTTCTGCCTCTGTGGGCCTGCTGGCTGCTGTTCCTTT<br>CTTGAGTGTGATTTTTTTTTTCTCTCCCTCAATAAAATAAATCAAA<br>CTCTGAGAC |
| 18 | mOTOF-202_2 transcript (NM_001313767.1), mouse otoferlin transcript variant 4, 6881 bp, encodes the protein of SEQ ID NO: 9 | TTGGTTGCCTTGGTCTCTGTGGGCAGCAGCAGGAGGAGGCGGC<br>AGCAGCCAGAGAAGAGGGAGGCGTGTGAGCCACACTCCACCAG<br>CGAGCTTCTTCCCGCTGCTCTGGAACTGCCCAGGCTCTCCCCA<br>CCAGCATGGCCCTGATTGTTCACCTCAAGACTGTCTCAGAGCTC<br>CGAGGCAAAGGTGACCGGATTGCCAAAGTCACTTTCCGAGGGC<br>AGTCTTTCTACTCCCGGGTCCTGGAGAACTGCGAGGGTGTGGC<br>TGACTTTGATGAGACGTTCCGGTGGCCAGTGGCCAGCAGCATC<br>GACCGGAATGAAGTGTTGGAGATTCAGATTTTCAACTACAGCAA<br>AGTCTTCAGCAACAAGCTGATAGGGACCTTCTGCATGGTGCTGC<br>AGAAAGTGGTGGAGGAGAATCGGGTAGAGGTGACCGACACGCT<br>GATGGATGACAGCAATGCTATCATCAAGACCAGCCTGAGCATGG<br>AGGTCCGGTATCAGGCCACAGATGGCACTGTGGGCCCCTGGGA<br>TGATGGAGACTTCCTGGGAGATGAATCCCTCCAGGAGGAGAAG<br>GACAGCCAGGAGACAGATGGGCTGCTACCTGGTTCCCGACCCA<br>GCACCCGGATATCTGGCGAGAAGAGCTTTCGCAGAGCGGGAAG<br>GAGTGTGTTCTCGGCCATGAAACTCGGCAAAACTCGGTCCCACA<br>AAGAGGAGCCCCAAAGACAAGATGAGCCAGCAGTGCTGGAGAT<br>GGAGGACCTGGACCACCTAGCCATTCAGCTGGGGGATGGGCTG<br>GATCCTGACTCCGTGTCTCTAGCCTCGGTCACCGCTCTCACCAG<br>CAATGTCTCCAACAAACGGTCTAAGCCAGATATTAAGATGGAGC<br>CCAGTGCTGGAAGGCCCATGGATTACCAGGTCAGCATCACAGT<br>GATTGAGGCTCGGCAGCTGGTGGGCTTGAACATGGACCCTGTG<br>GTGTGTGTGGAGGTGGGTGATGACAAGAAATACACGTCAATGAA<br>GGAGTCCACAAACTGCCCTTACTACAACGAGTACTTTGTCTTCG<br>ACTTCCATGTCTCTCCTGATGTCATGTTTGACAAGATCATCAAGA |

TABLE 2-continued

OTOF Sequences

| SEQ ID NO. | Sequence Name | Sequence |
|---|---|---|
| | | TCTCGGTTATCCATTCTAAGAACCTGCTTCGGAGCGGCACCCTG |
| | | GTGGGTTCCTTCAAAATGGATGTGGGGACTGTGTATTCCCAGCC |
| | | TGAACACCAGTTCCATCACAAATGGGCCATCCTGTCAGACCCCG |
| | | ATGACATCTCTGCTGGGTTGAAGGGTTATGTAAAGTGTGATGTC |
| | | GCTGTGGTGGGCAAGGGAGACAACATCAAGACACCCCACAAGG |
| | | CCAACGAGACGGATGAGGACGACATTGAAGGGAACTTGCTGCT |
| | | CCCCGAGGGCGTGCCCCCCGAACGGCAGTGGGCACGGTTCTA |
| | | TGTGAAAATTTACCGAGCAGAGGGACTGCCCCGGATGAACACAA |
| | | GCCTCATGGCCAACGTGAAGAAGGCGTTCATCGGTGAGAACAA |
| | | GGACCTCGTCGACCCCTATGTGCAAGTCTTCTTTGCTGGACAAA |
| | | AGGGCAAAACATCAGTGCAGAAGAGCAGCTATGAGCCGCTATG |
| | | GAATGAGCAGGTCGTCTTCACAGACTTGTTCCCCCCACTCTGCA |
| | | AACGCATGAAGGTGCAGATCCGGGACTCTGACAAGGTCAATGAT |
| | | GTGGCCATCGGCACCCACTTCATCGACCTGCGCAAGATTTCCAA |
| | | CGATGGAGACAAAGGCTTCCTGCCTACCCTCGGTCCAGCCTGG |
| | | GTGAACATGTACGGCTCCACGCGCAACTACACACTGCTGGACG |
| | | AGCACCAGGACTTGAATGAAGGCCTGGGGGAGGGTGTGTCCTT |
| | | CCGGGCCCGCCTCATGTTGGGACTAGCTGTGGAGATCCTGGAC |
| | | ACCTCCAACCCAGAGCTCACCAGCTCCACGGAGGTGCAGGTGG |
| | | AGCAGGCCACGCCTGTCTCGGAGAGCTGCACAGGGAGAATGGA |
| | | AGAATTTTTTCTATTTGGAGCCTTCTTGGAAGCCTCAATGATTGA |
| | | CCGGAAAAATGGGGACAAGCCAATTACCTTTGAGGTGACCATAG |
| | | GAAACTACGGCAATGAAGTCGATGGTATGTCCCGGCCCCTGAG |
| | | GCCTCGGCCCCGGAAAGAGCCTGGGGATGAAGAAGAGGTAGA |
| | | CCTGATTCAGAACTCCAGTGACGATGAAGGTGACGAAGCCGGG |
| | | GACCTGGCCTCGGTGTCCTCCACCCCACCTATGCGGCCCCAGA |
| | | TCACGGACAGGAACTATTTCCACCTGCCCTACCTGGAGCGCAAG |
| | | CCCTGCATCTATATCAAGAGCTGGTGGCCTGACCAGAGGCGGC |
| | | GCCTCTACAATGCCAACATCATGGATCACATTGCTGACAAGCTG |
| | | GAAGAAGGCCTGAATGATGTACAGGAGATGATCAAAACGGAGAA |
| | | GTCCTACCCGGAGCGCCGCCTGCGGGGTGTGCTAGAGGAACTC |
| | | AGCTGTGGCTGCCACCGCTTCCTCTCCCTCTCGGACAAGGACC |
| | | AGGGCCGCTCGTCCCGCACCAGGCTGGATCGAGAGCGTCTTAA |
| | | GTCCTGTATGAGGGAGTTGGAGAGCATGGGACAGCAGGCCAAG |
| | | AGCCTGAGGGCTCAGGTGAAGCGGCACACTGTTCGGGACAAGC |
| | | TGAGGTCATGCCAGAACTTTCTGCAGAAGCTACGCTTCCTGGCG |
| | | GATGAGCCCCAGCACAGCATTCCTGATGTGTTCATTTGGATGAT |
| | | GAGCAACAACAAACGTATCGCCTATGCCCGCGTGCCTTCCAAAG |
| | | ACCTGCTCTTCTCCATCGTGGAGGAGGAACTGGGCAAGGACTG |
| | | CGCCAAAGTCAAGACCCTCTTCCTGAAGCTGCCAGGGAAGAGG |
| | | GGCTTCGGCTCGGCAGGCTGGACAGTACAGGCCAAGCTGGAG |
| | | CTCTACCTGTGGCTGGGCCTCAGCAAGCAGCGAAAGGACTTCC |
| | | TGTGTGGTCTGCCCTGTGGCTTCGAGGAGGTCAAGGCAGCCCA |
| | | AGGCCTGGGCCTGCATTCCTTTCCGCCCATCAGCCTAGTCTACA |
| | | CCAAGAAGCAAGCCTTCCAGCTCCGAGCACACATGTATCAGGC |
| | | CCGAAGCCTCTTTGCTGCTGACAGCAGTGGGCTCTCTGATCCCT |
| | | TTGCCCGTGTCTTCTTCATCAACCAGAGCCAATGCACTGAGGTT |
| | | CTAAACGAGACACTGTGTCCCACCTGGGACCAGATGCTGGTATT |
| | | TGACAACCTGGAGCTGTACGGTGAAGCTCACGAGTTACGAGAT |
| | | GATCCCCCCATCATTGTCATTGAAATCTACGACCAGGACAGCAT |
| | | GGGCAAAGCCGACTTCATGGGCCGGACCTTCGCCAAGCCCCTG |
| | | GTGAAGATGGCAGATGAAGCATACTGCCCACCTCGCTTCCCGC |
| | | CGCAGCTTGAGTACTACCAGATCTACCGAGGCAGTGCCACTGC |
| | | CGGAGACCTACTGGCTGCCTTCGAGCTGCTGCAGATTGGGCCA |
| | | TCAGGGAAGGCTGACCTGCCACCCATCAATGGCCCAGTGGACA |
| | | TGGACAGAGGGCCCATCATGCCTGTGCCCGTGGGAATCCGGCC |
| | | AGTGCTCAGCAAGTACCGAGTGGAGGTGCTGTTCTGGGGCCTG |
| | | AGGGACCTAAAGAGGGTGAACCTGGCCCAGGTGGACCGACCAC |
| | | GGGTGGACATCGAGTGTGCAGGAAAGGGGGTACAATCCTCCCT |
| | | GATTCACAATTATAAGAAGAACCCCAACTTCAACACGCTGGTCAA |
| | | GTGGTTTGAAGTGGACCTCCCGGAGAATGAGCTCCTGCACCCA |
| | | CCCTTGAACATCCGAGTGGTAGATTGCCGGGCCTTTGGACGATA |
| | | CACCCTGGTGGGTTCCCACGCAGTCAGCTCACTGAGGCGCTTC |
| | | ATCTACCGACCTCCAGACCGCTCAGCCCCCAACTGGAACACCA |
| | | CAGGGGAGGTTGTAGTAAGCATGGAGCCTGAGGAGCCAGTTAA |
| | | GAAGCTGGAGACCATGGTGAAACTGGATGCGACTTCTGATGCT |
| | | GTGGTCAAGGTGGATGTGGCTGAAGATGAGAAGGAAAGGAAGA |
| | | AGAAGAAAAAGAAAGGCCCGTCAGAGGAGCCAGAGGAGGAAGA |
| | | GCCCGATGAGAGCATGCTGGATTGGTGGTCCAAGTACTTCGCC |
| | | TCCATCGACACAATGAAGGAGCAACTTCGACAACATGAGACCTC |
| | | TGGAACTGACTTGGAAGAGAAGGAAGAGATGGAAAGCGCTGAG |
| | | GGCCTGAAGGGACCAATGAAGAGCAAGGAGAAGTCCAGAGCTG |
| | | CAAAGGAGGAGAAAAAGAAGAAAAACCAGAGCCCTGGCCCTGG |
| | | CCAGGGATCGGAGGCTCCTGAGAAGAAGAAAGCCAAGATCGAT |
| | | GAGCTTAAGGTGTACCCCAAGGAGCTGGAATCGGAGTTTGACA |

TABLE 2-continued

| OTOF Sequences | | |
|---|---|---|
| SEQ ID NO. | Sequence Name | Sequence |
| | | GCTTTGAGGACTGGCTGCACACCTTCAACCTGTTGAGGGGCAA<br>GACGGGAGATGATGAGGATGGCTCCACAGAGGAGGAGCGCATA<br>GTAGGCCGATTCAAGGGCTCCCTCTGTGTGTACAAAGTGCCACT<br>CCCAGAAGATGTATCTCGAGAAGCTGGCTATGATCCCACCTATG<br>GAATGTTCCAGGGCATCCCAAGCAATGACCCCATCAATGTGCTG<br>GTCCGAATCTATGTGGTCCGGGCCACAGACCTGCACCCGGCCG<br>ACATCAATGGCAAAGCTGACCCCTATATTGCCATCAAGTTAGGC<br>AAGACCGACATCCGAGACAAGGAGAACTACATCTCCAAGCAGCT<br>CAACCCTGTGTTTGGGAAGTCCTTTGACATTGAGGCCTCCTTCC<br>CCATGGAGTCCATGTTGACAGTGGCCGTGTACGACTGGGATCT<br>GGTGGGCACTGATGACCTCATCGGAGAAACCAAGATTGACCTG<br>GAAAACCGCTTCTACAGCAAGCATCGCGCCACCTGCGGCATCG<br>CACAGACCTATTCCATACATGGCTACAATATCTGGAGGGACCCC<br>ATGAAGCCCAGCCAGATCCTGACACGCCTCTGTAAAGAGGGCA<br>AAGTGGACGGCCCCCACTTTGGTCCCCATGGGAGAGTGAGGGT<br>TGCCAACCGTGTCTTCACGGGGCCTTCAGAAATAGAGGATGAGA<br>ATGGTCAGAGGAAGCCCACAGATGAGCACGTGGCACTGTCTGC<br>TCTGAGACACTGGGAGGACATCCCCCGGGTGGGCTGCCGCCTT<br>GTGCCGGAACACGTGGAGACCAGGCCGCTGCTCAACCCTGACA<br>AGCCAGGCATTGAGCAGGGCCGCCTGGAGCTGTGGGTGGACAT<br>GTTCCCCATGGACATGCCAGCCCCTGGGACACCTCTGGATATAT<br>CCCCCAGGAAACCCAAGAAGTACGAGCTGCGGGTCATCGTGTG<br>GAACACAGACGAGGTGGTCCTGGAAGACGATGATTTCTTCACG<br>GGAGAGAAGTCCAGTGACATTTTTGTGAGGGGGTGGCTGAAGG<br>GCCAGCAGGAGGACAAACAGGACACAGATGTCCACTATCACTC<br>CCTCACGGGGGAGGGCAACTTCAACTGGAGATACCTCTTCCCC<br>TTCGACTACCTAGCGGCCGAAGAGAAGATCGTTATGTCCAAAAA<br>GGAGTCTATGTTCTCCTGGGATGAGACGGAGTACAAGATCCCTG<br>CGCGGCTCACCCTGCAGATCTGGGACGCTGACCACTTCTCGGC<br>TGACGACTTCCTGGGGGCTATCGAGCTGGACCTGAACCGGTTC<br>CCGAGGGGCGCTAAGACAGCCAAGCAGTGCACCATGGAGATGG<br>CCACCGGGGAGGTGGACGTACCCCTGGTTTCCATCTTTAAACAG<br>AAACGTGTCAAAGGCTGGTGGCCCCTCCTGGCCCGCAATGAGA<br>ATGATGAGTTTGAGCTCACAGGCAAAGTGGAGGCGGAGCTACA<br>CCTACTCACGGCAGAGGAGGCAGAGAAGAACCCTGTGGGCCTG<br>GCTCGCAATGAACCTGATCCCCTAGAAAAACCCAACCGGCCTGA<br>CACGGCATTCGTCTGGTTCCTGAACCCACTCAAATCTATCAAGT<br>ACCTCATCTGCACCCGGTACAAGTGGCTGATCATCAAGATCGTG<br>CTGGCGCTGCTGGGGCTGCTCATGCTGGCCCTCTTCCTTTACA<br>GCCTCCCAGGCTACATGGTCAAGAAGCTCCTAGGGGCCTGAAG<br>TGTGCCCCACCCCAGCCCGCTCCAGCATCCCTCCAGGGGCTGC<br>TGCGTATTTTGCCTTCCCTCACCTGGACTCTCTCCCAACTCCCT<br>GAGGAGCCCTCCCACGCCTGCCAGCCTTGAGCAAGACACCTGC<br>TTGCTGGACTTCATCCCCACCCCACACCCAAACTGTTGCTTGCC<br>TGATCTTGTCCCAGGCCTGCCTGGGGTTTGGGGCACAGTTGGC<br>CTCCAAAACCAGATACCCTCTTGTCTAAAGTACCAGGTTCCTCTG<br>CCCAACCCCAAGAGTGGTAGTGGCCCAACCCTCCCTGTGCTTTC<br>CAAATCTTGTCTTAAGGCACCAGTGAAATTAACCAAGAAACGCG<br>GAGCAATGCCCAAGGCTCTGATGAGTAGGAACACGTGGAAAGC<br>ACCAGGAATGCCAGCAGAGGCGAGGCGGCACACCTCTCTGCAG<br>AGCATCCAGGCCGAGCGGCGGGCAGCGGCCAGCTGCTTCTGC<br>GCATGCTCTCCTCTTGGCTCTGCTTCTTTCTCACAGTCACAGTCA<br>CTTCACAGCTTAGCCTTGGGCTTCCCATCACTTCCAGGGGTGCC<br>TCTGCCTTGGCCAGTGTGTGTCAGCTAGTACACAAGCTCCAAGT<br>GTGAATCAGGTGTACTGGCCGTCCTGAAGACTGACTGCCCTGTC<br>CTTCCTGCCGACAGCCACACCCGAGTGTACACTTAAAGCGGTG<br>CCCTTCTGCCTCTGTGGGCCTGCTGGCTGCTGTTCCTTTCTTGA<br>GTGTGATTTTTTTTTTCTCTCCCTCAATAAAATAAATCAAACTCTG<br>AGAC |

Expression of OTOF in Mammalian Cells

Mutations in OTOF have been linked to sensorineural hearing loss and auditory neuropathy. The compositions and methods described herein increase the expression of WT OTOF protein by administering a first nucleic acid vector that contains a polynucleotide encoding an N-terminal portion of an OTOF protein and a second nucleic acid vector that contains a polynucleotide encoding a C-terminal portion of an OTOF protein. In order to utilize nucleic acid vectors for therapeutic application in the treatment of sensorineural hearing loss and auditory neuropathy, they can be directed to the interior of the cell, and, in particular, to specific cell types. A wide array of methods has been established for the delivery of proteins to mammalian cells and for the stable expression of genes encoding proteins in mammalian cells.

Polynucleotides Encoding OTOF

One platform that can be used to achieve therapeutically effective intracellular concentrations of OTOF in mammalian cells is via the stable expression of the gene encoding OTOF (e.g., by integration into the nuclear or mitochondrial genome of a mammalian cell, or by episomal concatemer formation in the nucleus of a mammalian cell). The gene is a polynucleotide that encodes the primary amino acid sequence of the corresponding protein. In order to introduce exogenous genes into a mammalian cell, genes can be incorporated into a vector. Vectors can be introduced into a cell by a variety of methods, including transformation, transfection, transduction, direct uptake, projectile bombardment, and by encapsulation of the vector in a liposome. Examples of suitable methods of transfecting or transforming cells include calcium phosphate precipitation, electroporation, microinjection, infection, lipofection and direct uptake. Such methods are described in more detail, for example, in Green, et al., Molecular Cloning: A Laboratory Manual, Fourth Edition (Cold Spring Harbor University Press, New York 2014); and Ausubel, et al., Current Protocols in Molecular Biology (John Wiley & Sons, New York 2015), the disclosures of each of which are incorporated herein by reference.

OTOF can also be introduced into a mammalian cell by targeting vectors containing portions of a gene encoding an OTOF protein to cell membrane phospholipids. For example, vectors can be targeted to the phospholipids on the extracellular surface of the cell membrane by linking the vector molecule to a VSV-G protein, a viral protein with affinity for all cell membrane phospholipids. Such a construct can be produced using methods well known to those of skill in the field.

Recognition and binding of the polynucleotide encoding an OTOF protein by mammalian RNA polymerase is important for gene expression. As such, one may include sequence elements within the polynucleotide that exhibit a high affinity for transcription factors that recruit RNA polymerase and promote the assembly of the transcription complex at the transcription initiation site. Such sequence elements include, e.g., a mammalian promoter, the sequence of which can be recognized and bound by specific transcription initiation factors and ultimately RNA polymerase.

Polynucleotides suitable for use in the compositions and methods described herein also include those that encode an OTOF protein downstream of a mammalian promoter (e.g., a polynucleotide that encodes an N-terminal portion of an OTOF protein downstream of a mammalian promoter). Promoters that are useful for the expression of an OTOF protein in mammalian cells include constitutive promoters, cochlear hair cell-specific promoters, and inner hair cell-specific promoters. Constitutive promoters include the CAG promoter, the cytomegalovirus (CMV) promoter, the EF1α promoter, and the PGK promoter. Cochlear hair cell-specific promoters include the Myosin 15 (Myo15) promoter, the Myosin 7A (Myo7A) promoter, the Myosin 6 (Myo6) promoter, the POU4F3 promoter, the Atonal BHLH Transcription Factor 1 (ATOH1) promoter, the LIM Homeobox 3 (LHX3) promoter, the α9 acetylcholine receptor (α9AChR) promoter, and the α10 acetylcholine receptor (α10AChR) promoter. Inner hair cell-specific promoters include the FGF8 promoter, the VGLUT3 promoter, and the OTOF promoter. Alternatively, promoters derived from viral genomes can also be used for the stable expression of these agents in mammalian cells. Examples of functional viral promoters that can be used to promote mammalian expression of these agents include adenovirus late promoter, vaccinia virus 7.5K promoter, SV40 promoter, tk promoter of HSV, mouse mammary tumor virus (MMTV) promoter, LTR promoter of HIV, promoter of moloney virus, Epstein barr virus (EBV) promoter, and the Rous sarcoma virus (RSV) promoter.

In some embodiments, the Myo15 promoter for use in the compositions and methods described herein includes nucleic acid sequences from regions of the Myo15 locus that are capable of expressing a transgene specifically in hair cells, or variants thereof, such as a nucleic acid sequences that have at least 85% sequence identity (e.g., 85%, 90%, 95%, 96%, 97%, 98%, 99%, or more, sequence identity) to regions of the Myo15 locus that are capable of expressing a transgene specifically in hair cells. These regions include nucleic acid sequences immediately preceding the Myo15 translation start site and an upstream regulatory element that is located over 5 kb from the Myo15 translation start site. The Myo15 promoter for use in the compositions and methods described herein can optionally include a linker operably linking the regions of the Myo15 locus that are capable of expressing a transgene specifically in hair cells, or the regions of the Myo15 locus can be joined directly without an intervening linker.

In some embodiments, the Myo15 promoter for use in the compositions and methods described herein contains a first region (an upstream regulatory element) having at least 85% sequence identity (e.g., 85%, 90%, 95%, 96%, 97%, 98%, 99%, or more, sequence identity) to a region containing the first non-coding exon of the Myo15 gene (nucleic acids from −6755 to −7209 with respect to the Myo15 translation start site, the sequence of which is set forth in SEQ ID NO: 24) or a functional portion or derivative thereof joined (e.g., operably linked) to a second region having at least 85% sequence identity (e.g., 85%, 90%, 95%, 96%, 97%, 98%, 99%, or more, sequence identity) to the nucleic acid sequence immediately preceding the Myo15 translation start site (nucleic acids from −1 to −1157 with respect to the Myo15 translation start site, the sequence of which is set forth in SEQ ID NO: 25) or a functional portion or derivative thereof. The functional portion of SEQ ID NO: 24 may have the sequence of nucleic acids from −7166 to −7091 with respect to the Myo15 translation start site (set forth in SEQ ID NO: 26) and/or the sequence of nucleic acids from −7077 to −6983 with respect to the Myo15 translation start site (set forth in SEQ ID NO: 27). The first region may contain the nucleic acid sequence of SEQ ID NO: 26 fused to the nucleic acid sequence of SEQ ID NO: 27 with no intervening nucleic acids, as set forth in SEQ ID NO: 28, or the first region may contain the nucleic acid sequence of SEQ ID NO: 27 fused to the nucleic acid sequence of SEQ ID NO: 26 with no intervening nucleic acids, as set forth in SEQ ID NO: 29. Alternatively, the first region may contain the sequences of SEQ ID NO: 26 and SEQ ID NO: 27 joined by the endogenous intervening nucleic acid sequence (e.g., the first region may have the sequence of nucleic acids from −7166 to −6983 with respect to the Myo15 translation start site, as set forth in SEQ ID NO: 30) or a nucleic acid linker. In a Myo15 promoter in which the first region contains both SEQ ID NO: 26 and SEQ ID NO: 27, the two sequences can be included in any order (e.g., SEQ ID NO: 26 may be joined to (e.g., precede) SEQ ID NO: 27, or SEQ ID NO: 27 may be joined to (e.g., precede) SEQ ID NO: 26). The functional portion of SEQ ID NO: 25 may have the sequence of nucleic acids from −590 to −509 with respect to the Myo15 translation start site (set forth in SEQ ID NO: 31) and/or the sequence of nucleic acids from −266 to −161 with respect to the Myo15 translation start site (set forth in SEQ ID NO: 32). The second region may contain the nucleic acid sequence of SEQ ID NO: 31 fused to the nucleic acid sequence of SEQ ID NO: 32 with no intervening nucleic acids, as set forth in SEQ ID NO: 33, or the second region may contain the nucleic acid sequence of SEQ ID NO: 32 fused to the nucleic acid sequence of SEQ ID NO: 31 with no intervening nucleic acids, as set forth in SEQ ID NO: 34. Alternatively, the second region may contain the sequences of SEQ ID NO: 31 and SEQ ID NO: 32 joined by the endogenous intervening nucleic acid sequence (e.g., the second region may have the sequence of nucleic acids from −590 to −161 with respect to the Myo15 translation start site, as set forth in SEQ ID NO: 35) or a nucleic acid linker. In a Myo15 promoter in which the second region contains both SEQ ID NO: 31 and SEQ ID NO: 32, the two sequences can be included in any order (e.g., SEQ ID NO: 31 may be joined to (e.g., precede) SEQ ID NO: 32, or SEQ ID NO: 32 may be joined to (e.g., precede) SEQ ID NO: 31).

The first region and the second region of the Myo15 promoter can be joined directly or can be joined by a nucleic acid linker. For example, the Myo15 promoter can contain the sequence of SEQ ID NO: 24 or a functional portion or derivative thereof (e.g., any one or more of SEQ ID NOs: 26-30, e.g., SEQ ID NOs 26 and 27) fused to the sequence of SEQ ID NO: 25 or a functional portion or derivative thereof (e.g., any one or more of SEQ ID NOs: 31-35, e.g., SEQ ID NOs 31 and 32) with no intervening nucleic acids. For example, the nucleic acid sequence of the Myo15 promoter that results from direct fusion of SEQ ID NO: 24 to SEQ ID NO: 25 is set forth in SEQ ID NO: 36. Alternatively, a linker can be used to join the sequence of SEQ ID NO: 24 or a functional portion or derivative thereof (e.g., any one or more of SEQ ID NOs: 26-30, e.g., SEQ ID NOs 26 and 27) to the sequence of SEQ ID NO: 25 or a functional portion or derivative thereof (e.g., any one or more of SEQ ID NOs: 31-35, e.g., SEQ ID NOs 31 and 32).

The length of a nucleic acid linker for use in a Myo15 promoter described herein can be about 5 kb or less (e.g., about 5 kb, 4.5, kb, 4, kb, 3.5 kb, 3 kb, 2.5 kb, 2 kb, 1.5 kb, 1 kb, 900 bp, 800 bp, 700 bp, 600 bp, 500 bp, 450 bp, 400 bp, 350 bp, 300 bp, 250 bp, 200 bp, 150 bp, 100 bp, 90 bp, 80 bp, 70 bp, 60 bp, 50 bp, 40 bp, 30 bp, 25 bp, 20 bp, 15, bp, 10 bp, 5 bp, 4 bp, 3 bp, 2 bp, or less). Nucleic acid linkers that can be used in the Myo15 promoter described herein do not disrupt the ability of the Myo15 promoter of the invention to induce transgene expression in hair cells.

In some embodiments, the sequence of SEQ ID NO: 24 or a functional portion or derivative thereof (e.g., any one or more of SEQ ID NOs: 26-30, e.g., SEQ ID NOs 26 and 27) is joined (e.g., operably linked) to the sequence of SEQ ID NO: 25 or a functional portion or derivative thereof (e.g., any one or more of SEQ ID NOs: 31-35, e.g., SEQ ID NOs 31 and 32), and, in some embodiments, the order of the regions is reversed (e.g., the sequence of SEQ ID NO: 25 or a functional portion or derivative thereof (e.g., any one or more of SEQ ID NOs: 31-35, e.g., SEQ ID NOs 31 and 32) is joined (e.g., operably linked) to the sequence of SEQ ID NO: 24 or a functional portion or derivative thereof (e.g., any one or more of SEQ ID NOs: 26-30, e.g., SEQ ID NOs 26 and 27)). For example, the nucleic acid sequence of the Myo15 promoter that results from direct fusion of SEQ ID NO: 25 to SEQ ID NO: 24 is set forth in SEQ ID NO: 37. Regardless of order, the sequence of SEQ ID NO: 24 or a functional portion or derivative thereof and the sequence of SEQ ID NO: 25 or a functional portion or derivative thereof can be joined by direct fusion or a nucleic acid linker, as described above.

In some embodiments, the Myo15 promoter for use in the compositions and methods described herein contains a region having at least 85% sequence identity (e.g., 85%, 90%, 95%, 96%, 97%, 98%, 99%, or more, sequence identity) to a region containing the first non-coding exon of the Myo15 gene (nucleic acids from −6755 to −7209 with respect to the Myo15 translation start site, the sequence of which is set forth in SEQ ID NO: 24) or a functional portion or derivative thereof. The functional portion of SEQ ID NO: 24 may have the sequence of nucleic acids from −7166 to −7091 with respect to the Myo15 translation start site (set forth in SEQ ID NO: 26) and/or the sequence of nucleic acids from −7077 to −6983 with respect to the Myo15 translation start site (set forth in SEQ ID NO: 27). The Myo15 promoter may contain the nucleic acid sequence of SEQ ID NO: 26 fused to the nucleic acid sequence of SEQ ID NO: 27 with no intervening nucleic acids, as set forth in SEQ ID NO: 28, or the Myo15 promoter may contain the nucleic acid sequence of SEQ ID NO: 27 fused to the nucleic acid sequence of SEQ ID NO: 26 with no intervening nucleic acids, as set forth in SEQ ID NO: 29. Alternatively, the Myo15 promoter may contain the sequences of SEQ ID NO: 26 and SEQ ID NO: 27 joined by the endogenous intervening nucleic acid sequence (e.g., the first region may have the sequence of nucleic acids from −7166 to −6983 with respect to the Myo15 translation start site, as set forth in SEQ ID NO: 30) or a nucleic acid linker. In a Myo15 promoter that contains both SEQ ID NO: 26 and SEQ ID NO: 27, the two sequences can be included in any order (e.g., SEQ ID NO: 26 may be joined to (e.g., precede) SEQ ID NO: 27, or SEQ ID NO: 27 may be joined to (e.g., precede) SEQ ID NO: 26).

In some embodiments, the Myo15 promoter for use in the compositions and methods described herein contains a region having at least 85% sequence identity (e.g., 85%, 90%, 95%, 96%, 97%, 98%, 99%, or more, sequence identity) to the nucleic acid sequence immediately upstream of the Myo15 translation start site (nucleic acids from −1 to −1157 with respect to the Myo15 translation start site, the sequence of which is set forth in SEQ ID NO: 25) or a functional portion or derivative thereof. The functional portion of SEQ ID NO: 25 may have the sequence of nucleic acids from −590 to −509 with respect to the Myo15 translation start site (set forth in SEQ ID NO: 31) and/or the sequence of nucleic acids from −266 to −161 with respect to the Myo15 translation start site (set forth in SEQ ID NO: 32). The Myo15 promoter may contain the nucleic acid sequence of SEQ ID NO: 31 fused to the nucleic acid sequence of SEQ ID NO: 32 with no intervening nucleic acids, as set forth in SEQ ID NO: 33, or the Myo15 promoter may contain the nucleic acid sequence of SEQ ID NO: 32 fused to the nucleic acid sequence of SEQ ID NO: 31 with no intervening nucleic acids, as set forth in SEQ ID NO: 34. Alternatively, the Myo15 promoter may contain the sequences of SEQ ID NO: 31 and SEQ ID NO: 32 joined by the endogenous intervening nucleic acid sequence (e.g., the second region may have the sequence of nucleic acids from −590 to −161 with respect to the Myo15 translation start site, as set forth in SEQ ID NO: 35) or a nucleic acid linker. In a Myo15 promoter that contains both SEQ ID NO: 31 and SEQ ID NO: 32, the two sequences can be included in any order (e.g., SEQ ID NO: 31 may be joined to (e.g., precede) SEQ ID NO: 32, or SEQ ID NO: 32 may be joined to (e.g., precede) SEQ ID NO: 31).

The foregoing Myo15 promoter sequences are summarized in Table 3, below.

TABLE 3

| Exemplary nucleotide sequences for use in the Myo15 promoter described herein | | |
|---|---|---|
| SEQ ID NO. | Description of nucleic acid sequence | Nucleic Acid Sequence |
| 24 | Region containing non-coding exon 1 of Myo15 (-6755 to -7209) | CTGCAGCTCAGCCTACTACTTGCTTTCCAGGCTGTTCCTAGT TCCCATGTCAGCTGCTTGTGCTTTCCAGAGACAAAACAGGAA TAATAGATGTCATTAAATATACATTGGGCCCCAGGCGGTCAAT GTGGCAGCCTGAGCCTCCTTTCCATCTCTGTGGAGGCAGAC ATAGGACCCCCAACAAACAGCATGCAGGTTGGGAGCCAGCC ACAGGACCCAGGTAAGGGGCCCTGGGTCCTTAAGCTTCTGC CACTGGCTCCGGCATTGCAGAGAGAAGAGAAGGGGCGGCA GAGCTGAACCTTAGCCTTGCCTTCCTGGGTACCCTTCTGAGC CTCACTGTCTTCTGTGAGATGGGCAAAGTGCGGGTGTGACTC CTTGGCAACGGTGTTACACCAGGGCAGGTAAAGTTGTAGTTA TTTGTGGGGTACACCAGGACTGTTAAAGGTGTAACTAT |
| 25 | Region immediately preceding the translation start site of Myo15 (-1 to -1157) | GGTCTCACCCAGCATTTTCACTTCTAATAAGTTCAAATGTGAT ACGGCACCTTTCTAAAAATTAGTTTTCAGGGAAATAGGGTTCA AAACTGGTAGTGGTAGGGTCCATTCTCACGACCCCCAGGCCT GCTAACCCTGACCAAGCTACCTATTACTTACCCTCCTCTTTCT CCTCCTCCTCTTTCTCCTTCTCCTGCTTCCCCTCTTCCTTCTC CCTCCCTTCCTCTCCCTCCTCCCCCTCCTTGGCTGTGATCAG ATCCAGAGCCTGAATGAGCCTCCTGACCCCACACCCCCACTA GCATGGGCCTGCAAGTGCCCAGAAGTCCCTCCTGCCTCCTA AACTGCCCAGCCGATCCATTAGCTCTTCCTTCTTCCCAGTGA AAGAAGCAGGCACAGCCTGTCCCTCCCGTTCTACAGAAAGG AAGCTACAGCACAGGGAGGGCCAAAGGCCTTCCTGGGACTA GACAGTTGATCAACAGCAGGACTGGAGAGCTGGGCTCCATTT TTGTTCCTTGGTGCCCTGCCCCTCCCCATGACCTGCAGAGAC ATTCAGCCTGCCAGGCTTTATGAGGTGGGAGCTGGGCTCTC CCTGATGTATTATTCAGCTCCCTGGAGTTGGCCAGCTCCTGT TACACTGGCCACAGCCCTGGGCATCCGCTTCTCACTTCTAGT TTCCCCTCCAAGGTAATGTGGTGGGTCATGATCATTCTATCCT GGCTTCAGGGACCTGACTCCACTTTGGGGCCATTCGAGGGG TCTAGGGTAGATGATGTCCCCCTGTGGGGATTAATGTCCTGC TCTGTAAAACTGAGCTAGCTGAGATCCAGGAGGGCTTGGCCA GAGACAGCAAGTTGTTGCCATGGTGACTTTAAAGCCAGGTTG CTGCCCCAGCACAGGCCTCCCAGTCTACCCTCACTAGAAAAC AACACCCAGGCACTTTCCACCACCTCTCAAAGGTGAAACCCA AGGCTGGTCTAGAGAATGAATTATGGATCCTCGCTGTCCGTG CCACCCAGCTAGTCCCAGCGGCTCAGACACTGAGGAGAGAC TGTAGGTTCAGCTACAAGCAAAAAGACCTAGCTGGTCTCCAA GCAGTGTCTCCAAGTCCCTGAACCTGTGACACCTGCCCCAG GCATCATCAGGCACAGAGGGCCACC |
| 26 | Portion of SEQ ID NO: 24 (-7166 to -7091) | CCCATGTCAGCTGCTTGTGCTTTCCAGAGACAAAACAGGAAT AATAGATGTCATTAAATATACATTGGGCCCCAGG |
| 27 | Portion of SEQ ID NO: 24 (-7077 to -6983) | AGCCTGAGCCTCCTTTCCATCTCTGTGGAGGCAGACATAGGA CCCCCAACAAACAGCATGCAGGTTGGGAGCCAGCCACAGGA CCCAGGTAAGGG |
| 28 | Portion of SEQ ID NO: 24 (SEQ ID NO: 26 fused to SEQ ID NO: 27) | CCCATGTCAGCTGCTTGTGCTTTCCAGAGACAAAACAGGAAT AATAGATGTCATTAAATATACATTGGGCCCCAGGAGCCTGAG CCTCCTTTCCATCTCTGTGGAGGCAGACATAGGACCCCCAAC AAACAGCATGCAGGTTGGGAGCCAGCCACAGGACCCAGGTA AGGG |
| 29 | Portion of SEQ ID NO: 24 (SEQ ID NO: 27 fused to SEQ ID NO: 26) | AGCCTGAGCCTCCTTTCCATCTCTGTGGAGGCAGACATAGGA CCCCCAACAAACAGCATGCAGGTTGGGAGCCAGCCACAGGA CCCAGGTAAGGGCCCATGTCAGCTGCTTGTGCTTTCCAGAGA CAAAACAGGAATAATAGATGTCATTAAATATACATTGGGCCCC AGG |
| 30 | Portion of SEQ ID NO: 24 (-7166 to -6983) | CCCATGTCAGCTGCTTGTGCTTTCCAGAGACAAAACAGGAAT AATAGATGTCATTAAATATACATTGGGCCCCAGGCGGTCAAT GTGGCAGCCTGAGCCTCCTTTCCATCTCTGTGGAGGCAGAC ATAGGACCCCCAACAAACAGCATGCAGGTTGGGAGCCAGCC ACAGGACCCAGGTAAGGG |

TABLE 3-continued

Exemplary nucleotide sequences for use in the Myo15 promoter described herein

| SEQ ID NO. | Description of nucleic acid sequence | Nucleic Acid Sequence |
| --- | --- | --- |
| 31 | Portion of SEQ ID NO: 25 (-590 to -509) | TGAGGTGGGAGCTGGGCTCTCCCTGATGTATTATTCAGCTCC CTGGAGTTGGCCAGCTCCTGTTACACTGGCCACAGCCCTG |
| 32 | Portion of SEQ ID NO: 25 (-266 to -161) | CACAGGCCTCCCAGTCTACCCTCACTAGAAAACAACACCCAG GCACTTTCCACCACCTCTCAAAGGTGAAACCCAAGGCTGGTC TAGAGAATGAATTATGGATCCT |
| 33 | Portion of SEQ ID NO: 25 (SEQ ID NO: 31 fused to SEQ ID NO: 32) | TGAGGTGGGAGCTGGGCTCTCCCTGATGTATTATTCAGCTCC CTGGAGTTGGCCAGCTCCTGTTACACTGGCCACAGCCCTG CACAGGCCTCCCAGTCTACCCTCACTAGAAAACAACACCCAG GCACTTTCCACCACCTCTCAAAGGTGAAACCCAAGGCTGGTC TAGAGAATGAATTATGGATCCT |
| 34 | Portion of SEQ ID NO: 25 (SEQ ID NO: 32 fused to SEQ ID NO: 31) | CACAGGCCTCCCAGTCTACCCTCACTAGAAAACAACACCCAG GCACTTTCCACCACCTCTCAAAGGTGAAACCCAAGGCTGGTC TAGAGAATGAATTATGGATCCTTGAGGTGGGAGCTGGGCTCT CCCTGATGTATTATTCAGCTCCCTGGAGTTGGCCAGCTCCTG TTACACTGGCCACAGCCCTG |
| 35 | Portion of SEQ ID NO: 25 (-590 to -161) | TGAGGTGGGAGCTGGGCTCTCCCTGATGTATTATTCAGCTCC CTGGAGTTGGCCAGCTCCTGTTACACTGGCCACAGCCCTGG GCATCCGCTTCTCACTTCTAGTTTCCCCTCCAAGGTAATGTG GTGGGTCATGATCATTCTATCCTGGCTTCAGGGACCTGACTC CACTTTGGGGCCATTCGAGGGGTCTAGGGTAGATGATGTCC CCCTGTGGGGATTAATGTCCTGCTCTGTAAAACTGAGCTAGC TGAGATCCAGGAGGGCTTGGCCAGAGACAGCAAGTTGTTGC CATGGTGACTTTAAAGCCAGGTTGCTGCCCCAGCACAGGCCT CCCAGTCTACCCTCACTAGAAAACAACACCCAGGCACTTTCC ACCACCTCTCAAAGGTGAAACCCAAGGCTGGTCTAGAGAATG AATTATGGATCCT |
| 36 | SEQ ID NO: 24 fused to SEQ ID NO: 25 | CTGCAGCTCAGCCTACTACTTGCTTTCCAGGCTGTTCCTAGT TCCCATGTCAGCTGCTTGTGCTTTCCAGAGACAAAACAGGAA TAATAGATGTCATTAAATATACATTGGGCCCCAGGCGGTCAAT GTGGCAGCCTGAGCCTCCTTTCCATCTCTGTGGAGGCAGAC ATAGGACCCCCAACAAACAGCATGCAGGTTGGGAGCCAGCC ACAGGACCCAGGTAAGGGGCCCTGGGTCCTTAAGCTTCTGC CACTGGCTCCGGCATTGCAGAGAGAAGAGAAGGGGCGGCA GAGCTGAACCTTAGCCTTGCCTTCCTGGGTACCCTTCTGAGC CTCACTGTCTTCTGTGAGATGGGCAAAGTGCGGGTGTGACTC CTTGGCAACGGTGTTACACCAGGGCAGGTAAAGTTGTAGTTA TTTGTGGGGTACACCAGGACTGTTAAAGGTGTAACTATGGTC TCACCCAGCATTTTCACTTCTAATAAGTTCAAATGTGATACGG CACCTTTCTAAAAATTAGTTTTCAGGGAAATAGGGTTCAAAAC TGGTAGTGGTAGGGTCCATTCTCACGACCCCCAGGCCTGCT AACCCTGACCAAGCTACCTATTACTTACCCTCCTCTTTCTCCT CCTCCTCTTTCTCCTTCTCCTGCTTCCCCTCTTCCTTCTCCCT CCCTTCCTCTCCCTCCTCCCCCTCCTTGGCTGTGATCAGATC CAGAGCCTGAATGAGCCTCCTGACCCCACACCCCCACTAGC ATGGGCCTGCAAGTGCCCAGAAGTCCCTCCTGCCTCCTAAAC TGCCCAGCCGATCCATTAGCTCTTCCTTCTTCCCAGTGAAAG AAGCAGGCACAGCCTGTCCCTCCCGTTCTACAGAAAGGAAG CTACAGCACAGGGAGGGCCAAAGGCCTTCCTGGGACTAGAC AGTTGATCAACAGCAGGACTGGAGAGCTGGGCTCCATTTTTG TTCCTTGGTGCCCTGCCCCTCCCCATGACCTGCAGAGACATT CAGCCTGCCAGGCTTTATGAGGTGGGAGCTGGGCTCTCCCT GATGTATTATTCAGCTCCCTGGAGTTGGCCAGCTCCTGTTAC ACTGGCCACAGCCCTGGGCATCCGCTTCTCACTTCTAGTTTC CCCTCCAAGGTAATGTGGTGGGTCATGATCATTCTATCCTGG CTTCAGGGACCTGACTCCACTTTGGGGCCATTCGAGGGGTC TAGGGTAGATGATGTCCCCCTGTGGGGATTAATGTCCTGCTC TGTAAAACTGAGCTAGCTGAGATCCAGGAGGGCTTGGCCAG AGACAGCAAGTTGTTGCCATGGTGACTTTAAAGCCAGGTTGC TGCCCCAGCACAGGCCTCCCAGTCTACCCTCACTAGAAAACA ACACCCAGGCACTTTCCACCACCTCTCAAAGGTGAAACCCAA GGCTGGTCTAGAGAATGAATTATGGATCCTCGCTGTCCGTGC CACCCAGCTAGTCCCAGCGGCTCAGACACTGAGGAGAGACT GTAGGTTCAGCTACAAGCAAAAAGACCTAGCTGGTCTCCAAG CAGTGTCTCCAAGTCCCTGAACCTGTGACACCTGCCCCAGG CATCATCAGGCACAGAGGGCCACC |
| 37 | SEQ ID NO: 25 fused to SEQ ID NO: 24 | GGTCTCACCCAGCATTTTCACTTCTAATAAGTTCAAATGTGAT ACGGCACCTTTCTAAAAATTAGTTTTCAGGGAAATAGGGTTCA AAACTGGTAGTGGTAGGGTCCATTCTCACGACCCCCAGGCCT |

TABLE 3-continued

Exemplary nucleotide sequences for use in the Myo15 promoter described herein

| SEQ ID NO. | Description of nucleic acid sequence | Nucleic Acid Sequence |
|---|---|---|
| | | GCTAACCCTGACCAAGCTACCTATTACTTACCCTCCTCTTTCT<br>CCTCCTCCTCTTTCTCCTTCTCCTGCTTCCCCTCTTCCTTCTC<br>CCTCCCTTCCTCTCCCTCCTCCCCCTCCTTGGCTGTGATCAG<br>ATCCAGAGCCTGAATGAGCCTCCTGACCCCACACCCCCACTA<br>GCATGGGCCTGCAAGTGCCCAGAAGTCCCTCCTGCCTCCTA<br>AACTGCCCAGCCGATCCATTAGCTCTTCCTTCTTCCCAGTGA<br>AAGAAGCAGGCACAGCCTGTCCCTCCCGTTCTACAGAAAGG<br>AAGCTACAGCACAGGGAGGGCCAAAGGCCTTCCTGGGACTA<br>GACAGTTGATCAACAGCAGGACTGGAGAGCTGGGCTCCATTT<br>TTGTTCCTTGGTGCCCTGCCCCTCCCCATGACCTGCAGAGAC<br>ATTCAGCCTGCCAGGCTTTATGAGGTGGGAGCTGGGCTCTC<br>CCTGATGTATTATTCAGCTCCCTGGAGTTGGCCAGCTCCTGT<br>TACACTGGCCACAGCCCTGGGCATCCGCTTCTCACTTCTAGT<br>TTCCCCTCCAAGGTAATGTGGTGGGTCATGATCATTCTATCCT<br>GGCTTCAGGGACCTGACTCCACTTTGGGGCCATTCGAGGGG<br>TCTAGGGTAGATGATGTCCCCCTGTGGGGATTAATGTCCTGC<br>TCTGTAAAACTGAGCTAGCTGAGATCCAGGAGGGCTTGGCCA<br>GAGACAGCAAGTTGTTGCCATGGTGACTTTAAAGCCAGGTTG<br>CTGCCCCAGCACAGGCCTCCCAGTCTACCCTCACTAGAAAAC<br>AACACCCAGGCACTTTCCACCACCTCTCAAAGGTGAAACCCA<br>AGGCTGGTCTAGAGAATGAATTATGGATCCTCGCTGTCCGTG<br>CCACCCAGCTAGTCCCAGCGGCTCAGACACTGAGGAGAGAC<br>TGTAGGTTCAGCTACAAGCAAAAAGACCTAGCTGGTCTCCAA<br>GCAGTGTCTCCAAGTCCCTGAACCTGTGACACCTGCCCCAG<br>GCATCATCAGGCACAGAGGGCCACCCTGCAGCTCAGCCTAC<br>TACTTGCTTTCCAGGCTGTTCCTAGTTCCCATGTCAGCTGCTT<br>GTGCTTTCCAGAGACAAAACAGGAATAATAGATGTCATTAAAT<br>ATACATTGGGCCCCAGGCGGTCAATGTGGCAGCCTGAGCCT<br>CCTTTCCATCTCTGTGGAGGCAGACATAGGACCCCCAACAAA<br>CAGCATGCAGGTTGGGAGCCAGCCACAGGACCCAGGTAAGG<br>GGCCCTGGGTCCTTAAGCTTCTGCCACTGGCTCCGGCATTG<br>CAGAGAGAAGAGAAGGGGCGGCAGAGCTGAACCTTAGCCTT<br>GCCTTCCTGGGTACCCTTCTGAGCCTCACTGTCTTCTGTGAG<br>ATGGGCAAAGTGCGGGTGTGACTCCTTGGCAACGGTGTTAC<br>ACCAGGGCAGGTAAAGTTGTAGTTATTTGTGGGGTACACCAG<br>GACTGTTAAAGGTGTAACTAT |

Additional Myo15 promoters useful in conjunction with the compositions and methods described herein include nucleic acid molecules that have at least 85% sequence identity (e.g., 85%, 90%, 95%, 96%, 97%, 98%, 99%, or more, sequence identity) to the nucleic acid sequences set forth in Table 3, as well as functional portions or derivatives of the nucleic acid sequences set forth in Table 3. The Myo15 promoters listed in Table 3 are characterized in U.S. Provisional Application 62/663,679, which is incorporated herein by reference.

Once a polynucleotide encoding OTOF has been incorporated into the nuclear DNA of a mammalian cell or stabilized in an episomal monomer or concatemer, the transcription of this polynucleotide can be induced by methods known in the art. For example expression can be induced by exposing the mammalian cell to an external chemical reagent, such as an agent that modulates the binding of a transcription factor and/or RNA polymerase to the mammalian promoter and thus regulates gene expression. The chemical reagent can serve to facilitate the binding of RNA polymerase and/or transcription factors to the mammalian promoter, e.g., by removing a repressor protein that has bound the promoter. Alternatively, the chemical reagent can serve to enhance the affinity of the mammalian promoter for RNA polymerase and/or transcription factors such that the rate of transcription of the gene located downstream of the promoter is increased in the presence of the chemical reagent. Examples of chemical reagents that potentiate polynucleotide transcription by the above mechanisms include tetracycline and doxycycline. These reagents are commercially available (Life Technologies®, Carlsbad, CA) and can be administered to a mammalian cell in order to promote gene expression according to established protocols.

Other DNA sequence elements that may be included in the nucleic acid vectors for use in the compositions and methods described herein include enhancer sequences. Enhancers represent another class of regulatory elements that induce a conformational change in the polynucleotide containing the gene of interest such that the DNA adopts a three-dimensional orientation that is favorable for binding of transcription factors and RNA polymerase at the transcription initiation site. Thus, polynucleotides for use in the compositions and methods described herein include those that encode an OTOF protein and additionally include a mammalian enhancer sequence. Many enhancer sequences are now known from mammalian genes, and examples include enhancers from the genes that encode mammalian globin, elastase, albumin, α-fetoprotein, and insulin. Enhancers for use in the compositions and methods described herein also include those that are derived from the genetic material of a virus capable of infecting a eukaryotic cell. Examples include the SV40 enhancer on the late side of the replication origin (bp 100-270), the cytomegalovirus early promoter enhancer, the polyoma enhancer on the late side of the replication origin, and adenovirus enhancers. Additional enhancer sequences that induce activation of eukaryotic gene transcription are disclosed in Yaniv, et al., Nature 297:17 (1982). An enhancer may be spliced into a vector containing a polynucleotide encoding an OTOF protein, for example, at a position 5' or 3' to this gene. In a preferred orientation, the enhancer is positioned at the 5' side of the promoter, which in turn is located 5' relative to the polynucleotide encoding an OTOF protein.

The nucleic acid vectors described herein may include a Woodchuck Posttranscriptional Regulatory Element (WPRE). The WPRE acts at the mRNA level, by promoting nuclear export of transcripts and/or by increasing the efficiency of polyadenylation of the nascent transcript, thus increasing the total amount of mRNA in the cell. The addition of the WPRE to a vector can result in a substantial improvement in the level of transgene expression from several different promoters, both in vitro and in vivo. The WPRE can be located in the second nucleic acid vector between the polynucleotide encoding a C-terminal portion of an OTOF protein and the poly(A) sequence. In the compositions and methods described herein, the WPRE can have the sequence:

(SEQ ID NO: 23)

```
GATCCAATCAACCTCTGGATTACAAAATTTGTGAAAGATTGACTGGTAT
TCTTAACTATGTTGCTCCTTTTACGCTATGTGGATACGCTGCTTTAATG
CCTTTGTATCATGCTATTGCTTCCCGTATGGCTTTCATTTTCTCCTCCT
TGTATAAATCCTGGTTGCTGTCTCTTTATGAGGAGTTGTGGCCCGTTGT
CAGGCAACGTGGCGTGGTGTGCACTGTGTTTGCTGACGCAACCCCCACT
GGTTGGGGCATTGCCACCACCTGTCAGCTCCTTTCCGGGACTTTCGCTT
TCCCCCTCCCTATTGCCACGGCGGAACTCATCGCCGCCTGCCTTGCCCG
CTGCTGGACAGGGGCTCGGCTGTTGGGCACTGACAATTCCGTGGTGTTG
TCGGGGAAATCATCGTCCTTTCCTTGGCTGCTCGCCTGTGTTGCCACCT
GGATTCTGCGCGGGACGTCCTTCTGCTACGTCCCTTCGGCCCTCAATCC
AGCGGACCTTCCTTCCCGCGGCCTGCTGCCGGCTCTGCGGCCTCTTCCG
CGTCTTCGA.
```

The WPRE can also have the sequence:

(SEQ ID NO: 38)

```
AATCAACCTCTGGATTACAAAATTTGTGAAAGATTGACTGGTATTCTTA
ACTATGTTGCTCCTTTTACGCTATGTGGATACGCTGCTTTAATGCCTTT
GTATCATGCTATTGCTTCCCGTATGGCTTTCATTTTCTCCTCCTTGTAT
AAATCCTGGTTAGTTCTTGCCACGGCGGAACTCATCGCCGCCTGCCTTG
CCCGCTGCTGGACAGGGGCTCGGCTGTTGGGCACTGACAATTCCGTGGT
GTTTATTTGTGAAATTTGTGATGCTATTGCTTTATTTGTAACCATCTAG
CTTTATTTGTGAAATTTGTGATGCTATTGCTTTATTTGTAACCATTATA
AGCTGCAATAAACAAGTTAACAACAACAATTGCATTCATTTTATGTTTC
AGGTTCAGGGGGAGATGTGGGAGGTTTTTTAAA
```

In some embodiments, the nucleic acid vectors for use in the compositions and methods described herein include a reporter sequence, which can be useful in verifying OTOF gene expression, for example, in specific cells and tissues (e.g., in cochlear hair cells). Reporter sequences that may be provided in a transgene include DNA sequences encoding β-lactamase, β-galactosidase (LacZ), alkaline phosphatase, thymidine kinase, green fluorescent protein (GFP), chloramphenicol acetyltransferase (CAT), luciferase, and others well known in the art. When associated with regulatory elements which drive their expression, the reporter sequences provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA), and immunohistochemistry. For example, where the marker sequence is the LacZ gene, the presence of the vector carrying the signal is detected by assays for β-galactosidase activity. Where the transgene is green fluorescent protein or luciferase, the vector carrying the signal may be measured visually by color or light production in a luminometer.

Overlapping Dual Vectors

One approach for expressing large proteins in mammalian cells involves the use of overlapping dual vectors. This approach is based on the use of two nucleic acid vectors, each of which contains a portion of a polynucleotide that encodes a protein of interest and has a defined region of sequence overlap with the other polynucleotide. Homologous recombination can occur at the region of overlap and lead to the formation of a single nucleic acid molecule that encodes the full-length protein of interest.

Overlapping dual vectors for use in the methods and compositions described herein contain at least one kilobase (kb) of overlapping sequence (e.g., 1 kb, 1.5 kb, 2 kb, 2.5 kb, 3 kb or more of overlapping sequence). The nucleic acid vectors are designed such that the overlapping region is centered at an OTOF exon boundary, with an equal amount of overlap on either side of the boundary. The boundaries are chosen based on the size of the promoter and the locations of the portions of the polynucleotide that encode OTOF C2 domains. Overlapping regions are centered on exon boundaries that occur outside of the portion of the polynucleotide that encodes the C2C domain (e.g., after the portion of the polynucleotide that encodes the C2C domain). Exon boundaries within the portion of the polynucleotide that encodes the C2D domain can be selected as the center of the overlapping region, or exon boundaries located after the portion of the polynucleotide that encodes the C2D domain and before the portion of the polynucleotide that encodes the C2E domain can serve as the center of an overlapping region. The nucleic acid vectors for use in the methods and compositions described herein are also designed such that approximately half of the OTOF gene is contained within each vector (e.g., each vector contains a polynucleotide that encodes approximately half of the OTOF protein).

One exemplary overlapping dual vector system includes a first nucleic acid vector containing a CAG promoter operably linked to exons 1-28 and the 500 kb immediately 3' of the exon 28/29 boundary of a polynucleotide encoding an OTOF protein (e.g., human OTOF, e.g., SEQ ID NO: 1, or mouse OTOF, e.g., SEQ ID NO: 6); and a second nucleic acid vector containing the 500 kb immediately 5' of the exon 28/29 boundary and exons 29-48 of a polynucleotide encoding an OTOF protein (e.g., human OTOF, e.g., SEQ ID NO: 1, or mouse OTOF, e.g., SEQ ID NO: 6) and a poly(A) sequence (e.g., a bovine growth hormone (bGH) poly(A) signal sequence). In this overlapping dual vector system, the overlapping sequence is centered at the exon 28/29 boundary, which is after the portion of the polynucleotide that encodes the C2D domain. Another exemplary overlapping dual vector system includes a first nucleic acid vector containing a CAG promoter operably linked to exons 1-24 and the 500 kb immediately 3' of the exon 24/25 boundary of a polynucleotide encoding an OTOF protein (e.g., human OTOF, e.g., SEQ ID NO: 1, or mouse OTOF, e.g., SEQ ID NO: 6); and a second nucleic acid vector containing the 500 kb immediately 5' of the exon 24/25 boundary and exons 25-48 of a polynucleotide encoding an OTOF protein (e.g., human OTOF, e.g., SEQ ID NO: 1, or mouse OTOF, e.g., SEQ ID NO: 6) and a poly(A) sequence (e.g., a bGH poly(A) signal sequence). In this overlapping dual vector system, the overlapping sequence is centered at the exon 24/25 boundary, which is within the portion of the polynucleotide that encodes the C2D domain. The two exon boundaries described above can be used with any promoter that is a similar size to the CAG promoter (e.g., the CMV promoter), such as promoters that are 1 kb or shorter (e.g., approximately 1 kb, 950 bp, 900 bp, 850 bp, 800 bp, 750 bp, 700 bp, 650 bp, 600 bp, 550 bp 500 bp, 450 bp, 400 bp, 350 bp, 300 bp or shorter). For example, in either of the foregoing dual vector systems, the CMV promoter can be used in the place of the CAG promoter. A Myo15 promoter having a sequence that is 1 kb or shorter (e.g., a Myo15 promoter described hereinabove) can also be used in place of the CAG promoter. Alternatively, a different exon boundary can be chosen that is within or after the portion of the polynucleotide that encodes the C2D domain and before the portion of the polynucleotide that encodes the C2E domain. The nucleic acid vectors containing promoters of this size can optionally contain OTOF UTRs. For example, in the foregoing overlapping dual vector system in which the overlapping region is centered at the exon 28/29 boundary of OTOF, the second nucleic acid vector can contain the full-length OTOF 3' UTR (e.g., the 1035 bp human OTOF 3' UTR in dual vector systems encoding human OTOF, or the 1001 bp mouse OTOF 3' UTR in dual vector systems encoding mouse OTOF). In the foregoing overlapping dual vector system in which the overlapping region is centered at the exon 24/25 boundary of OTOF, neither the first nor the second nucleic acid vector contains an OTOF UTR.

In some embodiments, the first nucleic acid vector in the overlapping dual vector system contains a long promoter (e.g., a promoter that is longer than 1 kb, e.g., 1.1 kb, 1.25 kb, 1.5 kb, 1.75 kb, 2 kb, 2.5 kb, 3 kb or longer). In such overlapping dual vector systems, the overlapping region is centered at an exon boundary that is located after the portion of the polynucleotide that encodes the C2C domain and before the portion of the polynucleotide that encodes the C2D domain. For example, an overlapping dual vector system for use in the methods and compositions described herein includes a first nucleic acid vector containing a Myo15 promoter that is longer than 1 kb (e.g., SEQ ID NO: 36) operably linked to exons 1-21 and the 500 kb immediately 3' of the exon 21/22 boundary of a polynucleotide encoding an OTOF protein (e.g., human OTOF, e.g., SEQ ID NO: 1); and a second nucleic acid vector containing the 500 kb immediately 5' of the exon 21/22 boundary and exons 22-48 of a polynucleotide encoding an OTOF protein (e.g., human OTOF, e.g., SEQ ID NO: 1) and a poly(A) sequence (e.g., a bGH poly(A) signal sequence). In this overlapping dual vector system, neither the first nor the second nucleic acid vector includes an OTOF UTR. A short promoter (e.g., a CMV promoter, CAG promoter, or a Myo15 promoter having a sequence that is 1 kb or shorter) can also be used in this dual vector system (e.g., a dual vector system in which the overlapping region is centered at the exon 21/22 boundary). If a short promoter is used, additional elements, such as a 5' OTOF UTR, can be included in the first vector (e.g., the vector containing exons 1-21 and the 500 kb immediately 3' of the exon 21/22 boundary of a polynucleotide encoding an OTOF protein).

Trans-Splicing Dual Vectors

A second approach for expressing large proteins in mammalian cells involves the use of trans-splicing dual vectors. In this approach, two nucleic acid vectors are used that contain distinct nucleic acid sequences, and the polynucleotide encoding the N-terminal portion of the protein of interest and the polynucleotide encoding the C-terminal portion of the protein of interest do not overlap. Instead, the first nucleic acid vector includes a splice donor sequence 3' of the polynucleotide encoding the N-terminal portion of the protein of interest, and the second nucleic acid vector includes a splice acceptor sequence 5' of the polynucleotide encoding the C-terminal portion of the protein of interest. When the first and second nucleic acids are present in the same cell, their ITRs can concatemerize, forming a single nucleic acid structure in which the concatemerized ITRs are positioned between the splice donor and splice acceptor. Trans-splicing then occurs during transcription, producing a nucleic acid molecule in which the polynucleotides encoding the N-terminal and C-terminal portions of the protein of interest are contiguous, thereby forming the full-length coding sequence.

Trans-splicing dual vectors for use in the methods and compositions described herein are designed such that approximately half of the OTOF gene is contained within each vector (e.g., each vector contains a polynucleotide that encodes approximately half of the OTOF protein). The determination of how to split the polynucleotide sequence between the two nucleic acid vectors is made based on the size of the promoter and the locations of the portions of the polynucleotide that encode the OTOF C2 domains. When a short promoter is used in the trans-splicing dual vector system (e.g., a promoter that is 1 kb or shorter, e.g., approximately 1 kb, 950 bp, 900 bp, 850 bp, 800 bp, 750 bp, 700 bp, 650 bp, 600 bp, 550 bp 500 bp, 450 bp, 400 bp, 350 bp, 300 bp or shorter), such as a CAG promoter, a CMV promoter, or a Myo15 promoter having a sequence that is 1 kb or shorter (e.g., a Myo15 promoter described hereinabove), the OTOF polynucleotide sequence is divided between the two nucleic acid vectors at an exon boundary that occurs after the portion of the polynucleotide that encodes the C2D domain and before the portion of the polynucleotide that encodes the C2E domain, for example, the exon 26/27 boundary. The nucleic acid vectors containing promoters of this size can optionally contain OTOF UTRs (e.g., both the 5' and 3' OTOF UTRs, e.g., full-length UTRs). When a long promoter is used in the trans-splicing dual vector system (e.g., a promoter that is longer than 1 kb, e.g., 1.1 kb, 1.25 kb, 1.5 kb, 1.75 kb, 2 kb, 2.5 kb, 3 kb or longer), such as a Myo15 promoter that is longer than 1 kb (e.g., SEQ ID NO: 36), the OTOF polynucleotide sequence will be divided between the two nucleic acid vectors at an exon boundary that occurs after the portion of the polynucleotide that encodes the C2C domain, and either before the portion of the polynucleotide that encodes the C2D domain, such as the exon 19/20 boundary, or within the portion of the polynucleotide that encodes the C2D domain, such as the exon 25/26 boundary. A short promoter (e.g., a CMV promoter, CAG promoter, or a Myo15 promoter having a sequence that is 1 kb or shorter) can also be used in the dual vector systems designed for large promoters, in which case additional elements (e.g., OTOF UTR sequences) may be included in the first vector (e.g., the vector containing the portion of the polynucleotide the encodes the C2C domain).

One exemplary trans-splicing dual vector system that uses a short promoter includes a first nucleic acid vector containing a CAG promoter operably linked to exons 1-26 of a polynucleotide encoding an OTOF protein (e.g., human OTOF, e.g., SEQ ID NO: 1) and a splice donor sequence 3' of the polynucleotide sequence; and a second nucleic acid vector containing a splice acceptor sequence 5' of exons 27-48 of a polynucleotide encoding an OTOF protein (e.g., human OTOF, e.g., SEQ ID NO: 1) and a poly(A) sequence (e.g., a bGH poly(A) signal sequence). An alternative trans-splicing dual vector system includes a first nucleic acid vector containing a CAG promoter operably linked to exons 1-28 of a polynucleotide encoding an OTOF protein (e.g., mouse OTOF, e.g., SEQ ID NO: 6) and a splice donor sequence 3' of the polynucleotide sequence; and a second nucleic acid vector containing a splice acceptor sequence 5' of exons 29-48 of a polynucleotide encoding an OTOF protein (e.g., mouse OTOF, e.g., SEQ ID NO: 6) and a poly(A) sequence (e.g., a bGH poly(A) signal sequence). The CMV promoter or a Myo15 promoter having a sequence that is 1 kb or shorter (e.g., a Myo15 promoter described hereinabove) can be used in place of the CAG promoter either of the foregoing dual vector systems. These nucleic acid vectors can also contain full-length 5' and 3' OTOF UTRs in the first and second nucleic acid vectors, respectively (e.g., the first nucleic acid vector can contain the 5' human OTOF UTR (127 bp) in dual vector systems encoding human OTOF, or the 5' mouse UTR (134 bp) in dual vector systems encoding mouse OTOF; and the second nucleic acid vector can contain the 3' human OTOF UTR (1035 bp) in dual vector systems encoding human OTOF, or the 3' mouse OTOF UTR (1001 bp) in dual vector systems encoding mouse OTOF).

An exemplary trans-splicing dual vector system that uses a long promoter includes a first nucleic acid vector containing a Myo15 promoter that is longer than 1 kb (e.g., SEQ ID NO: 36) operably linked to exons 1-19 of a polynucleotide encoding an OTOF protein (e.g., human OTOF, e.g., SEQ ID NO: 1) and a splice donor sequence 3' of the polynucleotide sequence; and a second nucleic acid vector containing a splice acceptor sequence 5' of exons 20-48 of a polynucleotide encoding an OTOF protein (e.g., human OTOF, e.g., SEQ ID NO: 1) and a poly(A) sequence (e.g., a bGH poly(A) signal sequence). Alternatively, the trans-splicing dual vector system can include a first nucleic acid vector containing a Myo15 promoter that is longer than 1 kb (e.g., SEQ ID NO: 36) operably linked to exons 1-20 of a polynucleotide encoding an OTOF protein (e.g., mouse OTOF, e.g., SEQ ID NO: 6) and a splice donor sequence 3' of the polynucleotide sequence; and a second nucleic acid vector containing a splice acceptor sequence 5' of exons 21-48 of a polynucleotide encoding an OTOF protein (e.g., mouse OTOF, e.g., SEQ ID NO: 6) and a poly(A) sequence (e.g., a bGH poly(A) signal sequence). Neither the first nor the second nucleic acid vector in either of the foregoing Myo15 promoter trans-splicing dual vector systems contains an OTOF UTR. A short promoter (e.g., a CMV promoter, CAG promoter, or a Myo15 promoter having a sequence that is 1 kb or shorter) can also be used in the foregoing dual vector systems designed for large promoters. If these dual vector systems contain a short promoter, they may also include a 5' OTOF UTR in the first vector.

To accommodate an OTOF UTR, the OTOF coding sequence can be divided in a different position. For example, in a trans-splicing dual vector system in which the first nucleic acid vector contains a Myo15 promoter that is longer than 1 kb (e.g., SEQ ID NO: 36) operably linked to exons 1-25 of a polynucleotide encoding an OTOF protein (e.g., human OTOF, e.g., SEQ ID NO: 1) and a splice donor sequence 3' of the polynucleotide sequence; and the second nucleic acid vector contains a splice acceptor sequence 5' of exons 26-48 of a polynucleotide encoding an OTOF protein (e.g., human OTOF, e.g., SEQ ID NO: 1) and a poly(A) sequence (e.g., a bGH poly(A) signal sequence), the second nucleic acid can also contain a full-length OTOF 3' UTR (e.g., the 1035 bp human OTOF 3' UTR). For mouse OTOF, the trans-splicing dual vector system can contain a 3' UTR if the first nucleic acid vector contains a Myo15 promoter that is longer than 1 kb (e.g., SEQ ID NO: 36) operably linked to exons 1-24 of a polynucleotide encoding an OTOF protein (e.g., mouse OTOF, e.g., SEQ ID NO: 6) and a splice donor sequence 3' of the polynucleotide sequence; and the second nucleic acid vector contains a splice acceptor sequence 5' of exons 25-48 of a polynucleotide encoding an OTOF protein (e.g., mouse OTOF, e.g., SEQ ID NO: 6) and a poly(A) sequence (e.g., a bGH poly(A) signal sequence). In this dual vector system, the second nucleic acid can also contain a full-length OTOF 3' UTR (e.g., the 1001 bp mouse OTOF 3' UTR). A short promoter (e.g., a CMV promoter, CAG promoter, or a Myo15 promoter having a sequence that is 1 kb or shorter) can also be used in the foregoing dual vector systems designed for large promoters. If these dual vector systems contain a short promoter, they may also include a 5' OTOF UTR in the first vector.

Dual Hybrid Vectors

A third approach for expressing large proteins in mammalian cells involves the use of dual hybrid vectors. This approach combines elements of the overlapping dual vector strategy and the trans-splicing strategy in that it features both an overlapping region at which homologous recombination can occur and splice donor and splice acceptor sequences. In dual hybrid vector systems, the overlapping region is a recombinogenic region that is contained in both the first and second nucleic acid vectors, rather than a portion of the polynucleotide sequence encoding the protein of interest—the polynucleotide encoding the N-terminal portion of the protein of interest and the polynucleotide encoding the C-terminal portion of the protein of interest do not overlap in this approach. The recombinogenic region is 3' of the splice donor sequence in the first nucleic acid vector and 5' of the splice acceptor sequence in the second nucleic acid sequence. The first and second nucleic acid sequences can then join to form a single sequence based on one of two mechanisms: 1) recombination at the overlapping region, or 2) concatemerization of the ITRs. The remaining recombinogenic region(s) and/or the concatemerized ITRs can be removed by splicing, leading to the formation of a contiguous polynucleotide sequence that encodes the full-length protein of interest.

Recombinogenic regions that can be used in the compositions and methods described herein include the F1 phage AK gene having a sequence of: GGGATTTTGCCGATTTCGGCCTATTGGTTAA AAAATGAGCTGATTTAACAAAAATTTAACGCGAATTTTAACAAAAT (SEQ ID NO: 19) and alkaline phosphatase (AP) gene fragments as described in U.S. Pat. No. 8,236,557, which are incorporated herein by reference. In some embodiments, the AP gene fragment has the sequence of:

(SEQ ID NO: 39)

```
CCCCGGGTGCGCGGCGTCGGTGGTGCCGGCGGGGGCGCCAGGTCGCAG

GCGGTGTAGGGCTCCAGGCAGGCGGCGAAGGCCATGACGTGCGCTATGA

AGGTCTGCTCCTGCACGCCGTGAACCAGGTGCGCCTGCGGGCCGCGCGC
```

-continued

GAACACCGCCACGTCCTCGCCTGCGTGGGTCTCTTCGTCCAGGGGCACT

GCTGACTGCTGCCGATACTCGGGGCTCCCGCTCTCGCTCTCGGTAACAT

CCGGCCGGGCGCCGTCCTTGAGCACATAGCCTGGACCGTTTCCGTATAG

GAGGACCGTGTAGGCCTTCCTGTCCCGGGCCTTGCCAGCGGCCAGCCCG

ATGAAGGAGCTCCCTCGCAGGGGGTAGCCTCCGAAGGAGAAGACGTGGG

AGTGGTCGGCAGTGACGAGGCTCAGCGTGTCCTCCTCGCTGGTGAGCTG

GCCCGCCCTCTCAATGGCGTCGTCGAACATGATCGTCTCAGTCAGTGCC

CGGTAAGCCCTGCTTTCATGATGACCATGGTCGATGCGACCACCCTCCA

CGAAGAGGAAGAAGCCGCGGGGGTGTCTGCTCAGCAGGCGCAGGGCAGC

CTCTGTCATCTCCATCAGGGAGGGGTCCAGTGTGGAGTCTCGGTGGATC

TCGTATTTCATGTCTCCAGGCTCAAAGAGACCCATGAGATGGGTCACAG

ACGGGTCCAGGGAAGCCTGCATGAGCTCAGTGCGGTTCCACACGTACCG

GGCACCCTGGCGTTCGCCGAGCCATTCCTGCACCAGATTCTTCCCGTCC

AGCCTGGTCCCACCTTGGCTGTAGTCATCTGGGTACTCAGGGTCTGGGG

TTCCCATGCGAAACATGTACTTTCGGCCTCCA.

In some embodiments, the AP gene fragment has the sequence of:

(SEQ ID NO: 40)

CCCCGGGTGCGCGGCGTCGGTGGTGCCGGCGGGGGGCGCCAGGTCGCAG

GCGGTGTAGGGCTCCAGGCAGGCGGCGAAGGCCATGACGTGCGCTATGA

AGGTCTGCTCCTGCACGCCGTGAACCAGGTGCGCCTGCGGGCCGCGCGC

GAACACCGCCACGTCCTCGCCTGCGTGGGTCTCTTCGTCCAGGGGCACT

GCTGACTGCTGCCGATACTCGGGGCTCCCGCTCTCGCTCTCGGTAACAT

CCGGCCGGGCGCCGTCCTTGAGCACATAGCCTGGACCGTTTCCGTATAG

GAGGACCGTGTAGGCCTTCCTGTCCCGGGCCTTGCCAGCGGCCAGCCCG

ATGAAGGAGCTCCCTCGCAGGGGGTAGCCTCCGAAGGAGAAGACGTGGG

AGTGGTCGGCAGTGACGAGGCTCAGCGTGTCCTCCTCGCTGGTGA.

In some embodiments, the AP gene fragment has the sequence of:

(SEQ ID NO: 41)

GCTGGCCCGCCCTCTCAATGGCGTCGTCGAACATGATCGTCTCAGTCAG

TGCCCGGTAAGCCCTGCTTTCATGATGACCATGGTCGATGCGACCACCC

TCCACGAAGAGGAAGAAGCCGCGGGGGTGTCTGCTCAGCAGGCGCAGGG

CAGCCTCTGTCATCTCCATCAGGGAGGGGTCCAGTGTGGAGTCTCGGTG

GATCTCGTATTTCATGTCTCCAGGCTCAAAGAGACCCATGAGATGGGTC

ACAGACGGGTCCAGGGAAGCCTGCATGAGCTCAGTGCGGTTCCACACGT

ACCGGGCACCCTGGCGTTCGCCGAGCCATTCCTGCACCAGATTCTTCCC

GTCCAGCCTGGTCCCACCTTGGCTGTAGTCATCTGGGTACTCAGGGTCT

GGGGTTCCCATGCGAAACATGTACTTTCGGCCTCCA.

In some embodiments, the AP gene fragment has the sequence of:

(SEQ ID NO: 42)

CCCCGGGTGCGCGGCGTCGGTGGTGCCGGCGGGGGGCGCCAGGTCGCAG

GCGGTGTAGGGCTCCAGGCAGGCGGCGAAGGCCATGACGTGCGCTATGA

AGGTCTGCTCCTGCACGCCGTGAACCAGGTGCGCCTGCGGGCCGCGCGC

GAACACCGCCACGTCCTCGCCTGCGTGGGTCTCTTCGTCCAGGGGCACT

GCTGACTGCTGCCGATACTCGGGGCTCCCGCTCTCGCTCTCGGTAACAT

CCGGCCGGGCGCCGTCCTTGAGCACATAGCCTGGACCGTTTC

In some embodiments, the AP gene fragment has the sequence of:

(SEQ ID NO: 43)

CGTATAGGAGGACCGTGTAGGCCTTCCTGTCCCGGGCCTTGCCAGCGGC

CAGCCCGATGAAGGAGCTCCCTCGCAGGGGGTAGCCTCCGAAGGAGAAG

ACGTGGGAGTGGTCGGCAGTGACGAGGCTCAGCGTGTCCTCCTCGCTGG

TGAGCTGGCCCGCCCTCTCAATGGCGTCGTCGAACATGATCGTCTCAGT

CAGTGCCCGGTAAGCCCTGCTTTCATGATGACCATGGTCGATGCGACCA

CCCTCCACGAAGAGGAAGAAGCCGCGGGGGTGTCTGCTCAGCAGG.

In some embodiments, the AP gene fragment has the sequence of:

(SEQ ID NO: 44)

CGCAGGGCAGCCTCTGTCATCTCCATCAGGGAGGGGTCCAGTGTGGAGT

CTCGGTGGATCTCGTATTTCATGTCTCCAGGCTCAAAGAGACCCATGAG

ATGGGTCACAGACGGGTCCAGGGAAGCCTGCATGAGCTCAGTGCGGTTC

CACACGTACCGGGCACCCTGGCGTTCGCCGAGCCATTCCTGCACCAGAT

TCTTCCCGTCCAGCCTGGTCCCACCTTGGCTGTAGTCATCTGGGTACTC

AGGGTCTGGGGTTCCCATGCGAAACATGTACTTTCGGCCTCCA.

An exemplary splice donor sequence for use in the methods and compositions described herein (e.g., in trans-splicing and dual hybrid approaches) has the sequence: GTAAGTATCAAGGTTACAAGAC AGGTTTAAGGAGACCAATAGAAACTGGGCTTGTCGAGACAGAGAAGACTCTTGCGTTTCT (SEQ ID NO: 20). An exemplary splice acceptor sequence for use in the methods and compositions described herein (e.g., in trans-splicing and dual hybrid approaches) has the sequence: GATAGGCACCTATTGG TCTTACTGACATCCACTTTGCCTTTCTCTCCACAG (SEQ ID NO: 21). Additional examples of splice donor and splice acceptor sequences are known in the art.

Dual hybrid vectors for use in the methods and compositions described herein are designed such that approximately half of the OTOF gene is contained within each vector (e.g., each vector contains a polynucleotide that encodes approximately half of the OTOF protein). The determination of how to split the polynucleotide sequence between the two nucleic acid vectors is made based on the size of the promoter and the locations of the portions of the polynucleotide that encode the OTOF C2 domains. When a short promoter is used in the dual hybrid vector system (e.g., a promoter that is 1 kb or shorter, e.g., approximately 1 kb, 950 bp, 900 bp, 850 bp, 800 bp, 750 bp, 700 bp, 650 bp, 600 bp, 550 bp 500 bp, 450 bp, 400 bp, 350 bp, 300 bp or shorter), such as CAG, CMV, or a Myo15 promoter having a sequence that is 1 kb or shorter (e.g., a Myo15 promoter described hereinabove), the OTOF polynucleotide sequence is divided between the two nucleic acid vectors at an exon boundary that occurs after the portion of the polynucleotide that encodes the C2D domain and before the portion of the polynucleotide that encodes C2E domain, for example, the exon 26/27 boundary. The nucleic acid vectors containing promoters of this size can optionally contain OTOF UTRs (e.g., full-length 5' and 3' UTRs). When a long promoter is used in the trans-splicing dual vector system (e.g., a promoter that is longer than 1 kb, e.g., 1.1 kb, 1.25 kb, 1.5 kb, 1.75 kb, 2 kb, 2.5 kb, 3 kb or longer), such as a Myo15 promoter that is longer than 1 kb (e.g., SEQ ID NO: 36), the OTOF polynucleotide sequence will be divided between the two nucleic acid vectors at an exon boundary that occurs after the portion of the polynucleotide that encodes the C2C domain, and either before the portion of the polynucleotide that encodes the C2D domain, such as the exon 19/20 boundary, or within the portion of the polynucleotide that encodes the C2D domain, such as the exon 25/26 boundary. A short promoter (e.g., a CMV promoter, CAG promoter, or a Myo15 promoter having a sequence that is 1 kb or shorter) can also be used in the dual vector systems designed for large promoters, in which case additional elements (e.g., OTOF UTR sequences) may be included in the first vector (e.g., the vector containing the portion of the polynucleotide the encodes the C2C domain).

One exemplary dual hybrid vector system that uses a short promoter includes a first nucleic acid vector containing a CAG promoter operably linked to exons 1-26 of a polynucleotide encoding an OTOF protein (e.g., human OTOF, e.g., SEQ ID NO: 1), a splice donor sequence 3' of the polynucleotide sequence, and a recombinogenic region 3' of the splice donor sequence; and a second nucleic acid vector containing a recombinogenic region, a splice acceptor sequence 3' of the recombinogenic region, a polynucleotide 3' of the splice acceptor sequence that contains exons 27-48 of a polynucleotide encoding an OTOF protein (e.g., human OTOF, e.g., SEQ ID NO: 1), and a poly(A) sequence (e.g., a bGH poly(A) signal sequence). The first and second nucleic acid vectors can also contain the full-length 5' and 3' OTOF UTRs, respectively (e.g., the 127 bp human OTOF 5' UTR can be included in the first nucleic acid vector, and the 1035 bp human OTOF 3' UTR can be included in the second nucleic acid vector). Another exemplary dual hybrid vector system that uses a short promoter includes a first nucleic acid vector containing a CAG promoter operably linked to exons 1-28 of a polynucleotide encoding an OTOF protein (e.g., mouse OTOF, e.g., SEQ ID NO: 6), a splice donor sequence 3' of the polynucleotide sequence, and a recombinogenic region 3' of the splice donor sequence; and a second nucleic acid vector containing a recombinogenic region, a splice acceptor sequence 3' of the recombinogenic region, a polynucleotide 3' of the splice acceptor sequence that contains exons 29-48 of a polynucleotide encoding an OTOF protein (e.g., mouse OTOF, e.g., SEQ ID NO: 6), and a poly(A) sequence (e.g., a bGH poly(A) signal sequence). The first and second nucleic acid vectors can also contain the full-length 5' and 3' OTOF UTRs, respectively (e.g., the 134 bp mouse OTOF 5' UTR can be included in the first nucleic acid vector, and the 1001 bp mouse OTOF 3' UTR can be included in the second nucleic acid vector). The CMV promoter or a Myo15 promoter having a sequence that is 1 kb or shorter (e.g., a Myo15 promoter described hereinabove) can be used in place of the CAG promoter either of the foregoing dual vector systems.

An exemplary dual hybrid vector system that uses a long promoter includes a first nucleic acid vector containing a Myo15 promoter that is longer than 1 kb (e.g., SEQ ID NO: 36) operably linked to exons 1-19 of a polynucleotide encoding an OTOF protein (e.g., human OTOF, e.g., SEQ ID NO: 1), a splice donor sequence 3' of the polynucleotide sequence, and a recombinogenic region 3' of the splice donor sequence; and a second nucleic acid vector containing a recombinogenic region, a splice acceptor sequence 3' of the recombinogenic region, a polynucleotide 3' of the splice acceptor sequence that contains exons 20-48 of a polynucleotide encoding an OTOF protein (e.g., human OTOF, e.g., SEQ ID NO: 1), and a poly(A) sequence (e.g., a bGH poly(A) signal sequence). Another exemplary dual hybrid vector system that uses a long promoter includes a first nucleic acid vector containing a Myo15 promoter that is longer than 1 kb (e.g., SEQ ID NO: 36) operably linked to exons 1-20 of a polynucleotide encoding an OTOF protein (e.g., mouse OTOF, e.g., SEQ ID NO: 6), a splice donor sequence 3' of the polynucleotide sequence, and a recombinogenic region 3' of the splice donor sequence; and a second nucleic acid vector containing a recombinogenic region, a splice acceptor sequence 3' of the recombinogenic region, a polynucleotide 3' of the splice acceptor sequence that contains exons 21-48 of a polynucleotide encoding an OTOF protein (e.g., mouse OTOF, e.g., SEQ ID NO: 6), and a poly(A) sequence (e.g., a bGH poly(A) signal sequence). Neither the first nor the second nucleic acid vector in either of the foregoing Myo15 promoter dual hybrid vector systems contains an OTOF UTR. A short promoter (e.g., a CMV promoter, CAG promoter, or a Myo15 promoter having a sequence that is 1 kb or shorter) can also be used in the foregoing dual vector systems designed for large promoters. If these dual vector systems contain a short promoter, they may also include a 5' OTOF UTR in the first vector.

To accommodate an OTOF UTR, the OTOF coding sequence can be divided in a different position. For example, in a dual hybrid vector system in which the first nucleic acid vector contains a Myo15 promoter that is longer than 1 kb (e.g., SEQ ID NO: 36) operably linked to exons 1-25 of a polynucleotide encoding an OTOF protein (e.g., human OTOF, e.g., SEQ ID NO: 1), a splice donor sequence 3' of the polynucleotide sequence, and a recombinogenic region 3' of the splice donor sequence; and the second nucleic acid vector contains a recombinogenic region, a splice acceptor sequence 3' of the recombinogenic region, a polynucleotide 3' of the splice acceptor sequence that contains exons 26-48 of a polynucleotide encoding an OTOF protein (e.g., human OTOF, e.g., SEQ ID NO: 1), and a poly(A) sequence (e.g., a bGH poly(A) signal sequence), the second nucleic acid can also contain a full-length OTOF 3' UTR (e.g., the 1035 bp human OTOF UTR). For mouse OTOF, the dual hybrid vector system can contain a 3' UTR if the first nucleic acid vector contains a Myo15 promoter that is longer than 1 kb (e.g., SEQ ID NO: 36) operably linked to exons 1-24 of a polynucleotide encoding an OTOF protein (e.g., mouse OTOF, e.g., SEQ ID NO: 6), a splice donor sequence 3' of the polynucleotide sequence, and a recombinogenic region 3' of the splice donor sequence; and the second nucleic acid vector contains a recombinogenic region, a splice acceptor sequence 3' of the recombinogenic region, a polynucleotide 3' of the splice acceptor sequence that contains exons 25-48 of a polynucleotide encoding an OTOF protein (e.g., human OTOF, e.g., SEQ ID NO: 1), and a poly(A) sequence (e.g., a bGH poly(A) signal sequence). In this dual hybrid vector system, the second nucleic acid can also contain a full-length OTOF 3' UTR (e.g., the 1001 bp mouse OTOF UTR). A short promoter (e.g., a CMV promoter, CAG promoter, or a Myo15 promoter having a sequence that is 1 kb or shorter) can also be used in the foregoing dual vector systems designed for large promoters. If these dual vector systems contain a short promoter, they may also include a 5' OTOF UTR in the first vector.

The dual hybrid vectors used in the methods and compositions described herein can optionally include a degradation signal sequence in both the first and second nucleic acid vectors. The degradation signal sequence can be included to prevent or reduce the expression of portions of the OTOF protein from polynucleotides that failed to recombine and/or undergo splicing. The degradation signal sequence is positioned 3' of the recombinogenic region in the first nucleic acid vector, and is positioned between the recombinogenic region and the splice acceptor in the second nucleic acid vector. A degradation signal sequence that can be used in the compositions and methods described herein has the sequence of:

(SEQ ID NO: 22)
GCCTGCAAGAACTGGTTCAGCAGCCTGAGCCACTTCGTGATCCACCTG.

Exemplary pairs of overlapping, trans-splicing, and dual hybrid vectors are described in Table 4 below.

TABLE 4

Exemplary pairs of overlapping, trans-splicing, and hybrid dual vectors for use in the methods and compositions described herein

| Vector Pair Number | Vector Type | Vector Pair |
|---|---|---|
| 1 | Overlapping | First nucleic acid vector contains: CAG promoter operably linked to exons 1-24 and the 500 kb 3' of the exon 24/25 boundary of a polynucleotide encoding a human OTOF protein<br>Second nucleic acid vector contains: the 500 kb 5' of the exon 24/25 boundary and exons 25-48 of a polynucleotide encoding a human OTOF protein and a bGH poly(A) sequence |
| 2 | Overlapping | First nucleic acid vector contains: CAG promoter operably linked to exons 1-28 and the 500 kb 3' of the exon 28/29 boundary of a polynucleotide encoding a human OTOF protein<br>Second nucleic acid vector contains: the 500 kb 5' of the exon 28/29 boundary and exons 29-48 of a polynucleotide encoding a human OTOF protein and a bGH poly(A) sequence |
| 3 | Overlapping | First nucleic acid vector contains: Myo15 promoter operably linked to exons 1-21 and the 500 kb 3' of the exon 21/22 boundary of a polynucleotide encoding a human OTOF protein<br>Second nucleic acid vector contains: the 500 kb 5' of the exon 21/22 boundary and exons 22-48 of a polynucleotide encoding a human OTOF protein and a bGH poly(A) sequence |
| 4 | Trans-splicing | First nucleic acid vector contains: CAG promoter operably linked to exons 1-26 of a polynucleotide encoding a human OTOF protein and a splice donor sequence 3' of the polynucleotide<br>Second nucleic acid vector contains: a splice acceptor sequence 5' of exons 27-48 of a polynucleotide encoding a human OTOF protein and a bGH poly(A) sequence |
| 5 | Trans-splicing | First nucleic acid vector contains: Myo15 promoter operably linked to exons 1-19 of a polynucleotide encoding a human OTOF protein and a splice donor sequence 3' of the polynucleotide<br>Second nucleic acid vector contains: a splice acceptor sequence 5' of exons 20-48 of a polynucleotide encoding a human OTOF protein and a bGH poly(A) sequence |
| 6 | Trans-splicing | First nucleic acid vector contains: Myo15 promoter operably linked to exons 1-25 of a polynucleotide encoding a human OTOF protein and a splice donor sequence 3' of the polynucleotide<br>Second nucleic acid vector contains: a splice acceptor sequence 5' of exons 26-48 of a polynucleotide encoding a human OTOF protein and a bGH poly(A) sequence |
| 7 | Hybrid | First nucleic acid vector contains: CAG promoter operably linked to exons 1-26 of a polynucleotide encoding a human OTOF protein, a splice donor sequence 3' of the polynucleotide, and a recombinogenic region 3' of the splice donor sequence<br>Second nucleic acid vector contains: a recombinogenic region, a splice acceptor sequence 3' of the recombinogenic region, exons 27-48 of a polynucleotide encoding a human OTOF protein 3' of the splice acceptor sequence, and a bGH poly(A) sequence |
| 8 | Hybrid | First nucleic acid vector contains: Myo15 promoter operably linked to exons 1-19 of a polynucleotide encoding a human OTOF protein, a splice donor sequence 3' of the polynucleotide, and a recombinogenic region 3' of the splice donor sequence<br>Second nucleic acid vector contains: a recombinogenic region, a splice acceptor sequence 3' of the recombinogenic region, exons 20-48 of a polynucleotide encoding a human OTOF protein 3' of the splice acceptor sequence, and a bGH poly(A) sequence |
| 9 | Hybrid | First nucleic acid vector contains: Myo15 promoter operably linked to exons 1-25 of a polynucleotide encoding a human OTOF protein, a splice donor sequence 3' of the polynucleotide, and a recombinogenic region 3' of the splice donor sequence<br>Second nucleic acid vector contains: a recombinogenic region, a splice acceptor sequence 3' of the recombinogenic region, exons 26-48 of a polynucleotide encoding a human OTOF protein 3' of the splice acceptor sequence, and a bGH poly(A) sequence |

Vectors for the Expression of OTOF

In addition to achieving high rates of transcription and translation, stable expression of an exogenous gene in a mammalian cell can be achieved by integration of the polynucleotide containing the gene into the nuclear genome of the mammalian cell. A variety of vectors for the delivery and integration of polynucleotides encoding exogenous proteins into the nuclear DNA of a mammalian cell have been developed. Examples of expression vectors are disclosed in, e.g., WO 1994/011026 and are incorporated herein by reference. Expression vectors for use in the compositions and methods described herein contain a polynucleotide sequence that encodes a portion of OTOF, as well as, e.g., additional sequence elements used for the expression of these agents and/or the integration of these polynucleotide sequences into the genome of a mammalian cell. Certain vectors that can be used for the expression of OTOF include plasmids that contain regulatory sequences, such as promoter and enhancer regions, which direct gene transcription. Other useful vectors for expression of OTOF contain polynucleotide sequences that enhance the rate of translation of these genes or improve the stability or nuclear export of the mRNA that results from gene transcription. These sequence elements include, e.g., 5' and 3' untranslated regions and a polyadenylation signal site in order to direct efficient transcription of the gene carried on the expression vector. The expression vectors suitable for use with the compositions and methods described herein may also contain a polynucleotide encoding a marker for selection of cells that contain such a vector. Examples of a suitable marker include genes that encode resistance to antibiotics, such as ampicillin, chloramphenicol, kanamycin, or nourseothricin.

AAV Vectors for Nucleic Acid Delivery

In some embodiments, nucleic acids of the compositions and methods described herein are incorporated into recombinant AAV (rAAV) vectors and/or virions in order to facilitate their introduction into a cell. rAAV vectors useful in the compositions and methods described herein are recombinant nucleic acid constructs that include (1) a heterologous sequence to be expressed (e.g., a polynucleotide encoding an N-terminal or C-terminal portion of an OTOF protein) and (2) viral sequences that facilitate stability and expression of the heterologous genes. The viral sequences may include those sequences of AAV that are required in cis for replication and packaging (e.g., functional ITRs) of the DNA into a virion. Such rAAV vectors may also contain marker or reporter genes. Useful rAAV vectors have one or more of the AAV WT genes deleted in whole or in part, but retain functional flanking ITR sequences. The AAV ITRs may be of any serotype suitable for a particular application. For use in the methods and compositions described herein, the ITRs can be AAV2 ITRs. Methods for using rAAV vectors are described, for example, in Tal et al., J. Biomed. Sci. 7:279 (2000), and Monahan and Samulski, Gene Delivery 7:24 (2000), the disclosures of each of which are incorporated herein by reference as they pertain to AAV vectors for gene delivery.

The nucleic acids and vectors described herein can be incorporated into a rAAV virion in order to facilitate introduction of the nucleic acid or vector into a cell. The capsid proteins of AAV compose the exterior, non-nucleic acid portion of the virion and are encoded by the AAV cap gene. The cap gene encodes three viral coat proteins, VP1, VP2 and VP3, which are required for virion assembly. The construction of rAAV virions has been described, for instance, in U.S. Pat. Nos. 5,173,414; 5,139,941; 5,863,541; 5,869,305; 6,057,152; and 6,376,237; as well as in Rabinowitz et al., J. Virol. 76:791 (2002) and Bowles et al., J. Virol. 77:423 (2003), the disclosures of each of which are incorporated herein by reference as they pertain to AAV vectors for gene delivery.

rAAV virions useful in conjunction with the compositions and methods described herein include those derived from a variety of AAV serotypes including AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S. For targeting cochlear hair cells, AAV1, AAV2, AAV6, AAV9, Anc80, Anc80L65, DJ/9, 7m8, and PHP.B may be particularly useful. Serotypes evolved for transduction of the retina may also be used in the methods and compositions described herein. The first and second nucleic acid vectors in the compositions and methods described herein may have the same serotype or different serotypes. Construction and use of AAV vectors and AAV proteins of different serotypes are described, for instance, in Chao et al., Mol. Ther. 2:619 (2000); Davidson et al., Proc. Natl. Acad. Sci. USA 97:3428 (2000); Xiao et al., J. Virol. 72:2224 (1998); Halbert et al., J. Virol. 74:1524 (2000); Halbert et al., J. Virol. 75:6615 (2001); and Auricchio et al., Hum. Molec. Genet. 10:3075 (2001), the disclosures of each of which are incorporated herein by reference as they pertain to AAV vectors for gene delivery.

Also useful in conjunction with the compositions and methods described herein are pseudotyped rAAV vectors. Pseudotyped vectors include AAV vectors of a given serotype (e.g., AAV9) pseudotyped with a capsid gene derived from a serotype other than the given serotype (e.g., AAV1, AAV2, AAV3, AAV4, AAV5, AAV6, AAV7, AAV8, etc.). Techniques involving the construction and use of pseudotyped rAAV virions are known in the art and are described, for instance, in Duan et al., J. Virol. 75:7662 (2001); Halbert et al., J. Virol. 74:1524 (2000); Zolotukhin et al., Methods, 28:158 (2002); and Auricchio et al., Hum. Molec. Genet. 10:3075 (2001).

AAV virions that have mutations within the virion capsid may be used to infect particular cell types more effectively than non-mutated capsid virions. For example, suitable AAV mutants may have ligand insertion mutations for the facilitation of targeting AAV to specific cell types. The construction and characterization of AAV capsid mutants including insertion mutants, alanine screening mutants, and epitope tag mutants is described in Wu et al., J. Virol. 74:8635 (2000). Other rAAV virions that can be used in methods described herein include those capsid hybrids that are generated by molecular breeding of viruses as well as by exon shuffling. See, e.g., Soong et al., Nat. Genet., 25:436 (2000) and Kolman and Stemmer, Nat. Biotechnol. 19:423 (2001).

Pharmaceutical Compositions

The nucleic acid vectors described herein may be incorporated into a vehicle for administration into a patient, such as a human patient suffering from sensorineural hearing loss or auditory neuropathy, as described herein. Pharmaceutical compositions containing vectors, such as viral vectors, that contain a polynucleotide encoding a portion of an OTOF protein can be prepared using methods known in the art. For example, such compositions can be prepared using, e.g., physiologically acceptable carriers, excipients or stabilizers (Remington's Pharmaceutical Sciences 16th edition, Osol, A. Ed. (1980); incorporated herein by reference), and in a desired form, e.g., in the form of lyophilized formulations or aqueous solutions.

Mixtures of the nucleic acid vectors (e.g., viral vectors) described herein may be prepared in water suitably mixed with one or more excipients, carriers, or diluents. Dispersions may also be prepared in glycerol, liquid polyethylene glycols, and mixtures thereof and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (described in U.S. Pat. No. 5,466,468, the disclosure of which is incorporated herein by reference). In any case the formulation may be sterile and may be fluid to the extent that easy syringability exists. Formulations may be stable under the conditions of manufacture and storage and may be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For example, a solution containing a pharmaceutical composition described herein may be suitably buffered, if necessary, and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion. Some variation in dosage will necessarily occur depending on the condition of the subject being treated. For local administration to the inner ear, the composition may be formulated to contain a synthetic perilymph solution. An exemplary synthetic perilymph solution includes 20-200 mM NaCl, 1-5 mM KCl, 0.1-10 mM $CaCl_2$), 1-10 mM glucose, and 2-50 mM HEPEs, with a pH between about 6 and 9 and an osmolality of about 300 mOsm/kg. The person responsible for administration will, in any event, determine the appropriate dose for the individual subject. Moreover, for human administration, preparations may meet sterility, pyrogenicity, general safety, and purity standards as required by FDA Office of Biologics standards.

Methods of Treatment

The compositions described herein may be administered to a subject with sensorineural hearing loss or auditory neuropathy by a variety of routes, such as local administration to the inner ear (e.g., administration into the perilymph or endolymph, e.g., through the oval window, round window, or horizontal canal, e.g., administration to a cochlear hair cell), intravenous, parenteral, intradermal, transdermal, intramuscular, intranasal, subcutaneous, percutaneous, intratracheal, intraperitoneal, intraarterial, intravascular, inhalation, perfusion, lavage, and oral administration. The most suitable route for administration in any given case will depend on the particular composition administered, the patient, pharmaceutical formulation methods, administration methods (e.g., administration time and administration route), the patient's age, body weight, sex, severity of the disease being treated, the patient's diet, and the patient's excretion rate. Compositions may be administered once, or more than once (e.g., once annually, twice annually, three times annually, bi-monthly, monthly, or bi-weekly). In some embodiments, the first and second nucleic acid vectors are administered simultaneously (e.g., in one composition). In some embodiments, the first and second nucleic acid vectors are administered sequentially (e.g., the second nucleic acid vector is administered immediately after the first nucleic acid vector, or 5 minutes, 10 minutes, 15 minutes, 20 minutes, 25 minutes, 30 minutes, 45 minutes, 1 hour, 2 hours, 8 hours, 12 hours, 1 day, 2 days, 7 days, two weeks, 1 month or more after the first nucleic acid vector). The first and second nucleic acid vector can have the same serotype or different serotypes (e.g., AAV serotypes).

Subjects that may be treated as described herein are subjects having or at risk of developing sensorineural hearing loss or auditory neuropathy. The compositions and methods described herein can be used to treat subjects having a mutation in OTOF (e.g., a mutation that reduces OTOF function or expression, or an OTOF mutation associated with sensorineural hearing loss), subjects having a family history of autosomal recessive sensorineural hearing loss or deafness (e.g., a family history of OTOF-related hearing loss), or subjects whose OTOF mutational status and/or OTOF activity level is unknown. The methods described herein may include a step of screening a subject for a mutation in OTOF prior to treatment with or administration of the compositions described herein. A subject can be screened for an OTOF mutation using standard methods known to those of skill in the art (e.g., genetic testing). The methods described herein may also include a step of assessing hearing in a subject prior to treatment with or administration of the compositions described herein. Hearing can be assessed using standard tests, such as audiometry, ABR, electrochocleography (ECOG), and otoacoustic emissions. The compositions and methods described herein may also be administered as a preventative treatment to patients at risk of developing hearing loss or auditory neuropathy, e.g., patients who have a family history of inherited hearing loss or patients carrying an OTOF mutation who do not yet exhibit hearing loss or impairment.

Treatment may include administration of a composition containing the nucleic acid vectors (e.g., AAV viral vectors) described herein in various unit doses. Each unit dose will ordinarily contain a predetermined-quantity of the therapeutic composition. The quantity to be administered, and the particular route of administration and formulation, are within the skill of those in the clinical arts. A unit dose need not be administered as a single injection but may include continuous infusion over a set period of time. Dosing may be performed using a syringe pump to control infusion rate in order to minimize damage to the cochlea. In cases in which the nucleic acid vectors are AAV vectors (e.g., AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, or PHP.S vectors), the viral vectors may be administered to the patient at a dose of, for example, from about $1\times10^{10}$ vector genomes (VG) to $1\times10^{15}$ VG (e.g., $1\times10^{10}$ VG, $2\times10^{10}$ VG, $3\times10^{10}$ VG, $4\times10^{10}$ VG, $5\times10^{10}$ VG, $6\times10^{10}$ VG, $7\times10^{10}$ VG, $8\times10^{10}$ VG, $9\times10^{10}$ VG, $1\times10^{11}$ VG, $2\times10^{11}$ VG, $3\times10^{11}$ VG, $4\times10^{11}$ VG, $5\times10^{11}$ VG, $6\times10^{11}$ VG, $7\times10^{11}$ VG, $8\times10^{11}$ VG, $9\times10^{11}$ VG, $1\times10^{12}$ VG, $2\times10^{12}$ VG, $3\times10^{12}$ VG, $4\times10^{12}$ VG, $5\times10^{12}$ VG, $6\times10^{12}$ VG, $7\times10^{12}$ VG, $8\times10^{12}$ VG, $9\times10^{12}$ VG, $1\times10^{13}$ VG, $2\times10^{13}$ VG, $3\times10^{13}$ VG, $4\times10^{13}$ VG, $5\times10^{13}$ VG, $6\times10^{13}$ VG, $7\times10^{13}$ VG, $8\times10^{13}$ VG, $9\times10^{13}$ VG, $1\times10^{14}$ VG, $2\times10^{14}$ VG, $3\times10^{14}$ VG, $4\times10^{14}$ VG, $5\times10^{14}$ VG, $6\times10^{14}$ VG, $7\times10^{14}$ VG, $8\times10^{14}$ VG, $9\times10^{14}$ VG, $1\times10^{15}$ VG) in a volume of 1 μL to 200 μL (e.g., 1, 2, 3, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, or 200 μL).

The compositions described herein are administered in an amount sufficient to improve hearing, increase WT OTOF expression (e.g., expression in a cochlear hair cell, e.g., an inner hair cell), or increase OTOF function. Hearing may be evaluated using standard hearing tests (e.g., audiometry, ABR, electrochocleography (ECOG), and otoacoustic emissions) and may be improved by 5% or more (e.g., 5%, 10%, 15%, 20%, 30%, 40%, 50%, 60%, 70%, 80%, 90%, 100% or more) compared to hearing measurements obtained prior to treatment. In some embodiments, the compositions are administered in an amount sufficient to improve the subject's ability to understand speech. The compositions described herein may also be administered in an amount sufficient to slow or prevent the development or progression of sensorineural hearing loss or auditory neuropathy (e.g., in subjects who carry a mutation in OTOF or have a family history of autosomal recessive hearing loss but do not exhibit hearing impairment, or in subjects exhibiting mild to moderate hearing loss). OTOF expression may be evaluated using immunohistochemistry, Western blot analysis, quantitative real-time PCR, or other methods known in the art for detection protein or mRNA, and may be increased by 5% or more (e.g., 5%, 10%, 15%, 20%, 30%, 40%, 50%, 60%, 70%, 80%, 90%, 100% or more) compared to OTOF expression prior to administration of the compositions described herein. OTOF function may be evaluated directly (e.g., using electrophysiological methods or imaging methods to assess exocytosis) or indirectly based on hearing tests, and may be increased by 5% or more (e.g., 5%, 10%, 15%, 20%, 30%, 40%, 50%, 60%, 70%, 80%, 90%, 100% or more) compared to OTOF function prior to administration of the compositions described herein. These effects may occur, for example, within 1 week, 2 weeks, 3 weeks, 4 weeks, 5 weeks, 6 weeks, 7 weeks, 8 weeks, 9 weeks, 10 weeks, 15 weeks, 20 weeks, 25 weeks, or more, following administration of the compositions described herein. The patient may be evaluated 1 month, 2 months, 3 months, 4 months, 5 months, 6 months or more following administration of the composition depending on the dose and route of administration used for treatment. Depending on the outcome of the evaluation, the patient may receive additional treatments.

Kits

The compositions described herein can be provided in a kit for use in treating sensorineural hearing loss or auditory neuropathy (e.g., hearing loss associated with a mutation in OTOF). Compositions may include nucleic acid vectors described herein (e.g., a first nucleic acid vector containing a polynucleotide that encodes and N-terminal portion of an OTOF protein and a second nucleic acid vector containing a polynucleotide that encodes a C-terminal portion of an OTOF protein), optionally packaged in an AAV virus capsid (e.g., AAV1, AAV9, Anc80L65, DJ/9, or 7m8). The kit can further include a package insert that instructs a user of the kit, such as a physician, to perform the methods described herein. The kit may optionally include a syringe or other device for administering the composition.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regard as their invention.

Example 1: Generation of Nucleic Acid Vectors that Recombine to Produce Full-Length OTOF Gene fragments were synthesized and sub-cloned into an AAV2/cis-plasmid using restriction enzyme sites. Plasmids were maxi prepped to generate 1 mg of transfection grade plasmid. Inner ear-derived HEI-OC1 cells were seeded into a 12-well tissue culture dish 24 hours before plasmid transfection at a density of 200,000 cells/well. One microgram of each plasmid was transfected using Lipofectamine® 3000 according to standard manufacturer's protocol. For wells that received both 5' and 3' plasmids, 1 μg of each was transfected for a total of 2 μg of DNA. As a positive control, full-length Otoferlin cDNA was also transfected. Cells were incubated with plasmid for 48 hours.

Figure 20A:
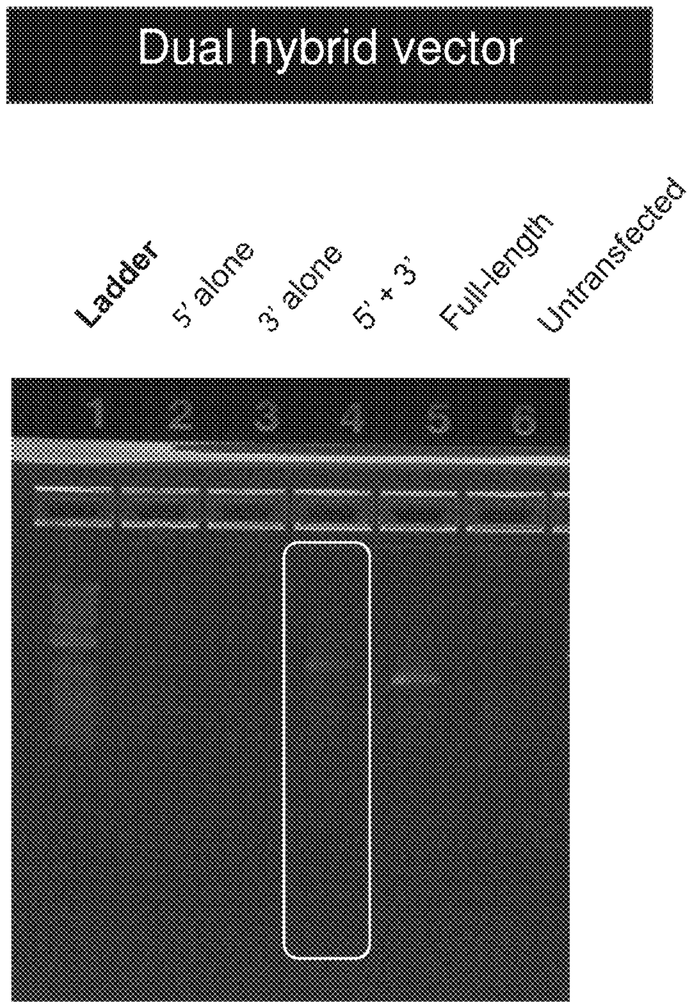
FIGS. 20A and 20B are images demonstrating that polynucleotides encoded by dual hybrid vectors (FIG. 20A) and overlapping vectors (FIG. 20B) undergo recombination in cell culture (top). Beneath each image is a schematic depicting the type of recombination that occurs in each dual vector system (bottom). Inner ear-derived House Ear Institute-Organ of Corti 1 (HEI-OC1) cells were transfected with plasmids containing either the 5' half of OTOF alone, the 3' half of OTOF alone, or both the 5' and 3' halves together. For the dual hybrid vector experiment, the 5' vector contained a Myo15 promoter (SEQ ID NO: 36) operably linked to exons 1-19 of a polynucleotide encoding the human OTOF protein of SEQ ID NO: 1, a splice donor sequence (SD), a recombinogenic region (AK), and a degradation signal sequence (CL1); and the 3' vector contained a recombinogenic region (AK), a degradation signal sequence (CL1), a splice acceptor sequence (SA), exons 20-48 of a polynucleotide encoding the human OTOF protein of SEQ ID NO: 1, and a WPRE sequence (SEQ ID NO: 23). For the overlapping dual vector experiment, the 5' vector contained a Myo15 promoter (SEQ ID NO: 36) operably linked to exons 1-21 of a polynucleotide encoding the human OTOF protein of SEQ ID NO: 1 and the 500 kb immediately 3' of the exon 21/22 boundary; and the 3' vector contained the 500 kb immediately 5' of the exon 21/22 boundary and exons 22-48 of a polynucleotide encoding the human OTOF protein of SEQ ID NO: 1, and a WPRE sequence (SEQ ID NO: 23). Full-length otoferlin was transfected as a positive control and untransfected cells were used a negative control. Genomic DNA was extracted from cells using a standard column from a gDNA isolation kit. PCR primers were designed to anneal outside of the region of splice sites or overlap and PCR was performed using standard molecular biology techniques. Amplicons were visualized using gel electrophoresis. The white box in the gel image indicates the lane in which 5' and 3' halves were transfected together and where a roughly 1 kb amplicon is seen, indicating recombination.
Figure 20A:
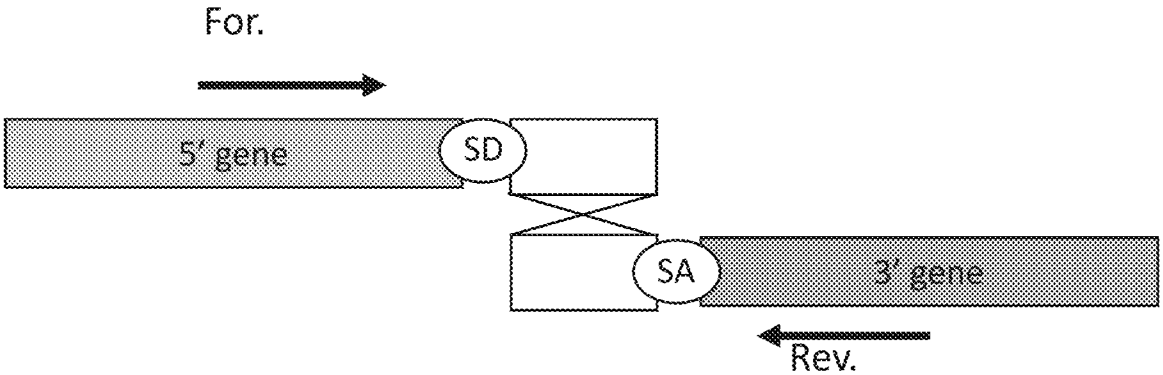
Figure 20B:
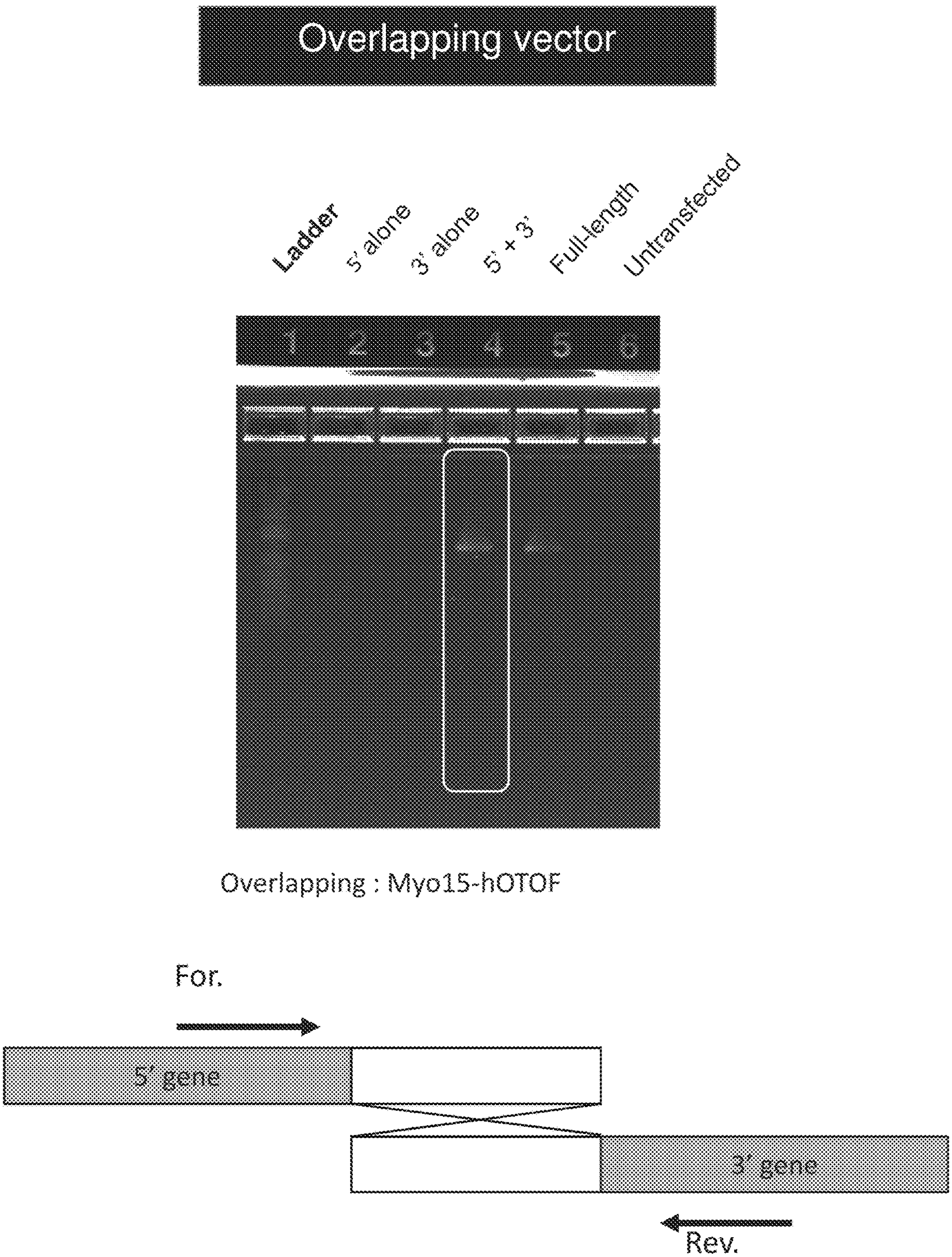

For PCR to check for recombination at the DNA level, genomic DNA was extracted from each well using the Qiagen® DNeasy® Blood and Tissue kit, according to standard manufacturer's protocol. PCR primers were designed to anneal to the plasmid outside of the region of overlap or splicing to generate an amplicon of ~1200 bp. PCR was performed using MyTaq® 2× mastermix according to manufacturer's recommendations: annealing temperature of 58° C., elongation step of 30 seconds, and cycle number of 35×. Ten microliters of PCR product was run on a pre-cast 1.2% agarose E-gel and imaged on a Bio-Rad® gel doc imaging station. Both dual hybrid vectors (FIG. 20A) and overlapping vectors (FIG. 20B) showed evidence of recombination when the 5' and 3' plasmids were transfected together.

Figure 21A:
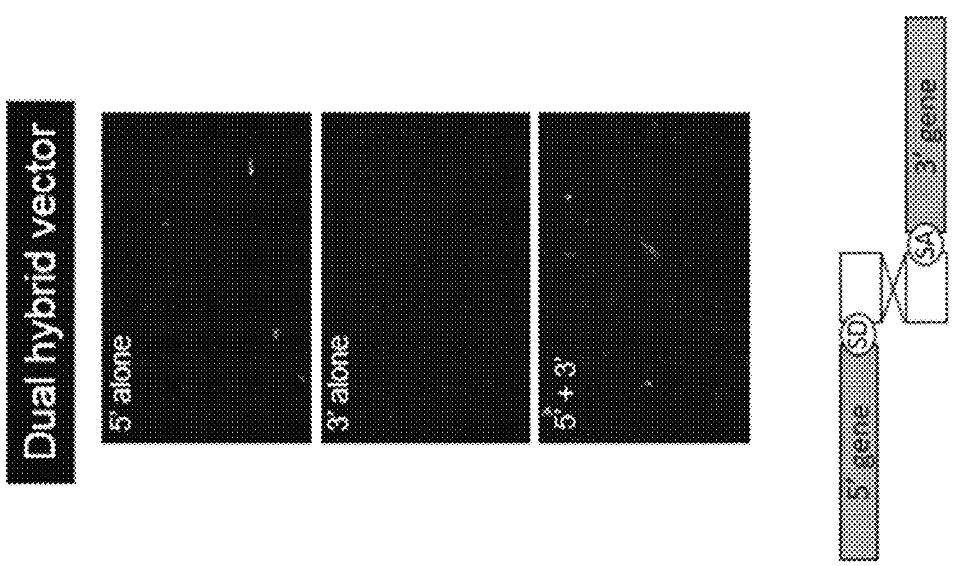
FIGS. 21A-21C are images demonstrating that polynucleotides encoded by dual hybrid vectors (FIG. 21A), trans-splicing vectors (FIG. 21B), and overlapping vectors (FIG. 21C) undergo recombination in cell culture and produce OTOF protein (top). Beneath each image is a schematic depicting the type of recombination that occurs in each dual vector system (bottom). Inner ear derived HEI-OC1 cells were transfected with plasmids containing either the 5' half of otoferlin alone, the 3' half of otoferlin alone, or both 5' and 3' halves together. For the dual hybrid vector experiment, the 5' vector contained a CAG promoter operably linked to the full-length human OTOF 5' UTR and exons 1-26 of a polynucleotide encoding the human OTOF protein of SEQ ID NO: 1, a splice donor sequence (SD), a recombinogenic region (AK), and a degradation signal sequence (CL1); and the 3' vector contained a recombinogenic region (AK), a degradation signal sequence (CL1), a splice acceptor sequence (SA), exons 27-48 of a polynucleotide encoding the human OTOF protein of SEQ ID NO: 1, the full-length human OTOF 3' UTR, and a WPRE sequence (SEQ ID NO: 23). For the trans-splicing dual vector experiment, the 5' vector contained a Myo15 promoter (SEQ ID NO: 36) operably linked to exons 1-24 of a polynucleotide encoding the mouse OTOF protein of SEQ ID NO: 6, and a splice donor sequence (SD); and the 3' vector contained a splice acceptor sequence (SA), exons 25-48 of a polynucleotide encoding the mouse OTOF protein of SEQ ID NO: 6, the full-length mouse OTOF 3' UTR, and a WPRE sequence (SEQ ID NO: 23). For the overlapping dual vector experiment, the 5' vector contained a CMV promoter operably linked to exons 1-24 of a polynucleotide encoding the mouse OTOF protein of SEQ ID NO: 6 and the 500 kb immediately 3' of the exon 24/25 boundary; and the 3' vector contained the 500 kb immediately 5' of the exon 24/25 boundary and exons 25-48 of a polynucleotide encoding the mouse OTOF protein of SEQ ID NO: 6, and a WPRE sequence (SEQ ID NO: 23). Cells were fixed in 4% PFA 48 hours post transfection and processed for immunohistochemistry. An antibody specific to OTOF protein labels some cells in the 5' alone transfected cells, no cells in the 3' alone transfected cells, and more cells than both previous conditions combined in the 5'+3' transfected cells.
Figure 21B:
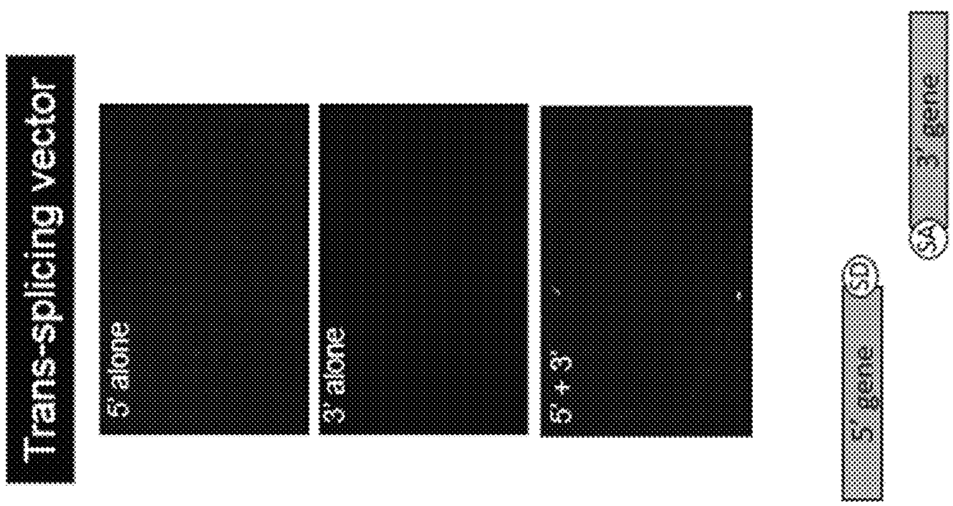
Figure 21C:
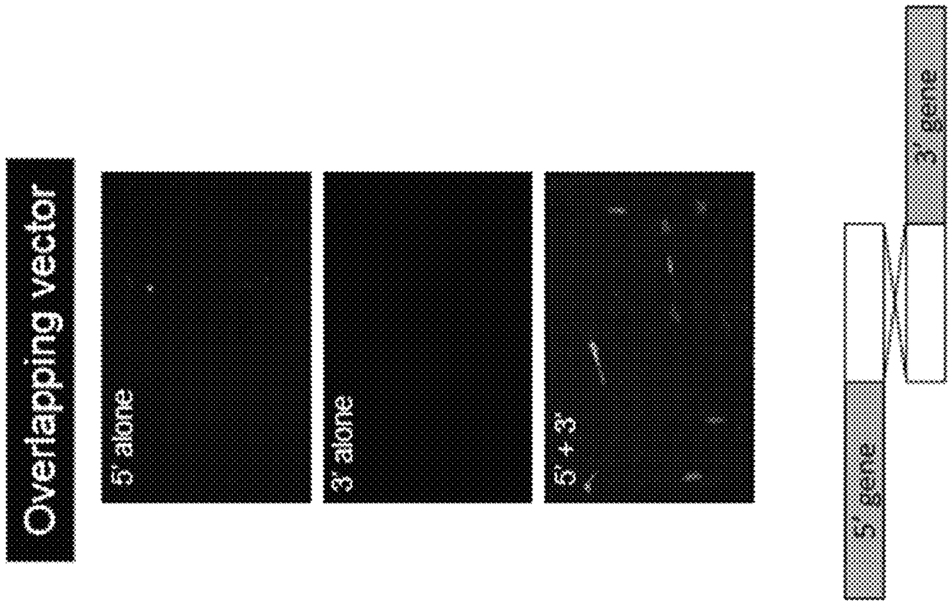

For immunofluorescence to check for recombination and generation of protein, cells were fixed with cold 4% PFA for 20 minutes at room temperature. Cells were washed three times with PBS and then permeabilized in a blocking solution of PBS with 10% normal donkey serum and 0.01% TritonX100. Cells were incubated in primary antibody overnight (mouse-anti-Otoferlin, Abcam® ab53233) at a concentration of 1:1000 at 4° C. Cells were washed three times with PBS and incubated in secondary antibody for three hours at room temperature (donkey-anti-mouse Alexa Fluor® 647, Thermo Fisher Scientific® A-31571). Cells were washed three times in PBS and stained with DAPI for 15 minutes at room temperature. Cells were imaged using a Zeiss® inverted Apotome® microscope. Increased staining was observed in cells transfected with both 5' and 3' plasmids compared to transfection of the 5' or 3' plasmid alone, indicating that the dual hybrid vector (FIG. 21A), trans-splicing vector (FIG. 21B), and overlapping vector (FIG. 21C) systems recombined in HEI-OC1 cells and generated OTOF protein.

Example 2: Administration of a Composition Containing Overlapping Dual Vectors that Express OTOF to a Subject with Sensorineural Hearing Loss According to the methods disclosed herein, a physician of skill in the art can treat a patient, such as a human patient, with sensorineural hearing loss (e.g., sensorineural hearing loss associated with a mutation in OTOF) so as to improve or restore hearing. To this end, a physician of skill in the art can administer to the human patient a composition containing a first AAV vector (e.g., AAV1 or AAV9) containing a Myo15 promoter (e.g., SEQ ID NO: 36) operably linked to exons 1-21 of a polynucleotide encoding an OTOF protein (e.g., human OTOF, e.g., SEQ ID NO: 1) and the 500 kb immediately 3' of the exon 21/22 boundary, and a second AAV vector (e.g., AAV1 or AAV9) containing the 500 kb immediately 5' of the exon 21/22 boundary and exons 22-48 of a polynucleotide encoding an OTOF protein (e.g., human OTOF, e.g., SEQ ID NO: 1) and a bGH poly(A) sequence. The composition containing the overlapping dual AAV vectors may be administered to the patient, for example, by local administration to the inner ear (e.g., injection into the perilymph), to treat sensorineural hearing loss.

Following administration of the composition to a patient, a practitioner of skill in the art can monitor the expression of OTOF, and the patient's improvement in response to the therapy, by a variety of methods. For example, a physician can monitor the patient's hearing by performing standard tests, such as audiometry, ABR, electrochocleography (ECOG), and otoacoustic emissions following administration of the composition. A finding that the patient exhibits improved hearing in one or more of the tests following administration of the composition compared to hearing test results prior to administration of the composition indicates that the patient is responding favorably to the treatment. Subsequent doses can be determined and administered as needed.

Example 3: Administration of a Composition Containing Trans-Splicing Dual Vectors that Express OTOF to a Subject with Sensorineural Hearing Loss According to the methods disclosed herein, a physician of skill in the art can treat a patient, such as a human patient, with sensorineural hearing loss (e.g., sensorineural hearing loss associated with a mutation in OTOF) so as to improve or restore hearing. To this end, a physician of skill in the art can administer to the human patient a composition containing a first AAV vector (e.g., AAV1 or AAV9) containing a Myo15 promoter (e.g., SEQ ID NO: 36) operably linked to exons 1-19 of a polynucleotide encoding an OTOF protein (e.g., human OTOF, e.g., SEQ ID NO: 1) and a splice donor sequence (e.g., SEQ ID NO: 20) 3' of the polynucleotide sequence, and a second AAV vector (e.g., AAV1 or AAV9) containing a splice acceptor sequence (e.g., SEQ ID NO: 21) 5' of exons 20-48 of a polynucleotide encoding an OTOF protein (e.g., human OTOF, e.g., SEQ ID NO: 1) and a bGH poly(A) sequence. The composition containing the trans-splicing dual AAV vectors may be administered to the patient, for example, by local administration to the inner ear (e.g., injection into the perilymph), to treat sensorineural hearing loss.

Following administration of the composition to a patient, a practitioner of skill in the art can monitor the expression of OTOF, and the patient's improvement in response to the therapy, by a variety of methods. For example, a physician can monitor the patient's hearing by performing standard tests, such as audiometry, ABR, electrochocleography (ECOG), and otoacoustic emissions following administration of the composition. A finding that the patient exhibits improved hearing in one or more of the tests following administration of the composition compared to hearing test results prior to administration of the composition indicates that the patient is responding favorably to the treatment. Subsequent doses can be determined and administered as needed.

Example 4: Administration of a Composition Containing Dual Hybrid Vectors that Express OTOF to a Subject with Sensorineural Hearing Loss According to the methods disclosed herein, a physician of skill in the art can treat a patient, such as a human patient, with sensorineural hearing loss (e.g., sensorineural hearing loss associated with a mutation in OTOF) so as to improve or restore hearing. To this end, a physician of skill in the art can

The invention claimed is:

1. A method of treating a subject having sensorineural hearing loss or auditory neuropathy or carrying an OTOF gene mutation, the method comprising administering to the subject a therapeutically effective amount of a composition comprising:

a first adeno-associated virus (AAV) vector comprising a myosin 15 (Myo15) promoter having at least 95% sequence identity to the sequence of SEQ ID NO: 36, wherein the Myo15 promoter is operably linked to a first coding polynucleotide that encodes an N-terminal portion of a human otoferlin (OTOF) protein; and a second AAV vector comprising a second coding polynucleotide that encodes a C-terminal portion of the human OTOF protein and a polyadenylation sequence positioned at a 3' end of the second coding polynucleotide, wherein neither the first AAV vector nor the second AAV vector encodes a full-length OTOF protein, and, when introduced into a mammalian cell, the first AAV vector and the second AAV vector undergo homologous recombination or concatemerization to form a recombined nucleic acid that encodes the full-length OTOF protein.

2. The method of claim 1, wherein the subject has an OTOF gene mutation.

3. The method of claim 1, wherein the subject has autosomal recessive deafness-9 (DFNB9).

4. The method of claim 1, wherein the first AAV vector further comprises a splice donor signal sequence positioned at a 3' end of the first coding polynucleotide; and the second AAV vector further comprises a splice acceptor signal sequence, wherein the second coding polynucleotide that encodes a C-terminal portion of the human OTOF protein is positioned at a 3' end of the splice acceptor signal sequence, wherein the first coding polynucleotide and the second coding polynucleotide do not overlap.

5. The method of claim 1, wherein the first AAV vector further comprises a splice donor signal sequence positioned at a 3' end of the first coding polynucleotide and a first recombinogenic region positioned 3' of the splice donor signal sequence; and the second AAV vector further comprises a second recombinogenic region and a splice acceptor signal sequence positioned 3' of the second recombinogenic region, wherein the second coding polynucleotide that encodes a C-terminal portion of the human OTOF protein is positioned at a 3' end of the splice acceptor signal sequence, wherein the first coding polynucleotide and the second coding polynucleotide do not overlap.

6. The method of claim 5, wherein the first coding polynucleotide and the second coding polynucleotide are divided at an OTOF exon boundary.

7. The method of claim 1, wherein the first coding polynucleotide and the second coding polynucleotide that encode the human OTOF protein do not comprise introns.

8. The method of claim 1, wherein the Myo15 promoter comprises the sequence of SEQ ID NO: 36.

9. A method of expressing OTOF in a cell, the method comprising introducing a composition into the cell comprising:

a first adeno-associated virus (AAV) vector comprising a myosin 15 (Myo15) promoter having at least 95% sequence identity to the sequence of SEQ ID NO: 36, wherein the Myo15 promoter is operably linked to a first coding polynucleotide that encodes an N-terminal portion of a human otoferlin (OTOF) protein; and a second AAV vector comprising a second coding polynucleotide that encodes a C-terminal portion of the human OTOF protein and a polyadenylation sequence positioned at a 3' end of the second coding polynucleotide, wherein neither the first AAV vector nor the second AAV vector encodes a full-length OTOF protein, and, when introduced into a mammalian cell, the first AAV vector and the second AAV vector undergo homologous recombination or concatemerization to form a recombined nucleic acid that encodes the full-length OTOF protein.

10. The method of claim 9, wherein the cell is a cochlear hair cell.

11. The method of claim 10, wherein the cell is an inner hair cell.

12. The method of claim 9, wherein the first AAV vector further comprises a splice donor signal sequence positioned at a 3' end of the first coding polynucleotide; and the second AAV vector further comprises a splice acceptor signal sequence, wherein the second coding polynucleotide that encodes a C-terminal portion of the human OTOF protein is positioned at a 3' end of the splice acceptor signal sequence, wherein the first coding polynucleotide and the second coding polynucleotide do not overlap.

13. The method of claim 9, wherein the first AAV vector further comprises a splice donor signal sequence positioned at a 3' end of the first coding polynucleotide and a first recombinogenic region positioned 3' of the splice donor signal sequence; and the second AAV vector further comprises a second recombinogenic region and a splice acceptor signal sequence positioned 3' of the second recombinogenic region, wherein the second coding polynucleotide that encodes a C-terminal portion of the human OTOF protein is positioned at a 3' end of the splice acceptor signal sequence, wherein the first coding polynucleotide and the second coding polynucleotide do not overlap.

14. The method of claim 13, wherein the first coding polynucleotide and the second coding polynucleotide are divided at an OTOF exon boundary.

15. The method of claim 9, wherein the first coding polynucleotide and the second coding polynucleotide that encode the human OTOF protein do not comprise introns.

16. The method of claim 9, wherein the Myo15 promoter comprises the sequence of SEQ ID NO: 36.

* * * * *